United States Patent
Tasken et al.

(10) Patent No.: US 9,556,111 B2
(45) Date of Patent: Jan. 31, 2017

(54) TERTIARY AMINES FOR USE IN THE TREATMENT OF CARDIAC DISORDERS

(71) Applicant: Universitetet I Oslo, Blindern (NO)

(72) Inventors: Kjetil Tasken, Rykkinn (NO); Birgitte Lygren, Kolbotn (NO); Ellen Ostensen, Lillestrom (NO); Jo Klaveness, Oslo (NO)

(73) Assignee: UNIVERSITETET I OSLO, Blindern (NO)

( * ) Notice: Subject to any disclaimer, the term of this patent is extended or adjusted under 35 U.S.C. 154(b) by 0 days.

(21) Appl. No.: 14/402,037

(22) PCT Filed: May 17, 2013

(86) PCT No.: PCT/EP2013/060263
§ 371 (c)(1),
(2) Date: Nov. 18, 2014

(87) PCT Pub. No.: WO2013/171332
PCT Pub. Date: Nov. 21, 2013

(65) Prior Publication Data
US 2015/0133510 A1  May 14, 2015

(30) Foreign Application Priority Data
May 18, 2012 (GB) .................................. 1208775.5

(51) Int. Cl.
| | |
|---|---|
| C07C 217/58 | (2006.01) |
| C07D 277/28 | (2006.01) |
| C07D 213/36 | (2006.01) |
| C07C 211/27 | (2006.01) |
| C07C 211/29 | (2006.01) |
| C07D 257/04 | (2006.01) |
| C07D 277/56 | (2006.01) |
| C07D 307/79 | (2006.01) |
| C07C 275/40 | (2006.01) |
| C07C 211/49 | (2006.01) |
| C07C 229/38 | (2006.01) |

(52) U.S. Cl.
CPC ........... *C07C 217/58* (2013.01); *C07C 211/27* (2013.01); *C07C 211/29* (2013.01); *C07C 211/49* (2013.01); *C07C 229/38* (2013.01); *C07C 275/40* (2013.01); *C07D 213/36* (2013.01); *C07D 257/04* (2013.01); *C07D 277/28* (2013.01); *C07D 277/56* (2013.01); *C07D 307/79* (2013.01)

(58) Field of Classification Search
CPC .... C07C 211/27; C07C 211/29; C07D 257/04; C07D 277/56; C07D 277/28
USPC ......... 546/329, 334; 548/202, 205; 564/443; 514/357
See application file for complete search history.

(56) References Cited

U.S. PATENT DOCUMENTS

| | | | |
|---|---|---|---|
| 6,107,104 A | 8/2000 | Lockerbie et al. | |
| 6,723,743 B1 | 4/2004 | Thurkauf et al. | |
| 6,958,214 B2 | 10/2005 | Braun | |
| 7,432,342 B2 | 10/2008 | Braun et al. | |
| 2005/0282814 A1 | 12/2005 | Wrasidlo et al. | |
| 2006/0154330 A1 | 7/2006 | Klussmann et al. | |
| 2009/0104177 A1 | 4/2009 | Klussmann et al. | |
| 2011/0158905 A1 | 6/2011 | Goldenberg et al. | |

FOREIGN PATENT DOCUMENTS

| | | |
|---|---|---|
| CN | 1865221 A | 11/2006 |
| DE | 2150293 A1 | 4/1973 |
| EP | 1777230 A1 | 4/2007 |
| EP | 2098226 A1 | 9/2009 |
| WO | WO0027852 A1 | 5/2000 |
| WO | WO03057673 A1 | 7/2003 |
| WO | WO2004081576 A2 | 9/2004 |
| WO | WO2006011043 A1 | 2/2006 |
| WO | WO2006032909 A2 | 3/2006 |
| WO | WO2006032923 A2 | 3/2006 |
| WO | WO2006122546 A1 | 11/2006 |
| WO | WO2007028969 A2 | 3/2007 |
| WO | WO2010073235 A1 | 7/2010 |
| WO | WO2012080762 A1 | 6/2012 |

OTHER PUBLICATIONS

Dorwald F. A. Side Reactions in Organic Synthesis, 2005, Wiley: VCH, Weinheim p. IX of Preface.*
The International Search Report and Written Opinion mailed Feb. 25, 2014 in connection with International Application No. PCT/EP2013/060263.
Singh, Chingakham B. et al. "Aqueous-Mediated N-Alkylation of Amines." Eur. J. Org. Chem. 2007, pp. 1369-1377.
"XP002719557." Database Registry, Chemical Abstracts Service, Colombus, Ohio, U.S., Aug. 3, 2005.
"XP002719558." Database Registry, Chemical Abstracts Service, Colombus, Ohio, U.S., Sep. 10, 2008.
"XP002719559." Database Registry, Chemical Abstracts Service, Colombus, Ohio, U.S., Sep. 10, 2008.

\* cited by examiner

*Primary Examiner* — Rita Desai
(74) *Attorney, Agent, or Firm* — Dorsey & Whitney LLP

(57) ABSTRACT

The present invention relates to tertiary amines of formula (I) for use in therapy, particularly for use in treating cardiovascular disorders. The compounds have been found to regulate phospholamban phosphorylation by interfering with the A-kinase anchor protein 18delta (AKAP18δ) binding to the PKA substrate phospholamban. The compounds share a tri(alkylaryl/alkylheteroaryl)amine structure.

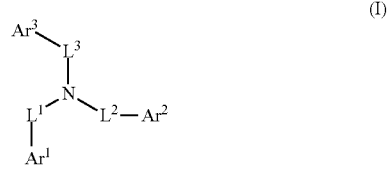

(I)

13 Claims, 4 Drawing Sheets

A

B

TERTIARY AMINES FOR USE IN THE TREATMENT OF CARDIAC DISORDERS

Figure 1:
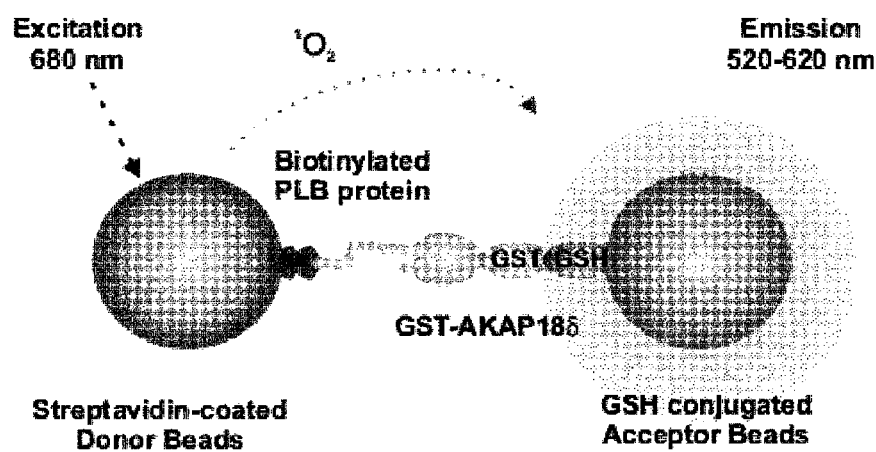
Figure 1:
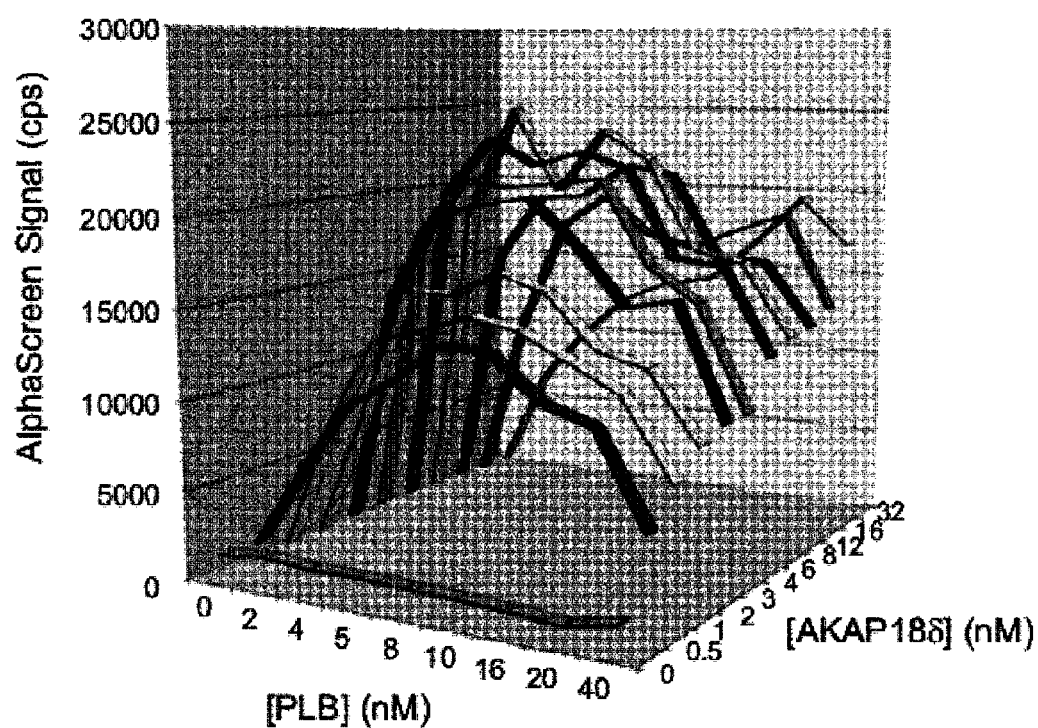

The invention relates to new chemical compounds, new pharmaceutical compositions and use of these compounds and their compositions for treatment of cardiac disorders especially reperfusion syndrome following myocardial infarction and post-infarction chronic heart failure. The specific compounds interfere with the A-kinase anchor protein (AKAP) 18delta (AKAP18δ) binding to the PKA substrate phospholamban.

The A-kinase anchor proteins (AKAPs) are a group of structurally diverse proteins which have the common function of binding to the regulatory subunit of protein kinase A (PKA) and confining the PKA holoenzyme to discrete locations within the cell. There are at least 50 different AKAPs, all of which have been cloned. Typical AKAPs include for example AKAP79, AKAP18, AKAP450, all of which are somewhat arbitrarily named after their apparent mobility by SDS-poly acrylamide gel electrophoresis. Later, the gene nomenclature committee has also introduced a separate nomenclature for AKAPs where they are consecutively numbered AKAP1, AKAP2, AKAP3 etc. In addition, some AKAPs like ezrin and Opa1 have already been assigned other names that are in use.

AKAPs act as targeting devices that assemble signaling elements on a scaffold (the AKAP) that itself targets to microdomains in cells. This allows specific targeting of substrates to be regulated by phosphorylation (by PKA) and dephosphorylation (by phosphatases). PKA binds via its regulatory subunits (RIα, RIIα, RIβ, RIIβ) directly to an amphipathic α-helix in the AKAP, which is a common feature of AKAPs. The AKAPs also bind other components including; phosphodiesterases (PDEs) which break down cAMP, phosphatases which dephosphorylate downstream PKA targets and also other kinases (PKC and MAPK). Some AKAPs are able to bind both regulatory subunits (RI & RII) of PKA and are dual-specific AKAPs (for example D-AKAP1, D-AKAP2, ezrin, OPA1).

For references related the various AKAPs and their biological functions see for example:

Tasken and Aandahl in Physiological Reviews volume 84, issue 1, page 137-167 (2004), Pidoux and Tasken in Journal of Molecular Endocrinology volume 44, issue 5, page 271-284 (2010), Feliciello et al in Journal of Molecular Biology, volume 308, issue 2, page 99-114 (2001), A. McCahill et al. in Cellular Signalling, volume 17, issue 9, page 1158-1173 (2005), L. Cardone et al. in Journal of Molecular Biology, volume 320, issue 3, page 663-675, A. M. Sardanelli et al. in FEBS Letters, volume 580, issue 24, page 5690-5696 (2006), B. Hu et al. in Biochemical and Biophysical Research Communications, volume 285, issue 5, page 1369-1376 (2001), S. Herrgaard et al. in FEBS Letters, volume 486, issue 2, page 107-111 (2000), B. Abrenica et al. in Journal of Molecular and Cellular Cardiology, volume 46, issue 5, 674-681 (2009), O. M. Seternes et al. in Cellular Signaling, volume 11, issue 3, page 211-219 (1999), K. Kurihara et al. in Biochemical Pharmacology, volume 66, issue 2, page 239-250 (2003), S. B. Moss et al. in Trends in Endocrinology & Metabolism, volume 12, issue 10, page 434-440 (2001), T. E. Lewis et al. in Urologic Oncology: Seminars and Original Investigations, volume 23, issue 6, page 407-412 (2005), F. W. Herberg et al. in Journal of Molecular Biology, volume 298, issue 2, page 329-339 (2000), C. R. Carlson et al. in Journal of Molecular Biology, volume 327, issue 3, page 609-618 (2003), R. B. Brown et al. in Biochemical and Biophysical Research Communications, volume 306, issue 2, page 394-401 (2003), T. Kurosu et al. in Brain Research, volume 1251, page 53-64 (2009), M. Hadad et al. in Mechanisms of Development, volume 128, issues 7-10, page 471-482 (2011), L. R. Johnson et al. in Development Biology, volume 192, issue 2, page 340-350 (1997), D. Diviani et al. in European Journal of Cell Biology, volume 85, issue 7, page 603-610 (2006), A. Feliciello et al. in Current Biology, volume 7, issue 12, page 1011-1014 (1997), G. K. Carnegie et al. in Molecular Cell, volume 15, issue 6, 889-899 (2004), A. Tamai et al. in International Congress Series, volume 1283, page 263-264 (2005), F. S. Kinderman et al. Molecular Cell, volume 24, issue 3, page 397-408 (2006), M. Colledge et al. in Neuron, volume 27, issue 1, page 107-119 (2000), Biochemical and Biophysical Research Communications, volume 225, issue 1, 313-319 ((1996), A. S. Cantrell et al. in Molecular and Cellular Neuroscience, volume 21, issue 1, page 63-80, K. Josefsen et al. in FEBS Letters, volume 584, issue 1, page 81-85 (2010), P. Klingbell et al. in Mechanisms of Development, volume 100, issue 2, page 323-326 (2001), G. K. Carnegie et al. in Molecular Cell, volume 32, issue 2, page 169-179 (2008), C. Riether et al. in Brain, Behavior, and Immunity, volume 25, issue 1, page 59-66 (2011), D. Diviani et al. in Current Biology, volume 10, issue 7, page 417-420 (2000), J. D. Scott et al in Handbook of Cell Signaling, volume 2, page 283-388 (2003), T-T Aye et al. in Journal of Molecular and Cellular Cardiology, volume 52, issue 2, 511-518 (2012), A. L. Bauman et al. in Neuropharmacology, volume 46, issue 3, page 299-310 (2004), J. D. Scott et al. in Handbook of Cell Signaling (Second Edition), page 1337-1347 (2010), M. G. Gold et al. in Molecular Cell, volume 24, issue 3, 383-395 (2006), A. Carrera et al. in Development Biology, volume 180, issue 1, page 284-296 (1996), M. L. Dell'Acqua et al. in European Journal of Cell Biology, volume 85, issue 7, page 627-633 (2006), N. W. Court et al. in Biochimica et Biophysica Acta (BBA)- Molecular Cell Research, volume 1744, issue 1, page 68-75 (2005)

There are a so far only a limited number of patent documents describing AKAPs. The most relevant documents are:

US2011/158905 (IBC Pharmaceuticals) describes a fusion protein comprising an anchoring domain (AD) moiety or a dimerization and docking domain (DDD) moiety, wherein the AD moiety consists of the amino acid sequence of the AD moiety of an AKAP (A-kinase anchoring protein) and the DDD moiety consists of the amino acid sequence of the DDD moiety of a human protein kinase A regulatory subunit; and an effector moiety. The effector moiety is selected from the group consisting of an antibody, an antigen-binding antibody fragment, a cytokine, a viral antigen, a xenoantigen, an RNase, a heat shock protein, the N-A1 domain of CEACAM5, the A3-B3 domain of CEACAM5, alpha2-macroglobulin, HSA (human serum albumin), a human protamine, and Fc fragment of a human antibody and a nucleic acid binding protein. The proteins might be useful for treatment of various diseases or conditions selected from the group consisting of cancer, autoimmune disease, immune dysregulation disease, organ-graft rejection, graft-versus-host disease, a neurodegenerative disease, a metabolic disease and a cardiovascular disease.

U.S. Pat. No. 7,432,342 (Sequenom) relates to A-kinase anchor protein (AKAPs) muteins, peptides thereof, and nucleic acids encoding the peptides, especially a polypeptide that is a mutein of a D-AKAP2 polypeptide, wherein the mutein exhibits modified binding to a regulatory subunit of PKA compared to a native D-AKAP2.

EP2098226 (Forsungsverbund Berlin E.V.) describes use of bicyclic compounds (I) or their salts, solvates, hydrates or formulations for preparing a medicament for the prophylaxis or treatment of diseases associated with defect of compartmentalized cyclic adenosine monophosphate (cAMP)-dependent signal transduction, is claimed. Use of bicyclic compounds of formula (I) or their salts, solvates, hydrates or formulations for preparing a medicament for the prophylaxis or treatment of diseases associated with defect of compartmentalized cyclic adenosine monophosphate (cAMP)-dependent signal transduction, is claimed. Formula (X) describes a general bicyclic formula in EP2098226, while formula (I) describes biphenyl compounds which are the most preferred compounds.

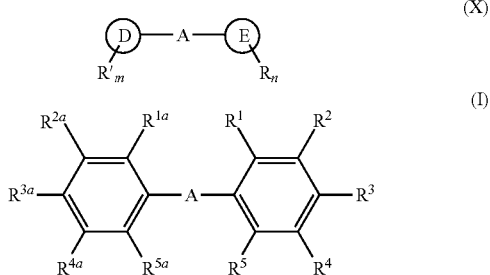

A: O, S, NH, CO, (hetero)alkyl, alkenyl, alkynyl, (hetero) aryl, cycloalkylene, (hetero)alkylcycloalkylene, heterocycloalkylene or (hetero)aralkylene group; R, R1: H, halo, $NH_2$, OH, $NO_2$, (hetero)alkyl, alkenyl, alkynyl (all preferred), SH, $N_3$, (hetero)aryl, (hetero)cycloalkyl, (hetero)alkylcycloalkyl or (hetero)aralkyl residue; D, E: (hetero) aryl, (hetero)cycloalkyl, (hetero)alkylcycloalkyl or (hetero) aralkyl (preferably substituted phenyl group); and m, n: 0-5 (preferably 1-3). The mechanism of action for these bicyclic compounds are protein kinease A and as AKAP interaction inhibitor. The indications for these agents are cardiovascular indications like hypertension and vasotropic activity.

WO2007/028969 (University of Oslo) relates to molecules which modify the binding between AKAP 18d and phosphodiesterase 4D or AKAP 18d and phospholamban and their use in altering PKA type II-mediated, activation of SERCA2 in a cell, for example to alleviate cardiovascular disease. Preferably such molecules include the motif RRASTIE. Molecules such as those which mimic binding of AKAP 18d to PKA, which allow enhanced phosphorylation of PLB are also discussed. No low-molecular weight compounds are specifically mentioned in this document.

WO2006/122546 describes non-peptide protein kinase A/protein kinase A anchor protein decouplers or disruptors. The compounds are listed in extensive tables of compounds. The chemical structures are structurally diverse and cannot be represented in any general formula. The compounds disclosed in these tables do not fall within the general formula of compounds of the present invention. The potential indications for use of these compounds are very broad including an extensive listing of very many different diseases, disorders and conditions.

WO2006/154330 (Forsungsverbund Berlin E.V.) relates to a nucleic acid sequence encoding a protein kinase A anchor protein, to the use of said nucleic acid sequence in a fusion protein, to a method of determining the interaction of said protein kinase A anchor protein with regulatory subunits of protein kinase A, and to a method of identifying cell-permeable substances.

WO2006/032923 (University of Oslo) describes a PKA I anchoring disrupting molecule or AKAP mimic, wherein said molecule or mimic is a polypeptide which comprises the following amino acid sequence: X1 X2 X3 Y A X4 X5 L A X6 X7 X8 I X9 X10 X11 X12 X13 (sequence (1)) or a peptidomimetic or analogue thereof is provided. Also provided are antibodies to the molecule, nucleic acid molecules comprising a sequence encoding the molecule and pharmaceutical compositions. A method of altering the PKA type I signaling pathway in a cell by administration of the anchoring disruption molecule or AKAP mimic, in particular to treat immunosuppressive disorders, proliferative diseases or autoimmune diseases is also described.

WO2006/032909 (University of Oslo) describes a PKA II anchoring disruption molecule or AKAP mimic, wherein said molecule or mimic is a polypeptide which comprises the following amino acid sequence: X1 X2 E X3 X4 A K Q I V X5 X6 X7 I X8 X9 X10 (sequence (1)) or a peptidomimetic or analogue thereof is provided. Also provided are antibodies to the molecule, nucleic acid molecules comprising a sequence encoding the molecule and pharmaceutical compositions. A method of altering the PKA type II signaling pathway in a cell by administration of the anchoring disruption molecule or AKAP mimic, in particular to treat cardiovascular and metabolic disorders is also described.

US2009/104177 (Forsungsverbund Berlin E.V.) relates to a nucleic acid sequence encoding peptides which inhibit the interaction of protein kinase A (PKA) and protein kinase A anchor proteins (AKAP), to a host organism comprising said nucleic acid sequence and optionally expressing said peptides, to the use of said peptides and of said host organism in investigating diseases associated with said AKAP-PKA interaction, and to the use of said peptides as pharmaceutical agent for the treatment of such diseases.

U.S. Pat. No. 6,958,214 (Sequenom) relates to polymorphic A-kinase anchor proteins (AKAPs) and nucleic acids encoding the proteins are provided herein. Methods of detecting polymorphic AKAPs and nucleic acids encoding the AKAPs, and kits for use in the detection methods are also provided. Further provided herein are methods of identifying subjects having or at risk of developing disorders of signal transduction. Methods of determining susceptibility to morbidity and/or increased or early mortality are also described.

WO2004/081576 (Sequenom) relates to polymorphic A-kinase anchor proteins (AKAPs) and nucleic acids encoding the proteins are provided herein. Methods of detecting polymorphic AKAPs and nucleic acids encoding the AKAPs, and kits for use in the detection methods are also provided. Further provided herein are methods of identifying subjects having or at risk of developing diseases or disorders, such as those related to signal transduction and/or cardiovascular disease. Methods of determining susceptibility to morbidity and/or increased or early mortality are also described.

U.S. Pat. No. 6,107,104 (ICOS) relates to compositions and methods useful for isolating calcineurin as well as inhibiting calcineurin activity. The compositions are peptides that contain regions that are homologous to calcineurin-binding regions of Akap79. Also provided are methods for determining if a cell contains a calcineurin-binding and PKA-binding anchoring protein that are useful for identifying additional proteins that bind both calcineurin and PKA. Another aspect of the present invention is methods of enhancing expression of interleukin 2 by T cells. Further provided are methods to identify proteins which interact with AKAP79, and methods to identify inhibitors of AKAP 79 interaction with other proteins.

The present invention relates to new chemical compounds, new pharmaceutical compositions and use of compounds and their compositions for treatment of cardiac disorders especially cardiac failure. The specific compounds interfere with the ability of the A-kinase anchor protein (AKAP) 186 to bind to the PKA substrate phospholamban and by disrupting this interaction specifically inhibits PKA phosphorylation of phospholamban upon adrenergic stimulation.

One aspect of the present invention relates to specific compounds interfering with A-kinase anchor proteins.

Thus, the present invention relates to a compound of formula (I) for use in therapy:

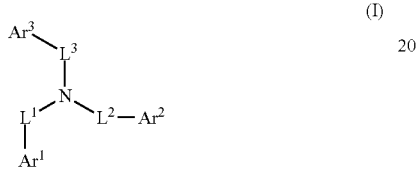
(I)

wherein

L$^1$, L$^2$ and L$^3$ independently denote C$_1$-C$_4$-alkylene optionally substituted with one phenyl;

Ar$^1$, Ar$^2$ and Ar$^3$ independently denote a 5-10 membered heteroaryl optionally substituted with —C(═O)Z or one or more R; or a 6-10 membered aryl optionally substituted with one or more R;

Z denotes OR$^a$ or NR$^b$R$^c$;

R$^a$ denotes H, C$_1$-C$_4$-alkyl, C$_3$-C$_6$-cycloalkyl, C$_2$-C$_4$-alkylene-O—C$_1$-C$_4$-alkyl, C$_2$-C$_4$-alkylene-CN; C$_1$-C$_4$-alkyl substituted with one or two Ar$^4$;

R$^b$ denotes H, C$_1$-C$_4$-alkyl, C$_3$-C$_6$-cycloalkyl, C$_2$-C$_4$-alkylene-CN; C$_2$-C$_4$-alkylene-O—C$_1$-C$_4$-alkyl; or C$_1$-C$_4$-alkyl substituted with one or two Ar$^4$;

R$^c$ denotes H, C$_1$-C$_8$ alkyl, C$_3$-C$_6$-cycloalkyl, Ar$^4$, C$_1$-C$_4$-alkyl substituted with one or two Ar$^4$; OH, O—C$_1$-C$_4$-alkyl, C$_2$-C$_4$-alkyl-O—C$_1$-C$_4$-alkyl, or C$_2$-C$_4$-alkyl-NR$^d$R$^a$;

or together NR$^b$R$^c$ denotes

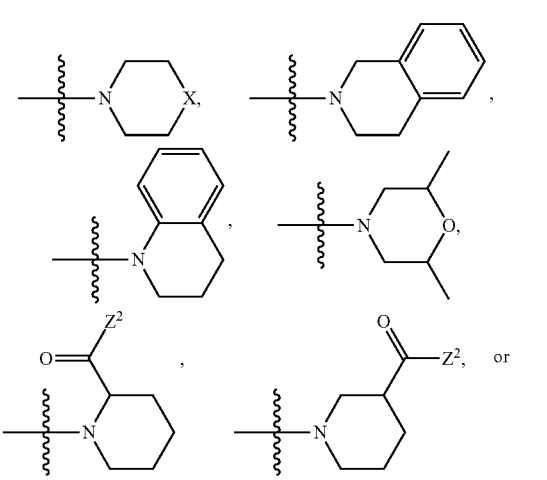

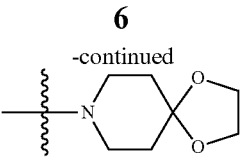

wherein X denotes CHZ$^1$, O, or NZ$^1$;

Z$^1$ denotes H, C(═O)H, C(═O)C$_1$-C$_4$-alkyl, C(═O)OR$^z$, Ar$^4$, C$_1$-C$_4$-alkyl, C$_3$-C$_6$-cycloalkyl, C$_1$-C$_4$-alkyl substituted with one or two Ar$^4$; C$_2$-C$_4$—NR$^d$R$^e$, or C$_2$-C$_4$—OR$^f$;

Z$^2$ denotes OR$^a$ or NR$^g$R$^g$;

Ar$^4$ denotes 5-6 membered heteroaryl; or phenyl optionally substituted with one or more R;

R$^d$, R$^e$ and R$^f$ independently denote H or C$_1$-C$_4$-alkyl;

R$^g$ denotes R$^b$;

R$^z$ denotes H, C$_1$-C$_4$-alkyl or C$_3$-C$_6$-cycloalkyl;

R independently denotes F, Cl, Br, I, C$_1$-C$_4$-haloalkyl, OR$^1$, SR$^1$, NO$_2$, NR$^2$R$^3$, R$^4$, C(═O)Y, SO$_3$H, C$_1$-C$_4$-alkyl, C$_1$-C$_4$-alkyl-phenyl, a 5-membered heteroaryl; or a phenyl substituted with a 5-membered heteroaryl;

R$^1$ denotes H, C$_1$-C$_4$-alkyl or C$_1$-C$_4$-alkyl-phenyl; or together two adjacent OR$^1$ groups denote —O—CH$_2$—O—;

R$^2$ and R$^3$ independently denote H or C$_1$-C$_4$-alkyl; or NR$^2$R$^3$ denotes —NHC(═O)—NHAr$^5$; or together two adjacent NR$^2$R$^3$ groups denote —NR$^2$—CH—N— or —NR$^2$—CH$_2$—NR$^2$—; or together with an adjacent OR$^1$ group, NR$^2$R$^3$ denotes —NR$^2$—CH$_2$—O— or —N—CH—O—; or together with an adjacent SR$^1$ group, NR$^2$R$^3$ denotes —NR$^2$—CH$_2$—S— or —N—CH—S—;

Ar$^5$ denotes phenyl optionally substituted with R$^h$;

R$^h$ denotes halogen or C$_1$-C$_4$ alkyl;

R$^4$ denotes C$_1$-C$_4$-alkyl; or together with an adjacent OR$^1$ group, R$^4$ denotes —CH$_2$CH$_2$—O—; or together two adjacent R$^4$ groups denote —(CH)$_4$— or —(CH$_2$)$_4$—;

Y denotes OR$^5$ or NR$^6$R$^7$;

R$^5$ denotes H or C$_1$-C$_4$-alkyl;

R$^6$ and R$^7$ independently denote H, C$_1$-C$_8$-alkyl or C$_3$-C$_6$ cycloalkyl.

The present invention also relates to a compound of formula (I') for use in therapy:

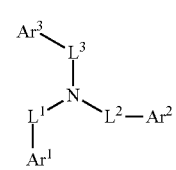
(I')

wherein

L$^1$, L$^2$ and L$^3$ independently denote C$_1$-C$_4$-alkylene optionally substituted with one phenyl;

Ar$^1$, Ar$^2$ and Ar$^3$ independently denote a 5-10 membered heteroaryl optionally substituted with —C(═O)Z or one or more R; or a 6-10 membered aryl optionally substituted with one or more R;

Z denotes OR$^a$ or NR$^b$R$^c$;

R$^a$ denotes H, C$_1$-C$_4$-alkyl, C$_3$-C$_6$-cycloalkyl, C$_2$-C$_4$-alkylene-O—C$_1$-C$_4$-alkyl, C$_2$-C$_4$-alkylene-CN; C$_1$-C$_4$-alkyl substituted with one or two Ar$^4$;

$R^b$ denotes H, $C_1$-$C_4$-alkyl, $C_3$-$C_6$-cycloalkyl, $C_2$-$C_4$-alkylene-CN; $C_2$-$C_4$-alkylene-O—$C_1$-$C_4$-alkyl; or $C_1$-$C_4$-alkyl substituted with one or two $Ar^4$;

$R^c$ denotes H, $C_1$-$C_8$ alkyl, $C_3$-$C_6$-cycloalkyl, $Ar^4$, $C_1$-$C_4$-alkyl substituted with one or two $Ar^4$; OH, O—$C_1$-$C_4$-alkyl, $C_2$-$C_4$-alkyl-O—$C_1$-$C_4$-alkyl, or $C_2$-$C_4$-alkyl-$NR^aR^a$;

or together $NR^bR^c$ denotes

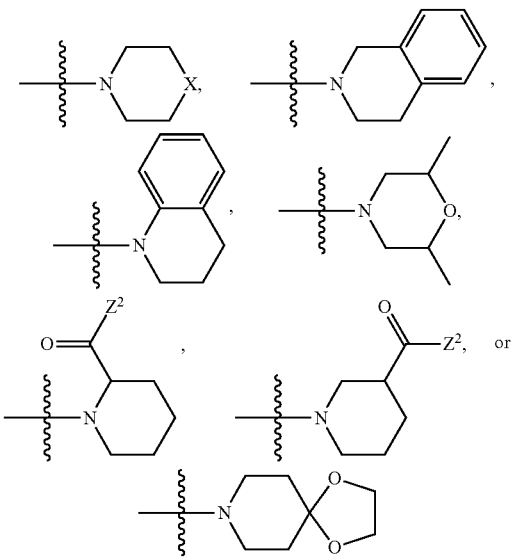

wherein X denotes $CHZ^1$, O, or $NZ^1$;

$Z^1$ denotes H, C(=O)H, C(=O)$C_1$-$C_4$-alkyl, C(=O)$OR^z$, $Ar^4$, $C_1$-$C_4$-alkyl, $C_3$-$C_6$-cycloalkyl, $C_1$-$C_4$-alkyl substituted with one or two $Ar^4$; $C_2$-$C_4$—$NR^dR^e$, or $C_2$-$C_4$—$OR^f$;

$Z^2$ denotes $OR^a$ or $NR^gR^g$;

$Ar^4$ denotes 5-6 membered heteroaryl; or phenyl optionally substituted with one or more R;

$R^d$, $R^e$ and $R^f$ independently denote H or $C_1$-$C_4$-alkyl;

$R^g$ denotes $R^b$;

$R^z$ denotes H, $C_1$-$C_4$-alkyl or $C_3$-$C_6$-cycloalkyl;

R independently denotes F, Cl, Br, I, $C_1$-$C_4$-haloalkyl, $OR^1$, $SR^1$, $NO_2$, $NR^2R^3$, $R^4$, C(=O)Y, $SO_3H$, $C_1$-$C_4$-alkyl, $C_1$-$C_4$-alkyl-phenyl, a 5-membered heteroaryl; or a phenyl substituted with a 5-membered heteroaryl;

$R^1$ denotes H, $C_1$-$C_4$-alkyl or $C_1$-$C_4$-alkyl-phenyl; or together two adjacent $OR^1$ groups denote —O—$CH_2$—O—;

$R^2$ and $R^3$ independently denote H or $C_1$-$C_4$-alkyl; or together two adjacent $NR^2R^3$ groups denote —$NR^2$—CH=N— or —$NR^2$—$CH_2$—$NR^2$—; or together with an adjacent $OR^1$ group, $NR^2R^3$ denotes —$NR^2$—$CH_2$—O— or —N=CH—O—; or together with an adjacent $SR^1$ group, $NR^2R^3$ denotes —$NR^2$—$CH_2$—S— or —N=CH—S—;

$R^4$ denotes $C_1$-$C_4$-alkyl; or together with an adjacent $OR^1$ group, $R^4$ denotes —$CH_2CH_2$—O—; or together two adjacent $R^4$ groups denote —$(CH)_4$— or —$(CH_2)_4$—;

Y denotes $OR^5$ or $NR^6R^7$;

$R^5$ denotes H or $C_1$-$C_4$-alkyl; and $R^6$ and $R^7$ independently denote H, $C_1$-$C_8$-alkyl or $C_3$-$C_6$ cycloalkyl.

Preferably, the present invention relates to a compound of formula (Ia) for use in therapy,

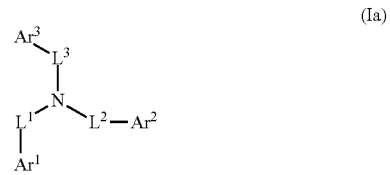

wherein $L^1$, $L^2$ and $L^3$ independently denote $C_1$-$C_4$-alkylene optionally substituted with one phenyl;

$Ar^1$, $Ar^2$ and $Ar^3$ independently denote a 5-10 membered heteroaryl optionally substituted with —C(=O)Z or one or more R; or a 6-10 membered aryl optionally substituted with one or more R;

Z denotes $OR^a$ or $NR^bR^c$;

$R^a$ denotes H or $C_1$-$C_4$-alkyl;

$R^b$ denotes H, $C_1$-$C_4$-alkyl, $C_2$-$C_4$-alkyl-CN; or $C_1$-$C_4$-alkyl substituted with one or two $Ar^4$;

$R^c$ denotes H, $C_1$-$C_8$ alkyl, $C_3$-$C_6$-cycloalkyl, $Ar^4$, $C_1$-$C_4$-alkyl substituted with one or two $Ar^4$; OH, O—$C_1$-$C_4$-alkyl, $C_2$-$C_4$-alkyl-O—$C_1$-$C_4$-alkyl, or $C_2$-$C_4$-alkyl-$NR^aR^a$;

or together $NR^bR^c$ denotes

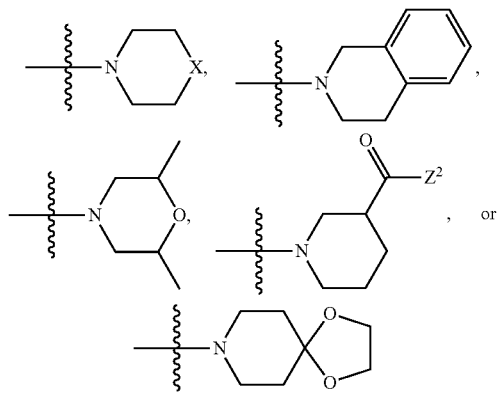

wherein X denotes $CHZ^1$, O, or $NZ^1$;

$Z^1$ denotes H, C(=O)H, C(=O)$C_1$-$C_4$-alkyl, C(=O)$OR^z$, $Ar^4$, $C_1$-$C_4$-alkyl, $C_1$-$C_4$-alkyl substituted with one or two $Ar^4$; $C_2$-$C_4$—$NR^dR^e$, or $C_2$-$C_4$—$OR^f$;

$Z^2$ denotes $OR^a$ or $NR^gR^g$;

$Ar^4$ denotes 5-6 membered heteroaryl; or phenyl optionally substituted with one or more R;

$R^d$, $R^e$ and $R^f$ independently denote H or $C_1$-$C_4$-alkyl;

$R^g$ denotes $R^b$;

$R^z$ denotes H or $C_1$-$C_4$-alkyl;

R independently denotes F, Cl, $CF_3$, $OR^1$, $NO_2$, $NR^2R^3$, $R^4$, C(=O)Y, $C_1$-$C_4$-alkyl, $C_1$-$C_4$-alkyl-phenyl, 5-tetrazolyl or

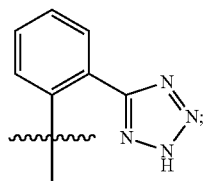 [SMILES: *c1ccccc1-c1nn[nH]n1]

$R^1$ denotes H, $C_1$-$C_4$-alkyl or $C_1$-$C_4$-alkyl-phenyl; or together two adjacent $OR^1$ groups denote —O—$CH_2$—O—;

$R^2$ and $R^3$ independently denote H or $C_1$-$C_4$-alkyl;

$R^4$ denotes $C_1$-$C_4$-alkyl; or together with an adjacent $OR^1$ group, $R^4$ denotes —$CH_2CH_2$—O—;

Y denotes $OR^5$ or $NR^6R^7$;

$R^5$ denotes H or $C_1$-$C_4$-alkyl;

$R^6$ and $R^7$ independently denote H, $C_1$-$C_8$-alkyl or $C_3$-$C_6$-cycloalkyl.

The following preferred embodiments relate to the compounds of formula (I), (I') and (Ia) as defined above:

Preferably, $Ar^1$, $Ar^2$ and $Ar^3$ independently denote a 5-9 membered heteroaryl optionally substituted with —C(=O)Z or one or more R; or a 6-10 membered aryl optionally substituted with one or more R.

Preferably, $Ar^1$, $Ar^2$ and $Ar^3$ independently denote a 5-6 membered heteroaryl optionally substituted with —C(=O)Z or one or more R; or a 6-10 membered aryl optionally substituted with one or more R.

Preferably, $Ar^1$, $Ar^2$ and $Ar^3$ independently denote a 5- or 6-membered heteroaryl optionally substituted with —C(=O)Z or one or more R; or a phenyl optionally substituted with one or more R.

Preferably, $Ar^1$, $Ar^2$ and $Ar^3$ independently denote a thiazole optionally substituted with —C(=O)Z; an oxazole optionally substituted with —C(=O)Z; or a phenyl optionally substituted with one or more R.

Preferably, $Ar^1$, $Ar^2$ and $Ar^3$ independently denote a thiazole optionally substituted with —C(=O)Z; or a phenyl optionally substituted with one or more R.

Preferably, when $Ar^1$, $Ar^2$, $Ar^3$ or $Ar^4$ are optionally substituted with one or more R, the (hetero)aryl ring has 0, 1 or 2 substituents.

Preferably, $Ar^1$ denotes phenyl optionally substituted with one or more R.

Preferably, $Ar^1$ denotes phenyl optionally substituted with one or two R.

Preferably, $Ar^2$ denotes phenyl optionally substituted with one or two R; or thiazole optionally substituted with —C(=O)Z.

Preferably, $Ar^2$ denotes phenyl optionally substituted with one or two R;

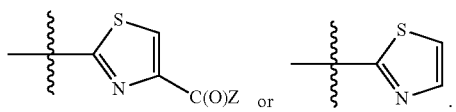

Preferably, $Ar^2$ denotes phenyl optionally substituted with one or two R; or

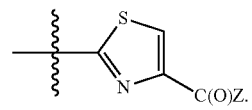

Preferably, $L^1$, $L^2$ and $L^3$ independently denote $C_1$-$C_3$-alkylene optionally substituted with one phenyl.

Preferably, $L^1$ denotes —$CH_2$—.

Preferably, $L^2$ denotes —$CH_2$—.

Preferably, $L^3$ denotes $C_1$-$C_3$-alkylene optionally substituted with one phenyl.

Thus, preferred compounds include a compound of formula (II)

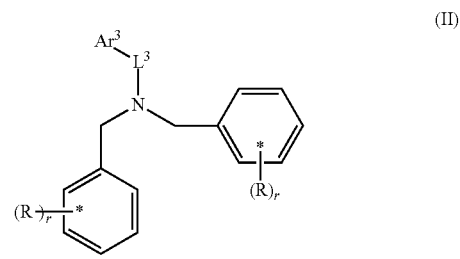

wherein r denotes 0, 1 or 2;

$L^3$ denotes $C_1$-$C_3$-alkyl optionally substituted with one phenyl; and $Ar^3$ and R are as defined above for the compound of formula (I).

Preferably, $Ar^3$ and R in the compound of formula (II) are as defined for the compound of formula (I').

Preferably, $Ar^3$ and R in the compound of formula (II) are as defined for the compound of formula (Ia).

Other preferred compounds include a compound of formula (III)

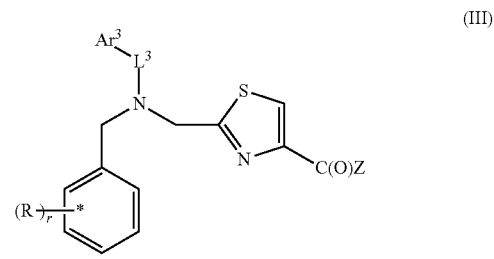

wherein r denotes 0, 1 or 2;

$L^3$ denotes $C_1$-$C_3$-alkylene optionally substituted with one phenyl; and $Ar^3$, R and Z are as defined above for the compound of formula (I).

Preferably, $Ar^3$, R and Z in the compound of formula (III) are as defined for the compound of formula (I').

Preferably, $Ar^3$, R and Z in the compound of formula (III) are as defined for the compound of formula (Ia).

The following preferred embodiments relate to the compounds of formula (I), (I') (Ia), (II) and (III) as defined above, including those embodiments of formulae (II) and (III) in which $Ar^3$ and R (and Z in the case of formula (III)) are as defined for the compound of formula (I'):

Preferably, $Ar^3$ denotes phenyl optionally substituted with one or two R; pyridyl, or 2-furyl.

Preferably, $Ar^3$ denotes phenyl optionally substituted with one or two R; or pyridyl.

Preferably, $Ar^3$ denotes phenyl optionally substituted with one or two R.

Preferably, $L^3$ denotes —CH$_2$—, —CH(CH$_3$)— or —CH$_2$CH$_2$CH(C$_6$H$_5$)—.

Preferably, $L^3$ denotes —CH$_2$— or —CH$_2$CH$_2$CH(C$_6$H$_5$)—; and
$Ar^3$ denotes phenyl optionally substituted with one or two R.

Preferably, Z denotes $OR^a$.

Preferably, $R^a$ denotes H or Me.

Preferably, Z denotes $NR^bR^c$.

Preferably, $R^b$ denotes H or $C_1$-$C_4$-alkyl; and
$R^c$ denotes H, $C_1$-$C_4$ alkyl, cyclopropyl, cyclohexyl, $Ar^4$, $C_1$-$C_4$-alkyl substituted with one or two $Ar^4$; OH, or O—$C_1$-$C_4$-alkyl;
or together $NR^bR^c$ denotes

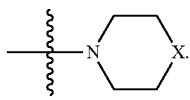

Preferably, $R^b$ denotes H or $C_1$-$C_4$-alkyl; and
$R^c$ denotes H, $C_1$-$C_6$ alkyl, $C_1$-$C_4$-alkyl substituted with one or two $Ar^4$;
or together $NR^bR^c$ denotes

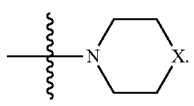

Preferably, $R^b$ denotes H; and
$R^c$ denotes H, $C_1$-$C_6$ alkyl, $C_1$-$C_4$-alkyl substituted with one or two $Ar^4$;
or together $NR^bR^c$ denotes

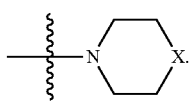

Preferably, together $NR^bR^c$ denotes

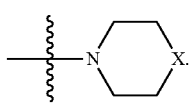

Preferably, X denotes $NZ^1$.

Preferably, $Z^1$ denotes H, C(═O)H, C(═O)C$_1$-C$_4$-alkyl, C(═O)OR$^z$, $Ar^4$, $C_1$-$C_4$-alkyl, or $C_1$-$C_4$-alkyl substituted with one or two $Ar^4$.

Preferably, $Z^1$ denotes H, C(═O)H, C(═O)C$_1$-C$_4$-alkyl, or C(═O)OR$^z$.

Preferably, $Z^1$ denotes H, $Ar^4$, $C_1$-$C_4$-alkyl, or $C_1$-$C_4$-alkyl substituted with one or two $Ar^4$.

Preferably, $Ar^4$ denotes phenyl optionally substituted with one or two R.

Preferably, $R^g$ denotes H or $C_1$-$C_4$-alkyl.

Preferably, $R^h$ denotes F or $C_1$-$C_4$-alkyl.

Preferably, $R^h$ denotes F or methyl.

Preferably, $R^z$ denotes H or methyl.

Preferably, R independently denotes F, Cl, CF$_3$, OR$^1$, NO$_2$, NR$^2$R$^3$, R$^4$, C(═O)Y, $C_1$-$C_4$-alkyl, $C_1$-$C_4$-alkyl-phenyl, or

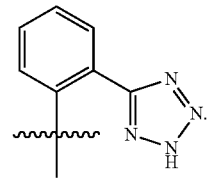 [SMILES: *c1ccccc1-c1nn[nH]n1]

Preferably, R independently denotes F, Cl, CF$_3$, OR$^1$, C(═O)Y, $C_1$-$C_4$-alkyl, $C_1$-$C_4$-alkyl-phenyl or

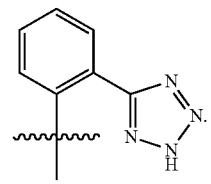 [SMILES: *c1ccccc1-c1nn[nH]n1]

Preferably, R independently denotes F, Cl, CF$_3$, OR$^1$, C(═O)Y, $C_1$-$C_4$-alkyl or $C_1$-$C_4$-alkyl-phenyl.

Preferably, Y denotes OR$^5$.

Preferably, R$^6$ and R$^7$ independently denote H and $C_1$-$C_6$-alkyl.

The above noted preferred embodiments can of course be combined with one another. Thus, particularly preferred embodiments of the invention include:

Embodiment 1

A compound of formula (I) for use in therapy, wherein
$L^1$, $L^2$ and $L^3$ independently denote $C_1$-$C_3$-alkylene optionally substituted with one phenyl; and
$Ar^1$ denotes phenyl optionally substituted with one or more R;
$Ar^2$ denotes phenyl optionally substituted with one or two R; or thiazole optionally substituted with —C(═O)Z;
$Ar^3$ denotes phenyl optionally substituted with one or two R; pyridyl, or 2-furyl;
Z denotes $OR^a$ or $NR^bR^c$;
$R^a$ denotes H or $C_1$-$C_4$-alkyl;
$R^b$ denotes H, $C_1$-$C_4$-alkyl, $C_2$-$C_4$-alkyl-CN; or $C_1$-$C_4$-alkyl substituted with one or two $Ar^4$;
$R^c$ denotes H, $C_1$-$C_8$ alkyl, $C_3$-$C_6$ cycloalkyl, $Ar^4$, $C_1$-$C_4$-alkyl substituted with one or two $Ar^4$; OH, O—$C_1$-$C_4$-alkyl, $C_2$-$C_4$-alkyl-O—$C_1$-$C_4$-alkyl, or $C_2$-$C_4$-alkyl-NR$^a$R$^a$;
or together $NR^bR^c$ denotes

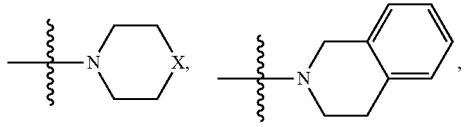

-continued

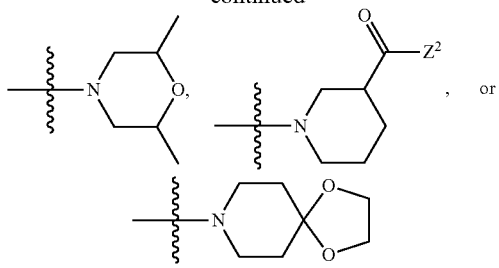

wherein X denotes $CHZ^1$, O, or $NZ^1$;
$Z^1$ denotes H, $C(=O)H$, $C(=O)C_1$-$C_4$-alkyl, $C(=O)OR^z$, $Ar^4$, $C_1$-$C_4$-alkyl, $C_1$-$C_4$-alkyl substituted with one or two $Ar^4$; $C_2$-$C_4$—$NR^dR^e$, or $C_2$-$C_4$—$OR^f$;
$Z^2$ denotes $OR^a$ or $NR^gR^g$;
$Ar^4$ denotes phenyl optionally substituted with one or two R;
$R^d$, $R^e$ and $R^f$ independently denote H or $C_1$-$C_4$-alkyl;
$R^g$ denotes $R^b$;
$R^z$ denotes H or $C_1$-$C_4$-alkyl;
R independently denotes F, Cl, $CF_3$, $OR^1$, $NO_2$, $NR^2R^3$, $R^4$, $C(=O)Y$, $C_1$-$C_4$-alkyl, $C_1$-$C_4$-alkyl-phenyl or

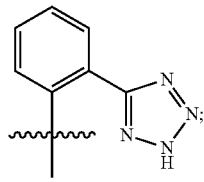 [SMILES: *c1ccccc1-c1nn[nH]n1]

$R^1$ denotes H, $C_1$-$C_4$-alkyl or $C_1$-$C_4$-alkyl-phenyl; or
together two adjacent $OR^1$ groups denote —O—$CH_2$—O—; or
together two adjacent $NR^2R^3$ groups denote —$NR^2$—CH—N— or —$NR^2$—$CH_2$—$NR^2$—; or
together with an adjacent $OR^1$ group, $NR^2R^3$ denotes —$NR^2$—$CH_2$—O— or —N—CH—O—;
$R^2$ and $R^3$ independently denote H or $C_1$-$C_4$-alkyl;
$R^4$ denotes $C_1$-$C_4$-alkyl; or
together with an adjacent $OR^1$ group, $R^4$ denotes —$CH_2CH_2$—O—;
Y denotes $OR^5$ or $NR^6R^7$;
$R^5$ denotes H or $C_1$-$C_4$-alkyl;
$R^6$ and $R^7$ independently denote H, $C_1$-$C_8$-alkyl or $C_3$-$C_6$ cycloalkyl.

Embodiment 2

A compound of formula (I) for use in therapy, wherein
$L^1$, $L^2$ and $L^3$ independently denote $C_1$-$C_3$-alkylene optionally substituted with one phenyl; and
$Ar^1$ denotes phenyl optionally substituted with one or more R;
$Ar^2$ denotes phenyl optionally substituted with one or two R;

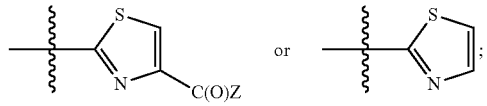

$Ar^3$ denotes phenyl optionally substituted with one or two R; pyridyl, or 2-furyl;
Z denotes $OR^a$ or $NR^bR^c$;
$R^a$ denotes H or $C_1$-$C_4$-alkyl;
$R^b$ denotes $R^b$ denotes H or $C_1$-$C_4$-alkyl; and
$R^c$ denotes H, $C_1$-$C_4$ alkyl, cyclopropyl, cyclohexyl, $Ar^4$, $C_1$-$C_4$-alkyl substituted with one or two $Ar^4$; OH, or O—$C_1$-$C_4$-alkyl;
or together $NR^bR^c$ denotes

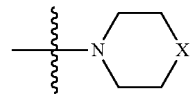

X denotes $CHZ^1$, O, or $NZ^1$;
$Z^1$ denotes $Z^1$ denotes H, $C(=O)H$, $C(=O)C_1$-$C_4$-alkyl, $C(=O)OR^z$, $Ar^4$, $C_1$-$C_4$-alkyl, or $C_1$-$C_4$-alkyl substituted with one or two $Ar^4$;
$Z^2$ denotes $OR^a$ or $NR^gR^g$;
$Ar^4$ denotes phenyl optionally substituted with one or two R;
$R^d$, $R^e$ and $R^f$ independently denote H or $C_1$-$C_4$-alkyl;
$R^g$ denotes $R^b$;
$R^z$ denotes H or $C_1$-$C_4$-alkyl;
R independently denotes F, Cl, $CF_3$, $OR^1$, $C(=O)Y$, $C_1$-$C_4$-alkyl, $C_1$-$C_4$-alkyl-phenyl or

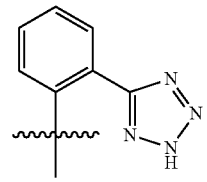 [SMILES: *c1ccccc1-c1nn[nH]n1]

$R^1$ denotes H, $C_1$-$C_4$-alkyl or $C_1$-$C_4$-alkyl-phenyl; or
together two adjacent $OR^1$ groups denote —O—$CH_2$—O—;
$R^2$ and $R^3$ independently denote H or $C_1$-$C_4$-alkyl;
$R^4$ denotes $C_1$-$C_4$-alkyl; or
together with an adjacent $OR^1$ group, $R^4$ denotes —$CH_2CH_2$—O—;
Y denotes $OR^5$ or $NR^6R^7$;
$R^5$ denotes H or $C_1$-$C_4$-alkyl;
$R^6$ and $R^7$ independently denote H and $C_1$-$C_6$-alkyl.

Embodiment 3

A compound of formula (I) for use in therapy, wherein
$L^1$ denotes —$CH_2$;
$L^2$ denotes —$CH_2$;
$L^3$ denotes —$CH_2$—, —$CH(CH_3)$— or —$CH_2CH_2CH(C_6H_5)$—;
$Ar^1$ denotes phenyl optionally substituted with one or two R;
$Ar^2$ denotes phenyl optionally substituted with one or two R;

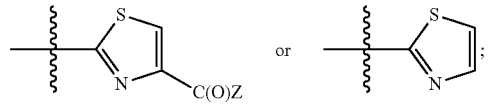

Ar$^3$ denotes phenyl optionally substituted with one or two R; pyridyl, or 2-furyl;
Z denotes OR$^a$ or NR$^b$R$^c$;
R$^a$ denotes H or C$_1$-C$_4$-alkyl;
R$^b$ denotes R$^b$ denotes H or C$_1$-C$_4$-alkyl; and
R$^c$ denotes H, C$_1$-C$_4$ alkyl, cyclopropyl, cyclohexyl, Ar$^4$, C$_1$-C$_4$-alkyl substituted with one or two Ar$^4$; OH, or O—C$_1$-C$_4$-alkyl;
or together NR$^b$R$^c$ denotes

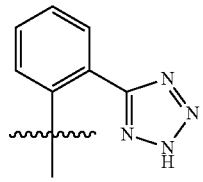 [SMILES: *c1ccccc1-c1nn[nH]n1]

X denotes CHZ$^1$, O, or NZ$^1$;
Z$^1$ denotes Z$^1$ denotes H, C(=O)H, C(=O)C$_1$-C$_4$-alkyl, C(=O)OR$^z$, Ar$^4$, C$_1$-C$_4$-alkyl, or C$_1$-C$_4$-alkyl substituted with one or two Ar$^4$;
Z$^2$ denotes OR$^a$ or NR$^g$R$^g$;
Ar$^4$ denotes phenyl optionally substituted with one or two R;
R$^d$, R$^e$ and R$^f$ independently denote H or C$_1$-C$_4$-alkyl;
R$^g$ denotes R$^b$;
R$^z$ denotes H or C$_1$-C$_4$-alkyl;
R independently denotes F, Cl, CF$_3$, OR$^1$, C(=O)Y, C$_1$-C$_4$-alkyl, C$_1$-C$_4$-alkyl-phenyl or

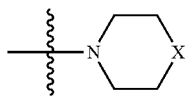

R$^1$ denotes H, C$_1$-C$_4$-alkyl or C$_1$-C$_4$-alkyl-phenyl; or
together two adjacent OR$^1$ groups denote —O—CH$_2$—O—;
R$^2$ and R$^3$ independently denote H or C$_1$-C$_4$-alkyl;
R$^4$ denotes C$_1$-C$_4$-alkyl; or
together with an adjacent OR$^1$ group, R$^4$ denotes —CH$_2$CH$_2$—O—;
Y denotes OR$^5$ or NR$^6$R$^7$;
R$^5$ denotes H or C$_1$-C$_4$-alkyl;
R$^6$ and R$^7$ independently denote H and C$_1$-C$_6$-alkyl.

Embodiment 4

A compound of formula (I) for use in therapy, wherein
L$^1$ denotes —CH$_2$;
L$^2$ denotes —CH$_2$;
L$^3$ denotes —CH$_2$—, —CH(CH$_3$)— or —CH$_2$CH$_2$CH(C$_6$H$_5$)—;
Ar$^1$ denotes phenyl optionally substituted with one or two R;
Ar$^2$ denotes phenyl optionally substituted with one or two R;

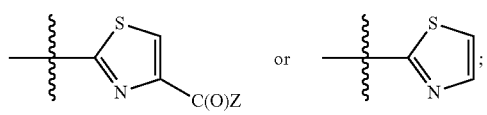

Ar$^3$ denotes phenyl optionally substituted with one or two R; pyridyl, or 2-furyl;
Z denotes NR$^b$R$^c$;
R$^b$ denotes H; and
R$^c$ denotes H, C$_1$-C$_6$ alkyl, C$_1$-C$_4$-alkyl substituted with one or two Ar$^4$;
or together NR$^b$R$^c$ denotes

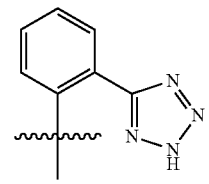 [SMILES: *c1ccccc1-c1nn[nH]n1]

X denotes NZ$^1$;
Z$^1$ denotes Z$^1$ denotes H, C(=O)H, C(=O)C$_1$-C$_4$-alkyl, C(=O)OR$^z$, Ar$^4$, C$_1$-C$_4$-alkyl, or C$_1$-C$_4$-alkyl substituted with one or two Ar$^4$;
Z$^2$ denotes OR$^a$ or NR$^g$R$^g$;
Ar$^4$ denotes phenyl optionally substituted with one or two R;
R$^d$, R$^e$ and R$^f$ independently denote H or C$_1$-C$_4$-alkyl;
R$^g$ denotes R$^b$;
R$^z$ denotes H or C$_1$-C$_4$-alkyl;
R independently denotes F, Cl, CF$_3$, OR$^1$, C(=O)Y, C$_1$-C$_4$-alkyl, C$_1$-C$_4$-alkyl-phenyl or

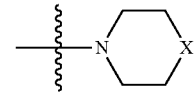

R$^1$ denotes H, C$_1$-C$_4$-alkyl or C$_1$-C$_4$-alkyl-phenyl; or
together two adjacent OR$^1$ groups denote —O—CH$_2$—O—;
R$^2$ and R$^3$ independently denote H or C$_1$-C$_4$-alkyl;
R$^4$ denotes C$_1$-C$_4$-alkyl; or
together with an adjacent OR$^1$ group, R$^4$ denotes —CH$_2$CH$_2$—O—;
Y denotes OR$^5$ or NR$^6$R$^7$;
R$^5$ denotes H or C$_1$-C$_4$-alkyl;
R$^6$ and R$^7$ independently denote H and C$_1$-C$_6$-alkyl.

Embodiment 5

A compound of formula (I) for use in therapy, wherein
L$^1$ denotes —CH$_2$;
L$^2$ denotes —CH$_2$;
L$^3$ denotes —CH$_2$—, —CH(CH$_3$)— or —CH$_2$CH$_2$CH(C$_6$H$_5$)—;
Ar$^1$ denotes phenyl optionally substituted with one or two R;
Ar$^2$ denotes phenyl optionally substituted with one or two R;

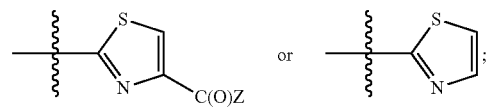

Ar$^3$ denotes phenyl optionally substituted with one or two R; pyridyl, or 2-furyl;
Z denotes NR$^b$R$^c$;
R$^b$ denotes H; and
R$^c$ denotes H, C$_1$-C$_6$ alkyl, C$_1$-C$_4$-alkyl substituted with one or two Ar$^4$;

or together NR$^b$R$^c$ denotes

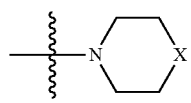

X denotes NZ$^1$;

Z$^1$ denotes Z$^1$ denotes H, C(=O)H, C(=O)C$_1$-C$_4$-alkyl, C(=O)OR$^z$, Ar$^4$, C$_1$-C$_4$-alkyl, or C$_1$-C$_4$-alkyl substituted with one or two Ar$^4$;

Z$^2$ denotes OR$^a$ or NR$^g$R$^g$;

Ar$^4$ denotes phenyl optionally substituted with one or two R;

R$^d$, R$^e$ and R$^f$ independently denote H or C$_1$-C$_4$-alkyl;

R$^g$ denotes R$^b$;

R$^z$ denotes H or C$_1$-C$_4$-alkyl;

R independently denotes F, Cl, CF$_3$, OR$^1$, C(=O)Y, C$_1$-C$_4$-alkyl or C$_1$-C$_4$-alkyl-phenyl;

R$^1$ denotes H, C$_1$-C$_4$-alkyl or C$_1$-C$_4$-alkyl-phenyl; or together two adjacent OR$^1$ groups denote —O—CH$_2$—O—;

R$^2$ and R$^3$ independently denote H or C$_1$-C$_4$-alkyl;

R$^4$ denotes C$_1$-C$_4$-alkyl; or together with an adjacent OR$^1$ group, R$^4$ denotes —CH$_2$CH$_2$—O—;

Y denotes OR$^5$ or NR$^6$R$^7$;

R$^5$ denotes H or C$_1$-C$_4$-alkyl;

R$^6$ and R$^7$ independently denote H and C$_1$-C$_6$-alkyl.

Typically, the compound of formula (I) (or formula (I')) contains at least one group capable of acting as a hydrogen bond donor, and/or at least one group capable of acting as a hydrogen bond acceptor.

Preferably, the compound of formula (I) (or formula (I')) will contain at least one, more preferably two, groups capable of acting as a hydrogen bond donor.

Preferably, the compound of formula (I) (or formula (I')) will contain at least one, more preferably two, groups capable of acting as a hydrogen bond acceptor.

By "hydrogen bond donor" is meant a group containing a hydrogen atom capable of forming a hydrogen bond, such as OH or NH. Hydrogen bond donors may also form part of a ring, such as tetrazole NH groups.

By "hydrogen bond acceptor" is meant a group capable of forming a hydrogen bond with a hydrogen atom, such as OMe or NMe$_2$. Hydrogen bond acceptors may also form part of a ring, such as pyridyl nitrogen atoms.

In some embodiments, the L$^1$Ar$^1$ and L$^2$Ar$^2$ moiety in the compound of formula (I) (or formula (I')) are identical.

In some embodiments, L$^1$Ar$^1$, L$^2$Ar$^2$ and L$^3$Ar$^3$ in the compound of formula (I) (or formula (I')) are all different.

In some embodiments, the compound of formula (I) (or formula (I')) does not have the following structure (i.e. in some embodiments the compounds having the following structure are excluded from the definition of any generic formula which may encompass them and do not form part of the claimed invention):

ethyl 1-[2-(dibenzylamino)ethyl]-4-(4-fluorobenzyl)-3-methyl-1H-pyrazole-5-carboxylate

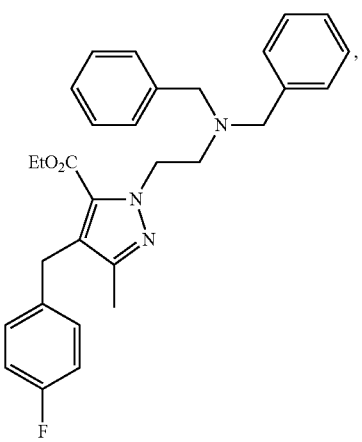 [SMILES: CCOC(=O)c1c(Cc2ccc(F)cc2)c(C)nn1CCN(Cc1ccccc1)Cc1ccccc1]

ethyl 1-[2-(dibenzylamino)ethyl]-4-(4-fluorobenzyl)-5-methyl-1H-pyrazole-3-carboxylate

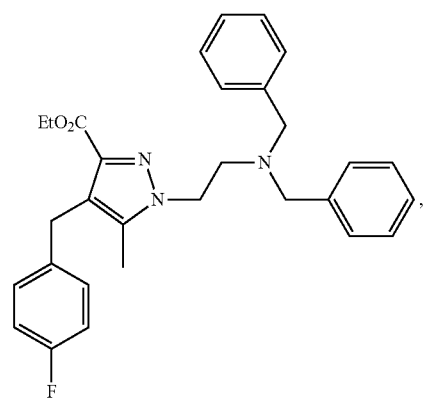 [SMILES: CCOC(=O)c1nn(CCN(Cc2ccccc2)Cc2ccccc2)c(C)c1Cc1ccc(F)cc1]

2-[({[4-(benzyloxy)phenyl]methyl}[3-fluorophenyl)methyl]amino)methyl]-1,3-thiazole-4-carboxylic acid

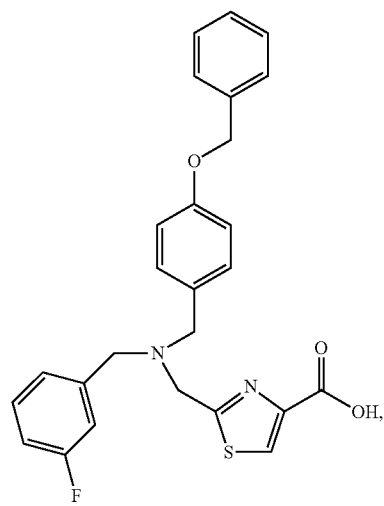 [SMILES: O=C(O)c1csc(CN(Cc2ccc(OCc3ccccc3)cc2)Cc2cccc(F)c2)n1]

19

2-[({[4-(benzyloxy)phenyl]methyl}(2,2-diphenyl-ethyl)amino)methyl]-1,3-thiazole-4-carboxylic acid

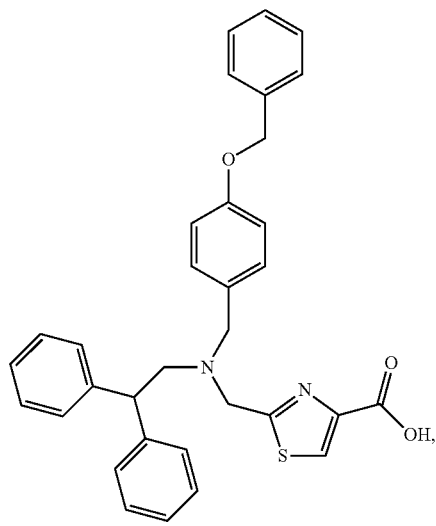 [SMILES: O=C(O)c1csc(CN(Cc2ccc(OCc3ccccc3)cc2)CC(c2ccccc2)c2ccccc2)n1]

2-[(dibenzylamino)methyl]-1,3-thiazole-4-carboxylic acid

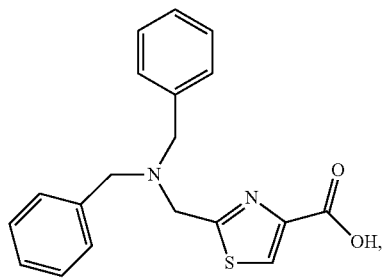 [SMILES: O=C(O)c1csc(CN(Cc2ccccc2)Cc2ccccc2)n1]

ethyl 2-[({[4-(benzyloxy)phenyl]methyl}[(4-fluorophenyl)methyl]amino)methyl-1,3-thiazole-4-carboxylate

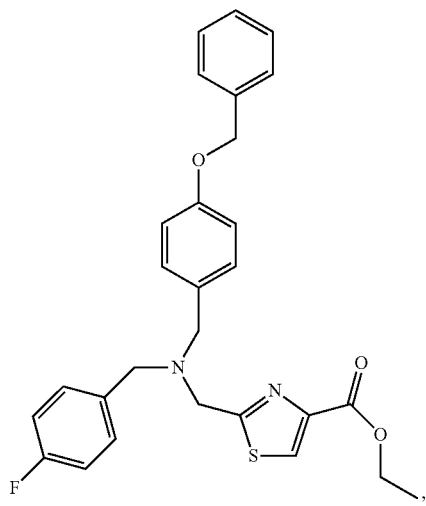 [SMILES: CCOC(=O)c1csc(CN(Cc2ccc(F)cc2)Cc2ccc(OCc3ccccc3)cc2)n1]

20

2-[({[4-(benzyloxy)phenyl]methyl}(pyridin-4-ylmethyl)amino)methyl]-1,3-thiazole-4-carboxylic acid

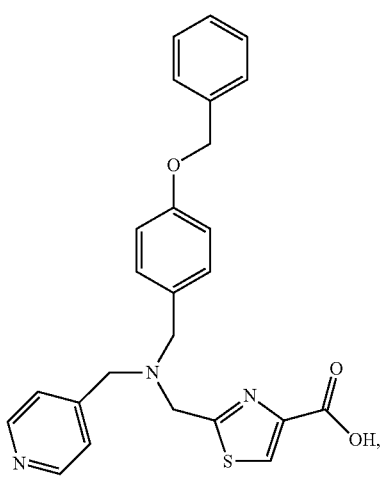 [SMILES: O=C(O)c1csc(CN(Cc2ccncc2)Cc2ccc(OCc3ccccc3)cc2)n1]

2-[({[4-(benzyloxy)phenyl]methyl}(pyridin-3-ylmethyl)amino)methyl]-1,3-thiazole-4-carboxylic acid

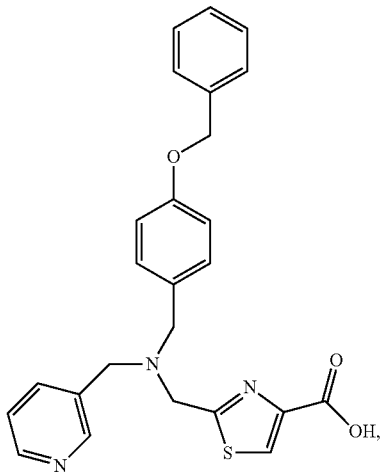 [SMILES: O=C(O)c1csc(CN(Cc2ccc(OCc3ccccc3)cc2)Cc2cccnc2)n1]

2-({[(4-fluorophenyl)methyl][(4-biphenyl)methyl]amino}methyl)-1,3-thiazole-4-carboxylic acid

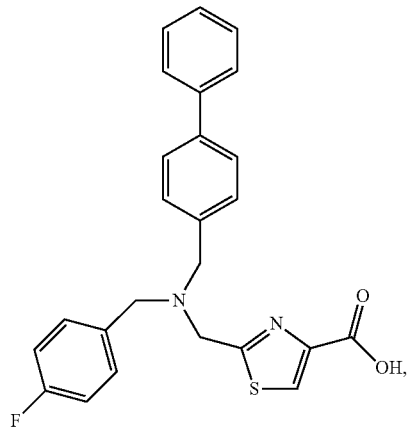 [SMILES: O=C(O)c1csc(CN(Cc2ccc(F)cc2)Cc2ccc(-c3ccccc3)cc2)n1]

21 ethyl 2-[({[4-(benzyloxy)phenyl]methyl}(pyridin-3-ylmethyl)amino)methyl]-1,3-thiazole-4-carboxylate

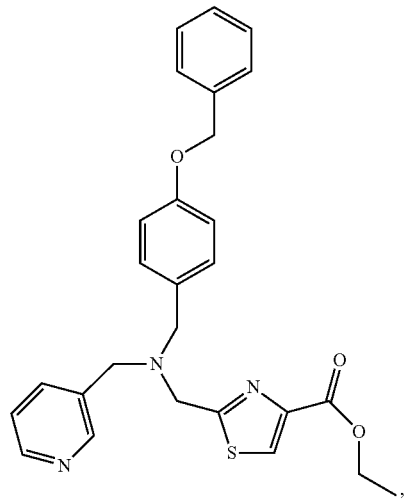 [SMILES: CCOC(=O)c1csc(CN(Cc2ccc(OCc3ccccc3)cc2)Cc2cccnc2)n1]

ethyl 2-[({[4-(benzyloxy)phenyl]methyl}(pyridin-4-ylmethyl)amino)methyl]-1,3-thiazole-4-carboxylate

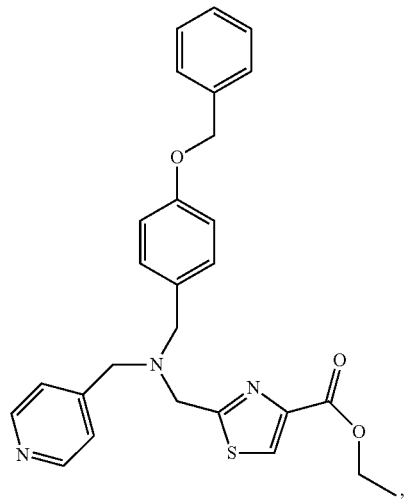 [SMILES: CCOC(=O)c1csc(CN(Cc2ccncc2)Cc2ccc(OCc3ccccc3)cc2)n1]

2-{[(4-benzyloxy-benzyl)-(4-fluoro-benzyl)-amino]-methyl}-thiazole-4-carboxylic acid ethylamide

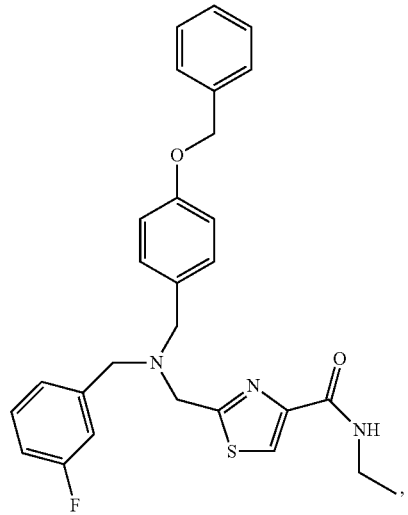 [SMILES: CCNC(=O)c1csc(CN(Cc2ccc(OCc3ccccc3)cc2)Cc2cccc(F)c2)n1]

22

{[4-(benzyloxy)phenyl]methyl}[4-fluorophenyl)methyl]{1-methyl-4-(trifluoromethyl)-1H-imidazol-2-yl]methyl}amine

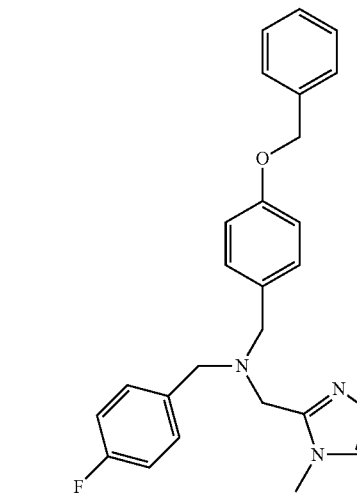

{[4-(benzyloxy)phenyl]methyl}[4-fluorophenyl)methyl]{4-(trifluoromethyl)-1H-imidazol-2-yl]methyl}amine

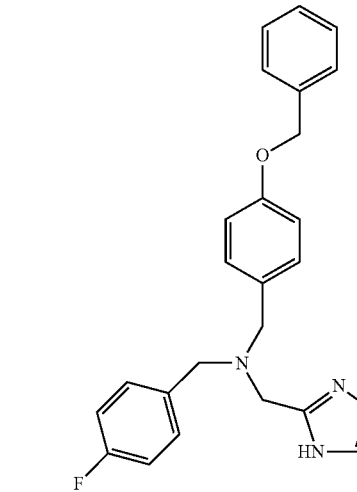

23
2-[({[4-(benzyloxy)phenyl]methyl}[4-fluorophenyl)methyl]amino)methyl]-1H-imidazole-4-carboxylic acid
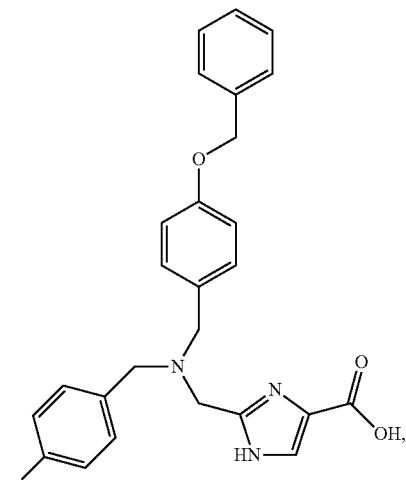
or
2-{[biphenyl-4-ylmethyl-(4-fluoro-benzyl)-amino]-methyl}-thiazole-4-carboxylic acid ethylester
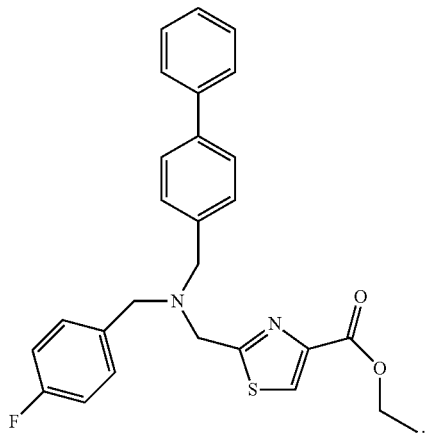 [SMILES: CCOC(=O)c1csc(CN(Cc2ccc(F)cc2)Cc2ccc(-c3ccccc3)cc2)n1]
Preferred compounds according to formula (I) have the following structure:
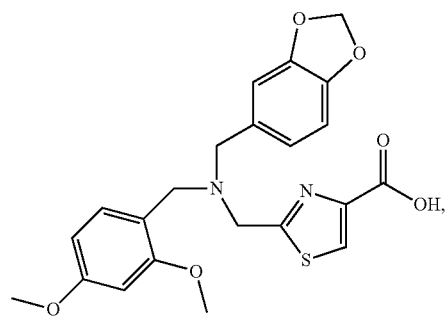
24
-continued
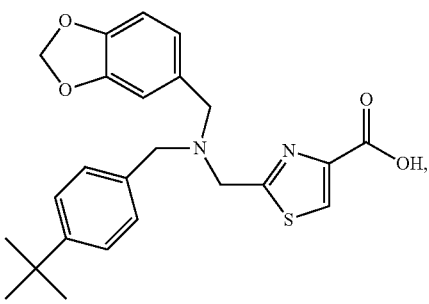
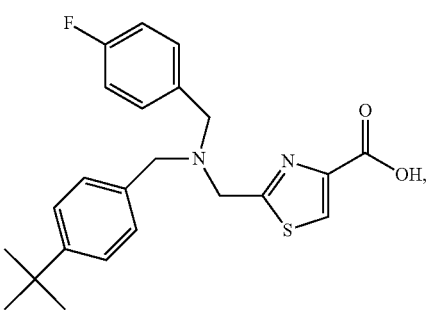
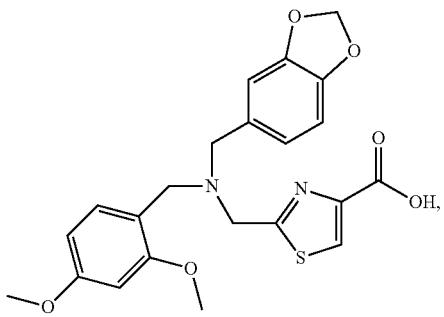
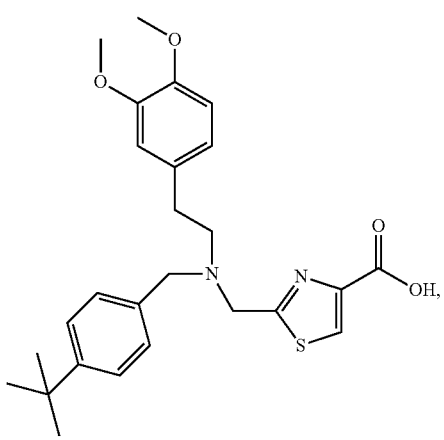
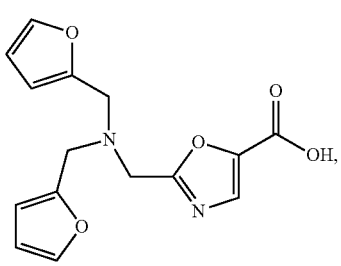

25
-continued
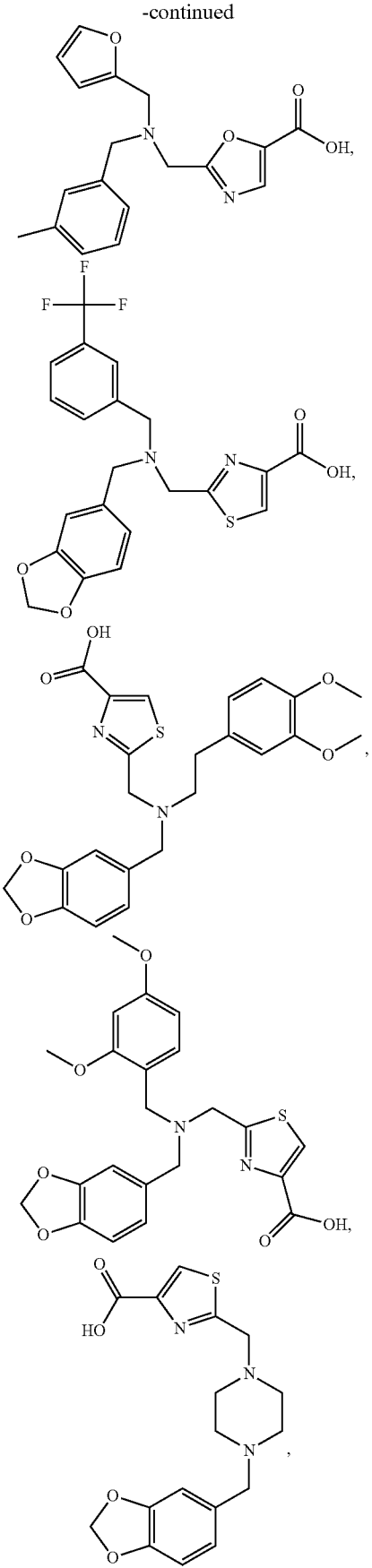
26
-continued
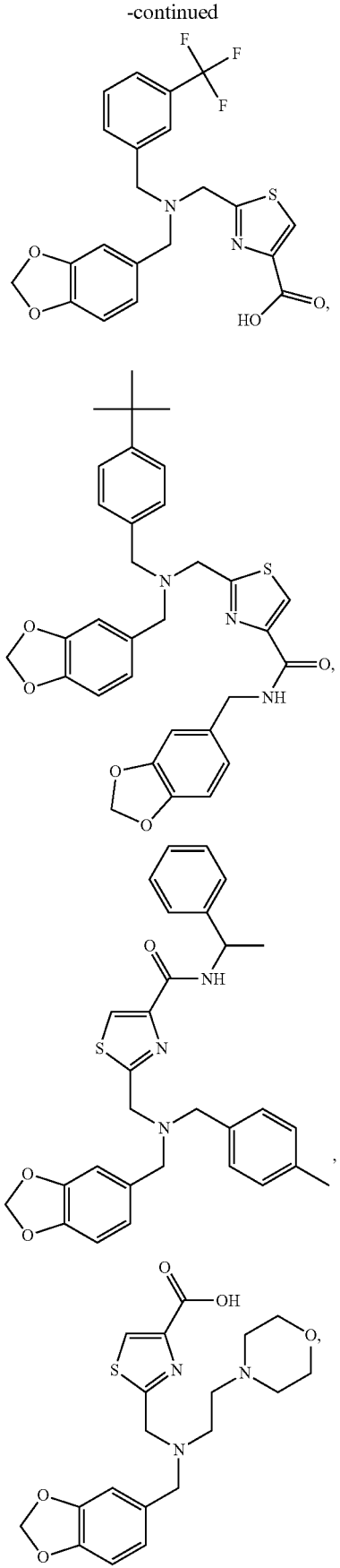

27
-continued
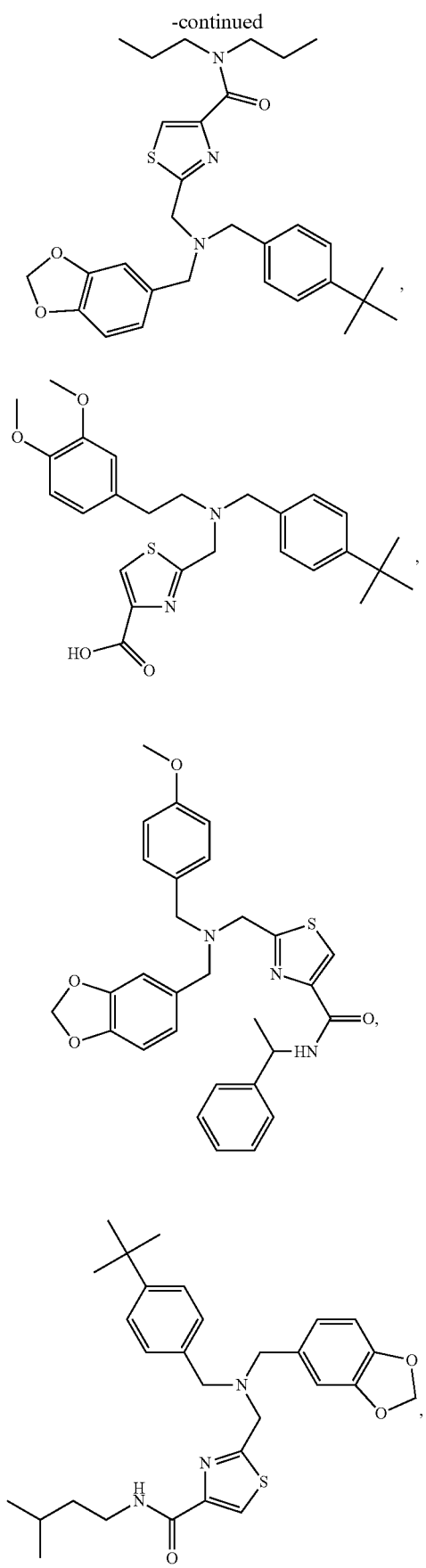
28
-continued
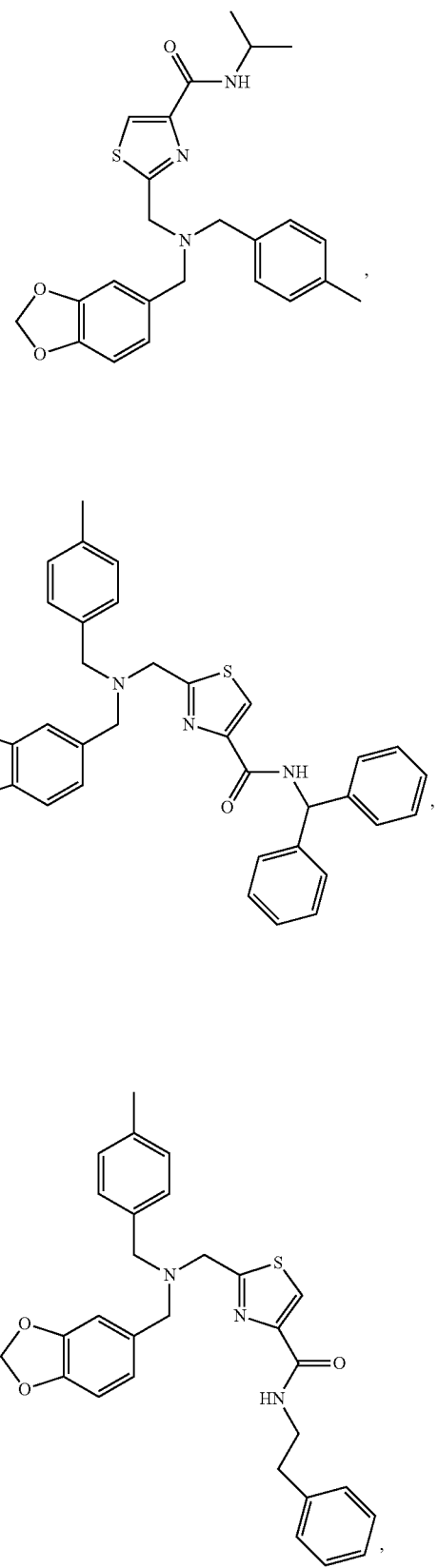

29
-continued
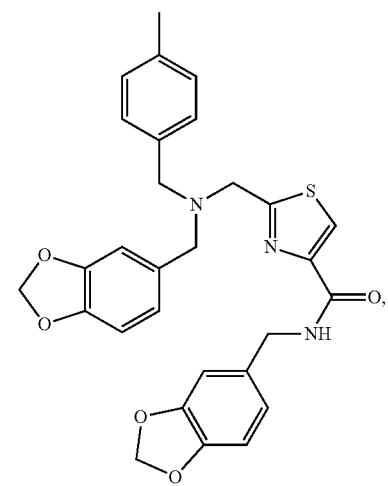
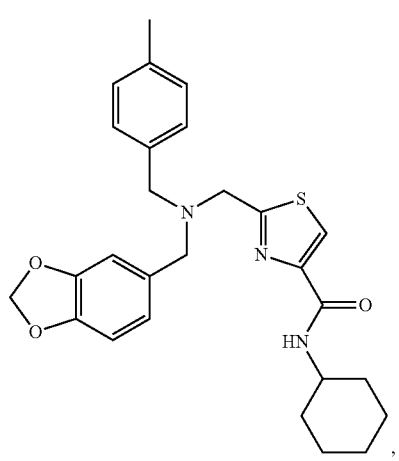
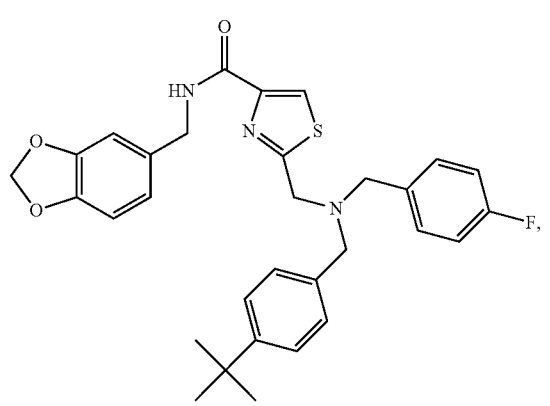
30
-continued
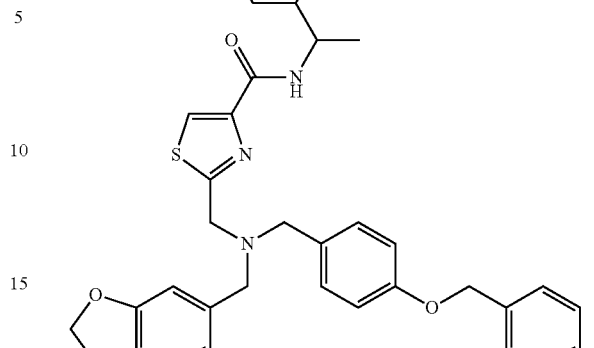
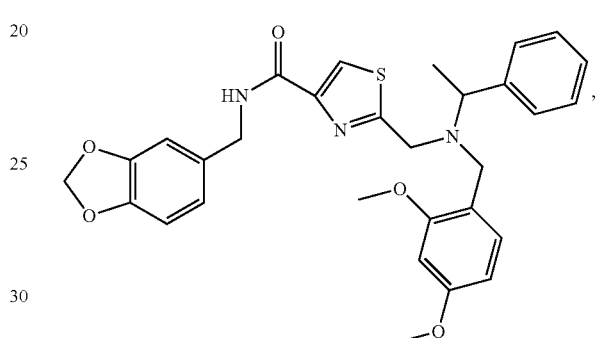
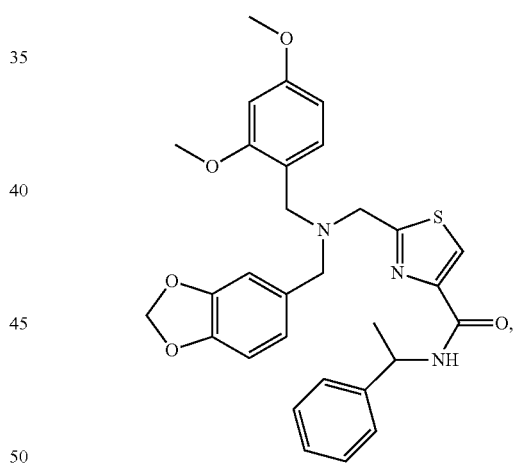
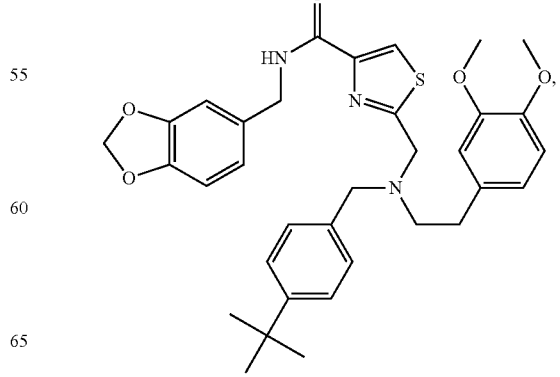

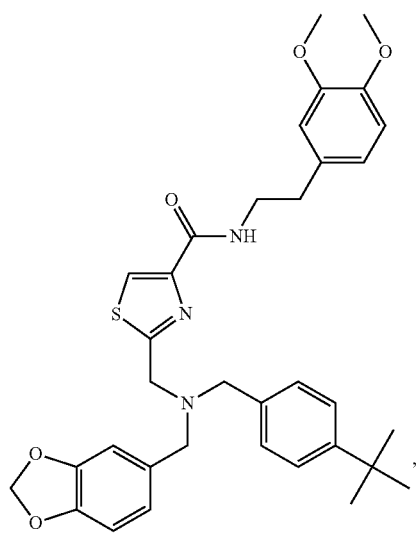
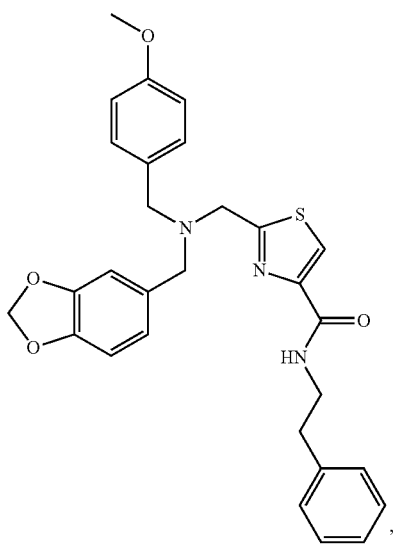
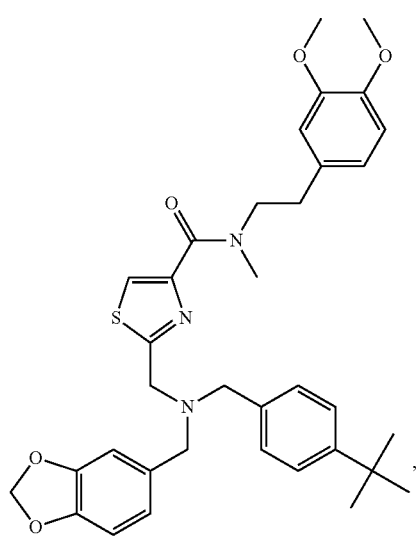
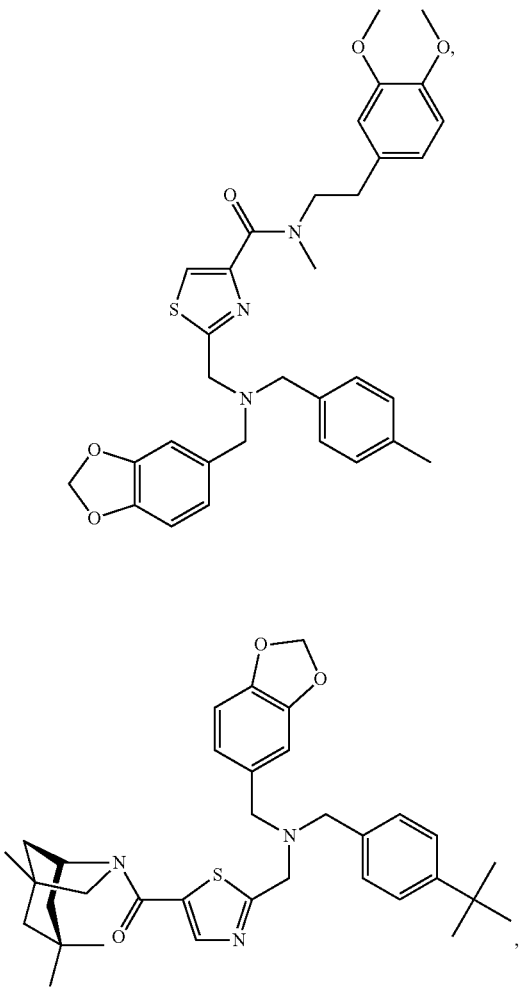

33
-continued
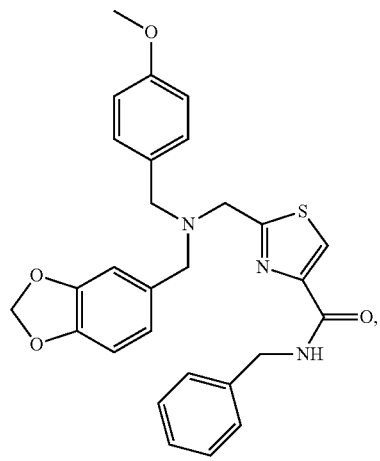
34
-continued
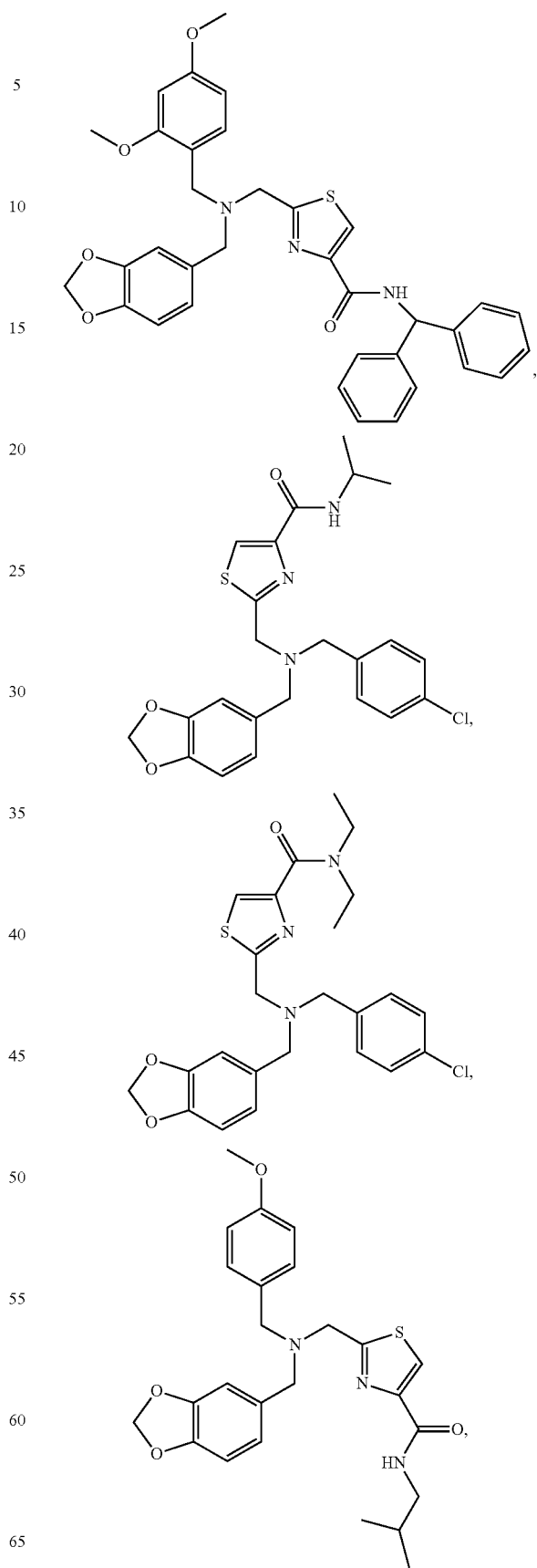

35
-continued
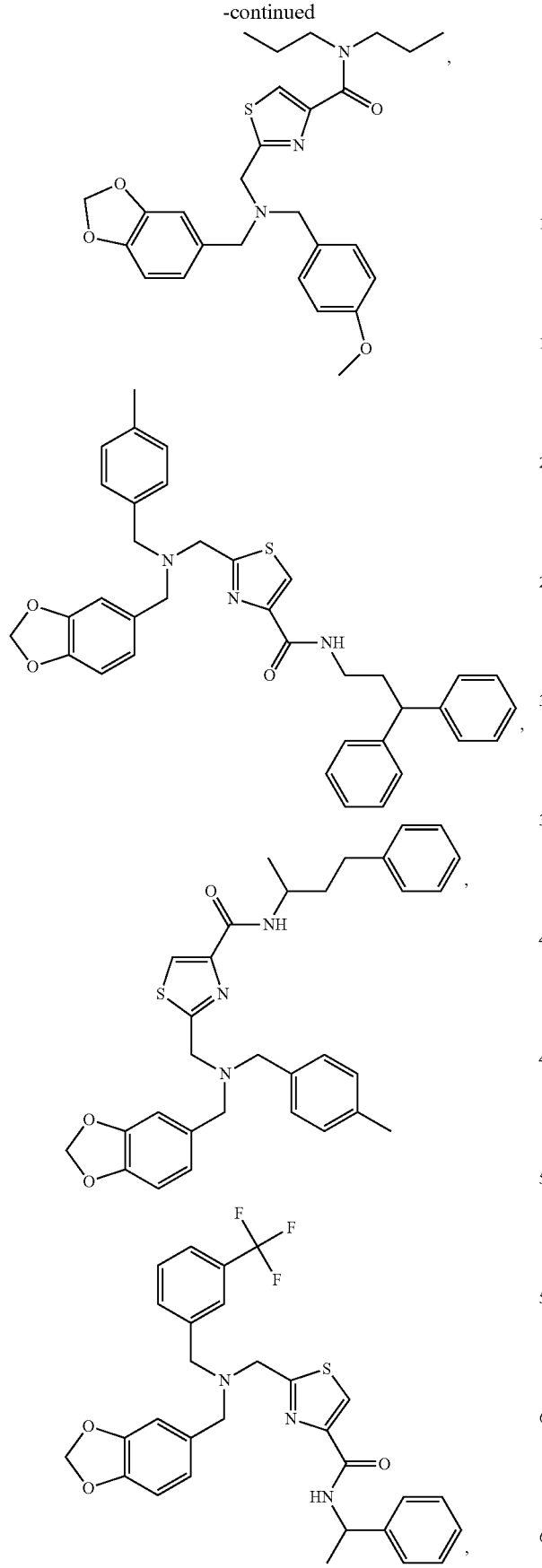
36
-continued
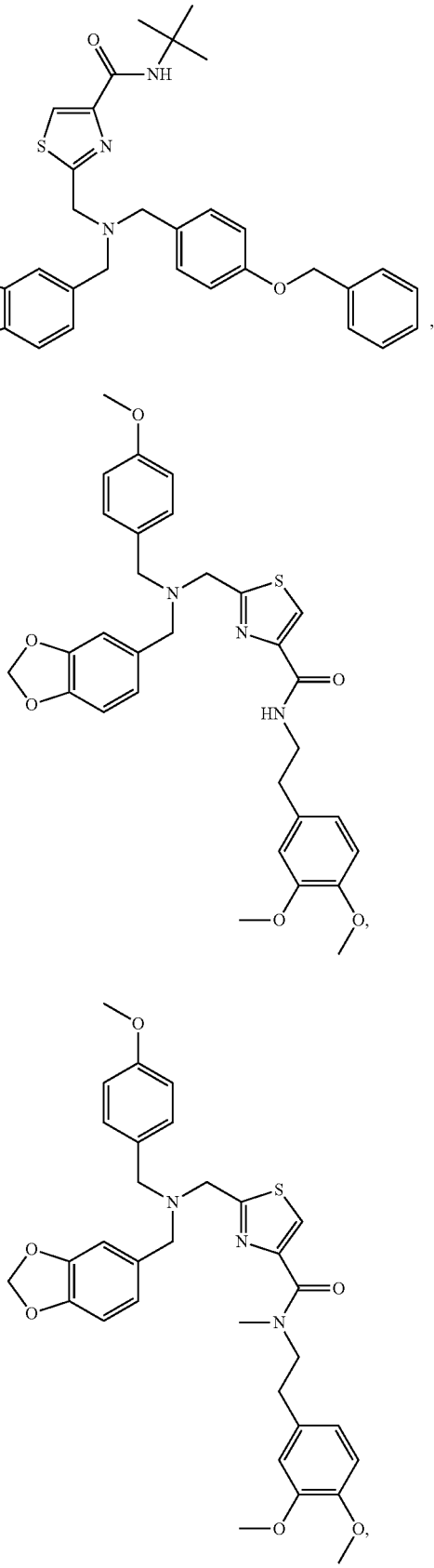

37
-continued
38
-continued
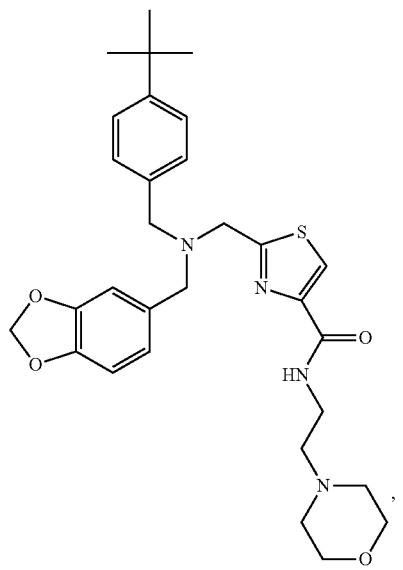
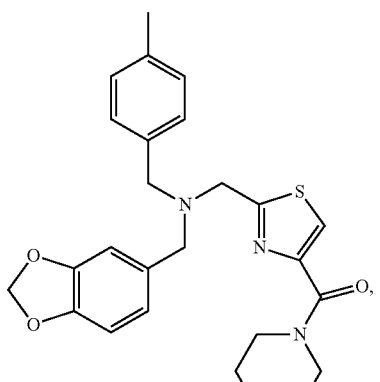
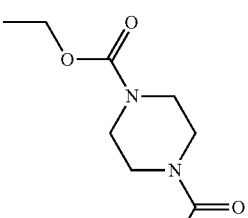
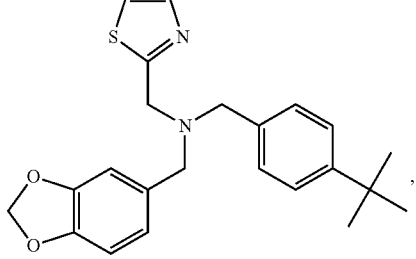
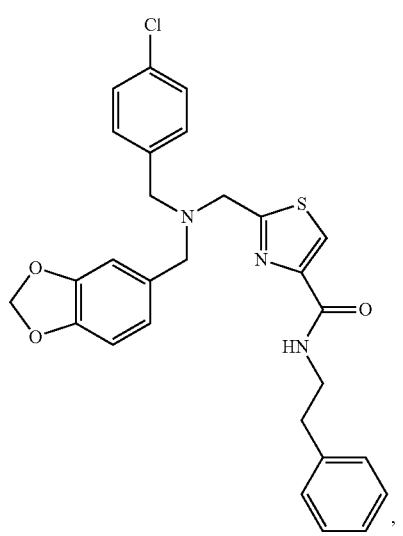
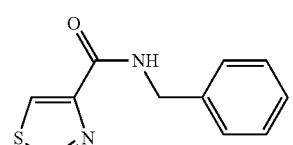
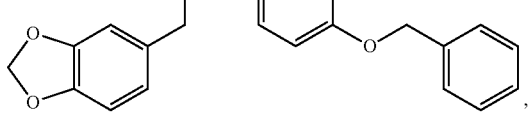

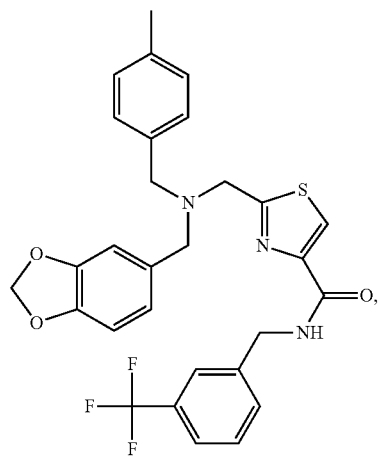
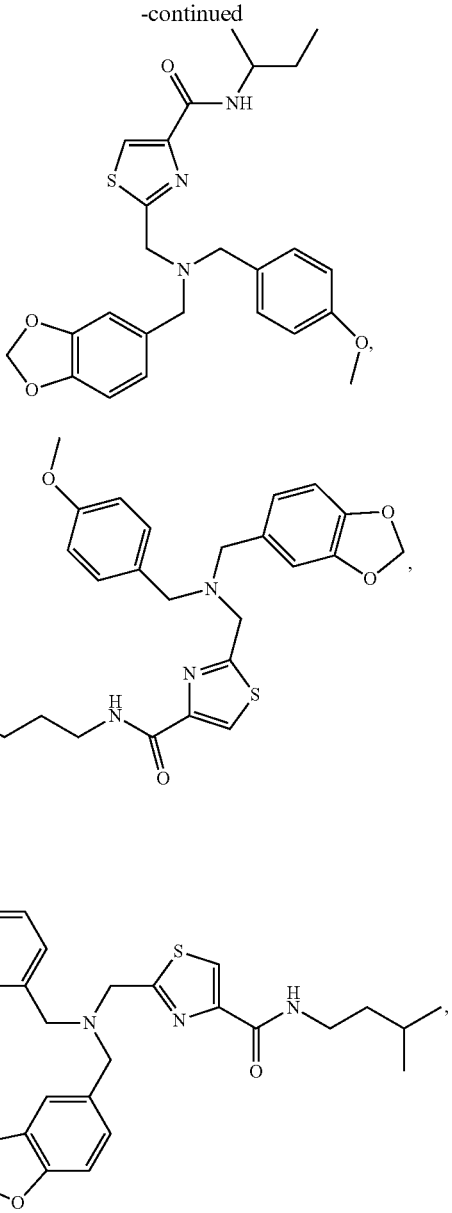
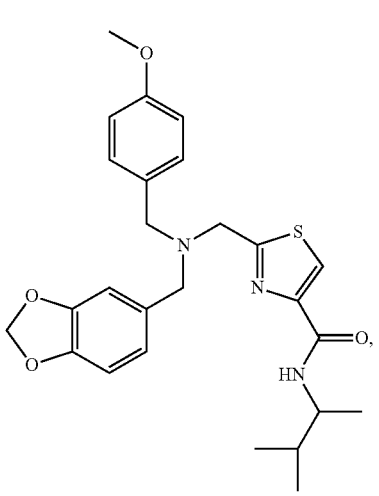

41
-continued
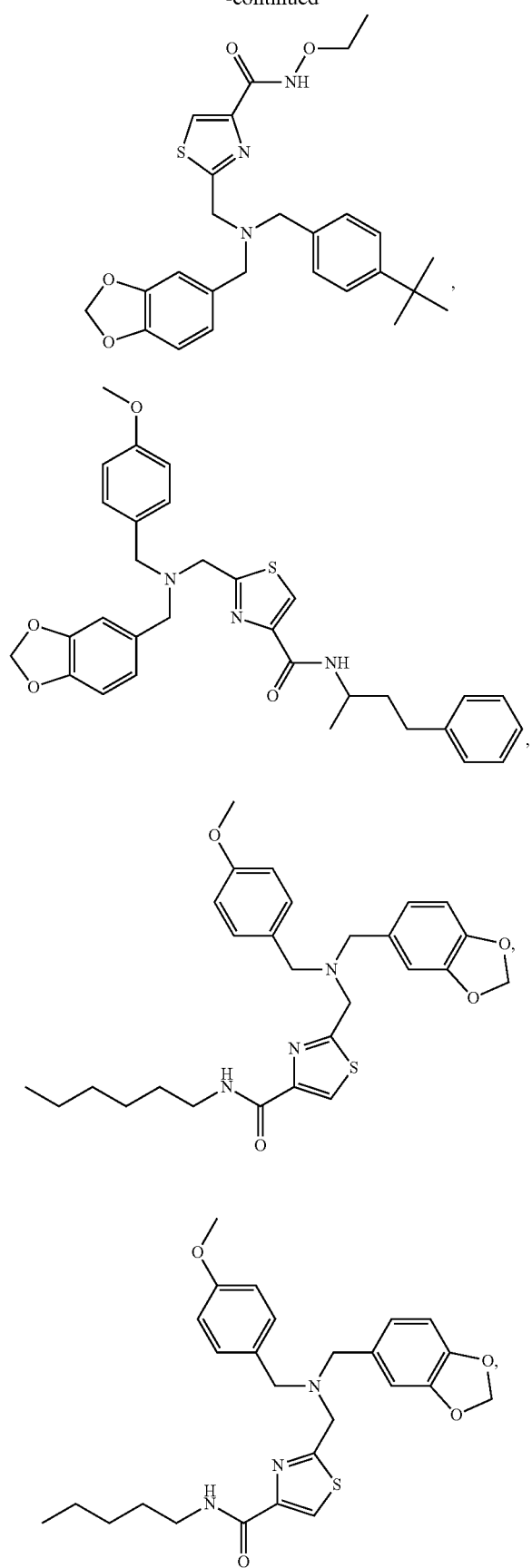
42
-continued
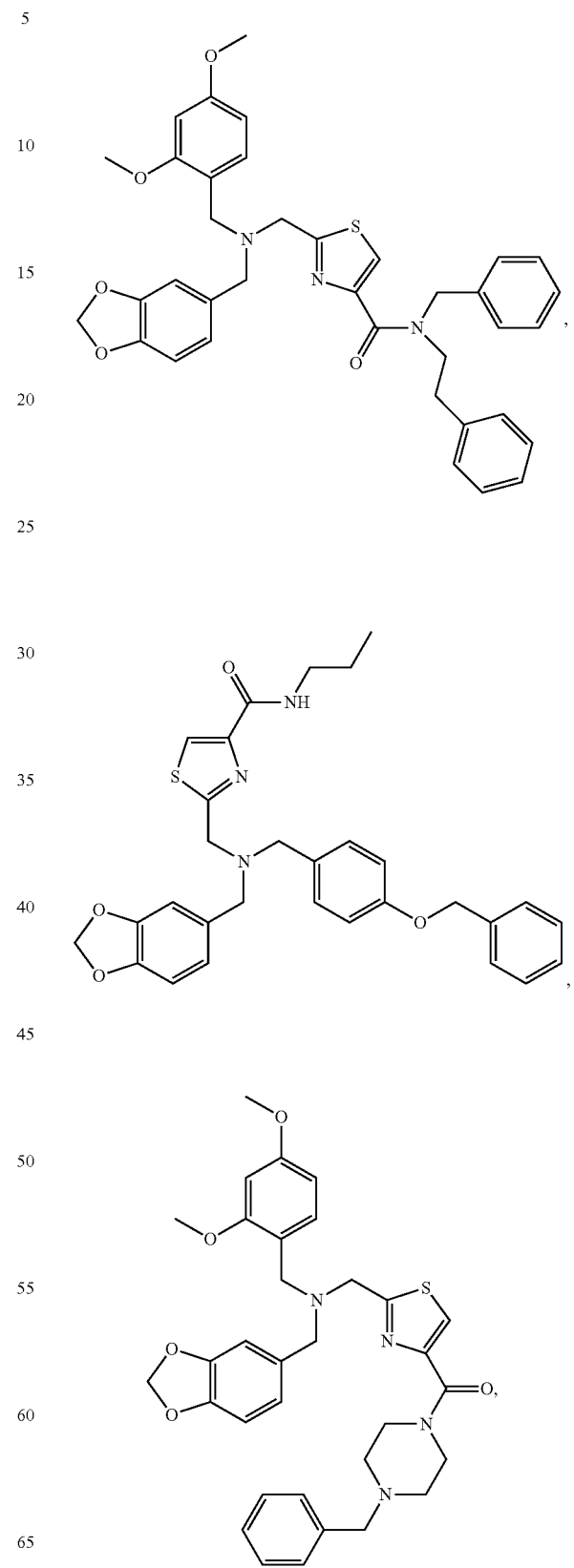

43
-continued
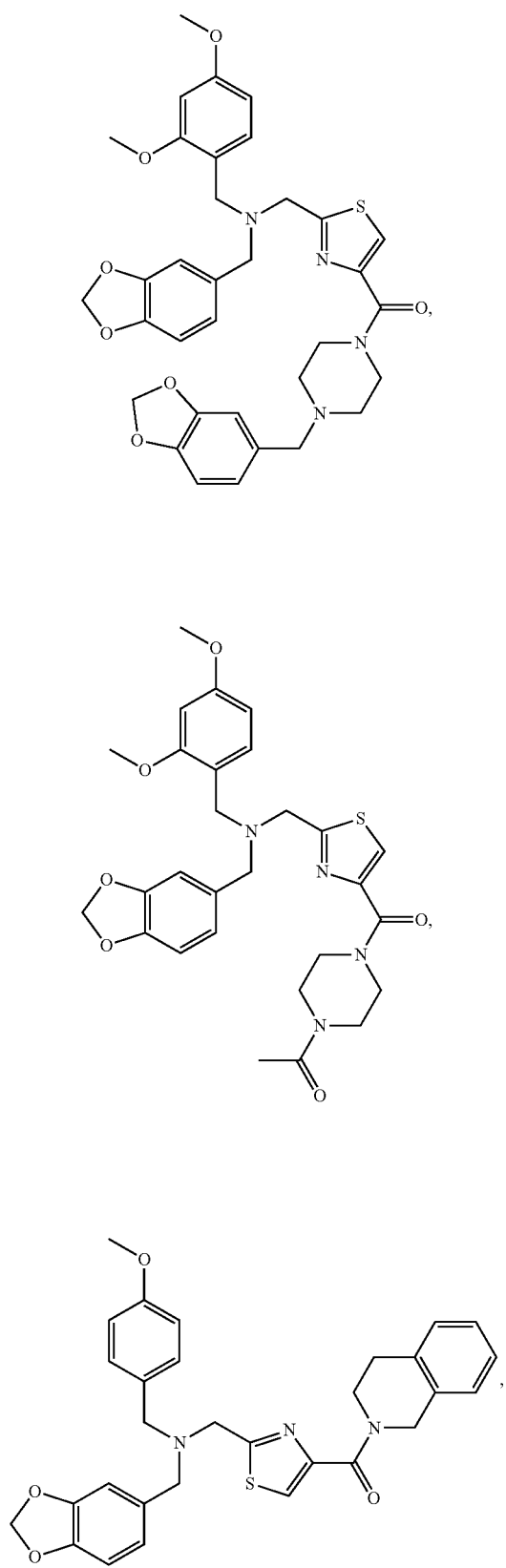
44
-continued
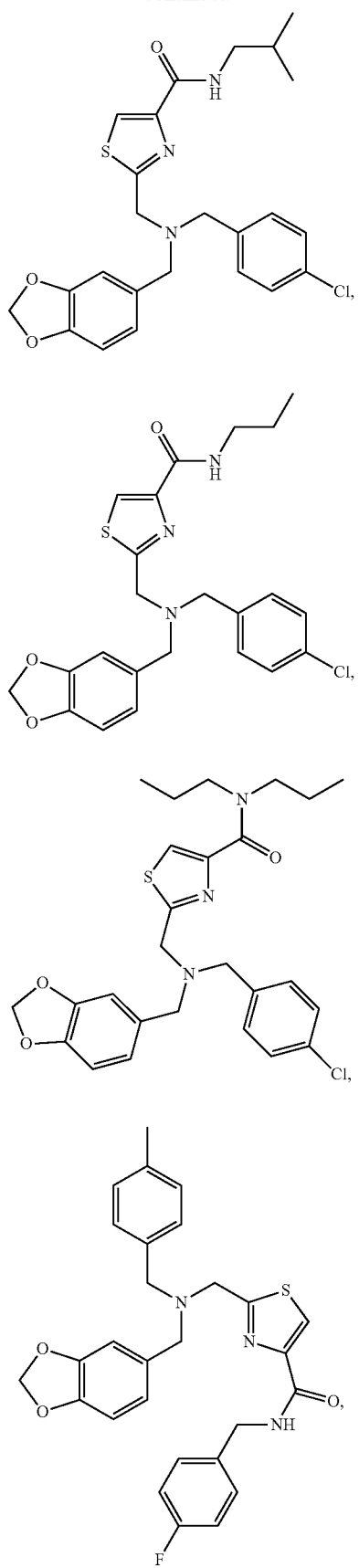

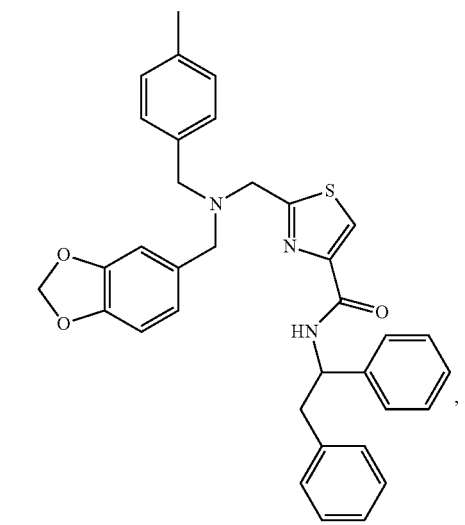
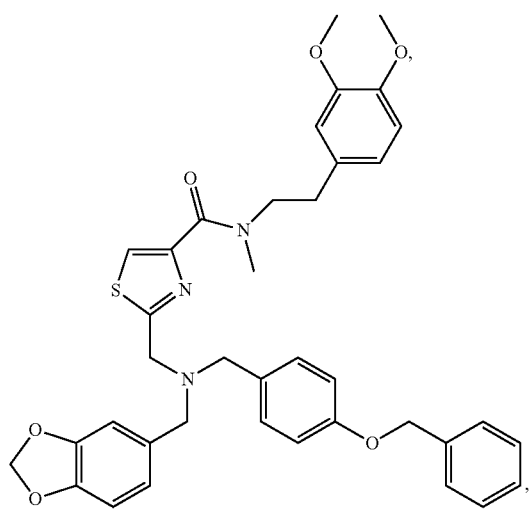
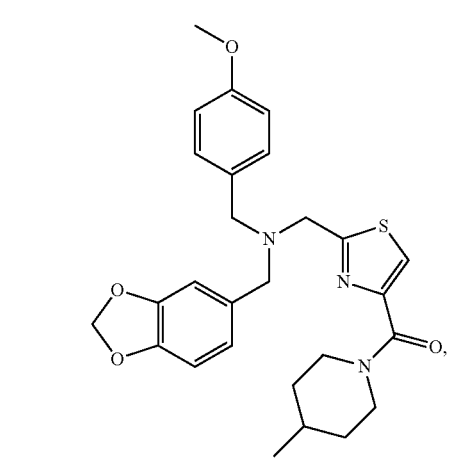
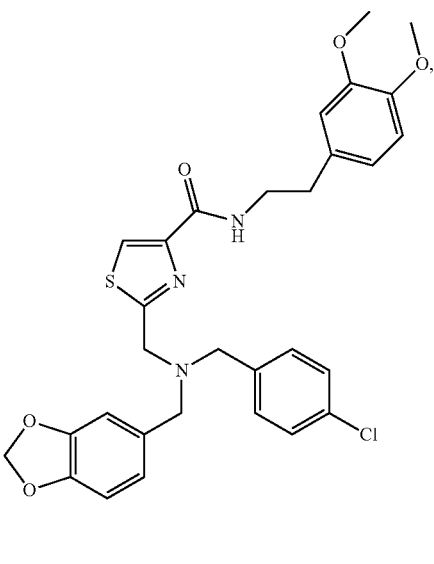
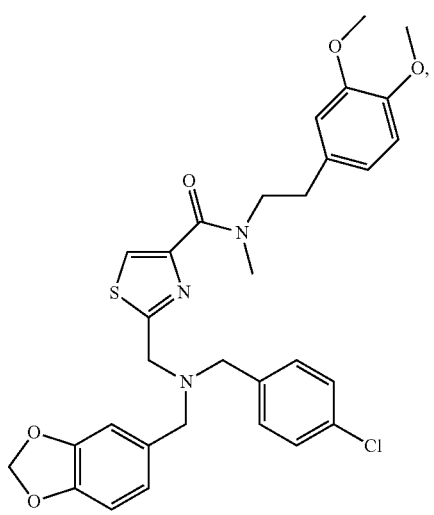
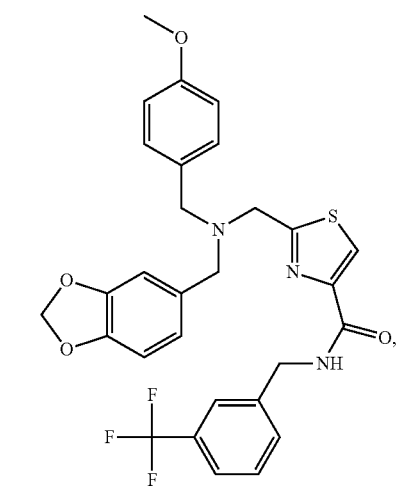

47
-continued
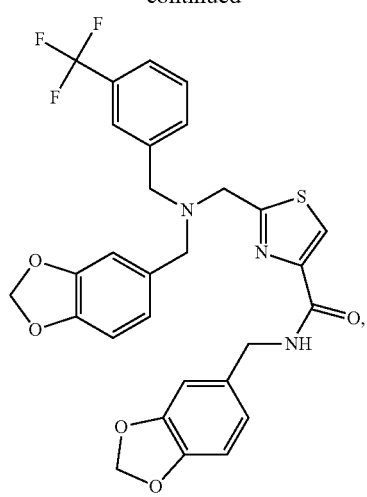
48
-continued
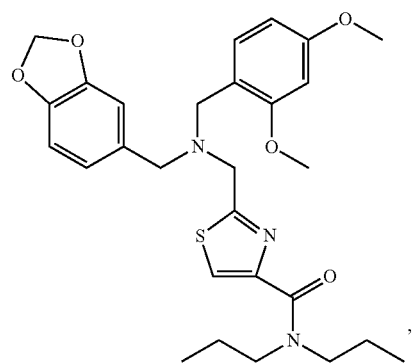
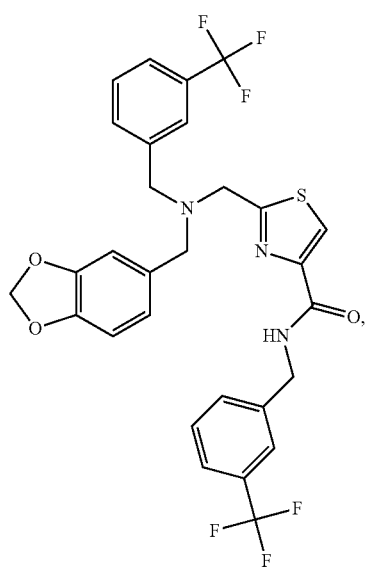
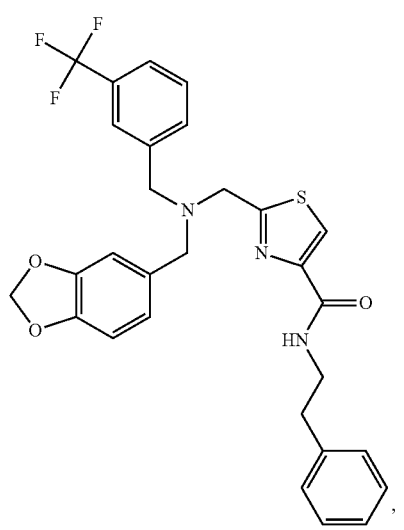
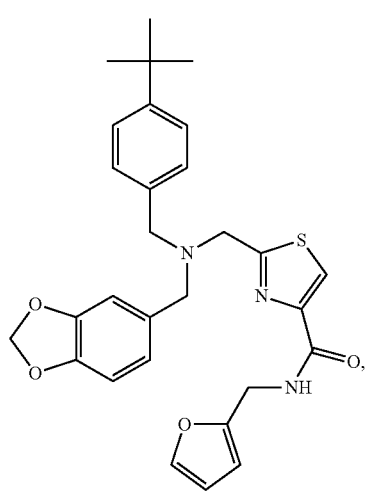
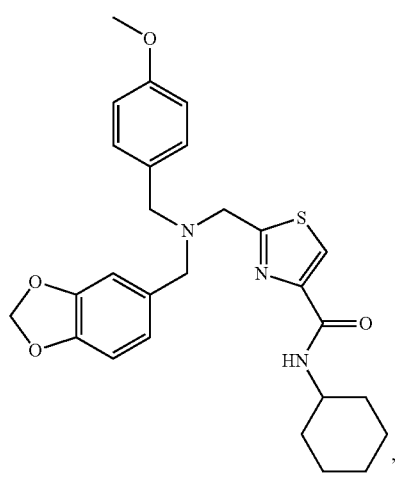

49
-continued
50
-continued
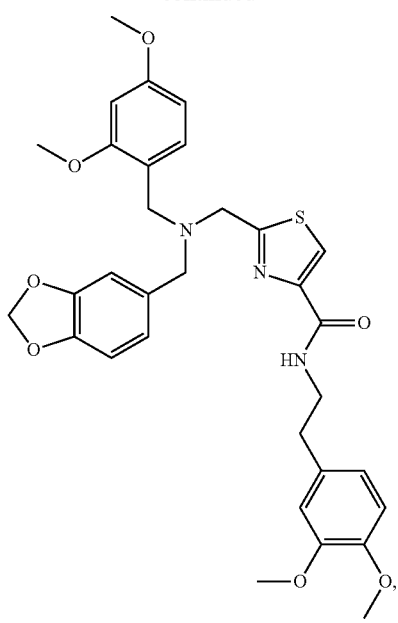
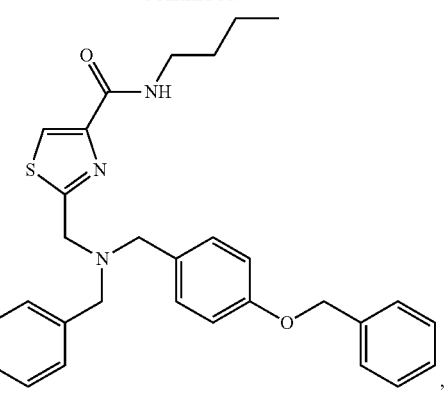
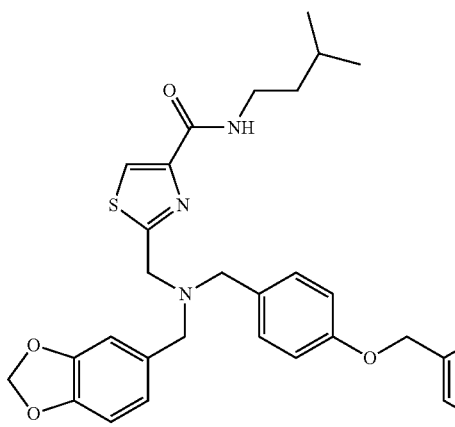
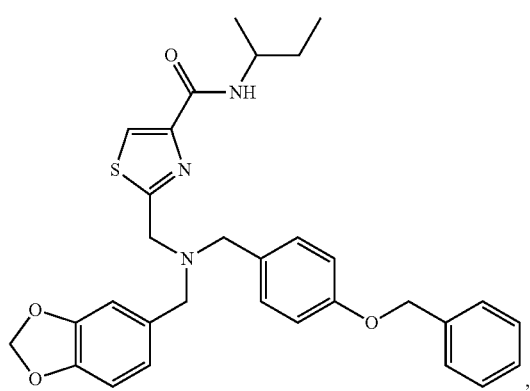
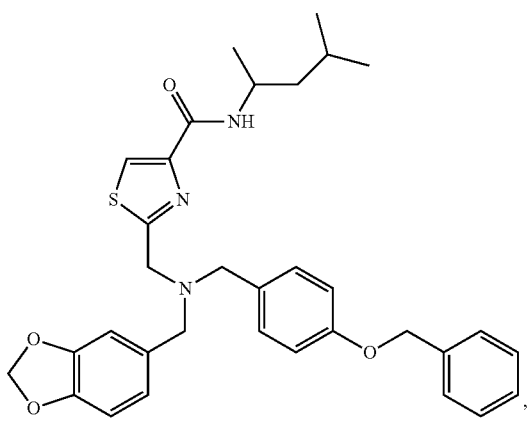

51
-continued
52
-continued
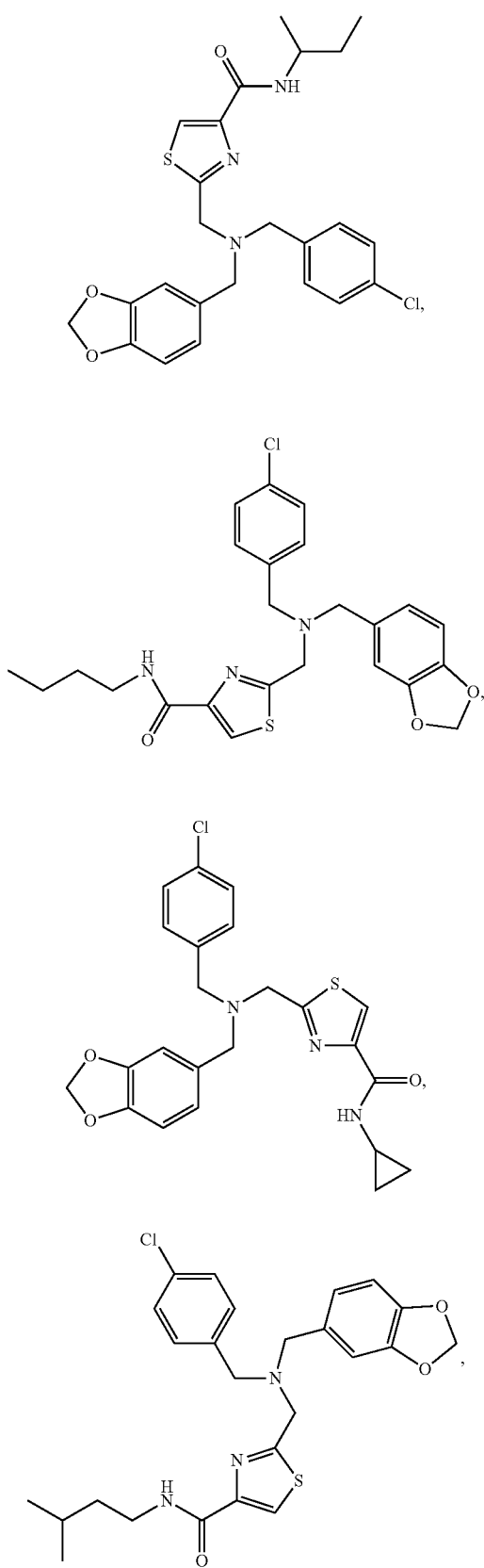
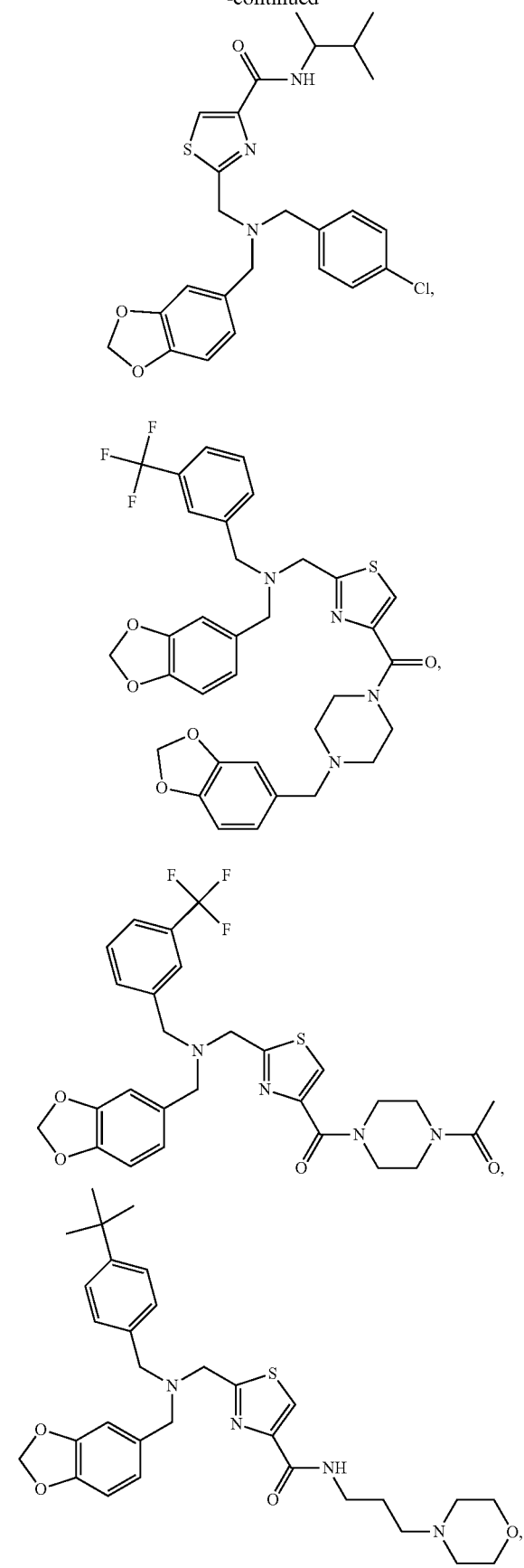

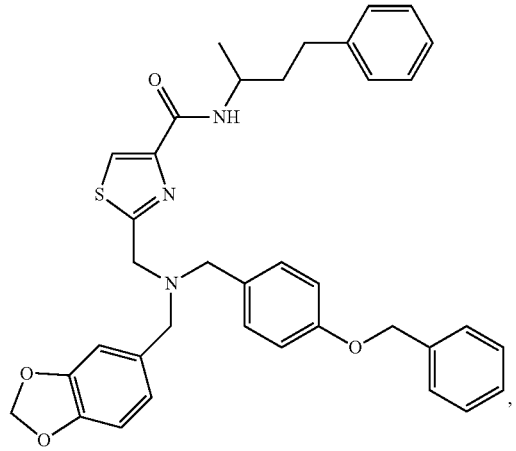
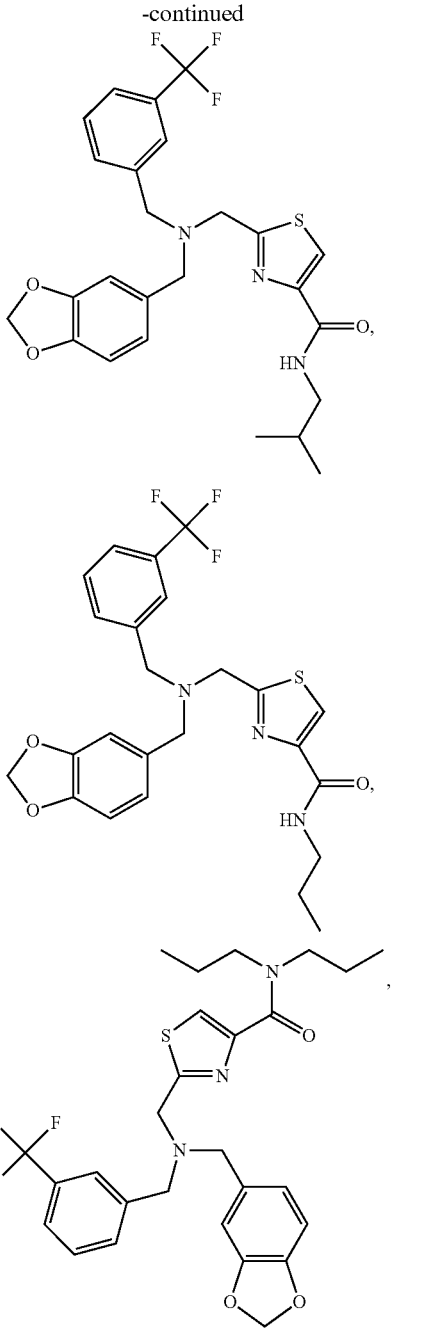
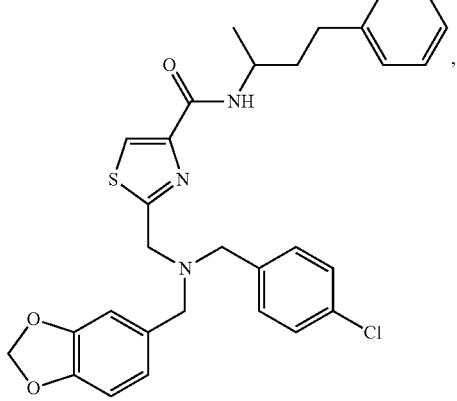

55
-continued
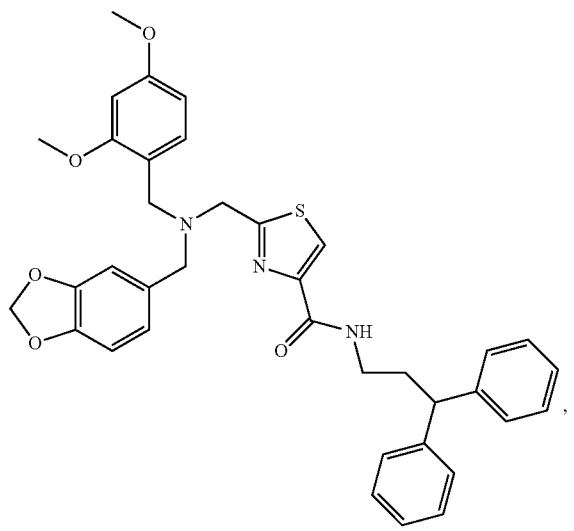
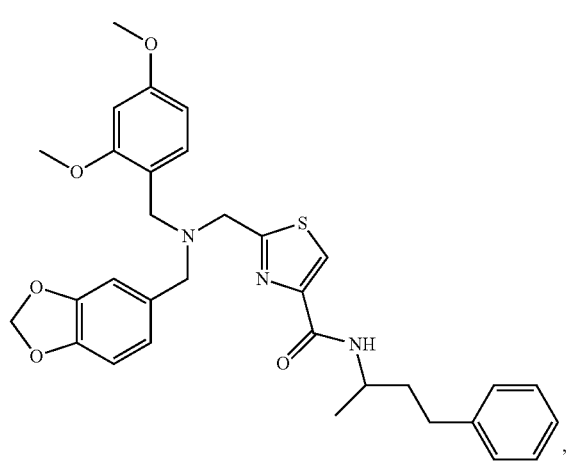
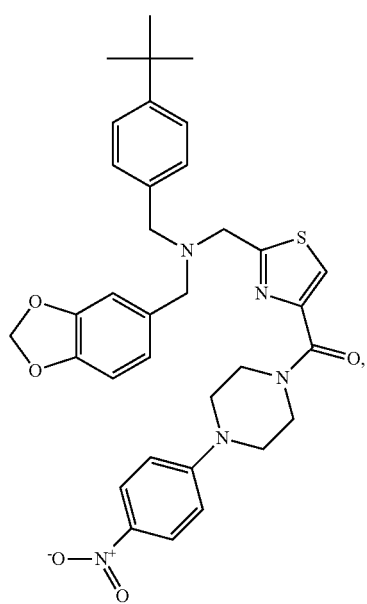
56
-continued
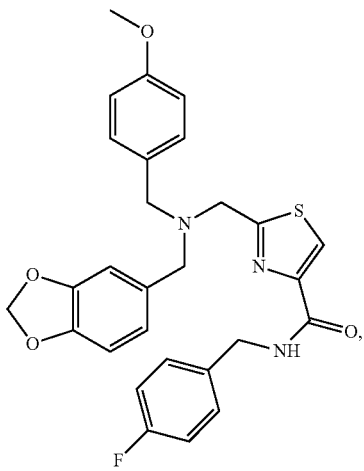
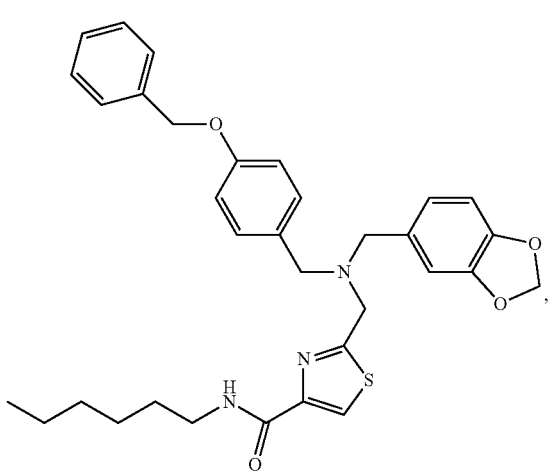
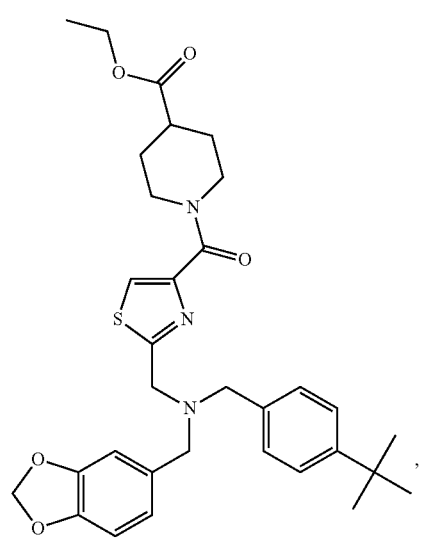

57
-continued
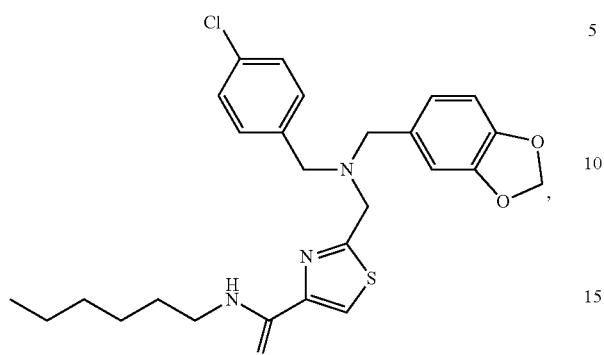
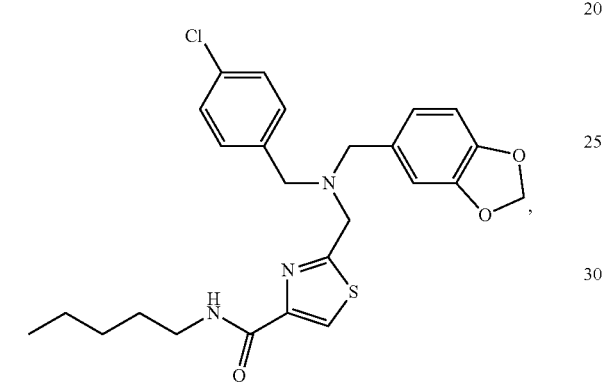
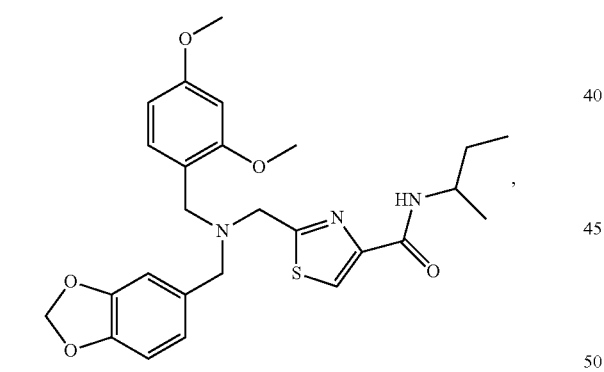
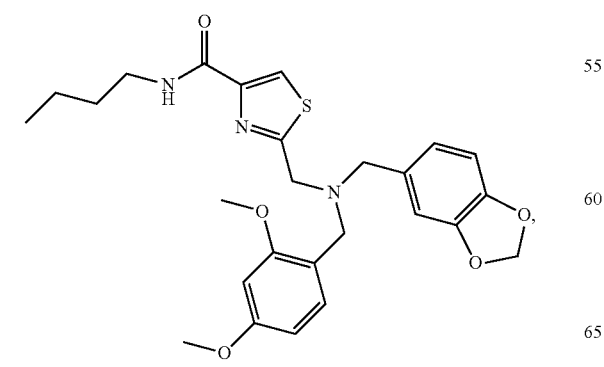
58
-continued
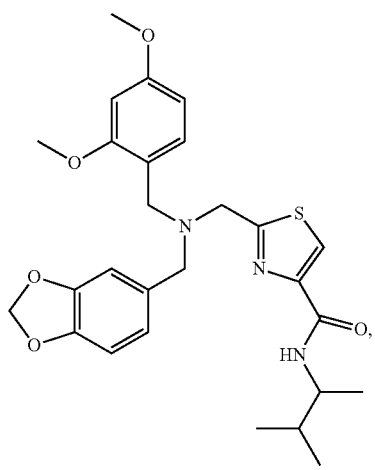
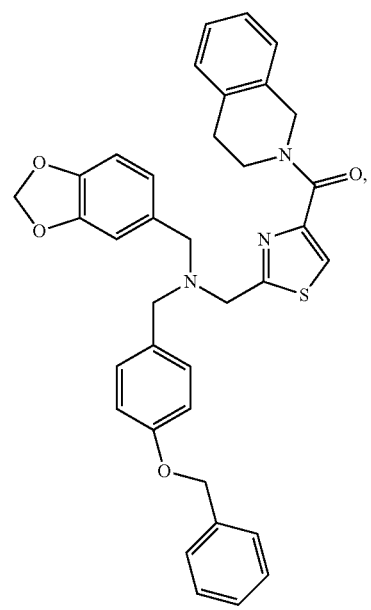
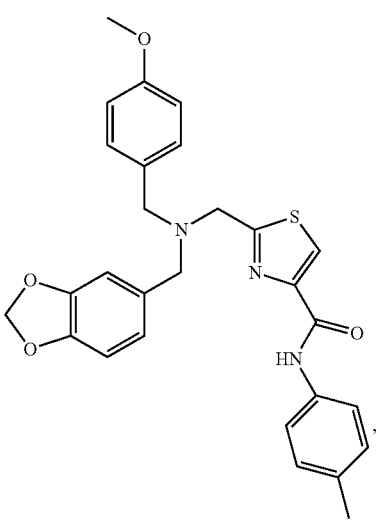

59
-continued
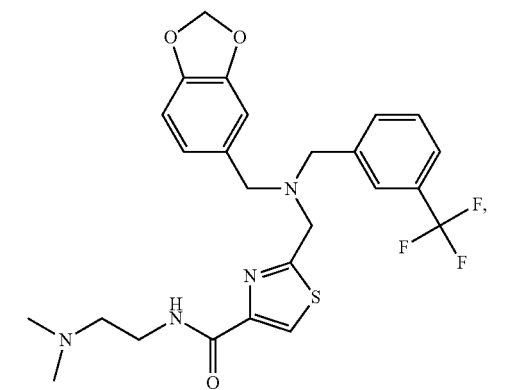
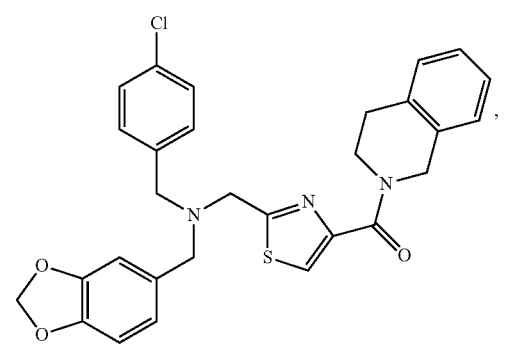
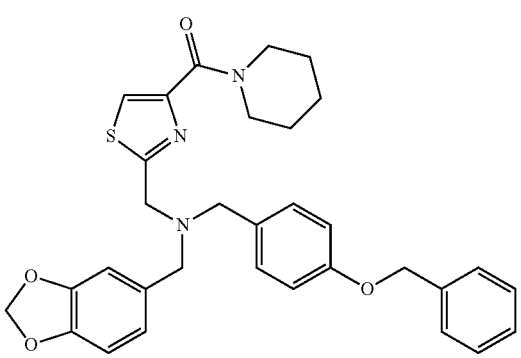
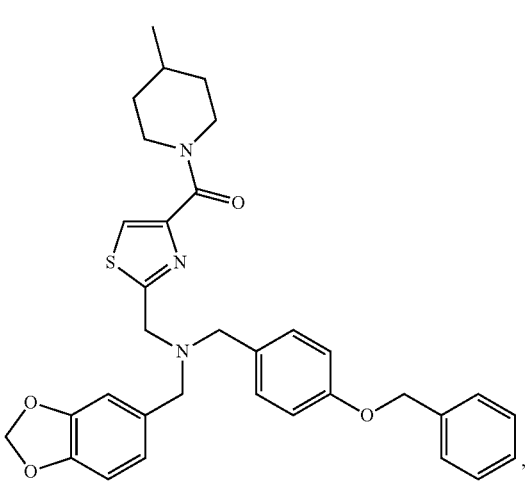
60
-continued
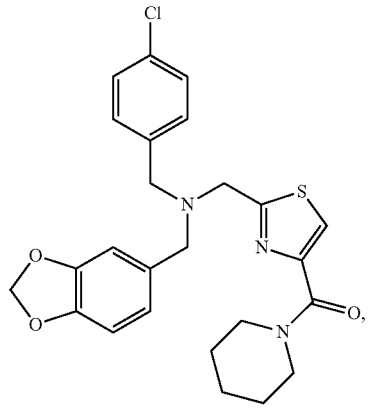
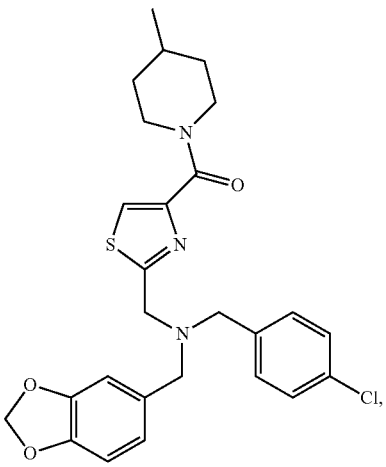
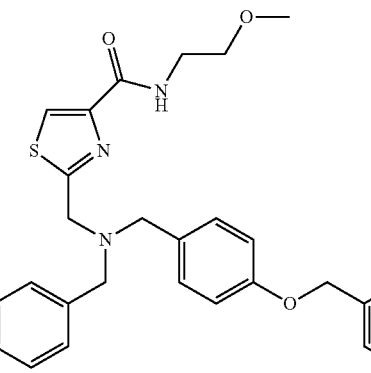
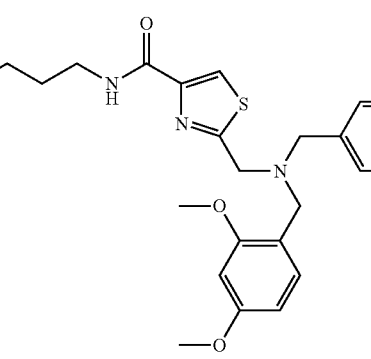

61
-continued
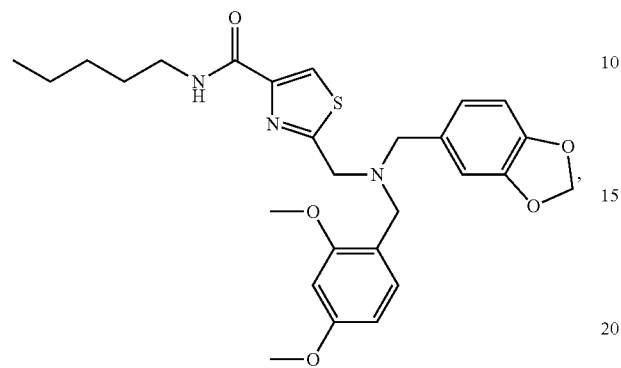
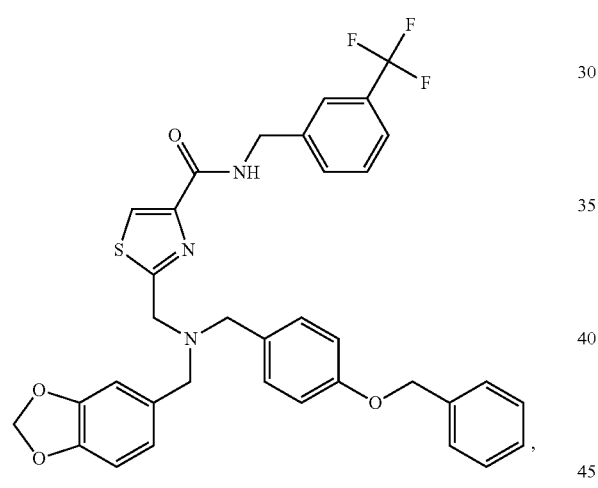
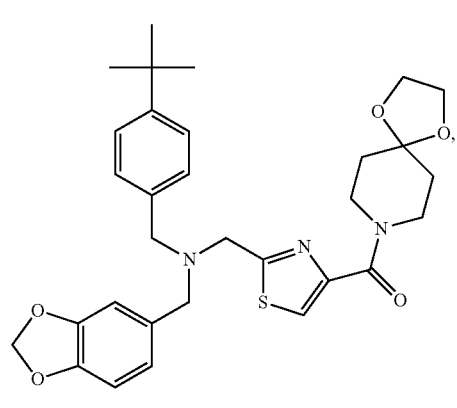
62
-continued
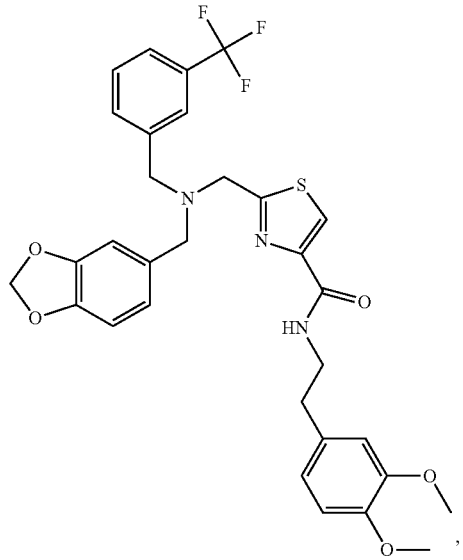
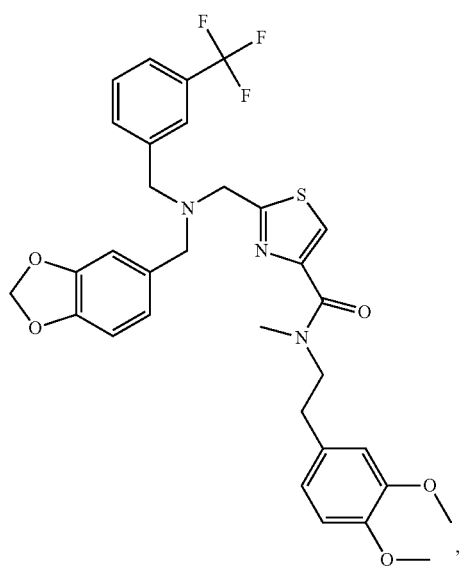
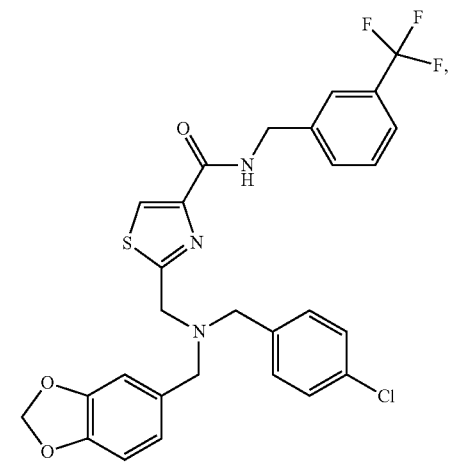

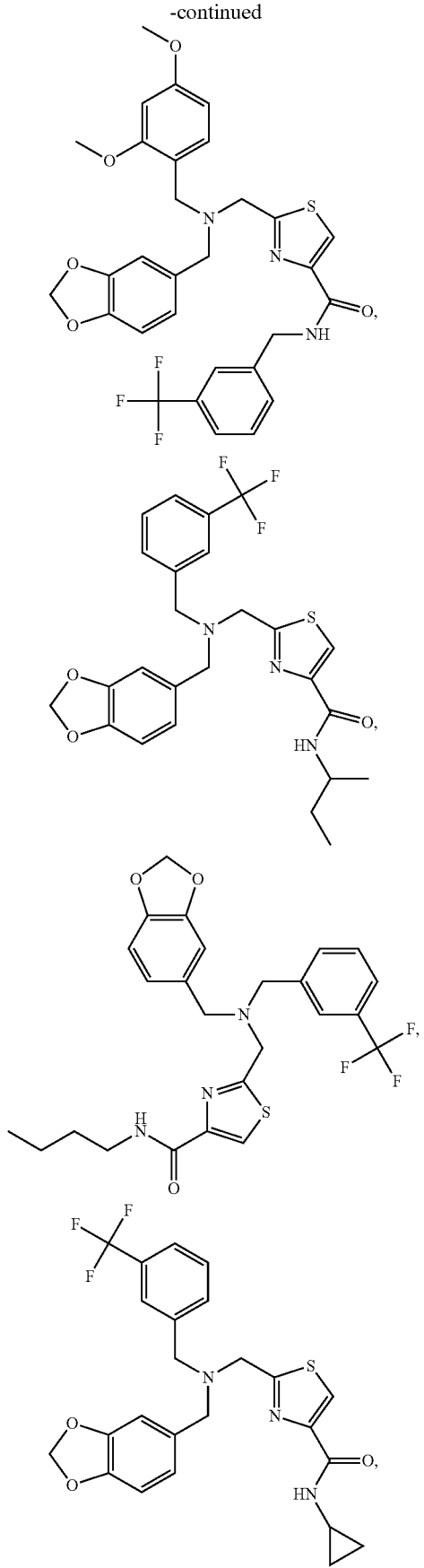
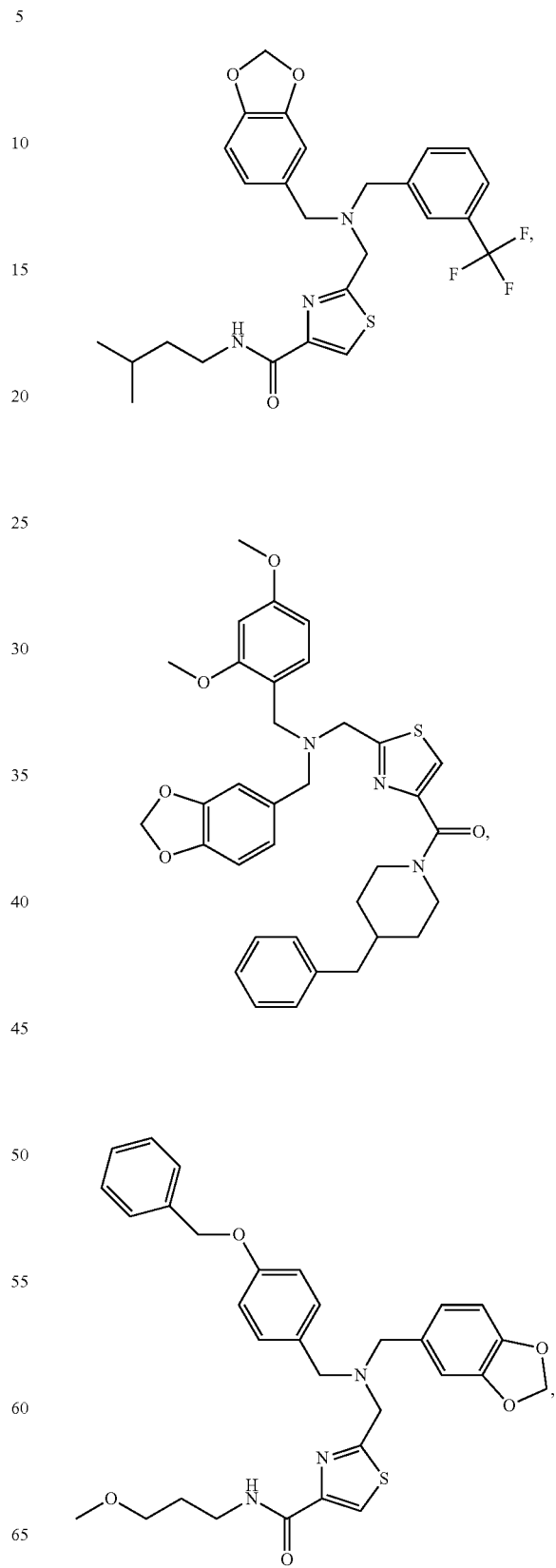

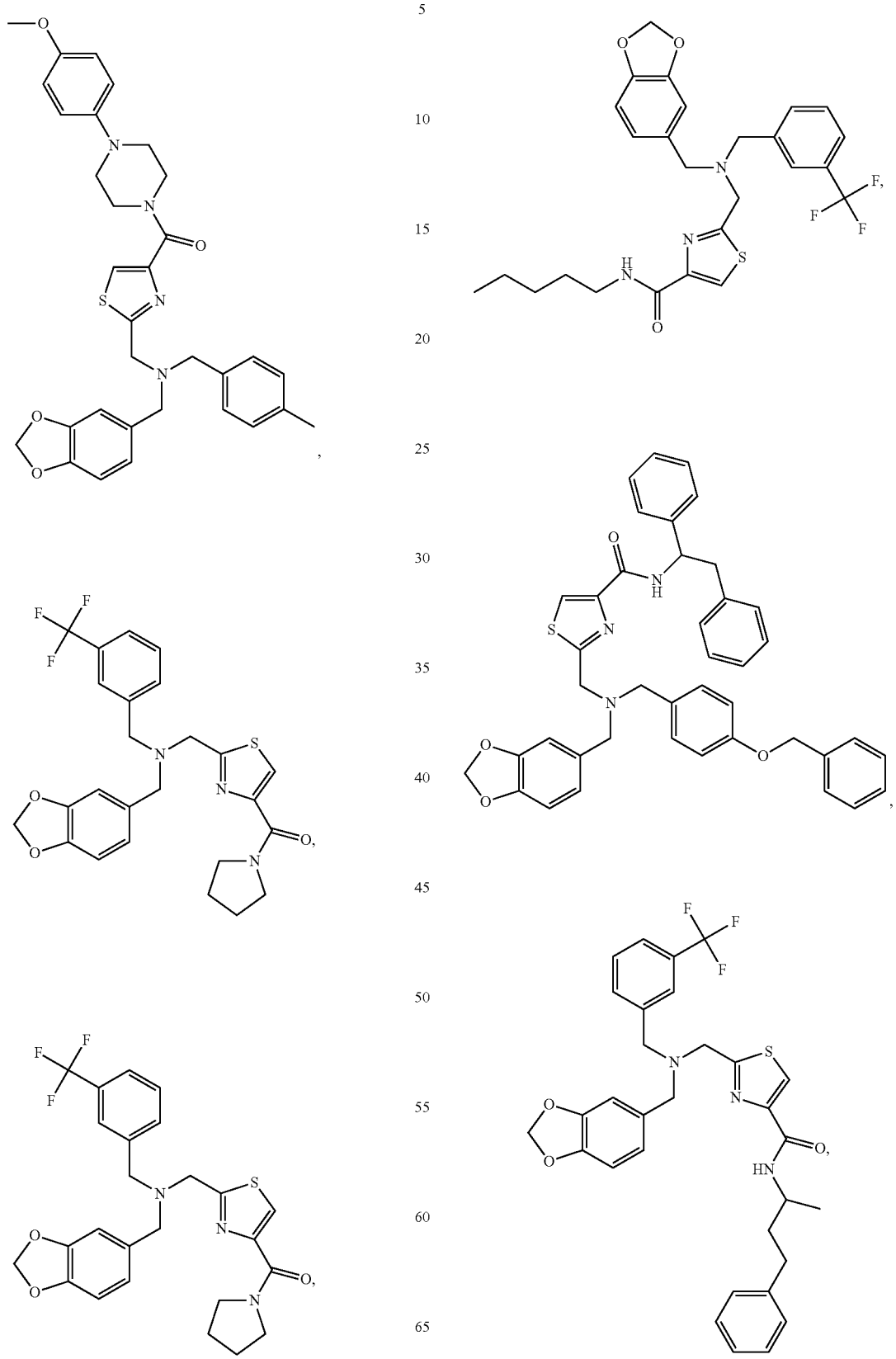

67
-continued
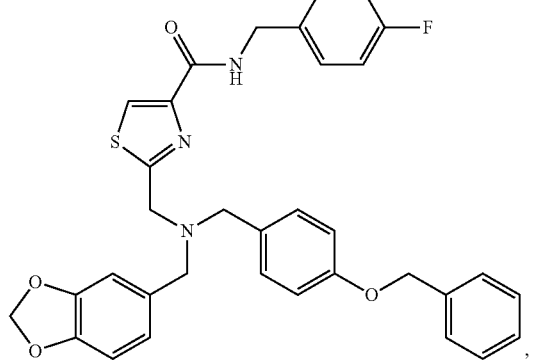
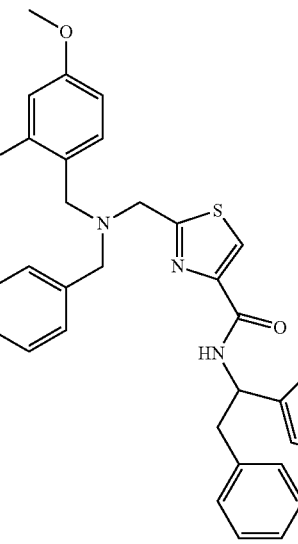
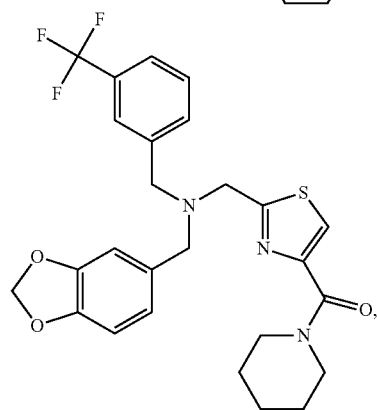
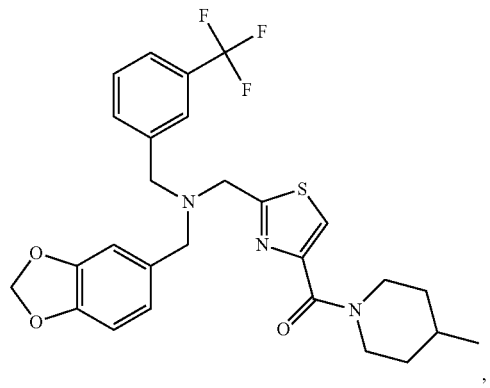
68
-continued
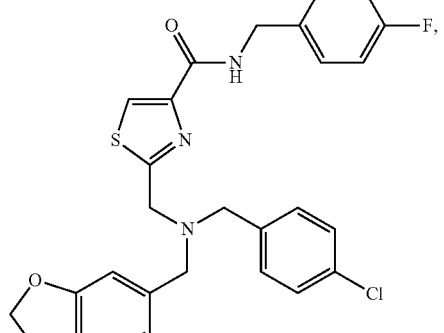
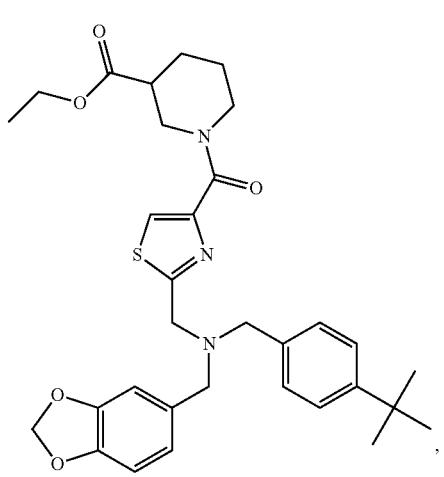
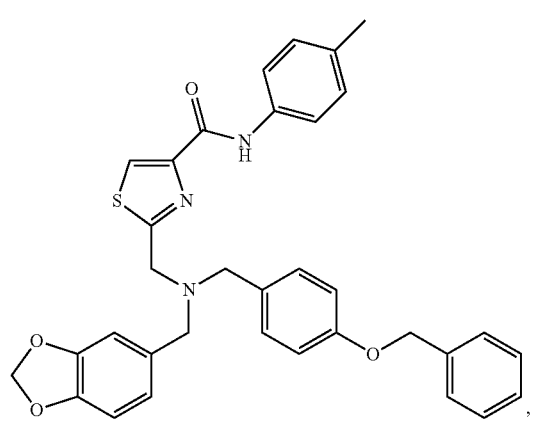
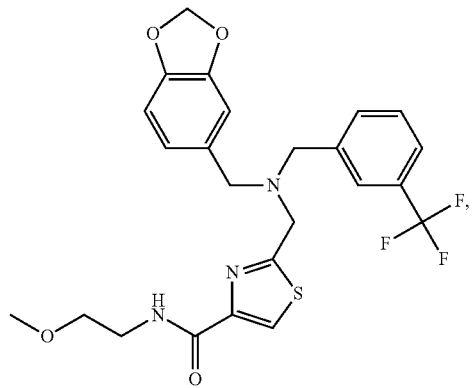

69
-continued
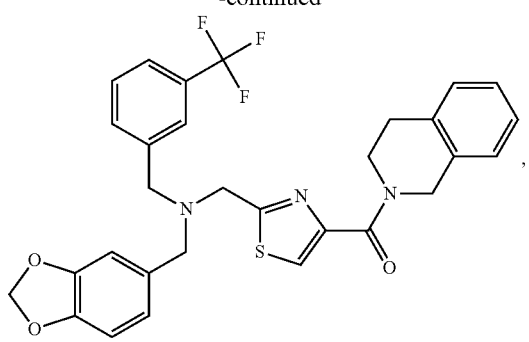
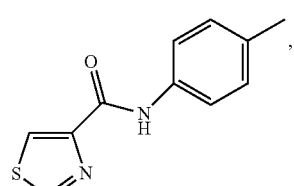
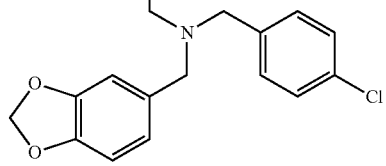
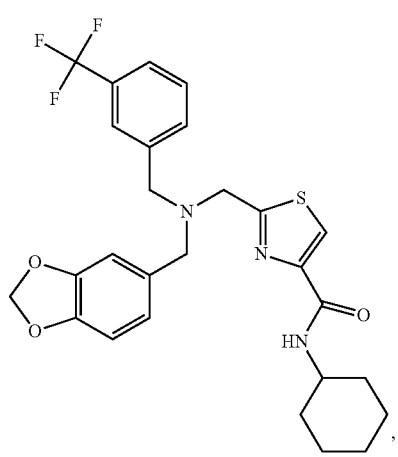
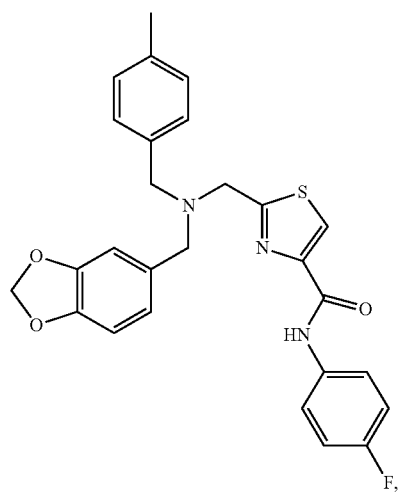
70
-continued
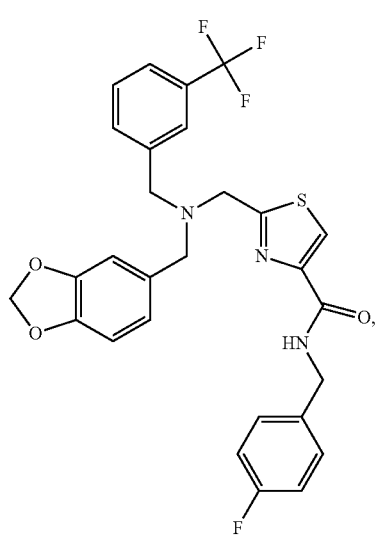
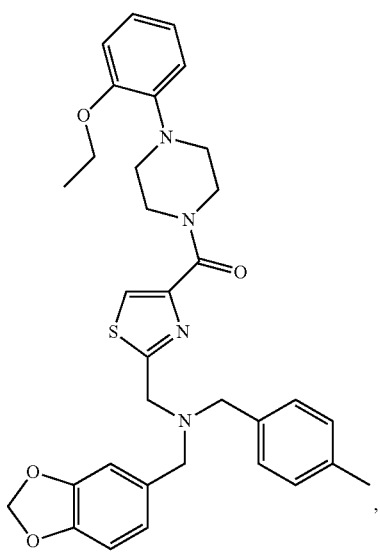
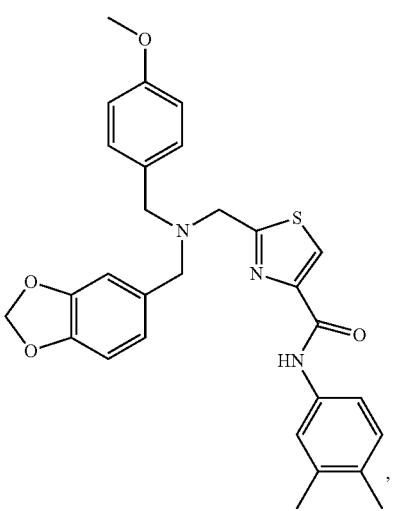

71
-continued
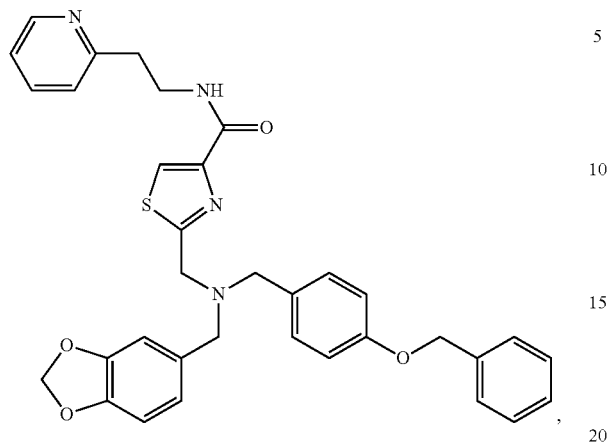
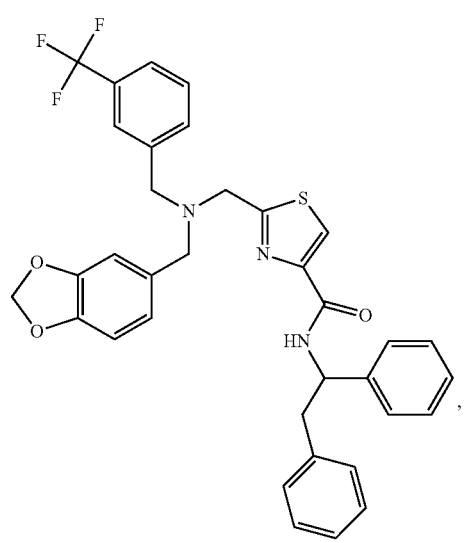
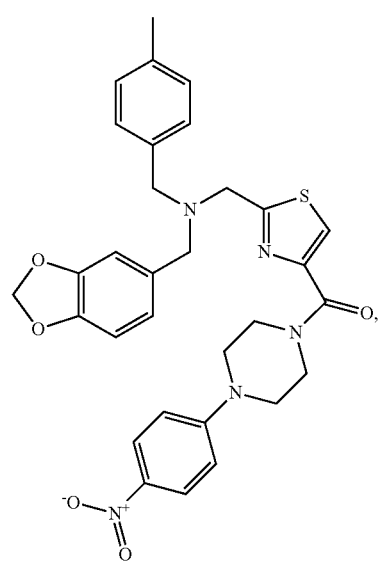
72
-continued
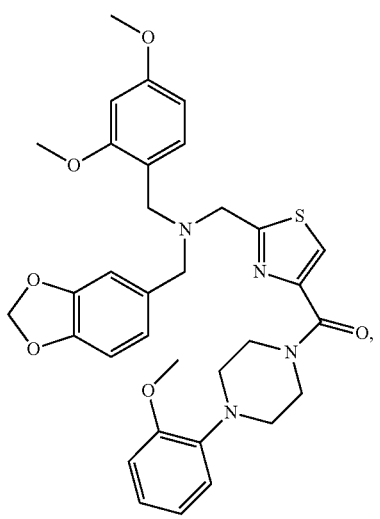
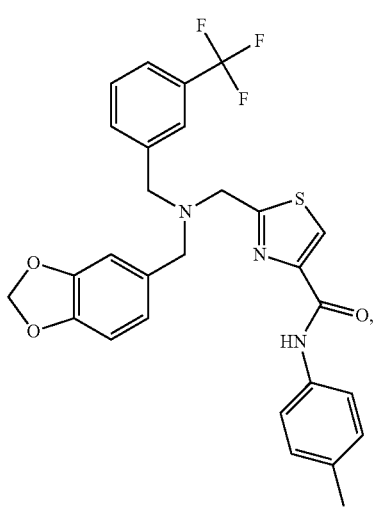
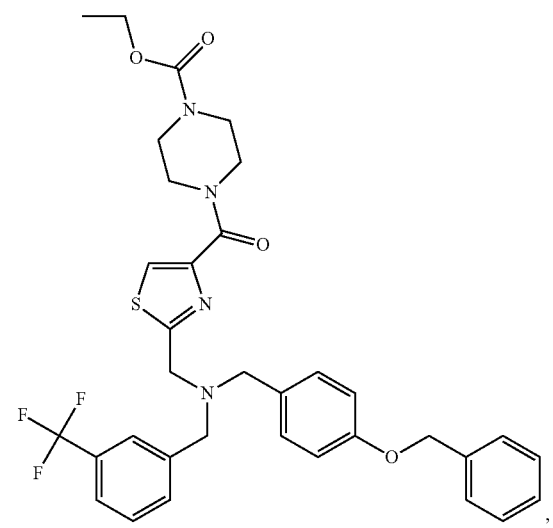

73
-continued
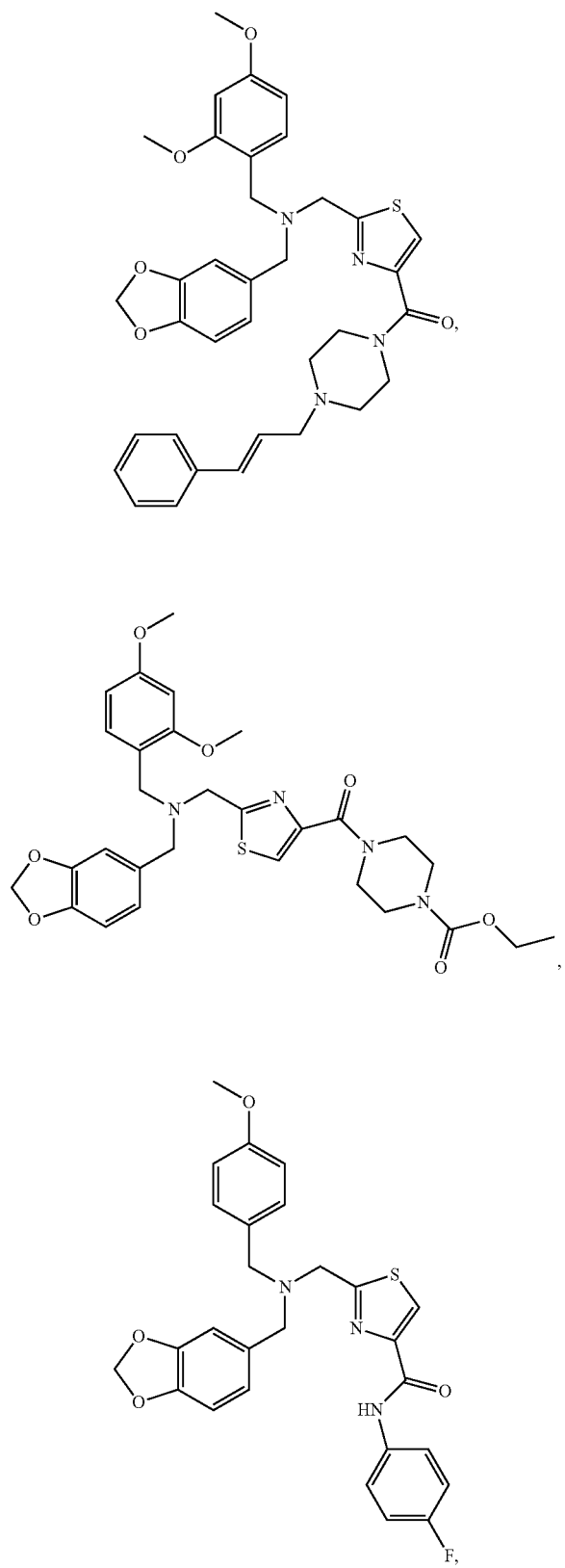
74
-continued
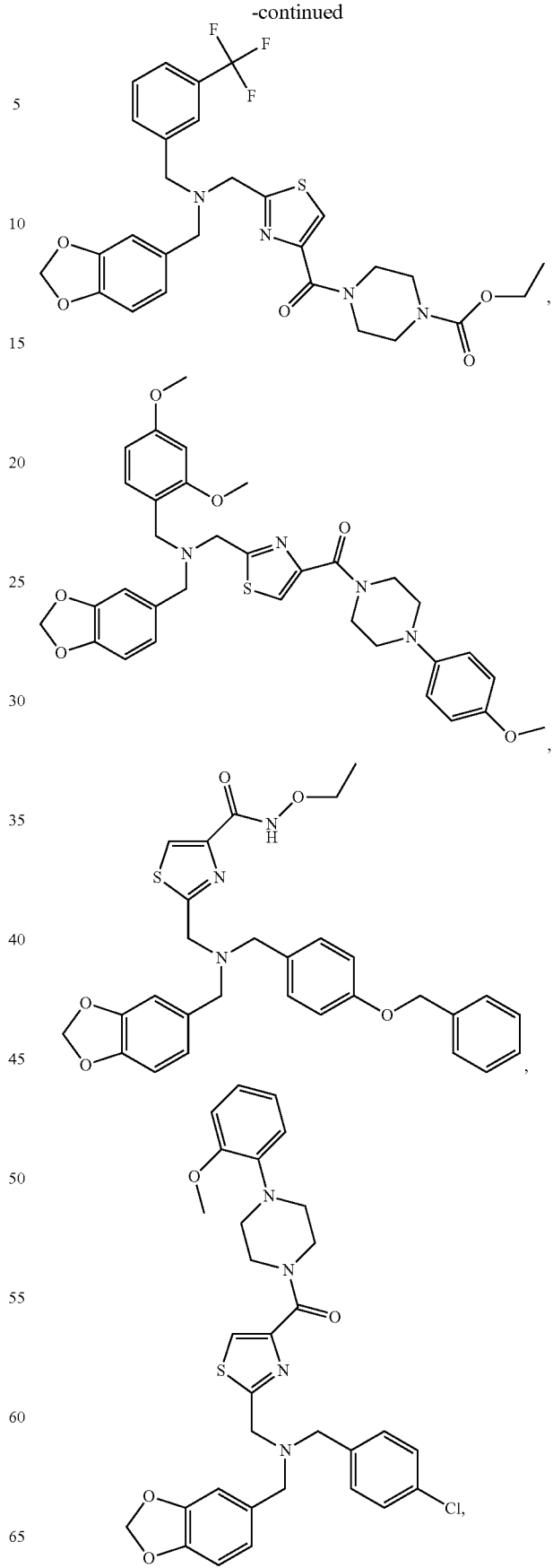

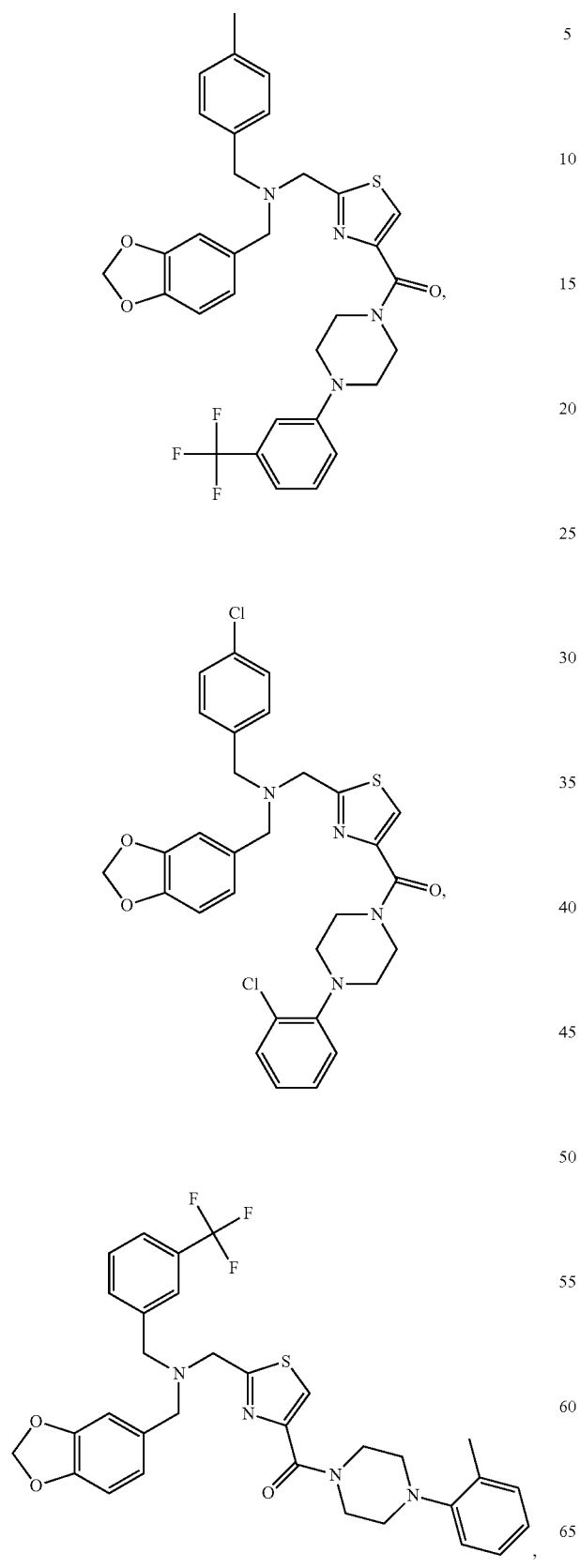
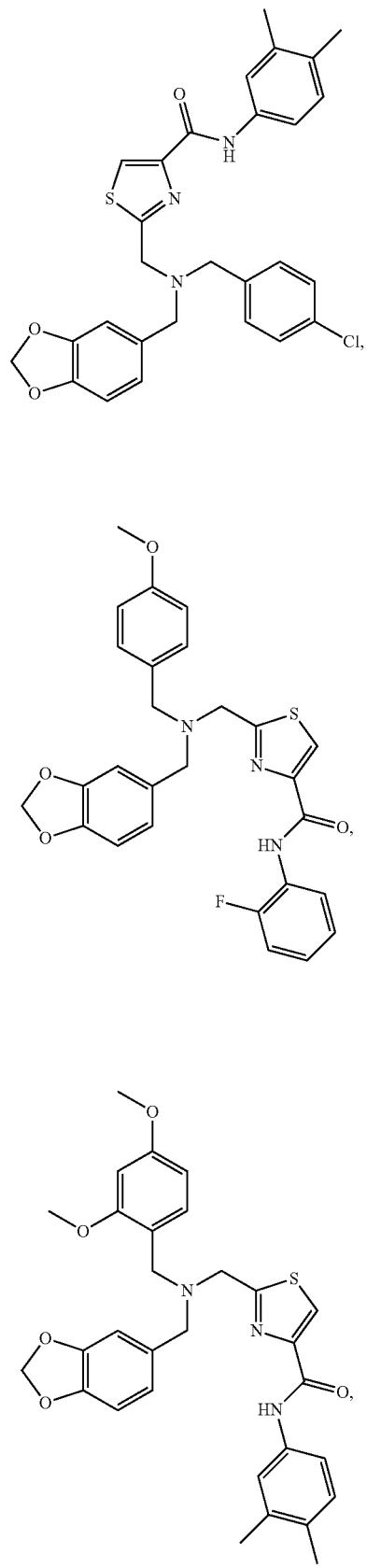

77
-continued
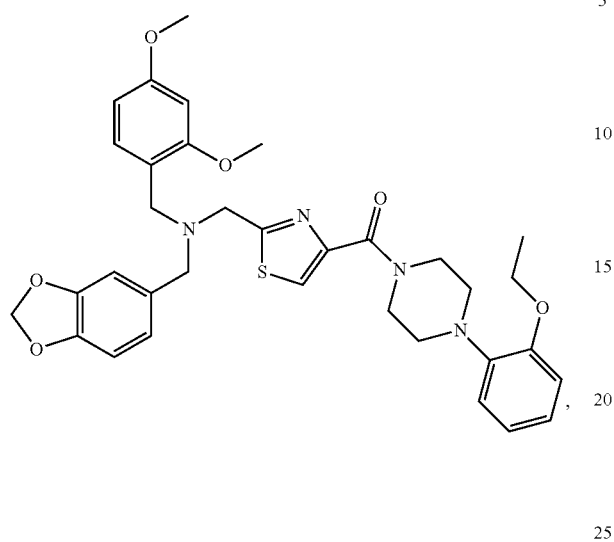
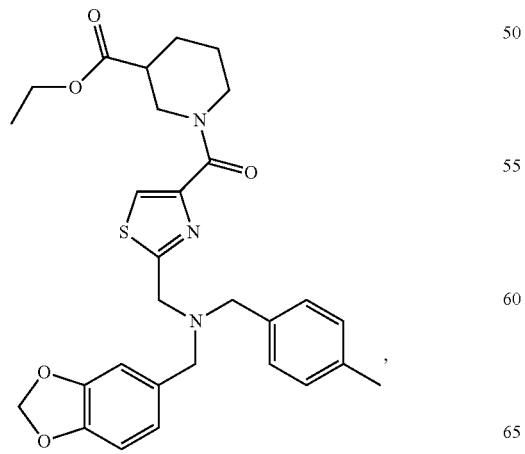
78
-continued
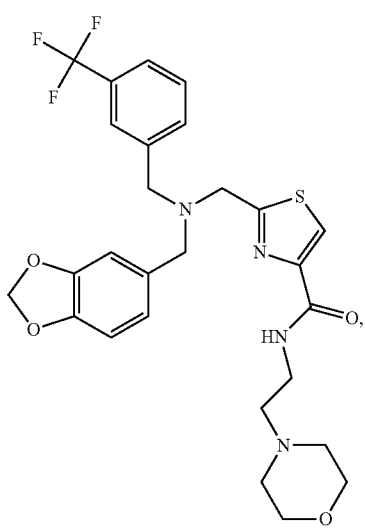
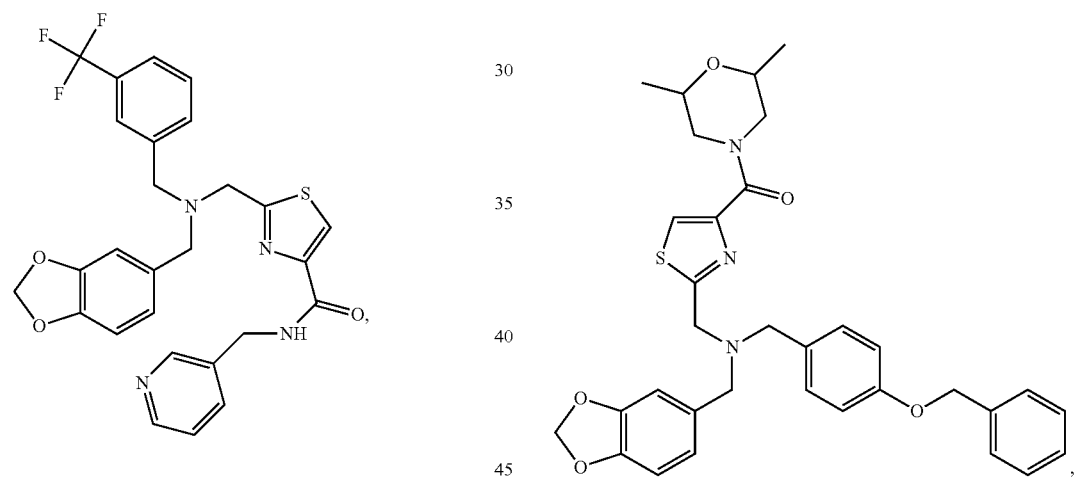
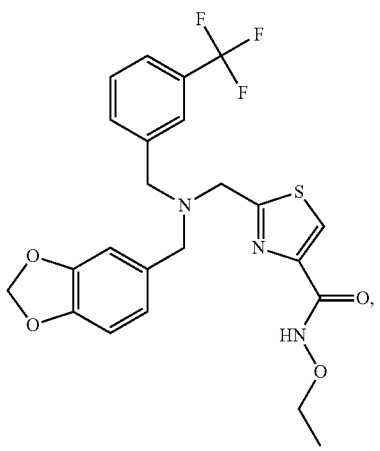

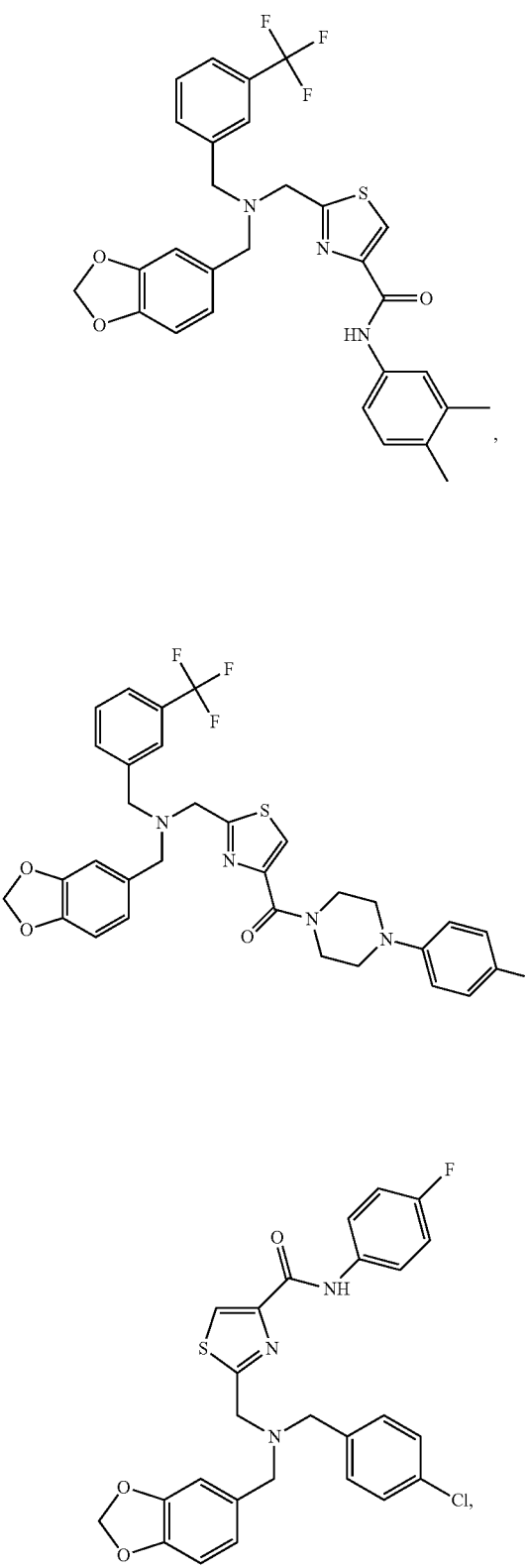
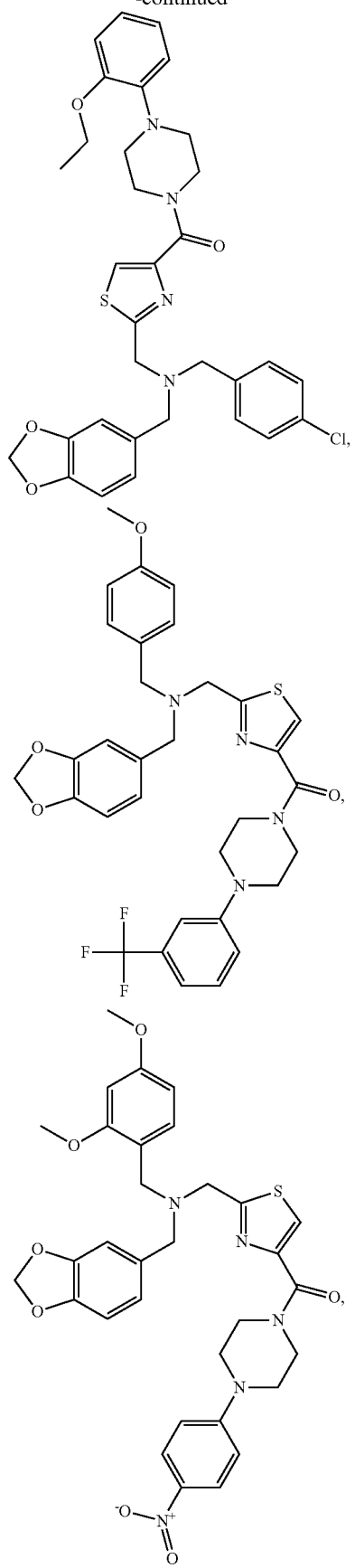

81
-continued
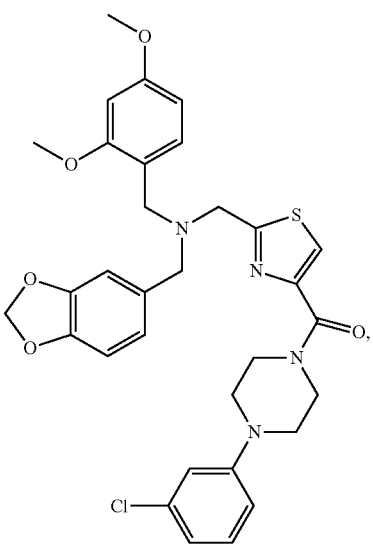
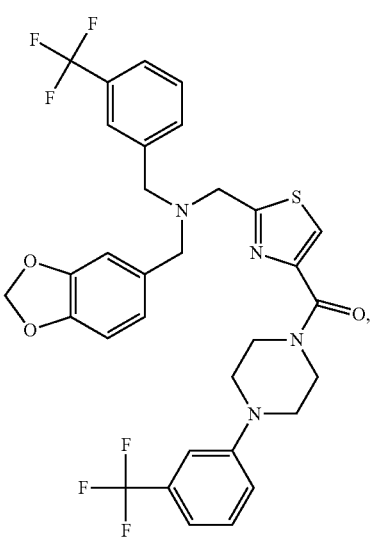
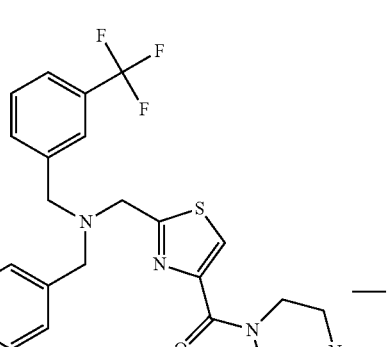
82
-continued
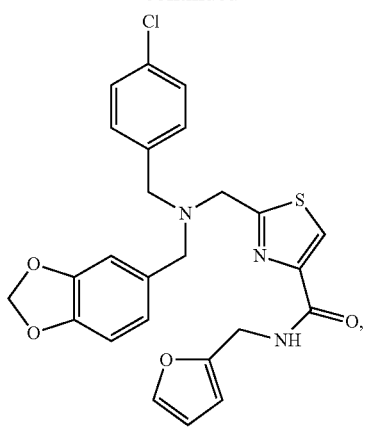
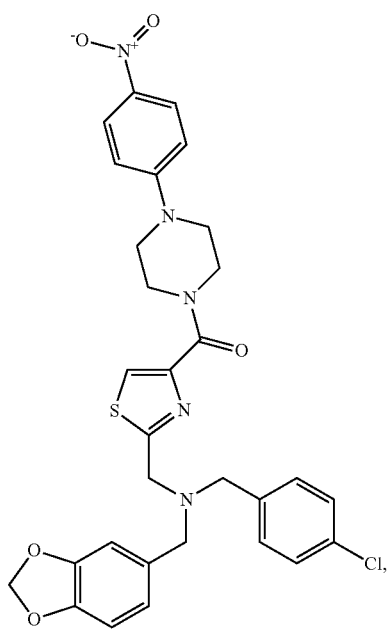
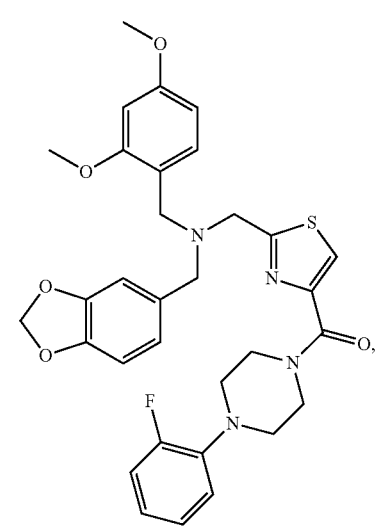

83
-continued
84
-continued
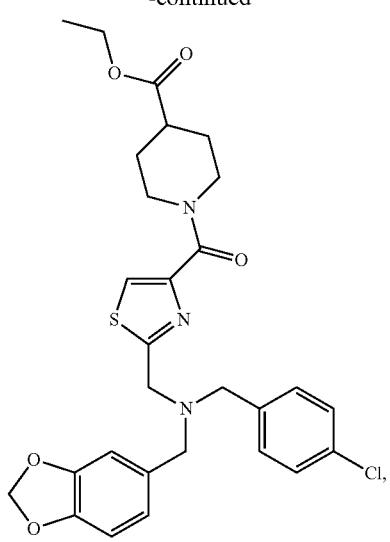
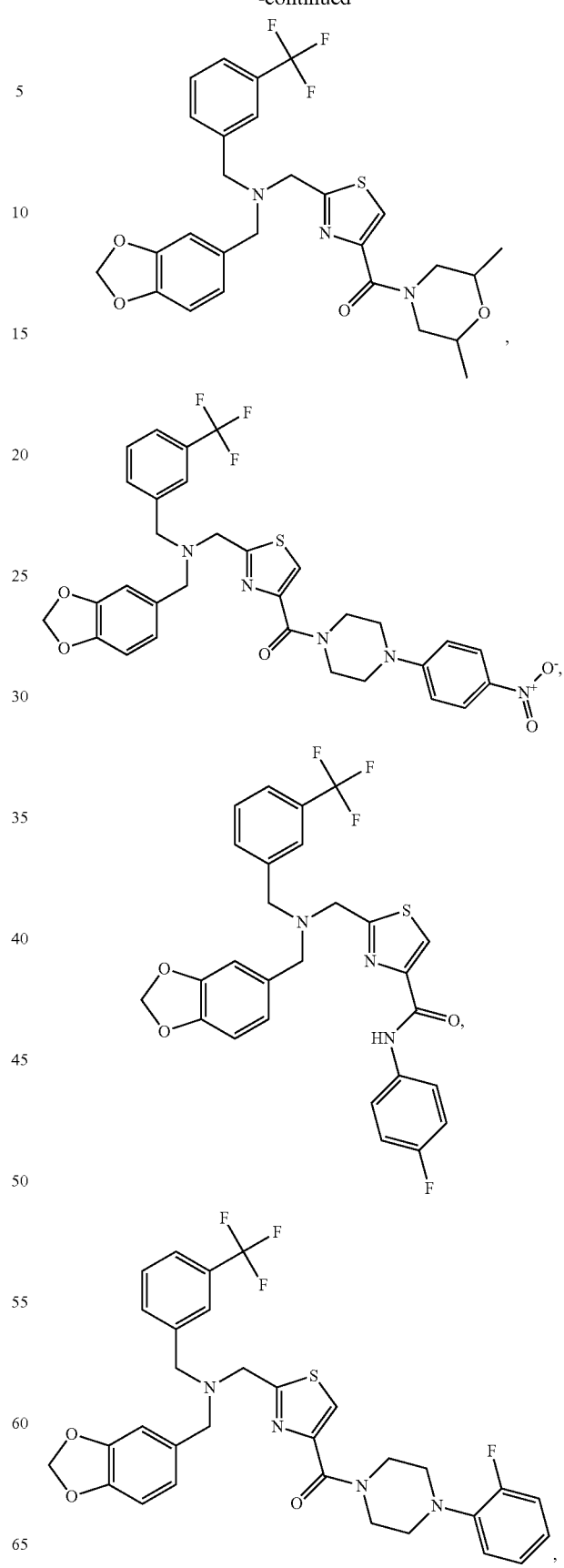

85
-continued
86
-continued
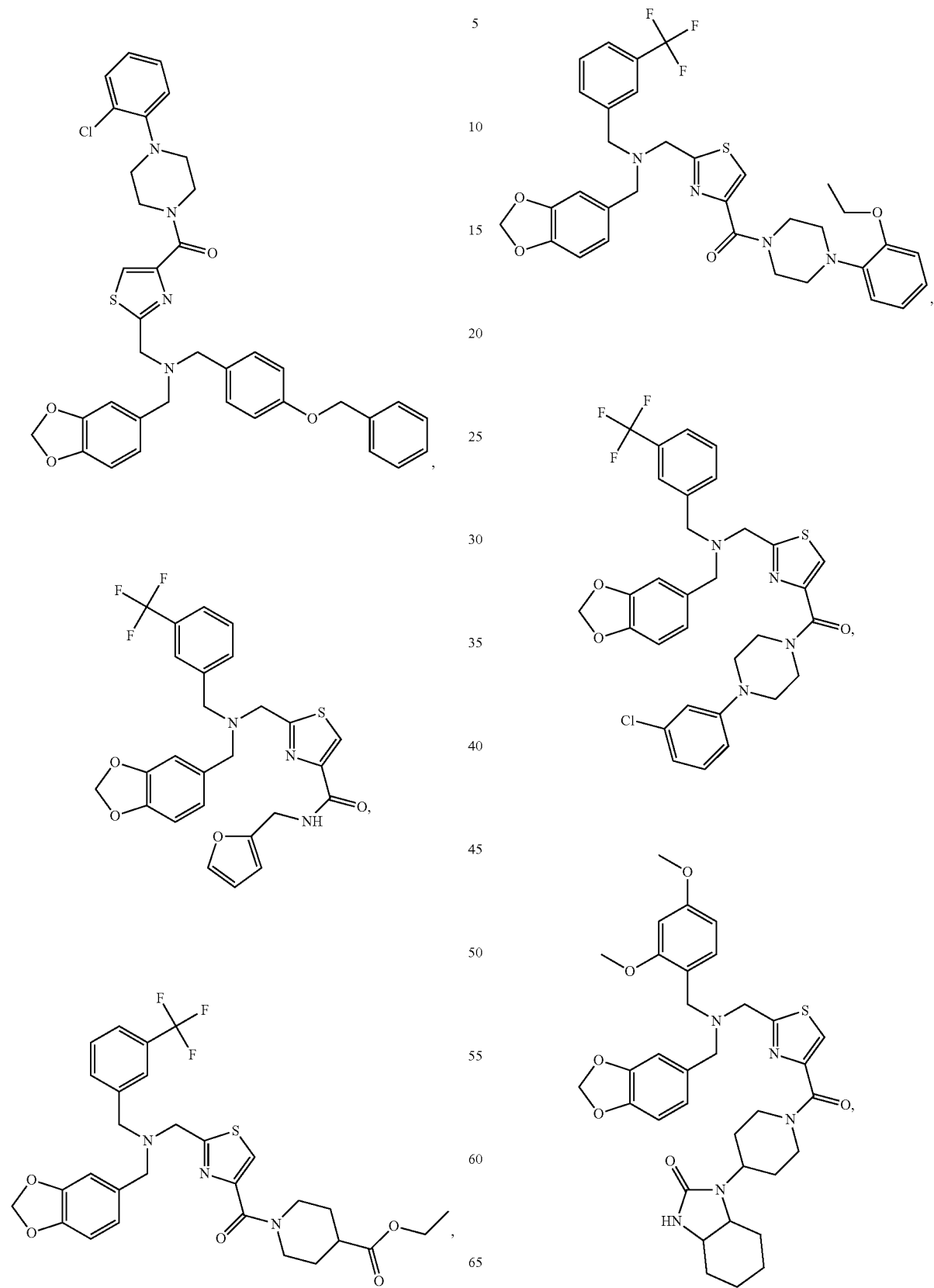

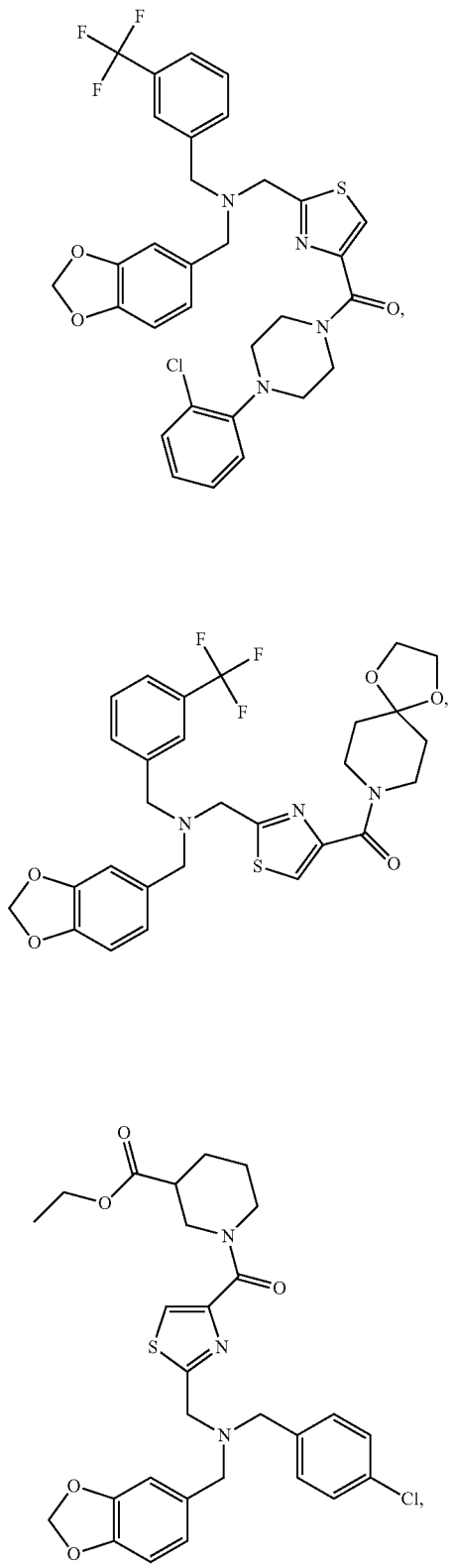
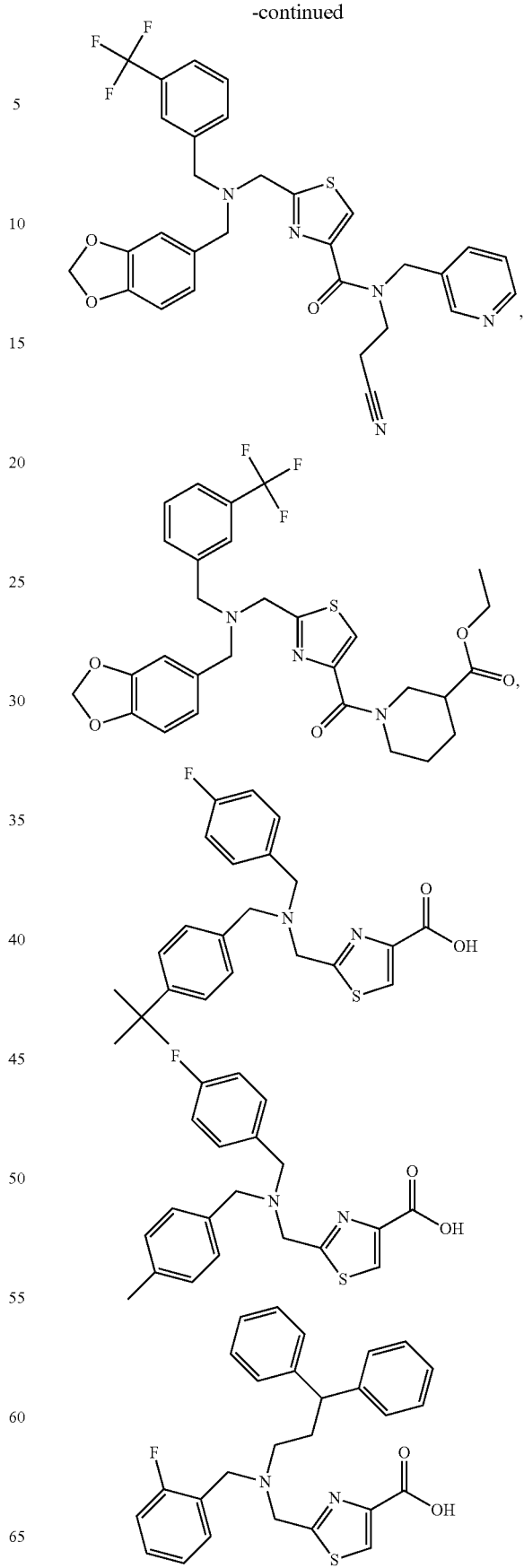

89
-continued
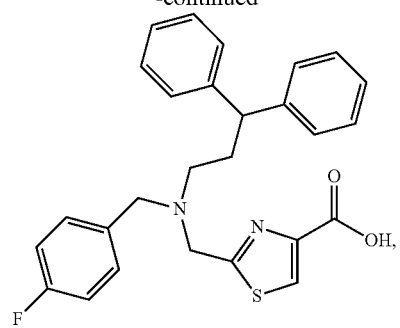
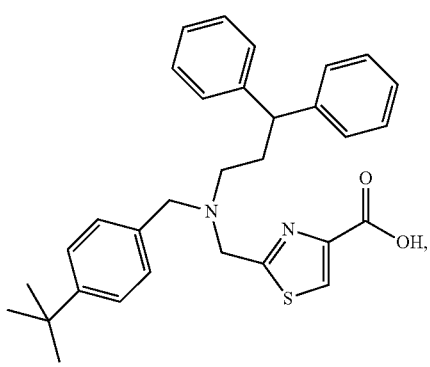
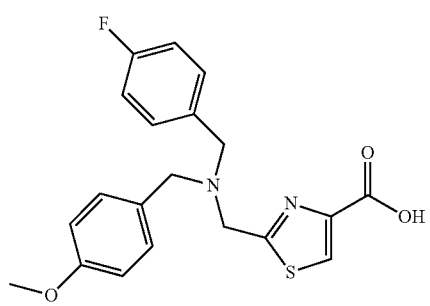
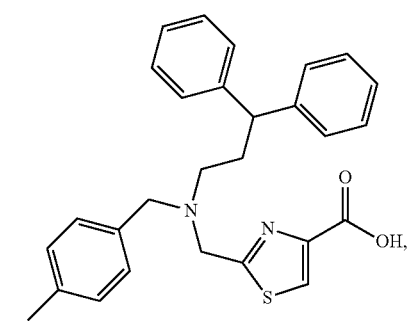
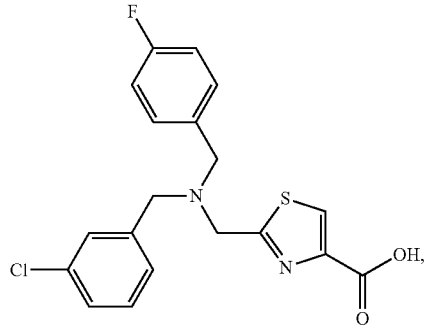
90
-continued
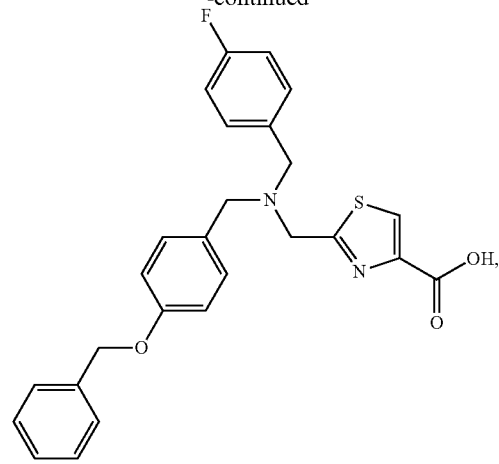
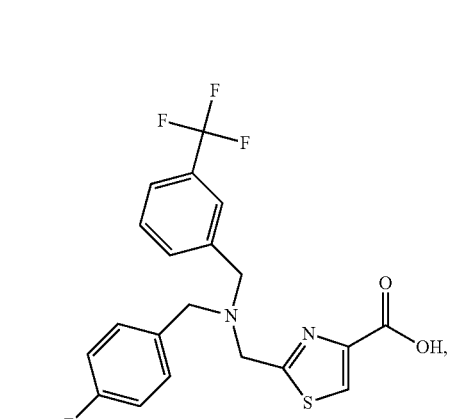
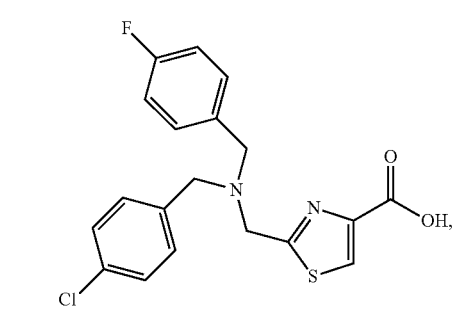
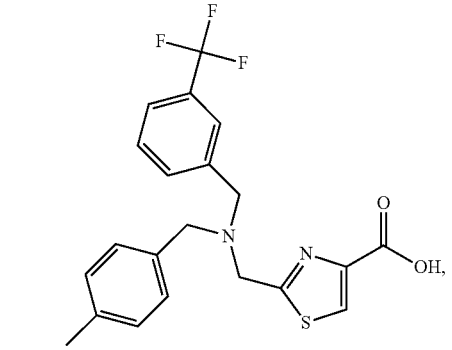

-continued
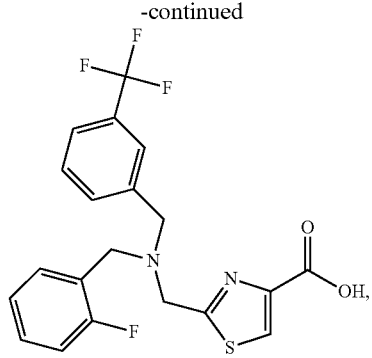
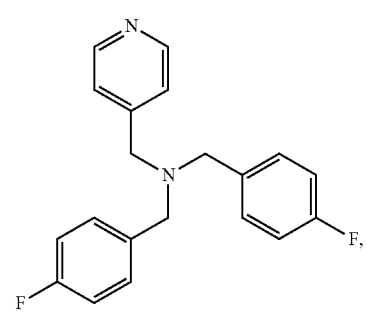
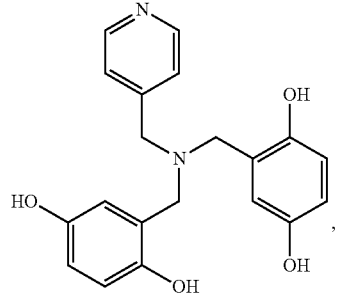
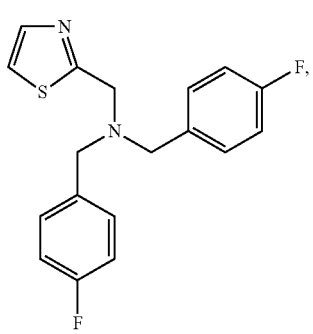
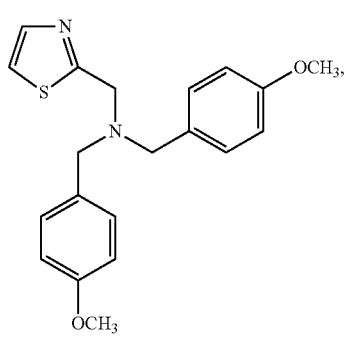
-continued
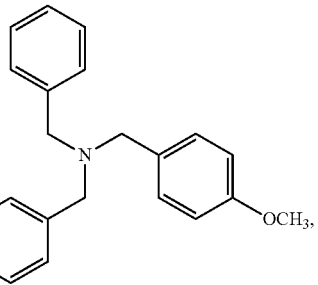
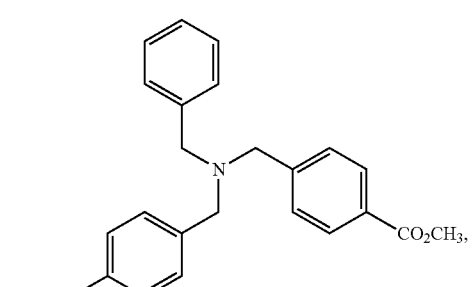
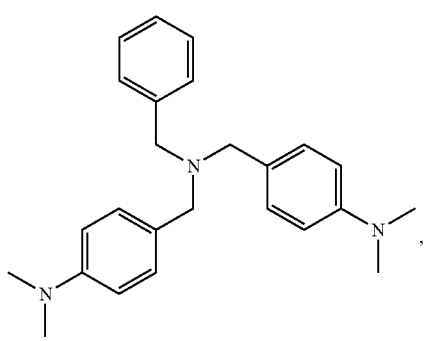
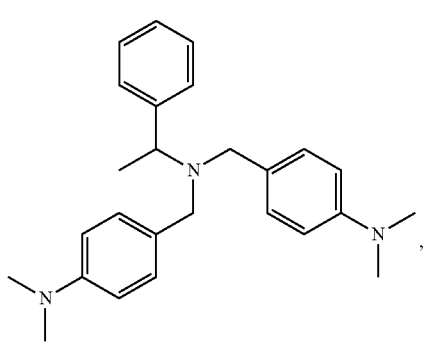
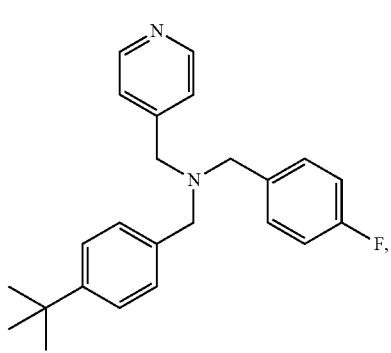

93
-continued
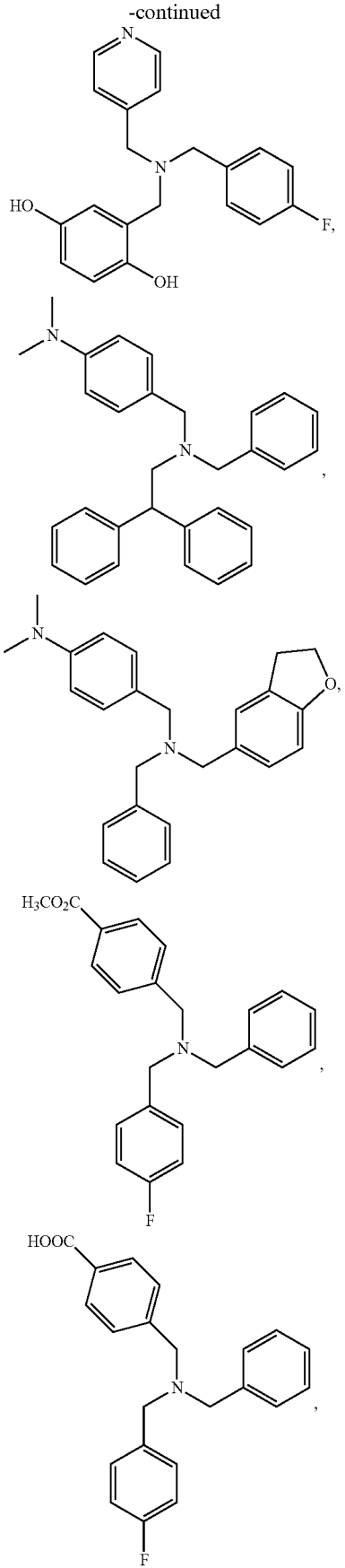
94
-continued
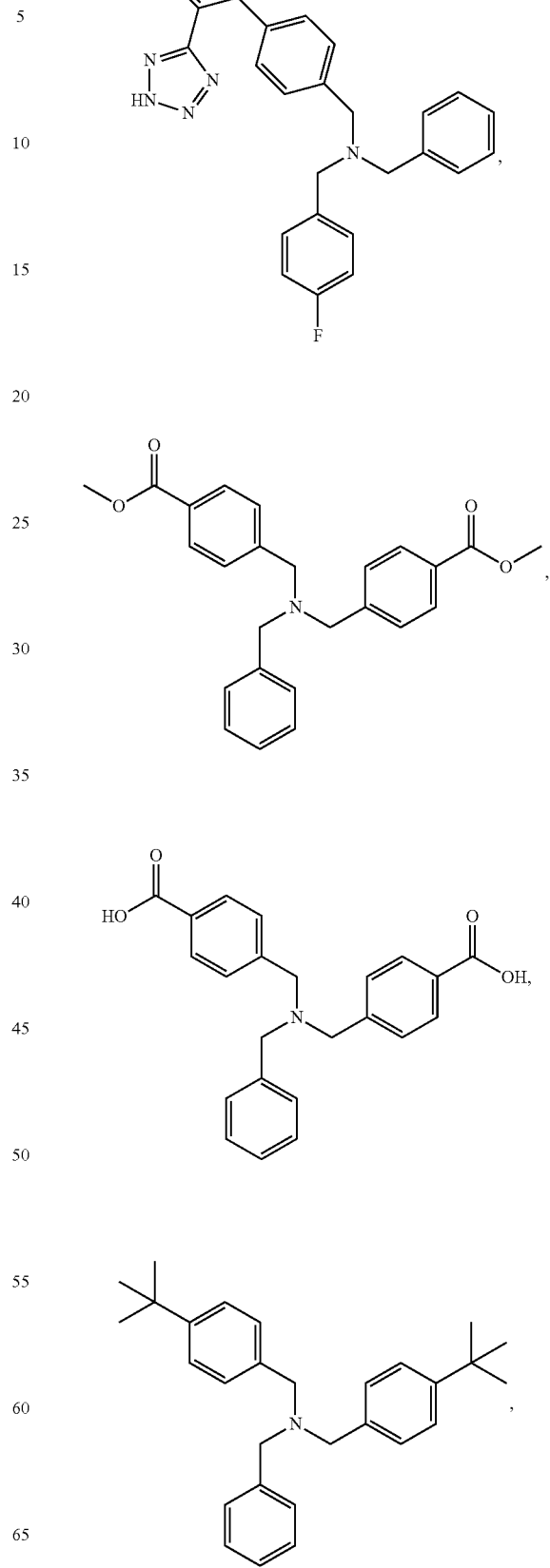

95
-continued
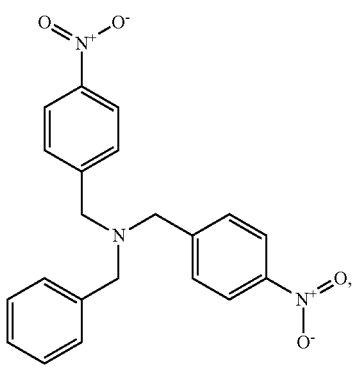
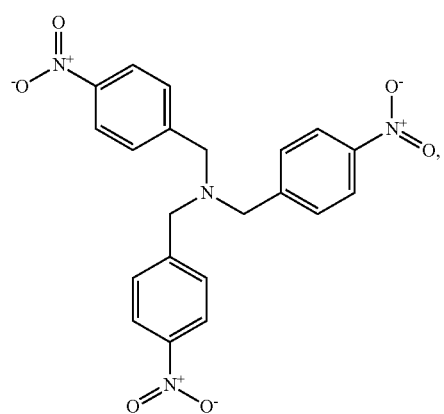
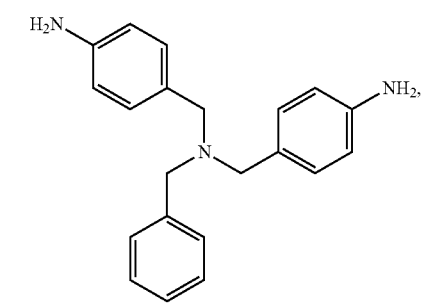
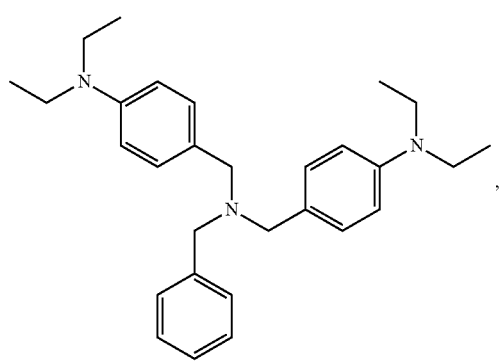
96
-continued
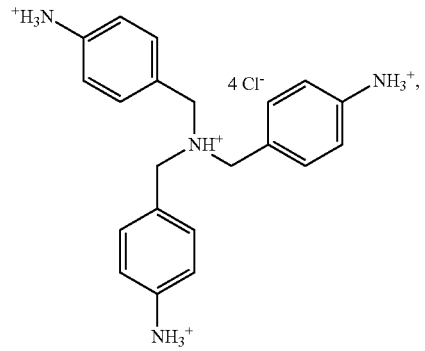
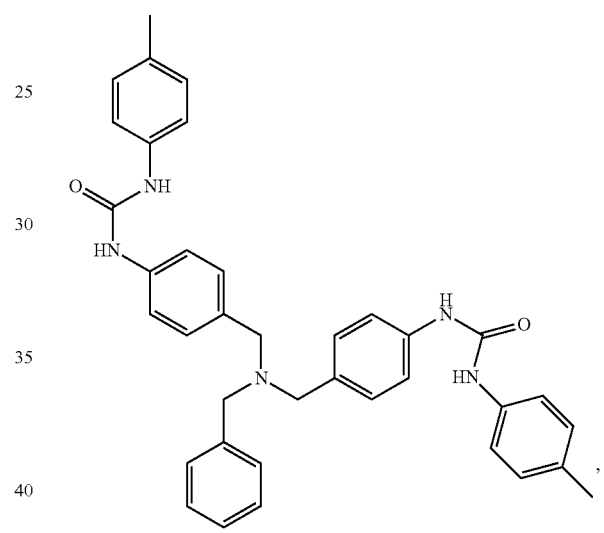
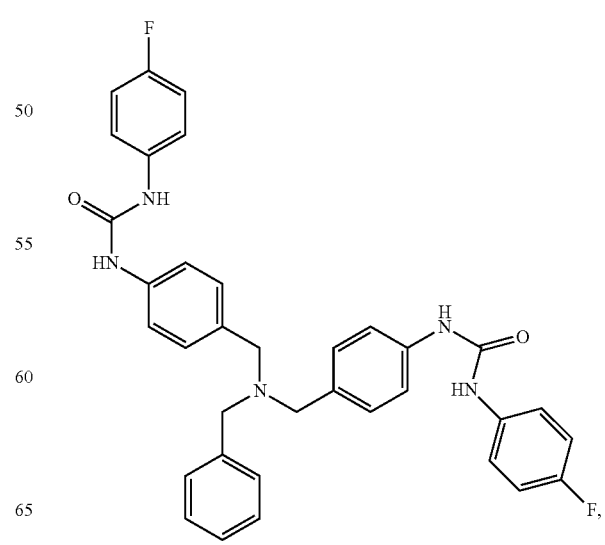

97
-continued
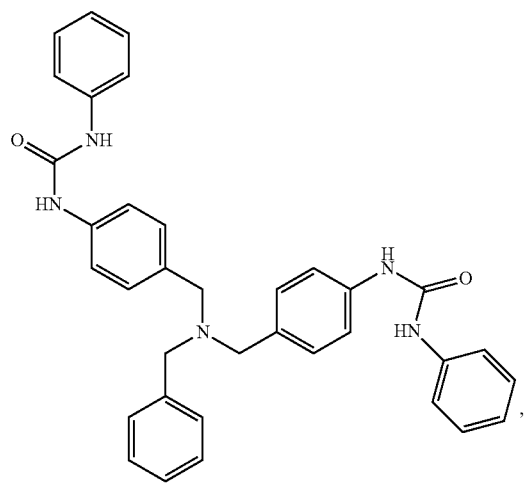
98
-continued
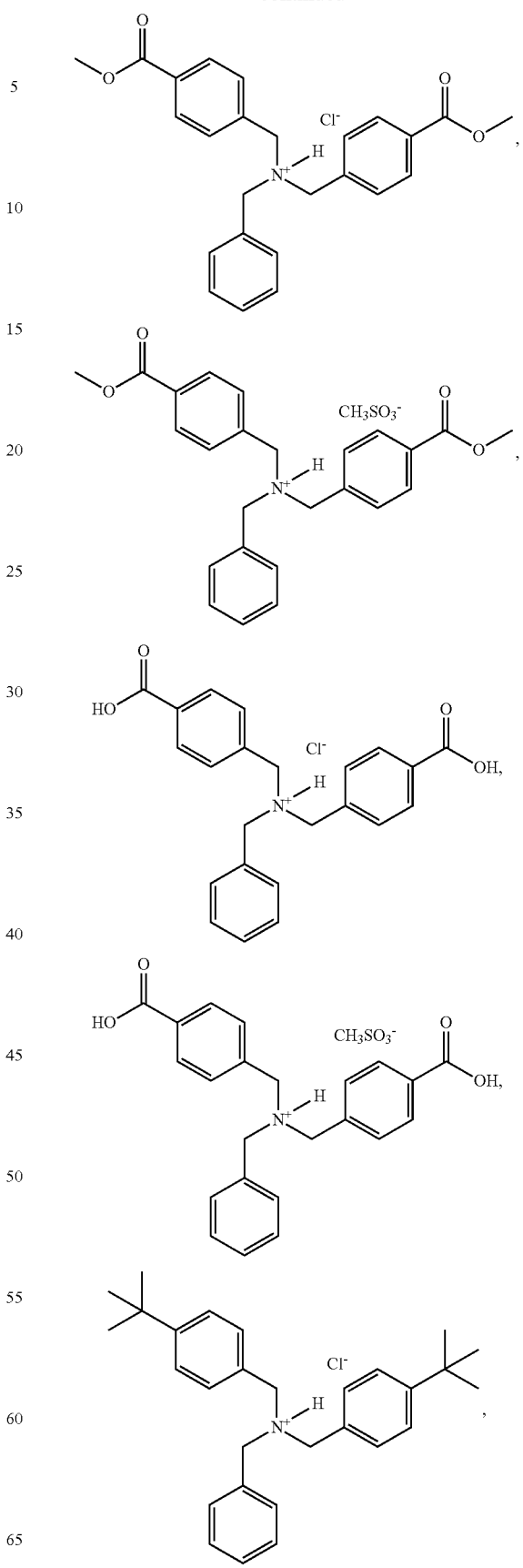

99
-continued
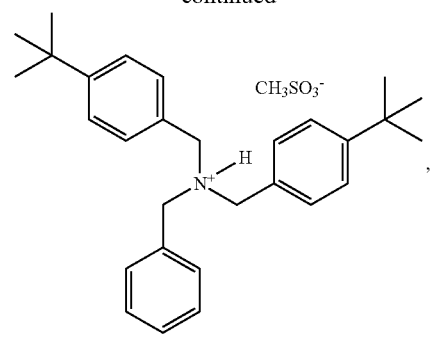
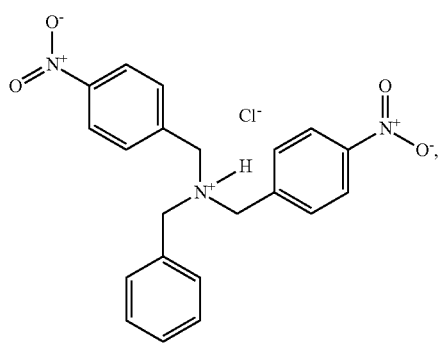
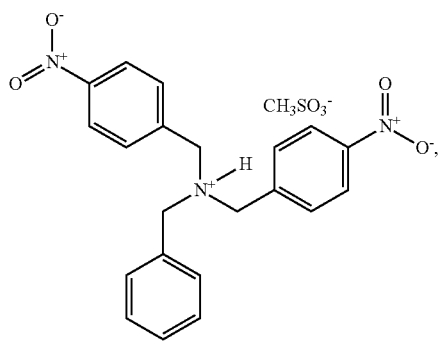
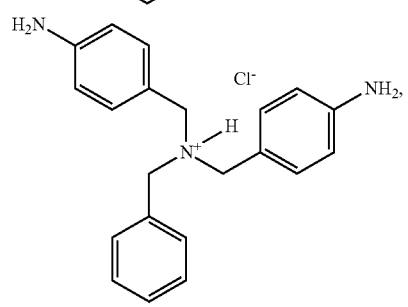
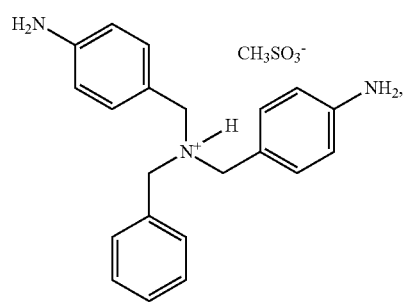
100
-continued
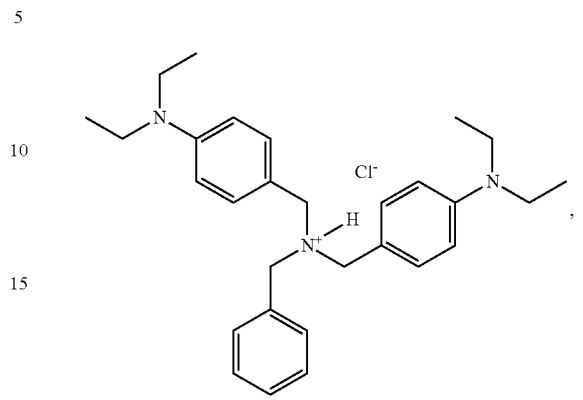
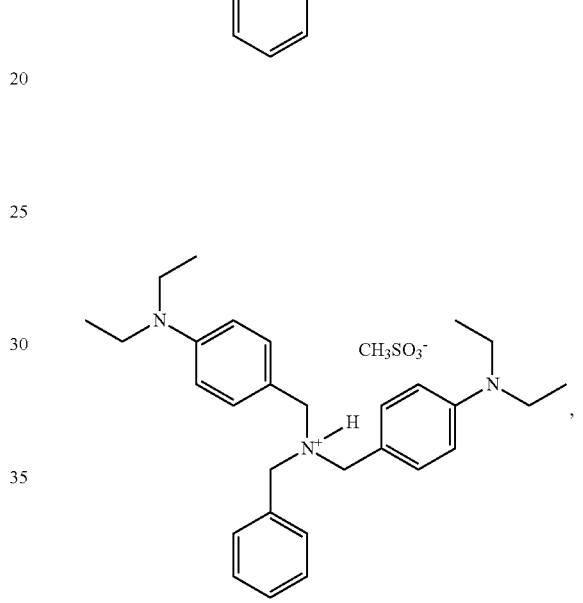
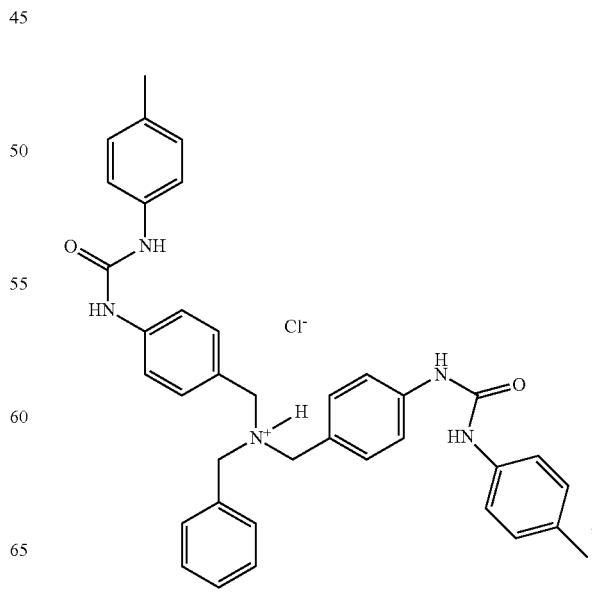

101
-continued
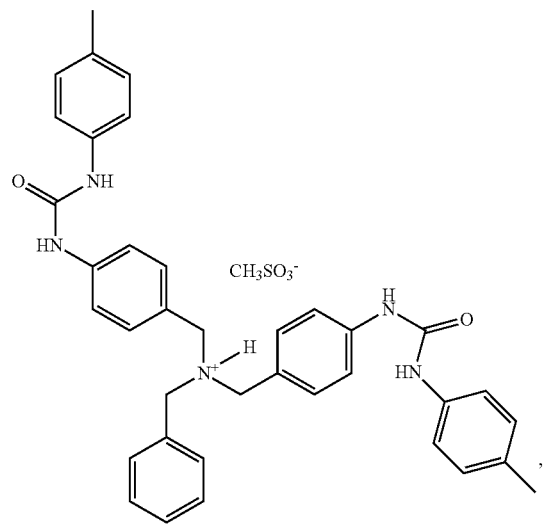
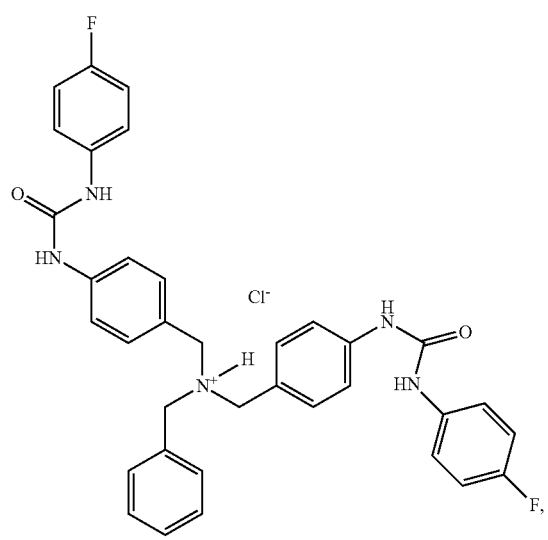
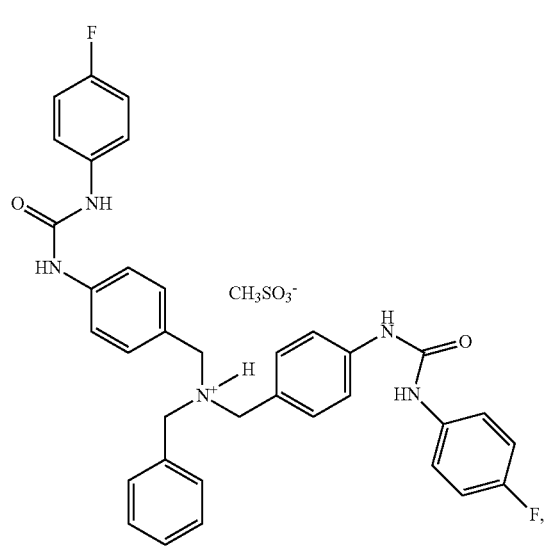
102
-continued
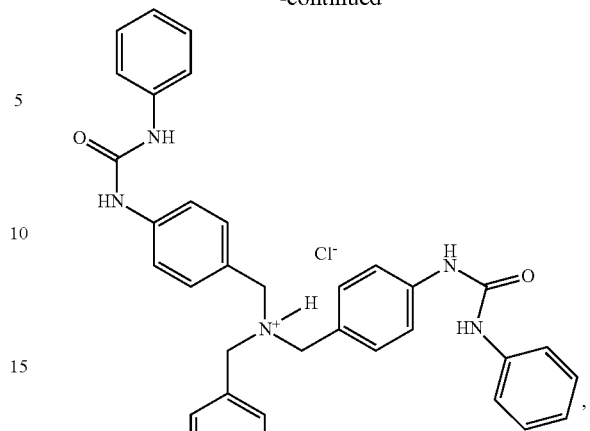
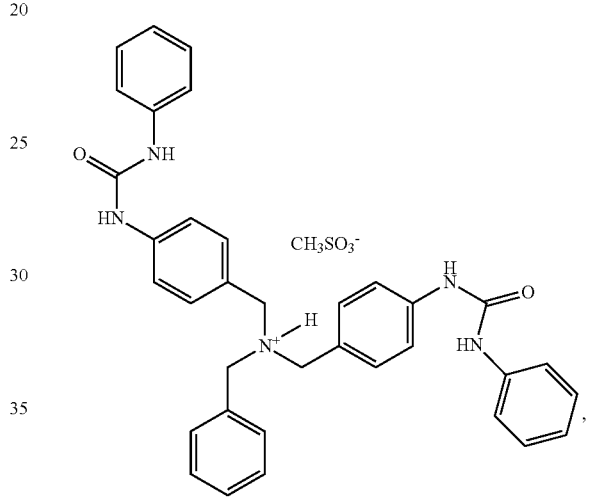
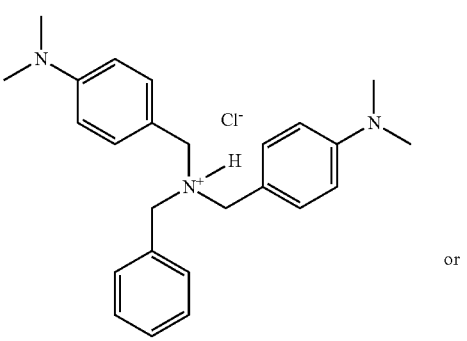
or
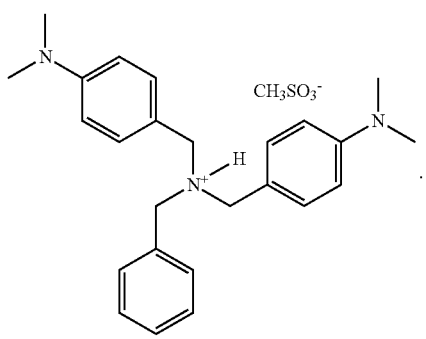

Particularly preferred compounds according to formula (I) have the following structure:
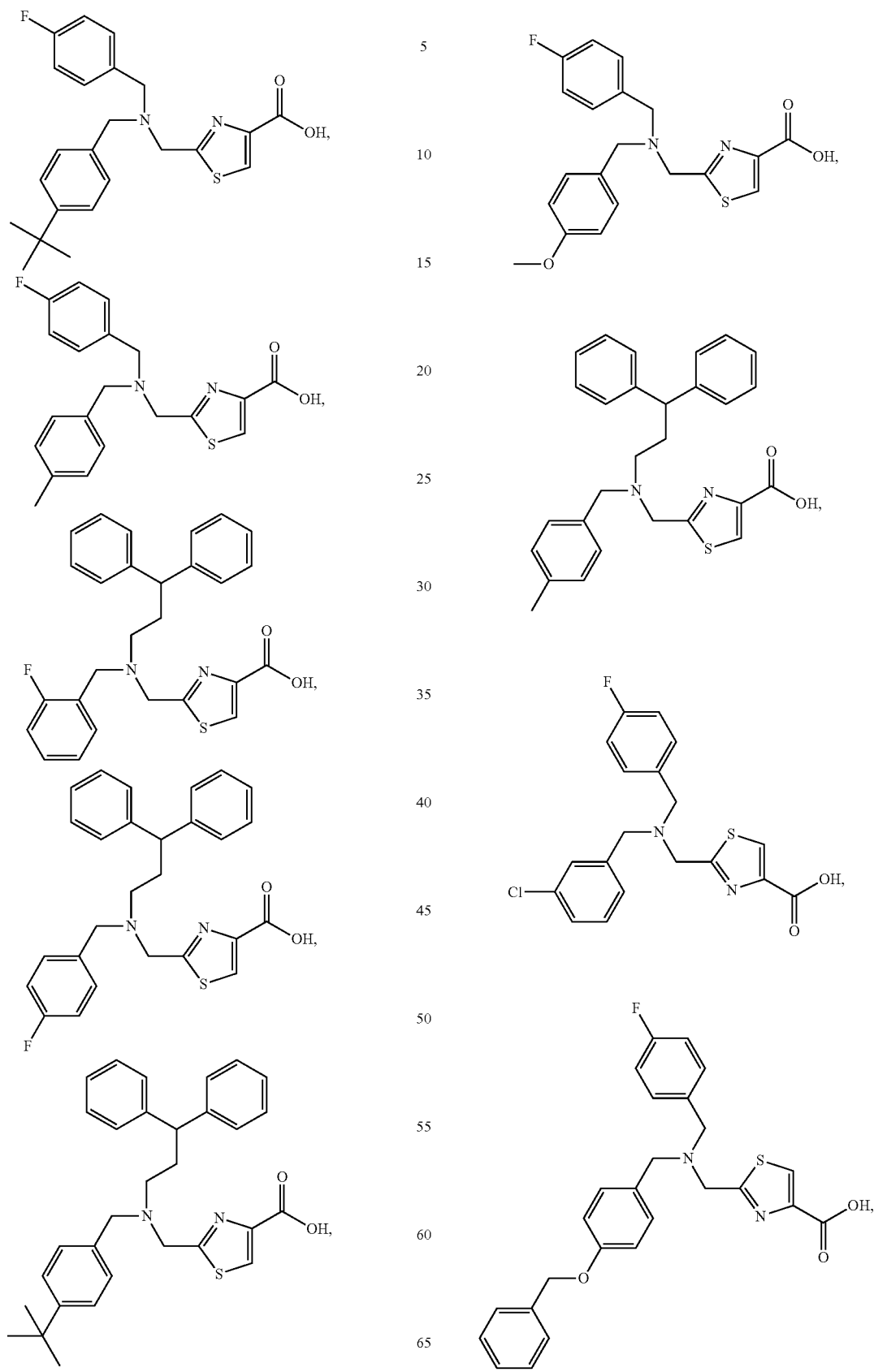

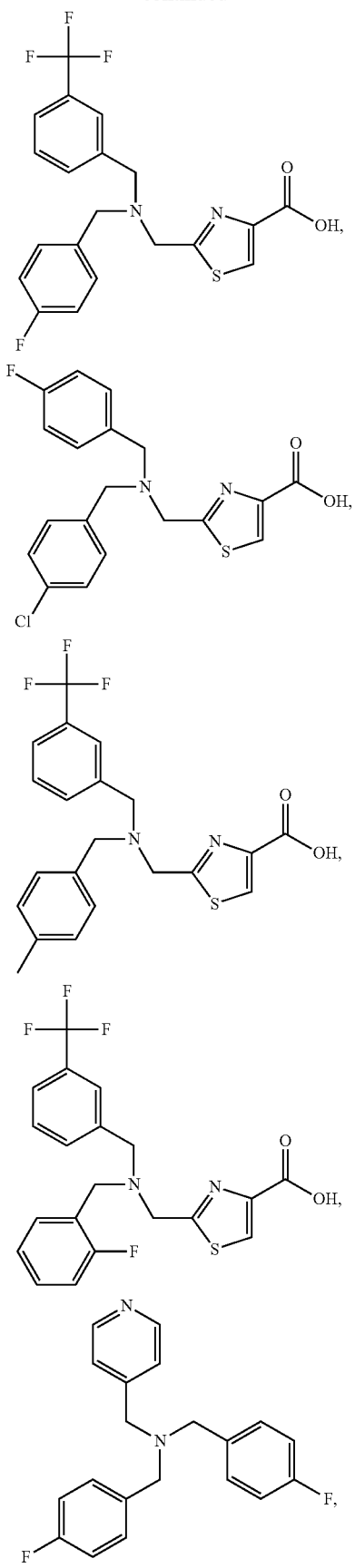
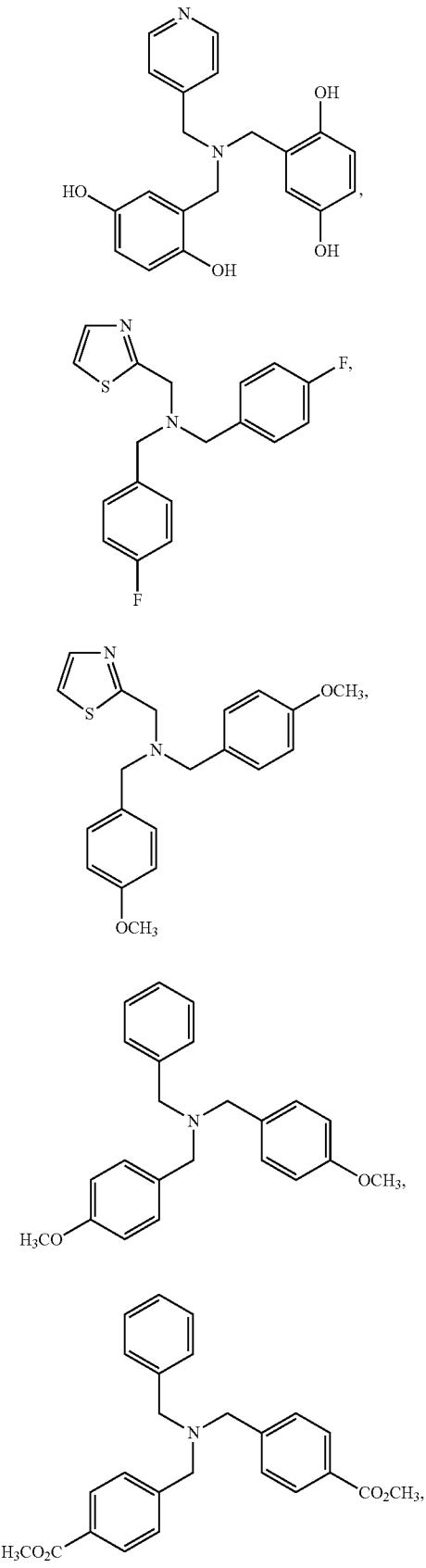

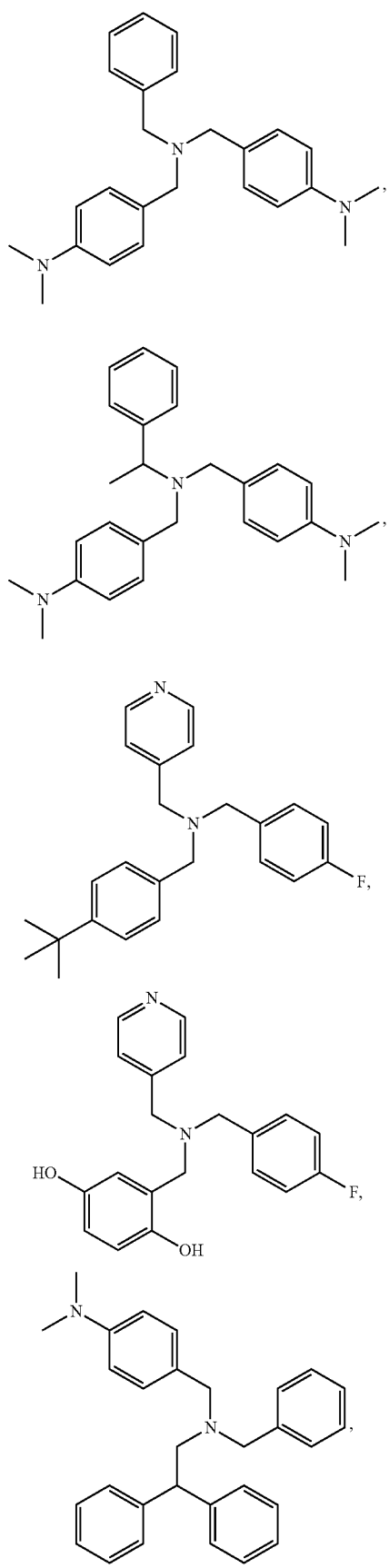
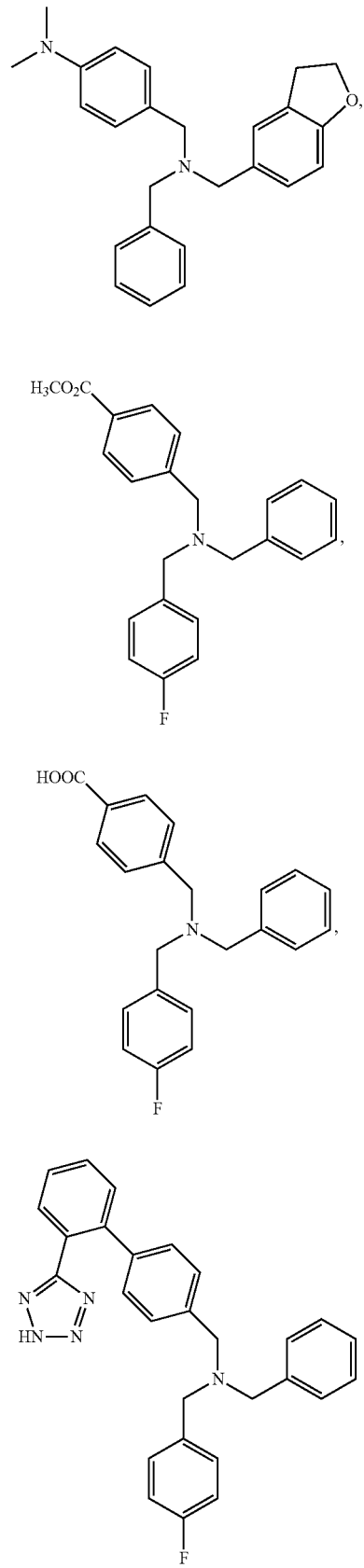 [SMILES: CN(C)c1ccc(CN(Cc2ccccc2)Cc2ccc3c(c2)CCO3)cc1 ; COC(=O)c1ccc(CN(Cc2ccccc2)Cc2ccc(F)cc2)cc1 ; O=C(O)c1ccc(CN(Cc2ccccc2)Cc2ccc(F)cc2)cc1 ; Fc1ccc(CN(Cc2ccccc2)Cc2ccc(-c3ccccc3-c3nn[nH]n3)cc2)cc1]

109
-continued
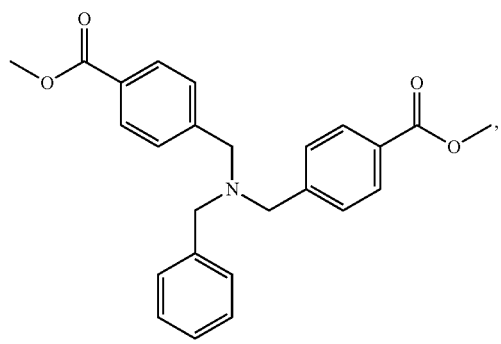
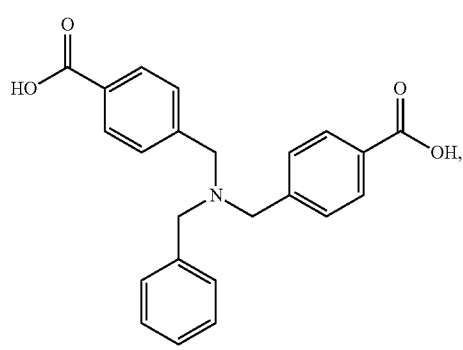
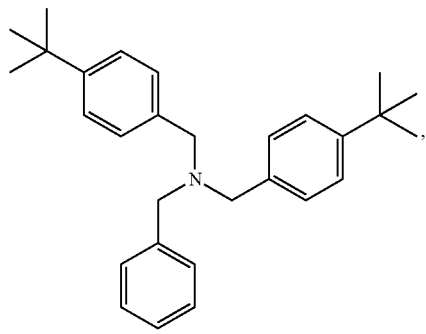
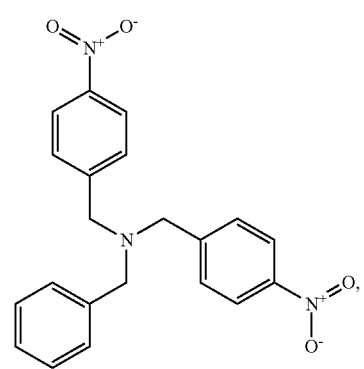
110
-continued
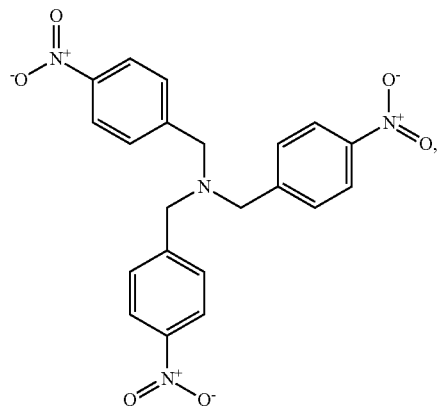
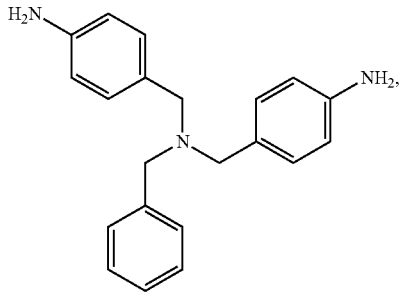
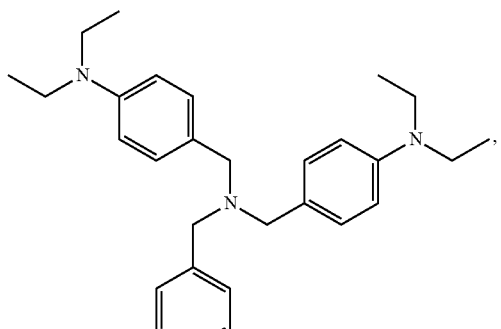
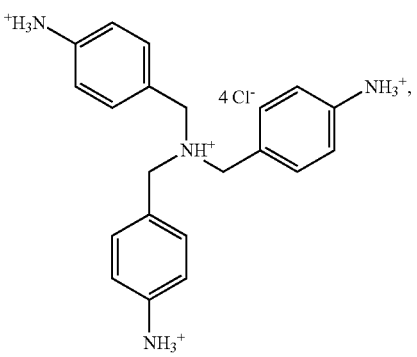

111
-continued
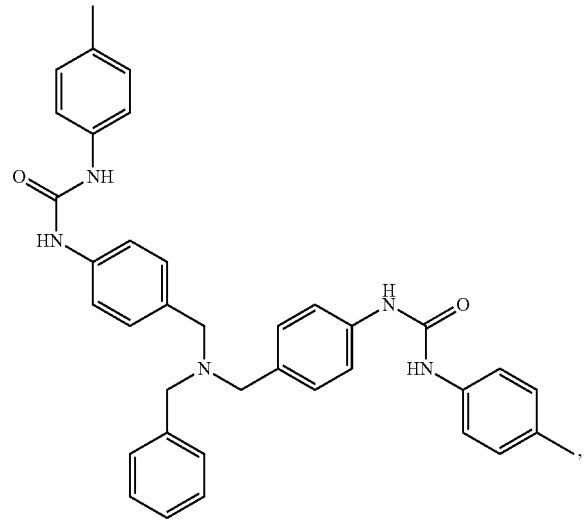
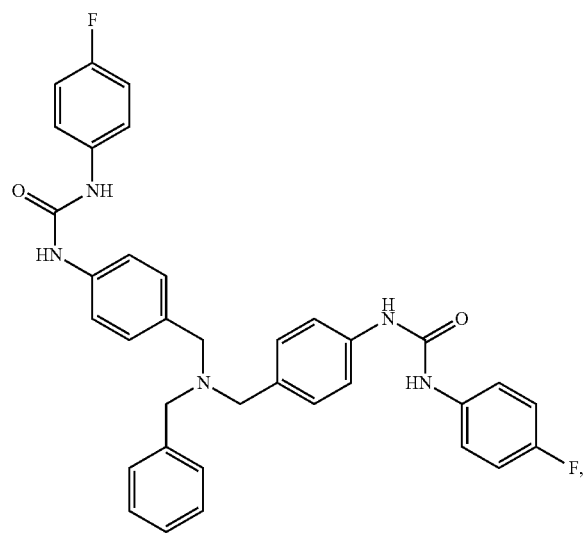
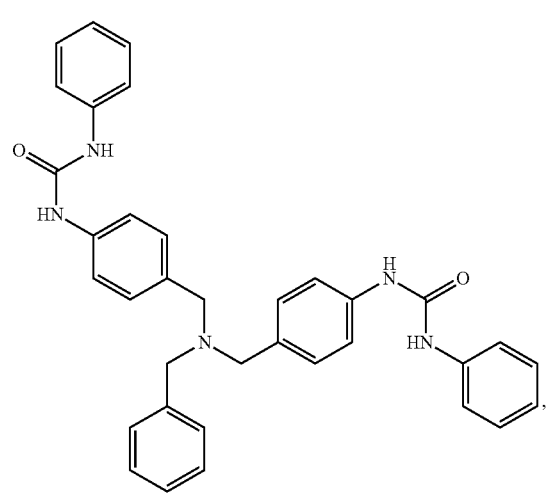
112
-continued
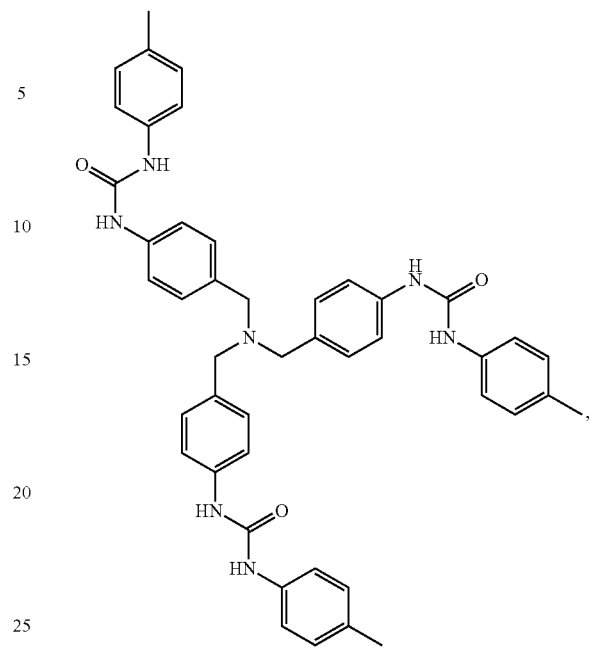
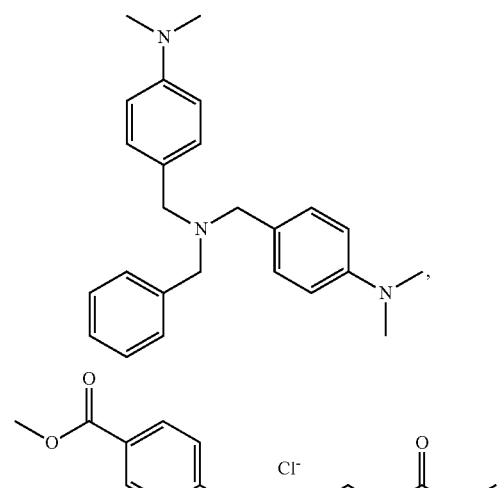
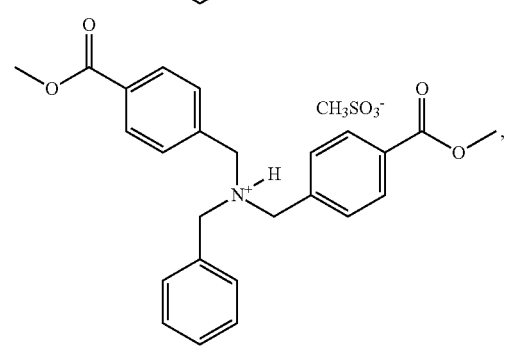

113
-continued
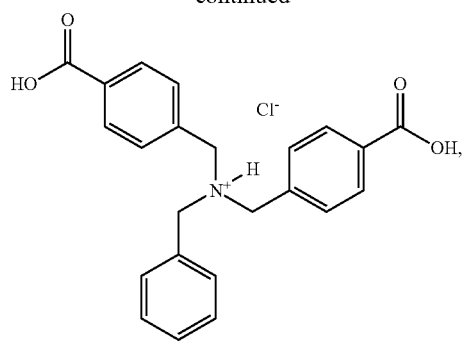
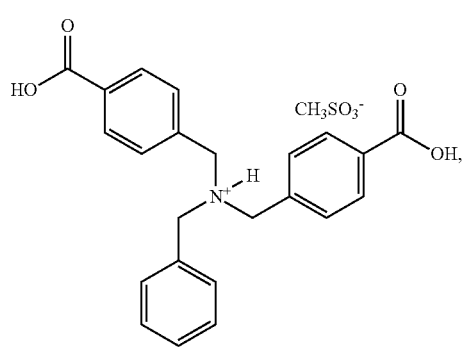
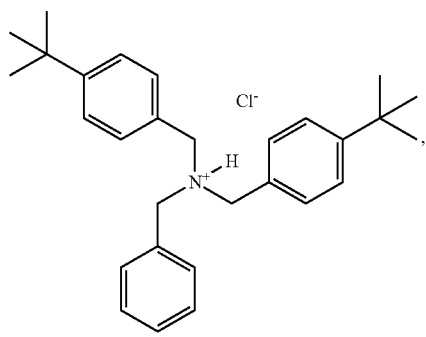
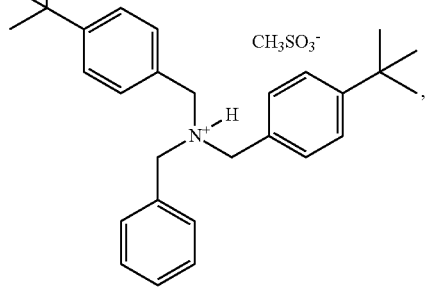
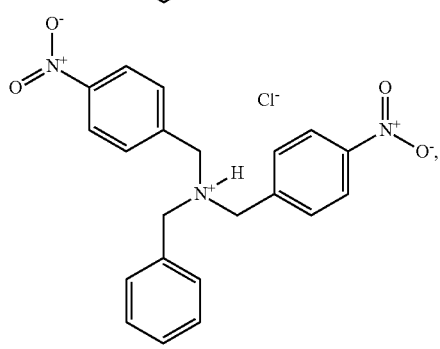
114
-continued
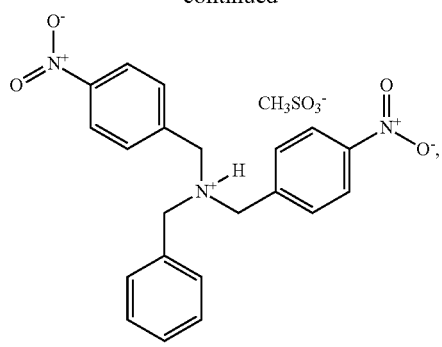
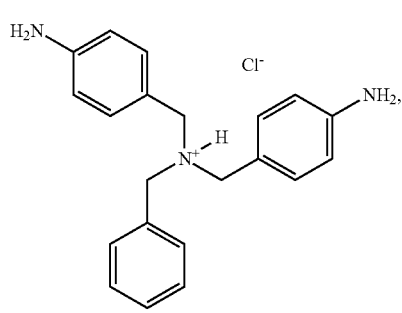
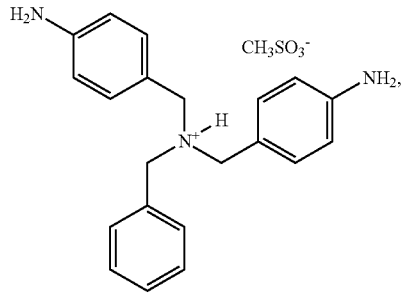
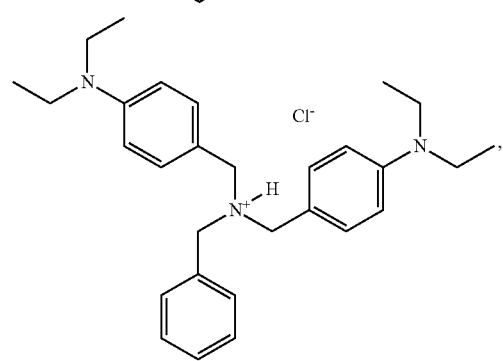
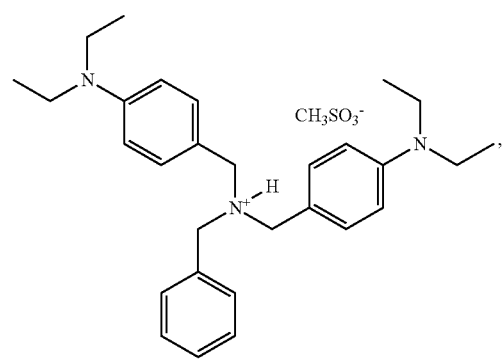

115
-continued
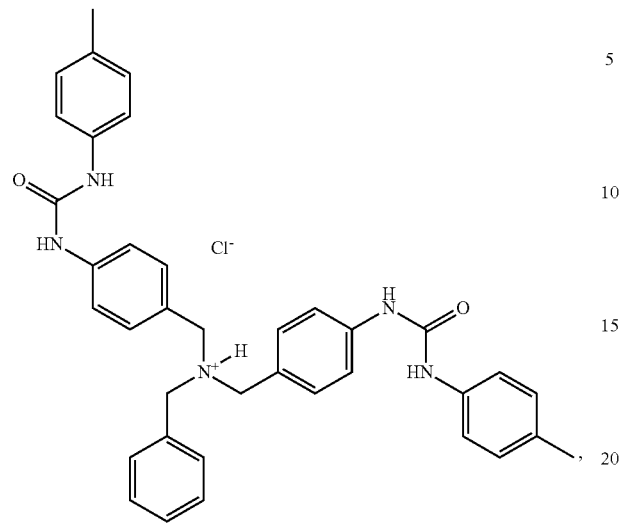
116
-continued
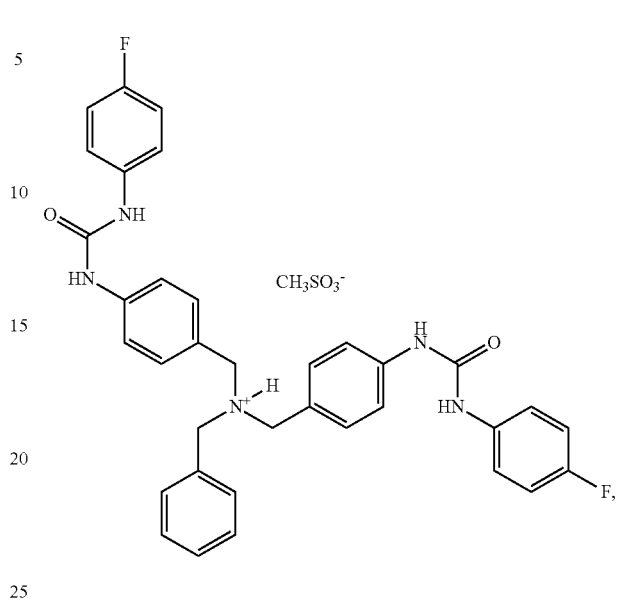
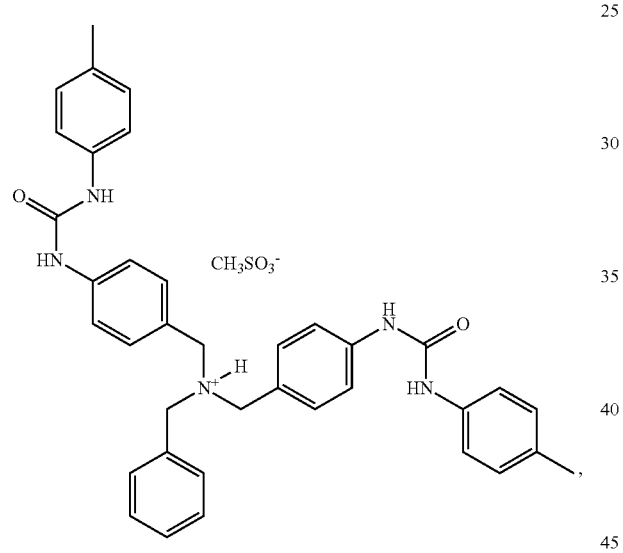
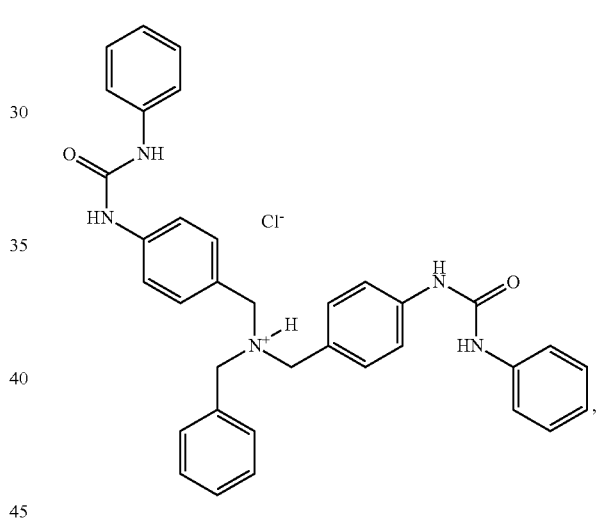
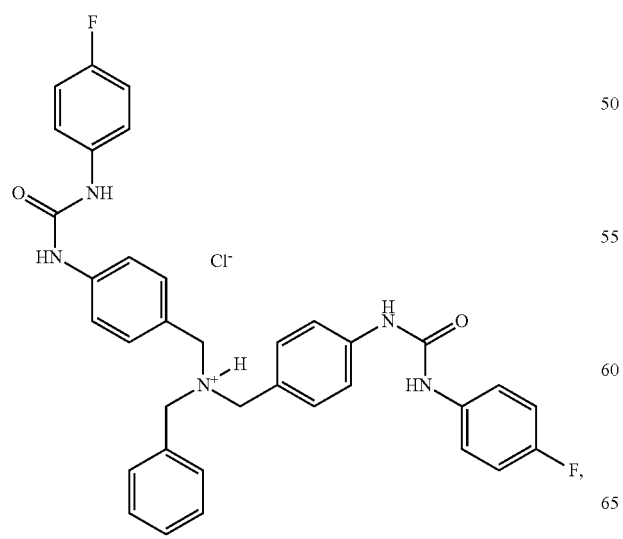
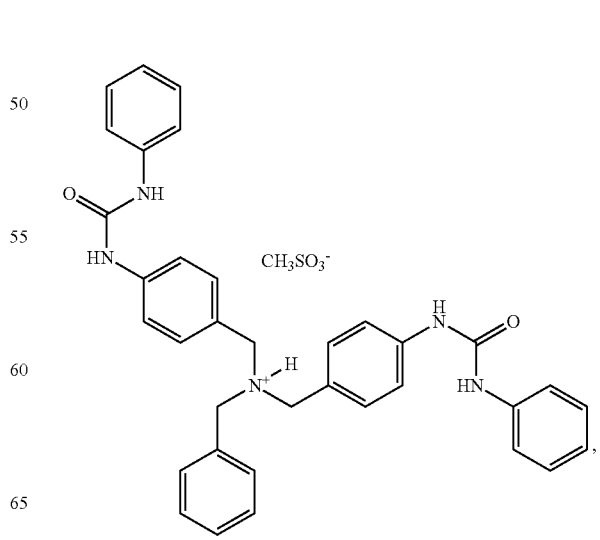

117
-continued
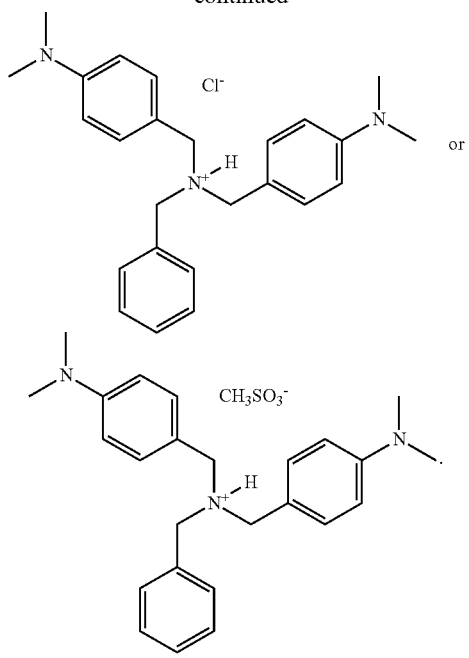
The invention relates to compounds of formula (I) for use in therapy. However, some of the compounds themselves are previously unknown. The invention therefore also provides novel compounds that find use in therapy, for example compounds of formula (I) having the following structure:
118
-continued
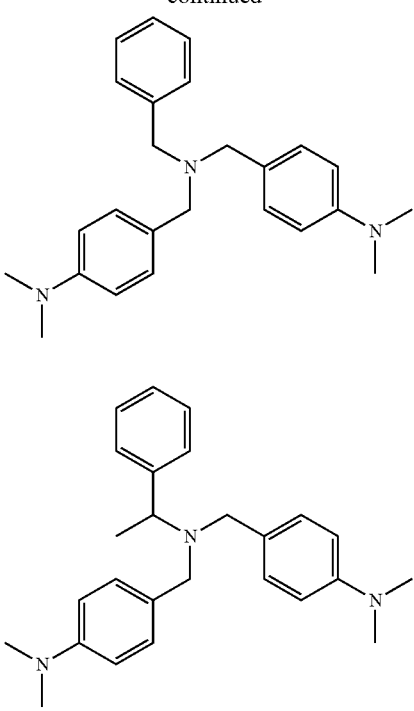
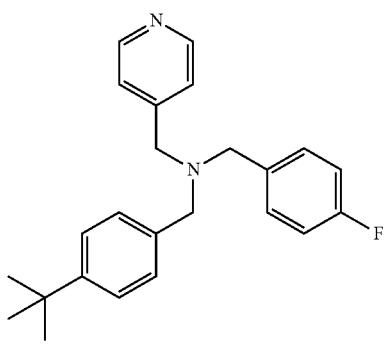
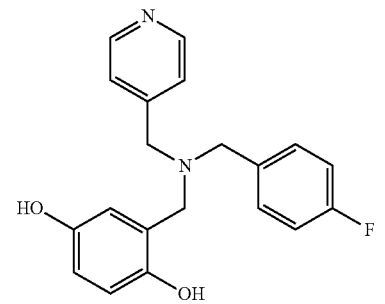
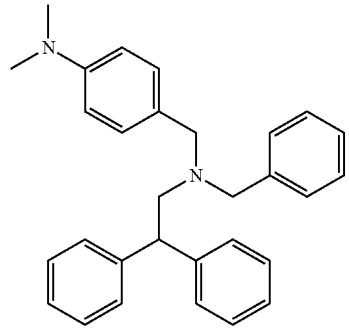

119
-continued
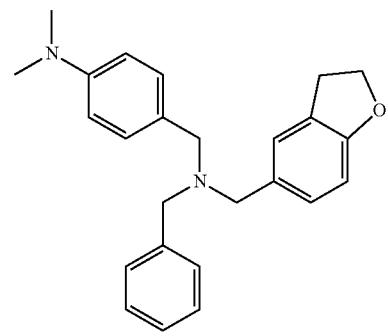
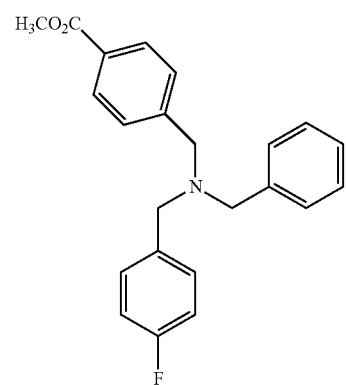
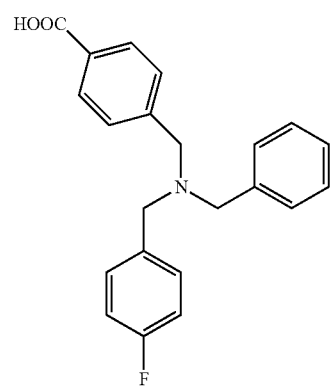
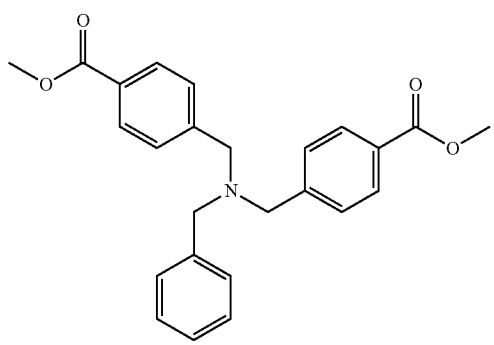
120
-continued
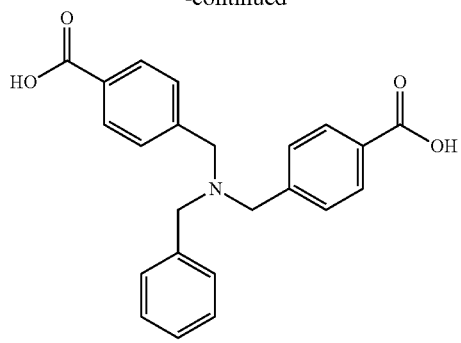
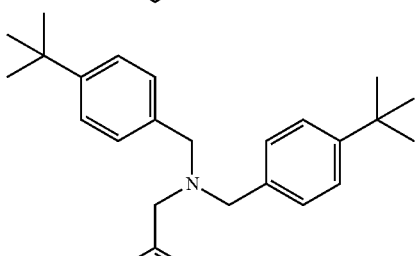
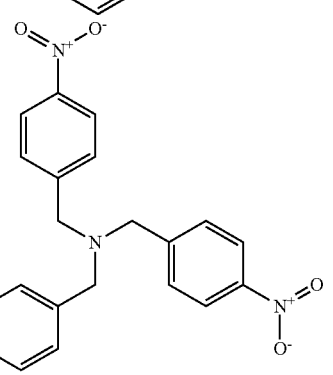
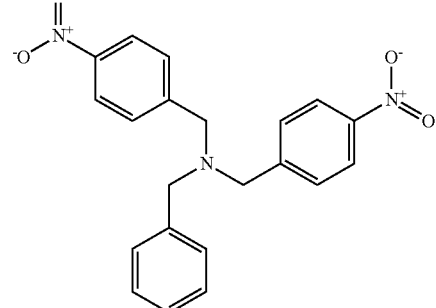
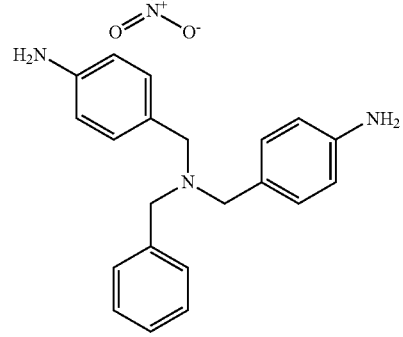

121
-continued
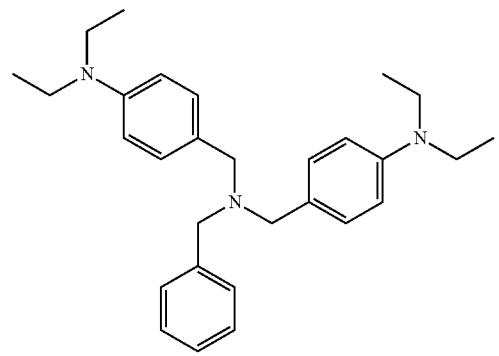
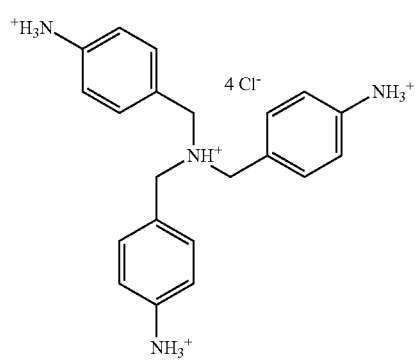
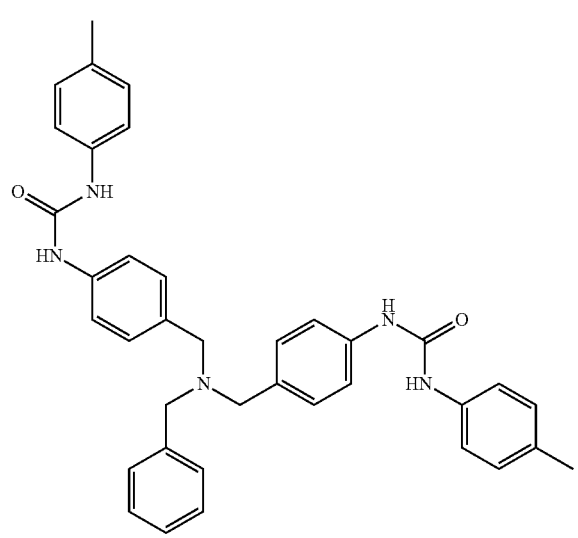
122
-continued
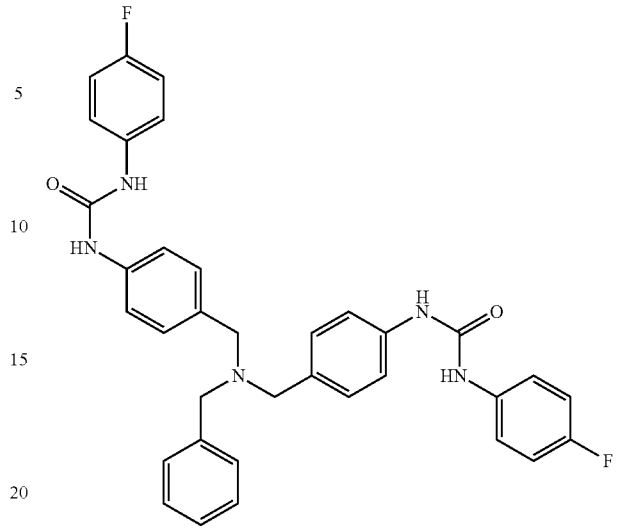
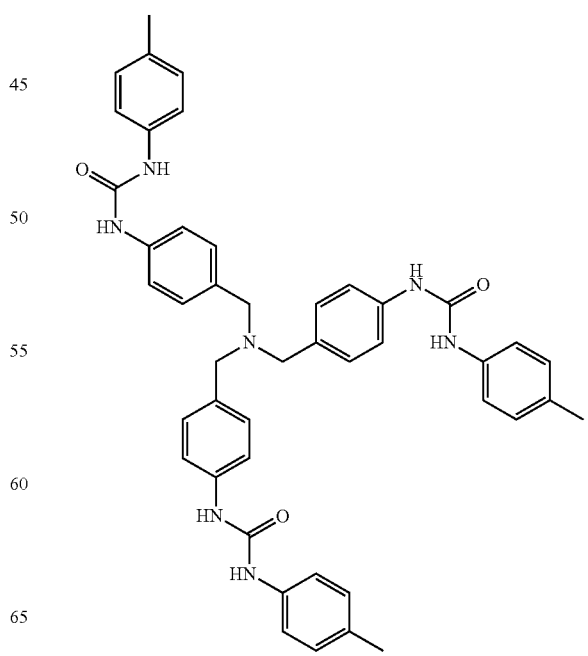

123
-continued
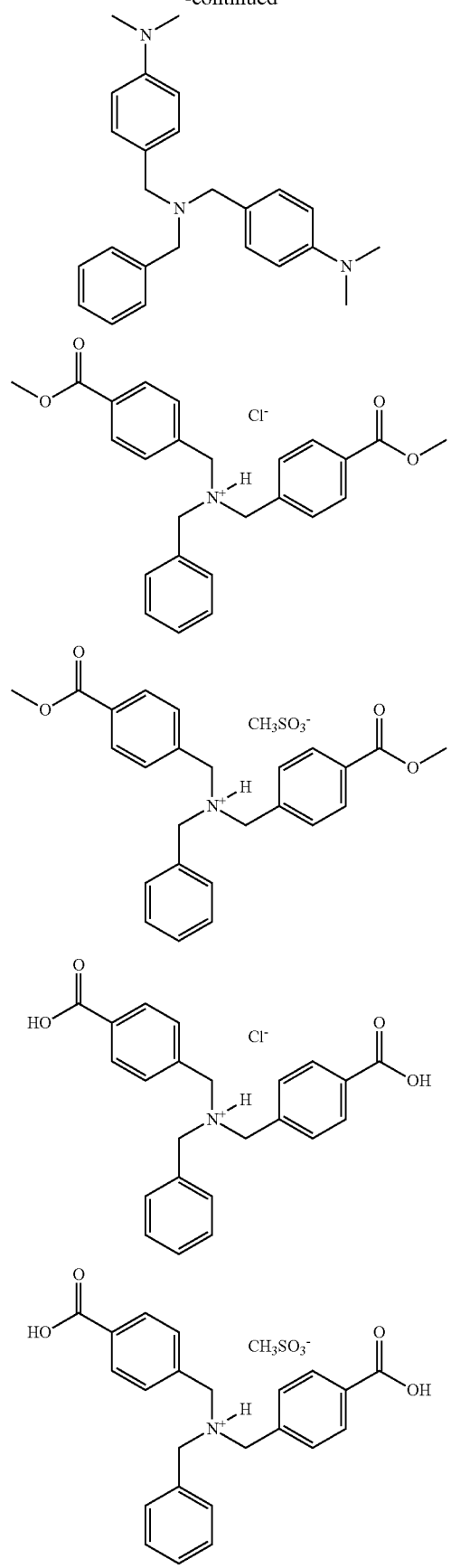
124
-continued
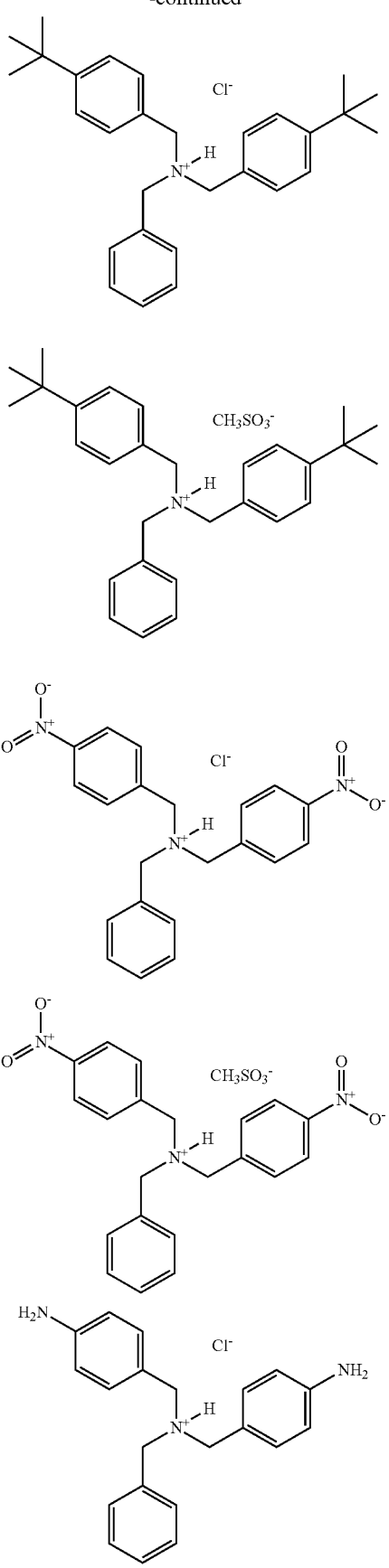

125
-continued
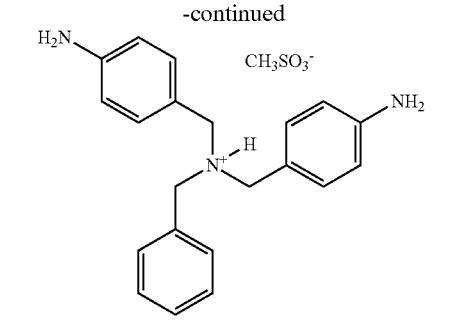
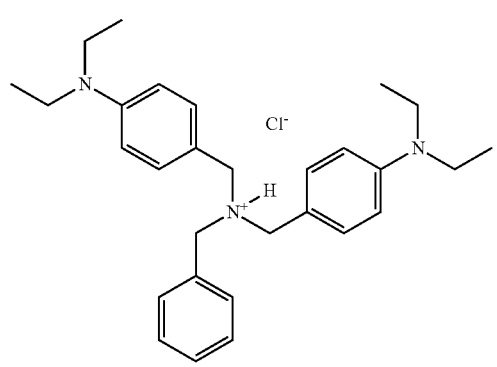
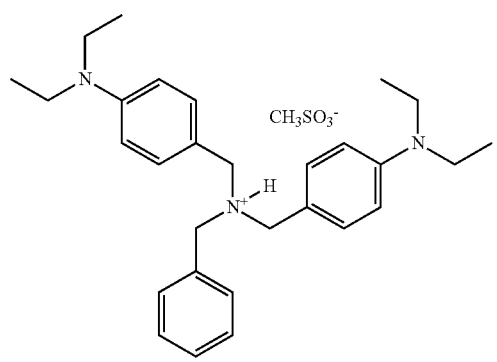
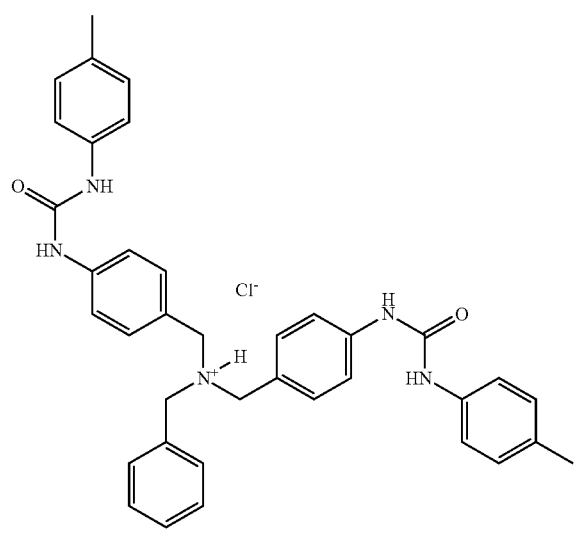
126
-continued
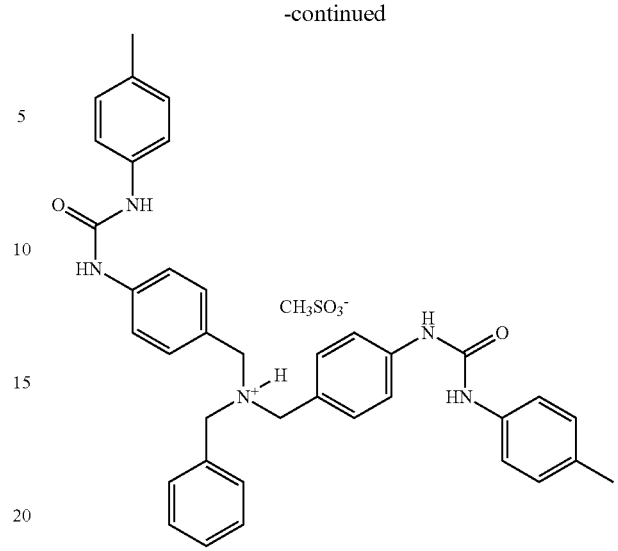
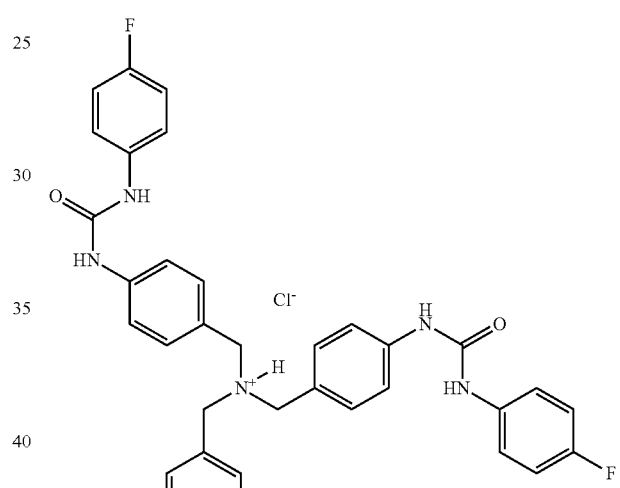
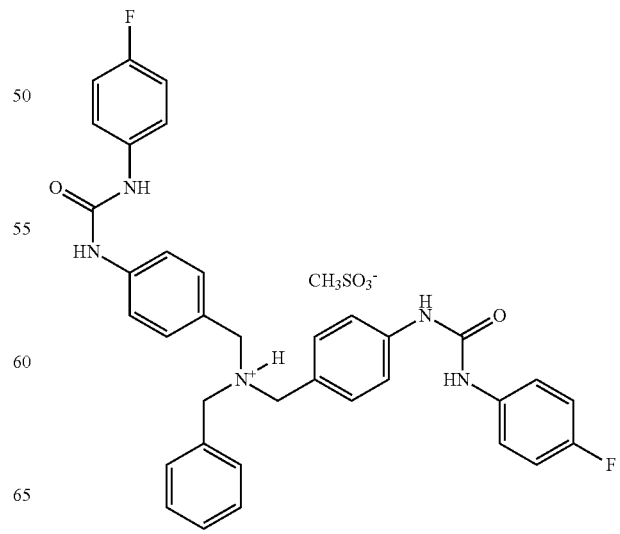

127
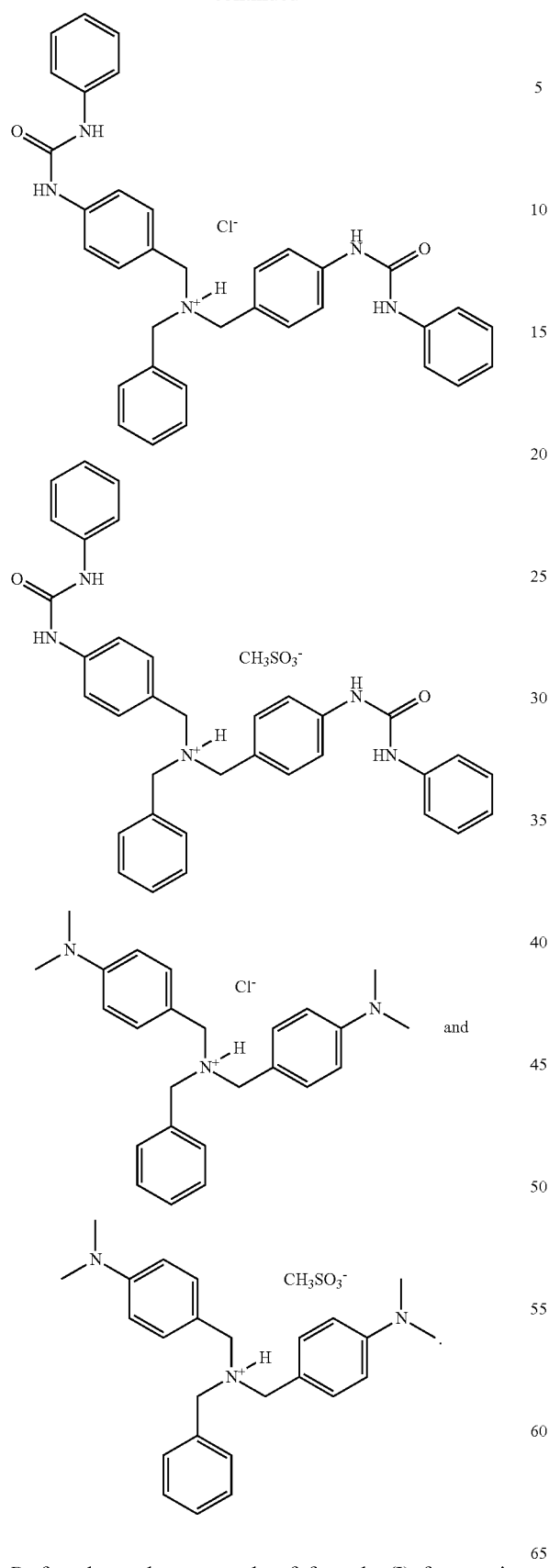
128
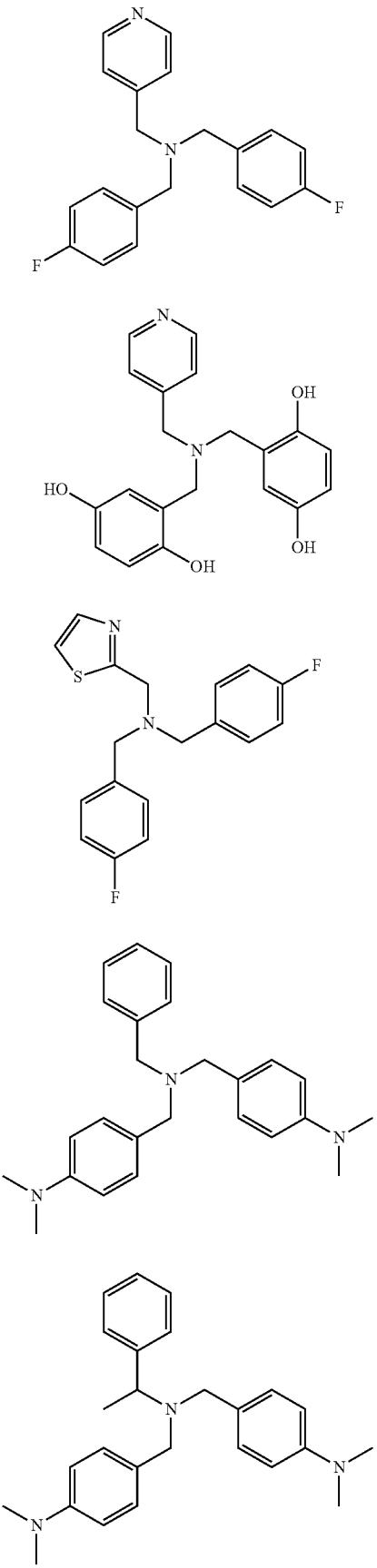
Preferred novel compounds of formula (I) for use in therapy are:

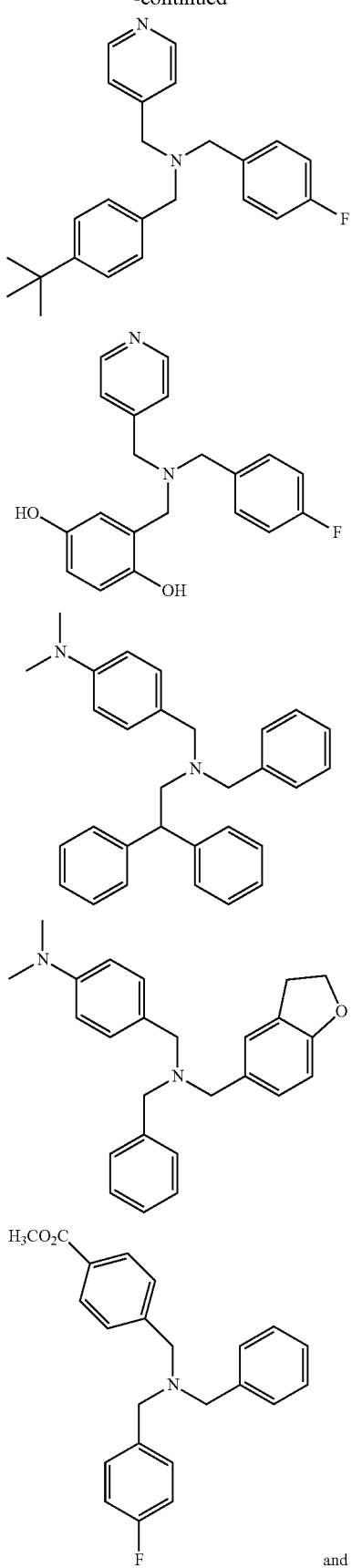

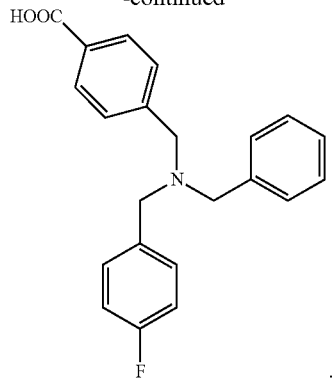

and

It is to be understood that where the preferred embodiments mentioned above are not mutually exclusive, they can be combined with one another. For example, the skilled person would understand that the above preferred embodiments in which $Ar^j$ (e.g. $Ar^1$) denotes phenyl optionally substituted with one or more R can be combined with the preferred embodiments in which R denotes independently denotes F, Cl, $CF_3$, $OR^1$, C(=O)Y, $C_1$-$C_4$-alkyl or $C_1$-$C_4$-alkyl-phenyl. The same holds true for the other non-mutually exclusive preferred embodiments mentioned above. The skilled person would understand which embodiments where mutually exclusive and would thus readily be able to determine the combinations of preferred embodiments that are contemplated by the present application.

As used herein, "alkyl" or "alkylene" is intended to include both branched and straight-chain saturated aliphatic hydrocarbon groups having the specified number of carbon atoms. For example, "$C_1$-$C_6$ alkyl" is intended to include $C_1$, $C_2$, $C_3$, $C_4$, $C_5$ and $C_6$ alkyl groups. Examples of alkyl include, but are not limited to, methyl, ethyl, n-propyl, i-propyl, n-butyl, i-butyl, sec-butyl, t-butyl, n-pentyl, n-hexyl, 2-methylbutyl, 2-methylpentyl, 2-ethylbutyl, 3-methylpentyl, and 4-methylpentyl.

By "haloalkyl" is meant both branched and straight chain saturated aliphatic hydrocarbon groups having the specified number of carbon atoms, wherein at least one of the hydrogen atoms has been replaced by F, Cl, Br or I. Preferably, haloalkyl refers to perfluoralkyl.

The term "cycloalkyl" refers to cyclized alkyl groups, including mono-, bi- or poly-cyclic ring systems. Example cycloalkyl groups include, but are not limited to, cyclopropyl, cyclobutyl, cyclopentyl, cyclohexyl, norbornyl, adamantyl and the like. Branched cycloalkyl groups such as 1-methylcyclopropyl and 2-methylcyclopropyl are included in the definition of "cycloalkyl".

As used herein, the term "aryl", is intended to mean an aromatic moiety containing, if specified, the specified number of carbon atoms; for example phenyl or naphthyl.

As used herein, the term "heteroaryl", is intended to mean an aromatic moiety containing, if specified, the specified number of atoms with at least one of the ring atoms being selected from N, O or S. Examples of heteroaryl rings include pyrrole, furan, thiophene, imidazole, pyrazole, 1,2,3-triazole, 1,2,4-triazole, tetrazole, thiazole, oxazole, isooxazole, benzofuran, isobenzofuran, indole, isoindole, benzothiophene, benzo[c]thiophene, benzinimdazole, indazole, purine, benzoxazole, benzothiazole, pyridine, pyrimidine, pyrazine, pyrazidine, quinoline, isoquinoline, quinoxaline, quinazoline and cinnoline.

The compounds of formula (I), (I'), (Ia), (II) and (III) are found to selectively target and disrupt Phospholamban-AKAP18δ, indicating that they would find use as cardioprotective agents following myocardial infarction.

Therefore, the present invention relates to a compound of formula (I), (I'), (Ia), (II) or (III) for use in therapy.

As mentioned above, these pharmaceutical compositions may be used for treating or preventing conditions in which PKA type II signalling which regulates SERCA2 is abnormal, in particular when the activity of this pathway is elevated or reduced. Furthermore, anchoring disruption may be beneficial also when the signalling is normal in cases when the heart is damaged and needs to be protected from adrenergic stimuli and pacing.

Thus, viewed from a further aspect, the present invention preferably provides a method of regulating SERCA2 activity in a human or non-human animal wherein a pharmaceutical composition as described hereinbefore is administered to said animal.

Viewed another way, the present invention provides a method of treating or preventing diseases or disorders exhibiting abnormal SERCA2 activity or which would benefit from a reduction or elevation in the activity of SERCA2 in a human or non-human animal wherein a pharmaceutical composition as described hereinbefore is administered to said animal.

Alternatively stated, the present invention provides the use of a pharmaceutical composition as defined herein for the preparation of a medicament for the regulation of SERCA2 activity, preferably as described hereinbefore.

Alternatively stated, the present invention provides the use of a pharmaceutical composition as defined herein for the preparation of a medicament for treating or preventing diseases or disorders exhibiting abnormal SERCA2 activity or which would benefit from a reduction or elevation in the activity of SERCA2.

Preferably, the present invention relates to a compound of formula (I), (I'), (Ia), (II) or (III) for use in treating or preventing diseases or disorders exhibiting abnormal SERCA2 activity or which would benefit from a reduction or elevation in the activity of SERCA2.

A number of the examples show that the regulation of SERCA2 activity provided by the compounds of the invention is associated with their effect on PKA type II signalling.

Thus, viewed from a further aspect the present invention preferably provides a method of treating or preventing diseases or disorders exhibiting abnormal PKA type II signalling that regulates SERCA2 activity or which would benefit from a reduction or elevation in the levels of SERCA2 mediated PKA type II signalling, preferably as described hereinbefore, in a human or non-human animal wherein a pharmaceutical composition as described hereinbefore is administered to said animal.

Alternatively stated, the present invention provides the use of a pharmaceutical composition as defined herein for the preparation of a medicament for the treatment or prevention of diseases or disorders exhibiting abnormal PKA type II signalling that regulates SERCA2 activity or which would benefit from a reduction or elevation in the levels of SERCA2 mediated PKA type II signalling, preferably as described hereinbefore.

Preferably, the present invention relates to a compound of formula (I), (I'), (Ia), (II) or (III) for use in treating or preventing cardiovascular disease.

As referred to herein "cardiovascular disease" refers to a disease or disorder of the heart or vascular system which may be congenital or acquired and encompasses diseases such as congenital heart failure, hypertension, myocardial infarction, congestive heart failure, reperfusion damage, dilated cardiomyopathy, post infarction heart failure, arrhythmia, atherosclerotic peripheral arterial disease and alveolar hypoxia leading to pulmonary hypertension and right ventricle failure.

As used herein, "treating" refers to the reduction, alleviation or elimination, preferably to normal levels, of one or more of the symptoms of said disease, disorder or condition which is being treated, e.g. normal blood pressure, cardiac function, etc., relative to the symptoms prior to treatment. Where not explicitly stated, treatment encompasses prevention. "Preventing" refers to absolute prevention, i.e. maintenance of normal levels with reference to the extent or appearance of a particular symptom (e.g. hypertension) or reduction or alleviation of the extent or timing (e.g. delaying) of the onset of that symptom.

Preferably, the present invention relates to a compound of formula (I), (I'), (Ia), (II) or (III) for use in treating conditions related to the heart.

By "conditions related to the heart" is meant and disease or disorder related of the heart which may be congenital or acquired and encompasses diseases such as congenital heart failure, myocardial infarction, post infarction heart failure, congestive heart failure, reperfusion damage, dilated cardiomyopathy and arrhythmia.

Preferably, the present invention relates to a compound of formula (I), (I'), (Ia), (II) or (III) for use in treating myocardial infarction.

Preferably, the present invention relates to a compound of formula (I), (I'), (Ia), (II) or (III) for use in treating congestive heart failure.

Preferably, the present invention relates to a compound of formula (I), (I'), (Ia), (II) or (III) for use in protecting against reperfusion damage.

Preferably, the present invention relates to a compound of formula (I), (I'), (Ia), (II) or (III) for use in protecting against post infarction heart failure.

Preferably, the present invention relates to a compound of formula (I), (I'), (Ia), (II) or (III) for use in protecting against congenital heart failure.

Preferably, the present invention relates to a compound of formula (I), (I'), (Ia), (II) or (III) for use in protecting against dilated cardiomyopathy.

Preferably, the present invention relates to a compound of formula (I), (I'), (Ia), (II) or (III) for use in protecting against arrhythmia heart failure.

Preferably, the present invention relates to a compound of formula (I), (I'), (Ia), (II) or (III) for use in interfering with A-kinase proteins.

Preferably, the present invention relates to a compound of formula (I), (I'), (Ia), (II) or (III) for use in inhibiting phospholamban phosphorylation.

Preferably, the present invention relates to a compound of formula (I), (I'), (Ia), (II) or (III) for use in inhibiting PKA phospholamban phosphorylation upon adrenergic stimulation.

Preferably, the present invention relates to a compound of formula (I), (I'), (Ia), (II) or (III) for use in inhibiting PKA-mediated phospholamban phosphorylation upon adrenergic stimulation.

Preferably, the present invention relates to a compound of formula (I), (I'), (Ia), (II) or (III) for use in regulating SERCA2 activity.

Preferably, the present invention relates to a compound of formula (I), (I'), (Ia), (II) or (III) for use in mediating adrenergic pacing of the heart.

Preferably, the present invention relates to a compound of formula (I), (I'), (Ia), (II) or (III) for use in regulating the adrenergic pacing of the heart.

Preferably, the present invention relates to a compound of formula (I), (I'), (Ia), (II) or (III) for use in preventing arrhythmia.

Preferably, the present invention relates to a compound of formula (I), (I'), (Ia), (II) or (III) for use in inhibiting protein kinase A binding to A-kinase anchor proteins.

Preferably, the present invention relates to a compound of formula (I), (I'), (Ia), (II) or (III) for use in inhibiting AKAP18δ binding to phospholamban.

The present invention also relates to methods of treating/inhibiting/protecting against/mediating (as the case may be) the above conditions, comprising administering to a human or non-human animal (e.g. a mammal) in need thereof a compound according to formula (I), (I'), (II), or (III).

Subjects which may be treated are preferably mammalian, preferably humans and companion or agricultural animals such as dogs, cats, monkeys, horses, sheep, goats, cows, rabbits, rats and mice.

Preferred mammals are humans.

The present invention also relates to the use of a compound according to formula (I), (I'), (II), or (III) for treating/inhibiting/protecting against/mediating (as the case may be) the above conditions.

The present invention also relates to a compound according to formula (I), (I'), (II), or (III) for use in the manufacture of a medicament for use in treating/inhibiting/protecting against/mediating (as the case may be) the above conditions.

As shown by the examples below, the compounds of the invention are capable of influencing phospholamban phosphorylation. This is believed to be the first time this the activity of this target has been modulated by chemical moieties.

Thus, viewed from a further aspect the present invention preferably provides a method of treating or preventing diseases or disorders associated with phospholamban phosphorylation, comprising administering to a subject in need thereof a pharmaceutically effective amount of a compound with molecular weight below 1000 Daltons (or g/mol) or pharmaceutically acceptable salts thereof.

By "diseases or disorders associated with phospholamban phosphorylation" is meant conditions which arise due to abnormal phospholamban phosphorylation, such as but not limited to post infarction heart failure and congestive heart failure, as well as conditions that may occur in patients showing normal phospholamban phosphorylation but which would benefit from a cardioprotective effect due to inhibition of phospholamban phosphorylation, such as but not limited to congenital heart failure, myocardial infarction, reperfusion damage, dilated cardiomyopathy, and arrhythmia.

Preferred diseases or disorders associated with phospholamban phosphorylation are cardiovascular diseases.

Preferred diseases or disorders associated with phospholamban phosphorylation are cardiovascular diseases selected from congenital heart failure, myocardial infarction, post infarction heart failure, congestive heart failure, reperfusion damage, dilated cardiomyopathy and arrhythmia.

The invention also relates to a method of regulating phospholamban phosphorylation comprising administering to a subject a pharmaceutically effective amount of a compound with molecular weight below 1000 Daltons, or pharmaceutically acceptable salts thereof.

The invention also relates to a method of inhibiting phospholamban phosphorylation comprising administering to a subject a pharmaceutically effective amount of a compound with molecular weight below 1000 Daltons, or pharmaceutically acceptable salts thereof.

In preferred embodiments, these methods use a nitrogen-containing compound. More preferably, said nitrogen-containing compound is an amine. Even more preferably, said amine is a tertiary amine.

Most preferably, said amine is an alkylaryl or alkylheteroaryl tertiary amine.

Thus, in a preferred aspect, the invention relates to a method of treating or preventing diseases or disorders associated with phospholamban phosphorylation, comprising administering to a subject in need thereof a pharmaceutically effective amount of a alkylaryl or alkylheteroaryl tertiary amine with molecular weight below 1000 Daltons or pharmaceutically acceptable salts thereof.

In such embodiments, "alkylaryl" means an alkylene group bonded to an aromatic ring containing only carbon atoms, which may optionally be substituted. By "alkylheteroaryl" is meant an alkylene group bonded to an aromatic ring containing carbon atoms and at least one heteroatom, which may optionally be substituted.

In preferred embodiments, the alkylaryl or alkylheteroaryl tertiary amine is a compound of formula (I), (I'), (Ia), (II) or (III).

The present invention also relates to pharmaceutical compositions comprising a compound according to formula (I), (I'), (Ia), (II), or (III) and one or more pharmaceutically acceptable excipients and/or diluents.

By "pharmaceutically acceptable" is meant that the ingredient must be compatible with other ingredients in the composition as well as physiologically acceptable to the recipient.

Pharmaceutical compositions for use according to the invention may be formulated in conventional manner using readily available ingredients. Thus, the active ingredient may be incorporated, optionally together with other active substances as a combined preparation, with one or more conventional carriers, diluents and/or excipients, to produce conventional galenic preparations such as tablets, pills, powders, lozenges, sachets, cachets, elixirs, suspensions (as injection or infusion fluids), emulsions, solutions, syrups, aerosols (as a solid or in a liquid medium), ointments, soft and hard gelatin capsules, suppositories, sterile injectable solutions, sterile packaged powders, and the like. Biodegradable polymers (such as polyesters, polyanhydrides, polylactic acid, or polyglycolic acid) may also be used for solid implants. The compositions may be stabilized by use of freeze-drying, undercooling or Permazyme.

Suitable excipients, carriers or diluents are lactose, dextrose, sucrose, sorbitol, mannitol, starches, gum acacia, calcium phosphate, calcium carbonate, calcium lactose, corn starch, aglinates, tragacanth, gelatin, calcium silicate, microcrystalline cellulose, polyvinylpyrrolidone, cellulose, water syrup, water, water/ethanol, water/glycol, water/polyethylene, glycol, propylene glycol, methyl cellulose, methylhydroxybenzoates, propyl hydroxybenzoates, talc, magnesium stearate, mineral oil or fatty substances such as hard fat or suitable mixtures thereof. Agents for obtaining sustained release formulations, such as carboxypolymethylene, carboxymethyl cellulose, cellulose acetate phthalate, or polyvinylacetate may also be used. The compositions may additionally include lubricating agents, wetting agents, viscosity increasing agents, colouring agents, granulating agents, disintegrating agents, binding agents, osmotic active agents, emulsifying agents, suspending agents, preserving agents, sweetening agents, flavouring agents, adsorption enhancers, e.g. for nasal delivery (bile salts, lecithins, surfactants, fatty acids, chelators) and the like. The compositions of the invention may be formulated so as to provide quick, sustained or delayed release of the active ingredient after administration of the patient by employing procedures well known in the art.

The active ingredient in such compositions may comprise from about 0.01% to about 99% by weight of the formulation, preferably from about 0.1 to about 50%, for example 10%.

The invention also extends to pharmaceutical compositions as described above for use as a medicament.

It will be understood that preferred methods/uses/compositions described above utilise the preferred compounds of formula (I), (I'), (Ia), (II) and (III) defined above, particularly the specific compounds mentioned above.

The administration may be by any suitable method known in the medicinal arts, including for example oral, parenteral (e.g. intramuscular, subcutaneous, intraperitoneal or intravenous) percutaneous, buccal, rectal or topical administration or administration by inhalation.

The preferred routes of administration are oral administration and intravenous administration. Preferred formulations for the composition of the invention are therefore as a tablet, a capsule or an intravenous solution.

The tablets are typically prepared by direct compression or a granulation procedure, for example using standard fluid bed technology. The tablets are preferably coated with film coating or another coating such as an enteric coating.

The capsules are preferably gelatine capsules.

The composition for injection can be a ready to use solution or a dry material to be dissolved before administration. All intravenous compositions are sterile. Any sterilization method may be used, such as heat sterilization and aseptic preparation.

The compositions of the invention may contain the compound of formula (I) (or formula (I')) as a physiologically acceptable salt thereof. Such salts might typically be HCl, HBr, sulphate salt, phosphate salt, nitrate salt and salts with sulphonic acids like for example methane sulphonic acid. Other salts include organic salts like acetate, citrate and fumarate. The salt form of the compound of formula (I) (or formula (I')) is preferred for intravenous administration.

The unit dose will vary depending upon choice of compound and disease or disorder being treated.

Typically, the unit dose will vary from 0.1 mg to 500 mg; more preferably from 1 mg to 300 mg. A typical daily dose will be from 0.1 mg to 2 grams, more preferably 1 mg to 1 g, even more preferably 1 mg to 600 mg.

Typical daily doses per kg body weight of the patient vary from 5 mg/kg/day to 50 mg/kg/day, preferably from 10 mg/kg/day to 40 mg/kg/day.

Typically, the tablet or capsule weight is between 70 mg and 1 gram. Typically, the injection or infusion volume is between 0.3 ml and 500 ml.

The dosing regime will vary depending upon the clinical situation. Typical average dosing will be once, twice or three times a day, preferably once or twice a day.

The precise dosage of the active compound to be administered and the length of the course of treatment will of course, depend on a number of factors including for example, the age and weight of the patient, the specific condition requiring treatment and its severity, and the route of administration.

The compounds of formula (I) (such as those of formula (I')) typically show an $EC_{50}$ value (as determined by the AlphaScreen described in the Examples) of 200 µM or below, preferably 100 µM or below, more preferably 50 µM or below, more preferably 25 µM or below, most preferably 10 µM or below, such as 5 µM or below.

The method of treatment according to the invention may advantageously be combined with administration of one or more active ingredients which are effective in treating the disorder or disease to be treated. Thus, pharmaceutical compositions of the invention may additionally contain one or more of such active ingredients.

Co-administration with other cardiovascular drugs is particularly preferred. For example, it is preferable to co-administer the compounds of formula (I) (or formula (I')) with drugs that treat hypertension, heart failure, arrhythmia and post infarction. It is more preferable to co-administer the compounds of formula (I) (or formula (I')) with drugs that treat hypertension, heart failure, arrhythmia and post infarction myocardial reperfusion syndrome.

The most preferred drugs to be administered together with the compounds of formula (I) or (I') are beta-blockers, calcium antagonists, ACE-inhibitors, ATII/-blockers and anti-arrhythmic drugs.

The following Examples are given by way of illustration only in which the Figures referred to are as follows:

FIG. 1: Set-up of GST-AKAP18δ: PLB-biotin interaction assay by AlphaScreen (A) and cross-titration of the preparations of GST-AKAP18δ and biotinylated PLB (B)

Figure 2:
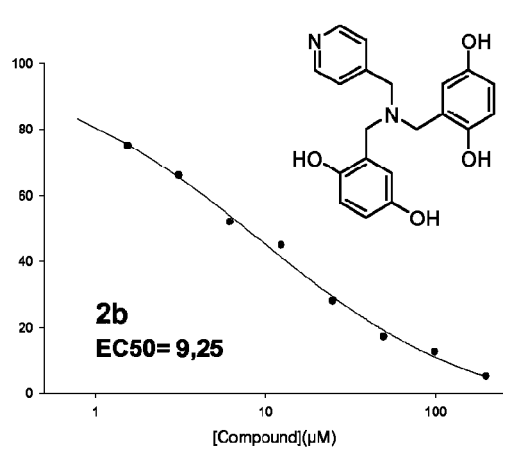

FIG. 2: Concentration-response curves of compound 2b in the AKAP18δ-PLB AlphaScreen assay. Compound concentration (x-axis) is logarithmic.

Figure 3:
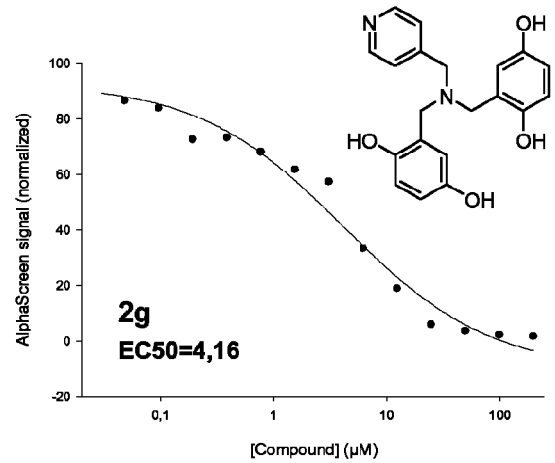

FIG. 3: Concentration-response curves of compound 2g in the AKAP18δ-PLB AlphaScreen assay. Compound concentration (x-axis) is logarithmic.

Figure 4:
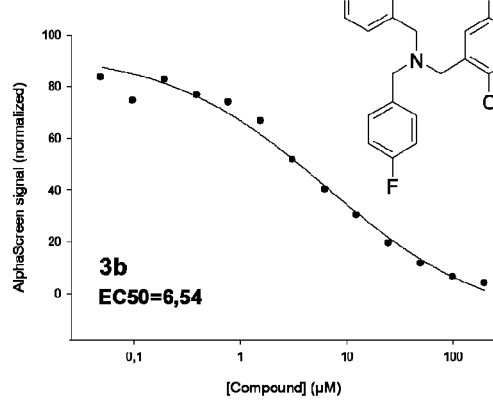

FIG. 4: Concentration-response curves of compound 3b in the AKAP18δ-PLB AlphaScreen assay. Compound concentration (x-axis) is logarithmic.

Figure 5:
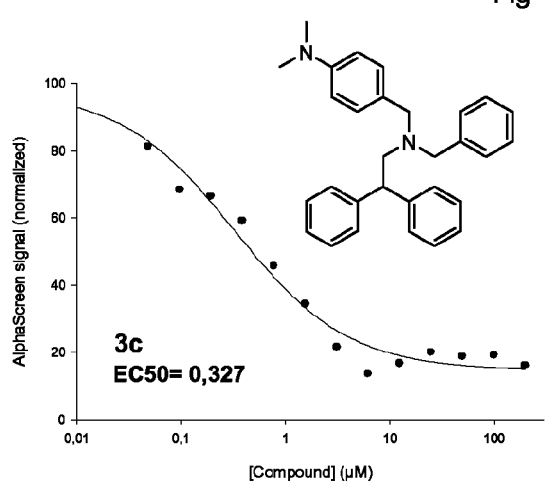

FIG. 5: Concentration-response curves of compound 3c in the AKAP18δ-PLB AlphaScreen assay. Compound concentration (x-axis) is logarithmic.

Figure 6:
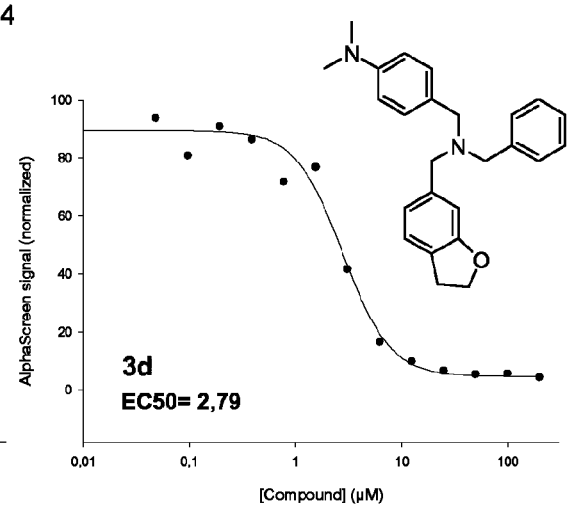

FIG. 6: Concentration-response curves of compound 3d in the AKAP18δ-PLB AlphaScreen assay. Compound concentration (x-axis) is logarithmic.

Figure 7:
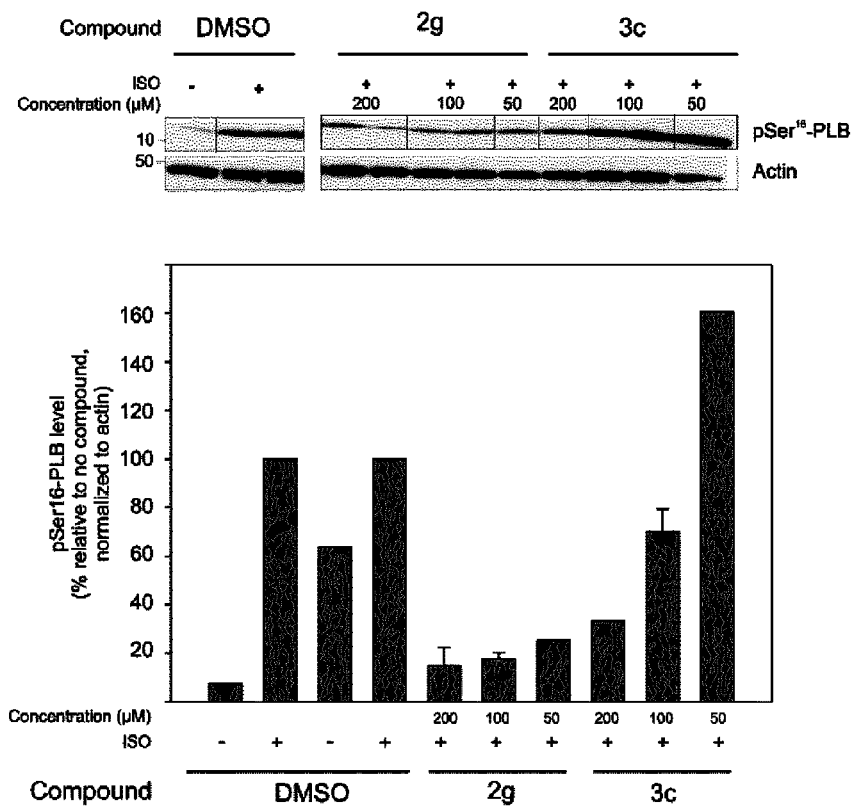

FIG. 7: Disruption of the AKAP18δ-PLB complex influences PLB-$Ser^{16}$ phosphorylation. Rat neonatal cardiomyocytes treated with compounds 24 hours prior stimulation with isoproterenol (100 nM, 5 minutes). The histogram shows levels of phosphorylated $Ser^{16}$-PLB quantified by densiometery relative to actin levels.

Figure 8:
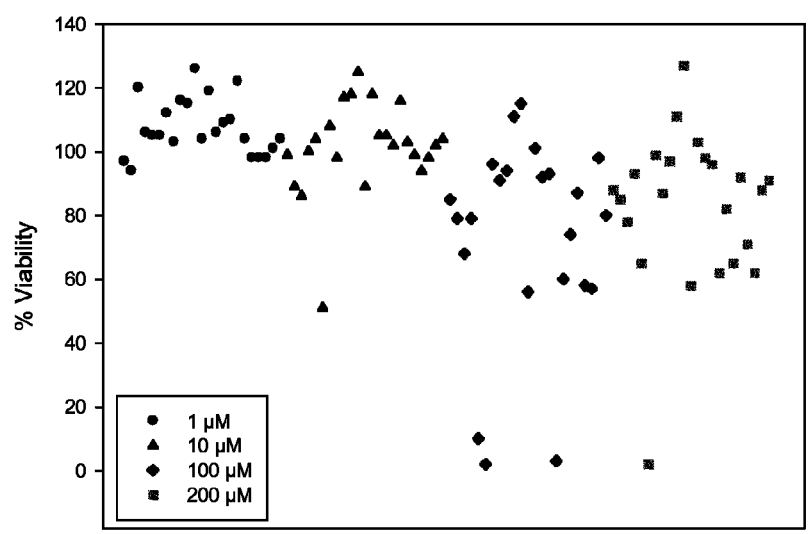

FIG. 8: Percent viability after 24 hours incubation with synthesized compounds.

Figure 9:
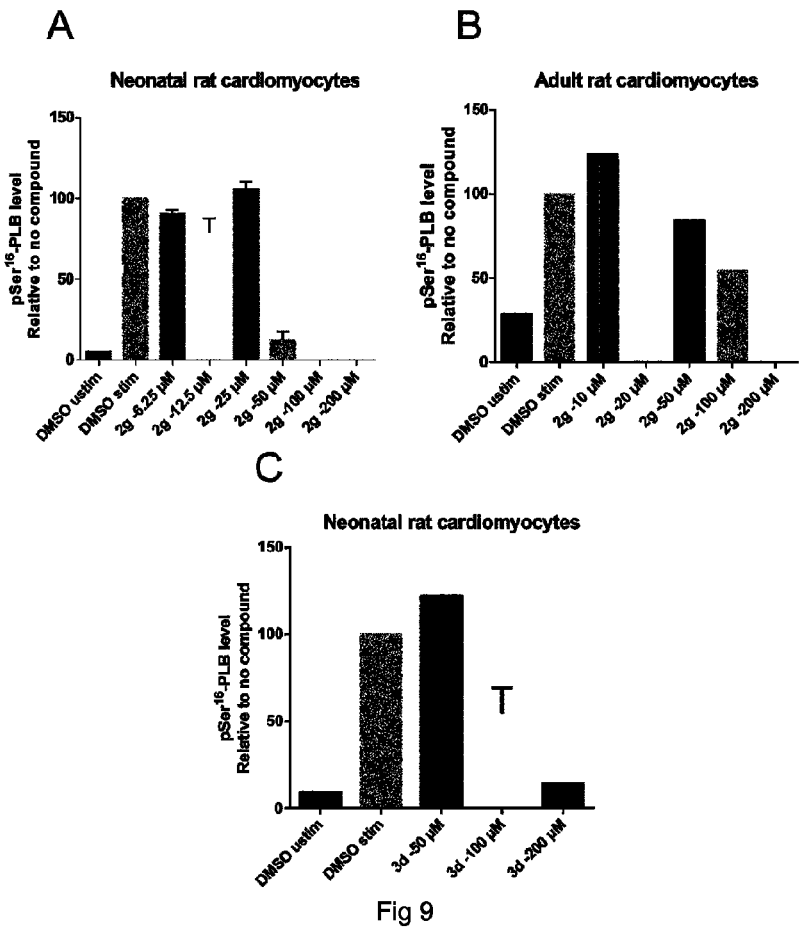

FIG. 9: Disruption of the AKAP18δ-PLB complex influences PLB-$Ser^{16}$ phosphorylation. Rat neonatal cardiomyocytes treated with compound 2g (A) or 3d (C) 24 hours prior stimulation with isoproterenol (100 nM, 5 minutes). Rat adult cardiomyocytes treated with compound 2g (B) 1 hour prior to stimulation with isoproterenol (10 nM, 5 minutes). The histograms show levels of phosphorylated $Ser^{16}$-PLB quantified by densitometry on Western blots (relative to actin levels).

Figure 10:
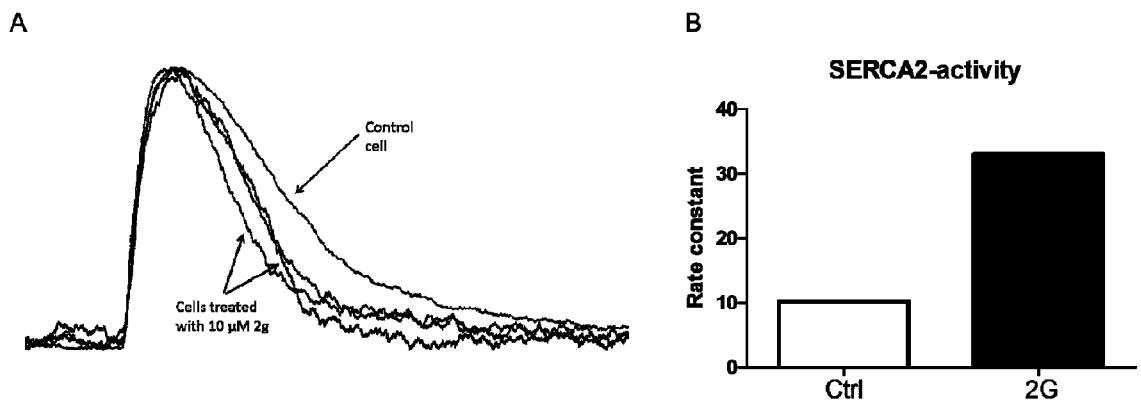
Figure 1:
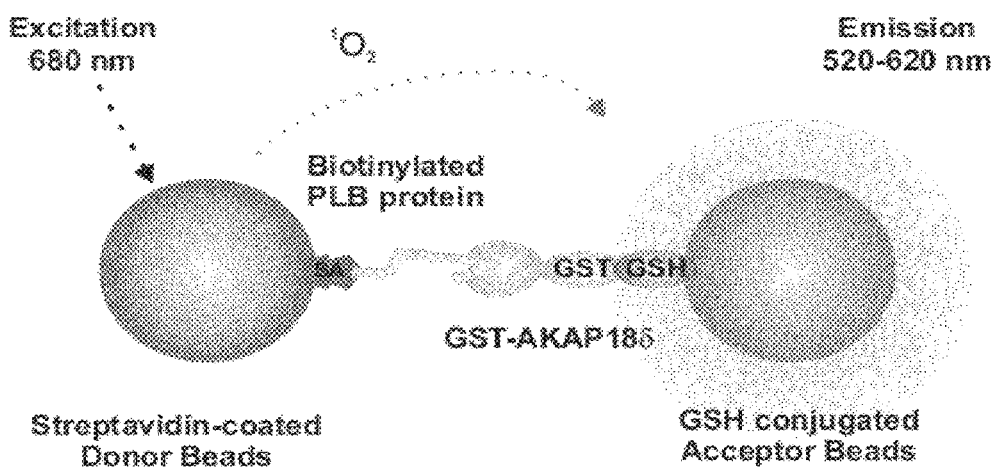
Figure 1:
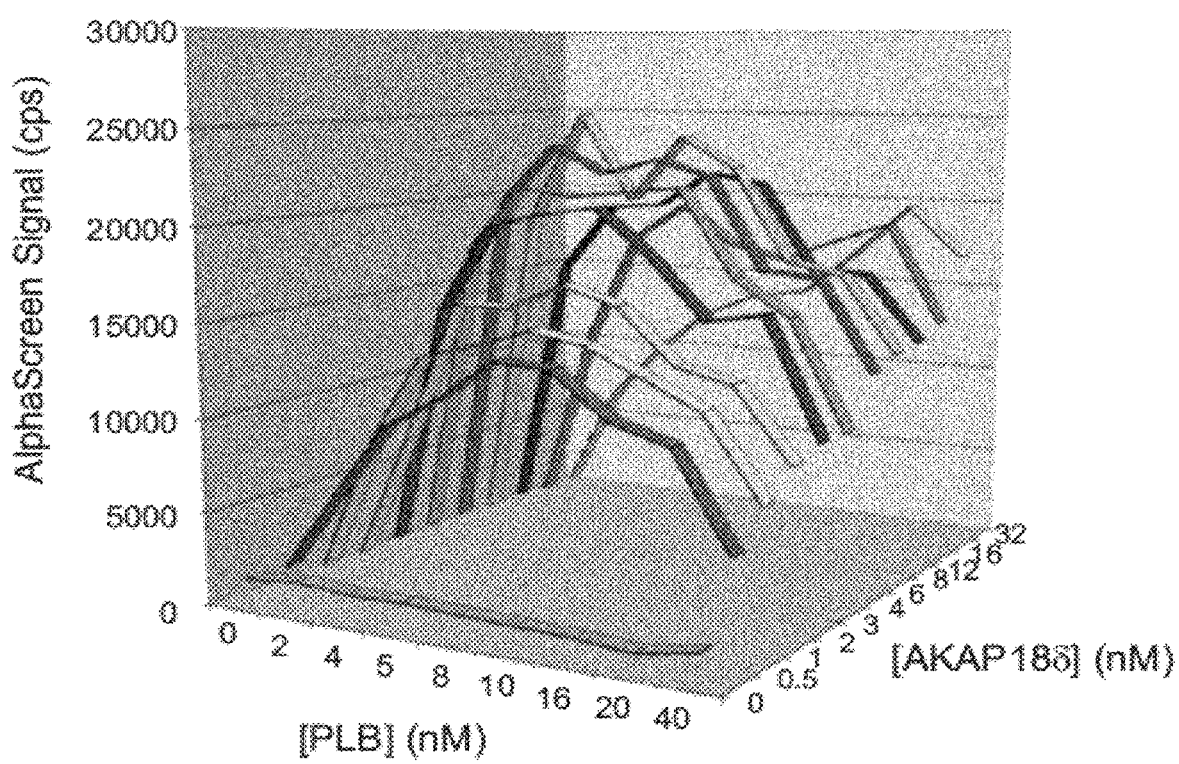
Figure 7:
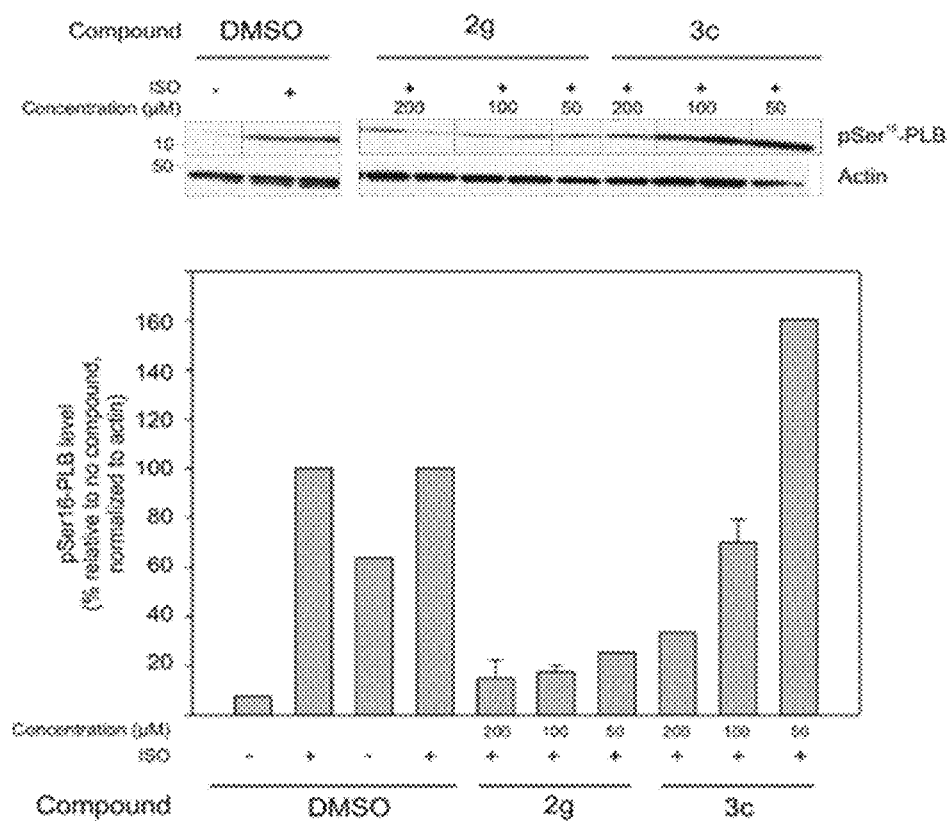
Figure 8:
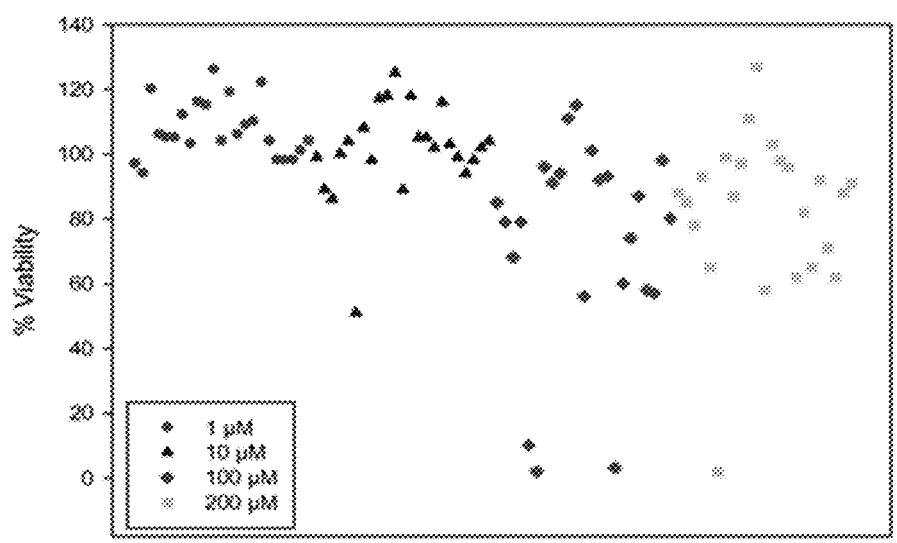
Figure 9:
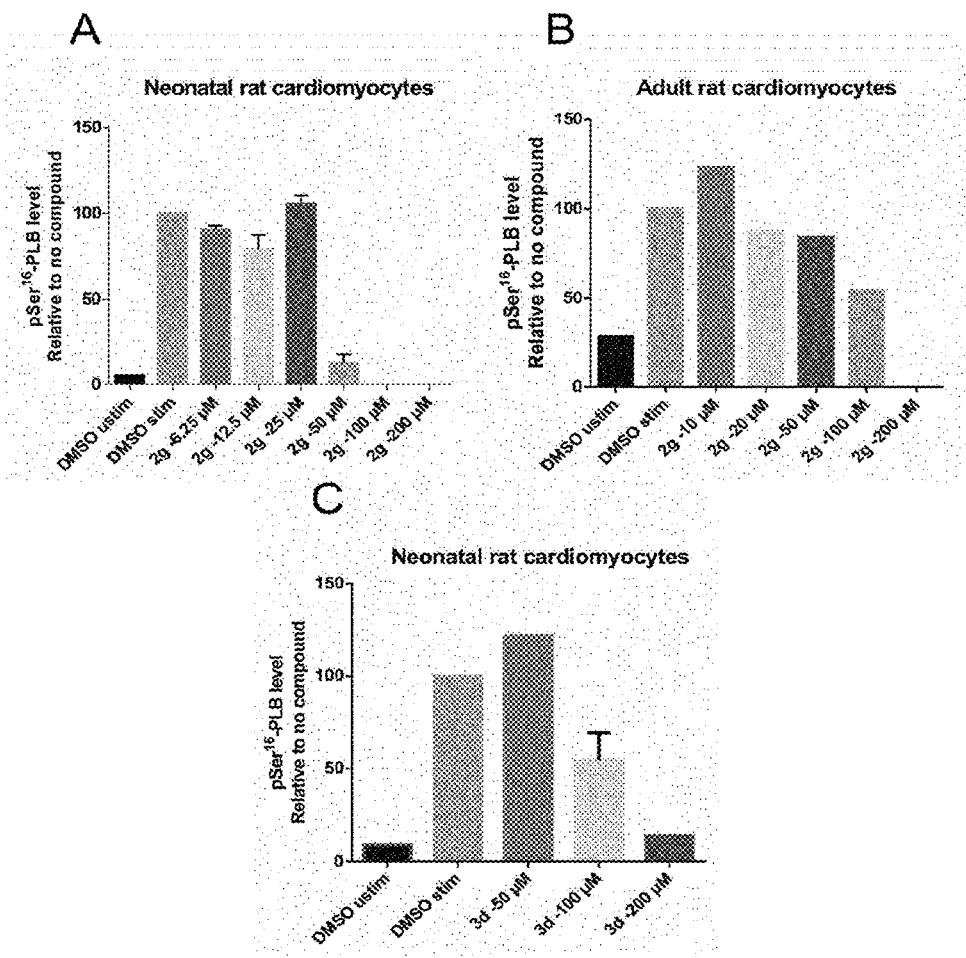
Figure 10:
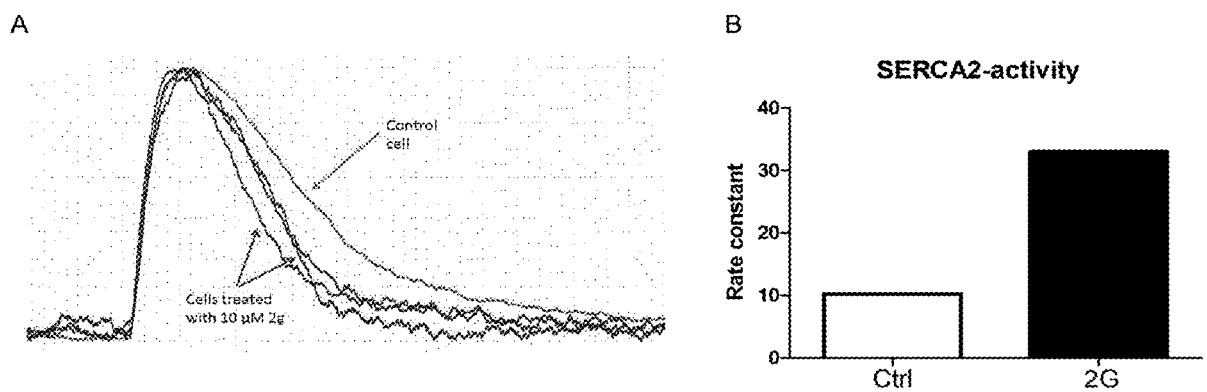

FIG. 10: Compound 2g regulates SERCA2-activity. A novel patch clamp based technique was performed to directly assess SERCA-activity independently of receptor stimulation in intact cardiomyocytes. By dialyzing cardiomyocytes with a fixed level of cAMP with and without presence of compound 2g, preliminary data indicates ability of compound 2g to regulate SERCA2-activity in intact adult cardiomyocytes.

EXAMPLES

Binding Assay

Stable and optimal assay conditions were determined by cross-titrating GST-AKAP18δ and biotinylated PLB using 10 µg/ml glutathione acceptor beads and 10 µg/ml streptavidin donor beads in an AlphaScreen assay. The excitation wavelength was 680 nm, with the emission wavelength being 520-560 nm. Signal intensity in each well was registered and the optimal concentration to use was chosen to be the concentration prior to the peak of the signal. The set up of the assay and cross-titration results are shown in FIGS. 1A and 1B.

Concentrations to give a reliable signal were determined to be between 2 and 16 nM for AKAP18δ-GST and 4 and 20 nM PLB-biotin for relevant preparations of protein, for example 4 nM and 20 nM, respectively.

Example 1

Screening

A compound library consisting of 79,000 different small molecular compounds was screened with the above assay. The following compounds of formulae (I) were identified as having relatively low $EC_{50}$ values (2.0 µM-137 µM).

TABLE 1

| Group of compounds of formulae (I) | |
|---|---|
| Structure | $EC_{50}$ |
| [structure] | 41.6 µM |
| [structure] | 36.4 µM |
| [structure] | 137 µM |

TABLE 1-continued

| Group of compounds of formulae (I) | |
|---|---|
| Structure | EC$_{50}$ |
| | 39.5 μM |
| | 10.6 μM |
| | 60.5 μM |
| | 18 μM |

TABLE 1-continued

| Group of compounds of formulae (I) | |
|---|---|
| Structure | EC$_{50}$ |
| (4-fluorobenzyl)(4-chlorobenzyl)aminomethyl thiazole-4-carboxylic acid | 94.3 µM |
| (3,3-diphenylpropyl)(4-tert-butylbenzyl)aminomethyl thiazole-4-carboxylic acid | 21.1 µM |
| (3-trifluoromethylbenzyl)(4-methylbenzyl)aminomethyl thiazole-4-carboxylic acid | 98.3 µM |
| (4-fluorobenzyl)(4-methoxybenzyl)aminomethyl thiazole-4-carboxylic acid | 25.6 µM |

TABLE 1-continued

| Group of compounds of formulae (I) | |
|---|---|
| Structure | EC$_{50}$ |
| [structure: 2-fluorobenzyl, 3-(trifluoromethyl)benzyl amine linked to thiazole-4-carboxylic acid] | 215.9 μM |
| [structure: 3,3-diphenylpropyl, 4-methylbenzyl amine linked to thiazole-4-carboxylic acid] | 35.4 μM |
| [structure: bis(4-nitrobenzyl)benzylamine] | 7.5 μM |
| [structure: N-benzyl-bis(4-carboxybenzyl)amine] | 29.6 μM |

TABLE 1-continued
| Group of compounds of formulae (I) | |
|---|---|
| Structure | EC$_{50}$ |
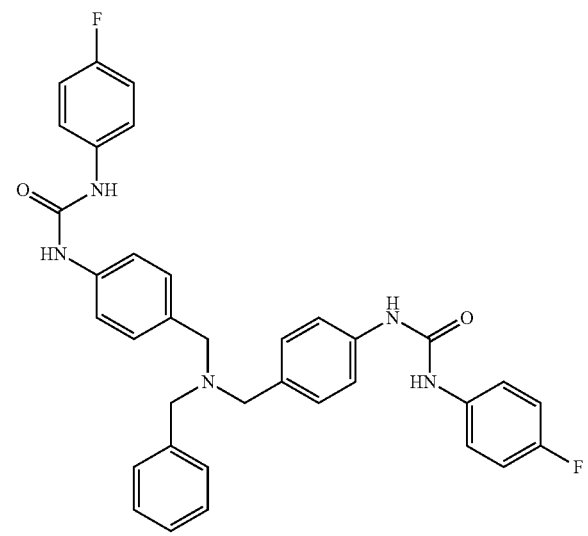 [SMILES: O=C(Nc1ccc(F)cc1)Nc1ccc(CN(Cc2ccccc2)Cc2ccc(NC(=O)Nc3ccc(F)cc3)cc2)cc1]
9.3 µM
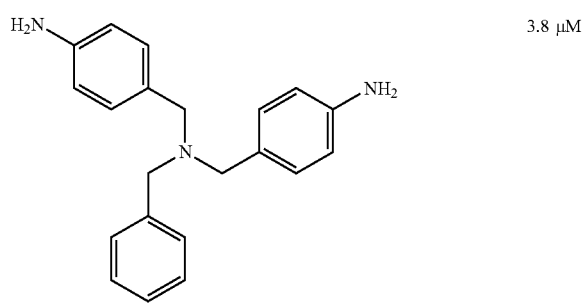
3.8 µM
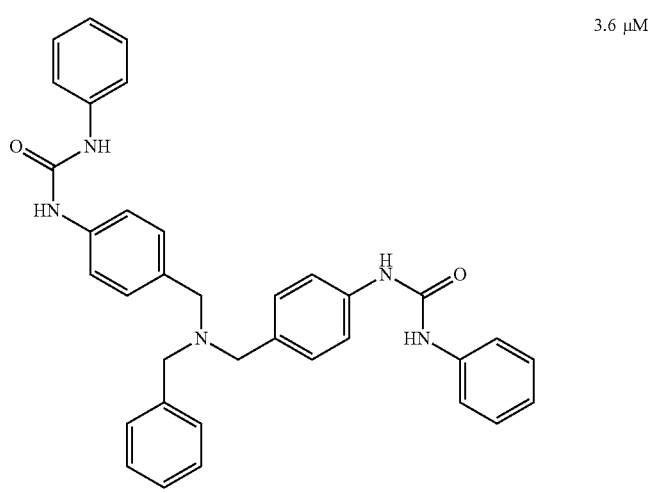
3.6 µM TABLE 1-continued
| Group of compounds of formulae (I) | |
|---|---|
| Structure | EC$_{50}$ |
| 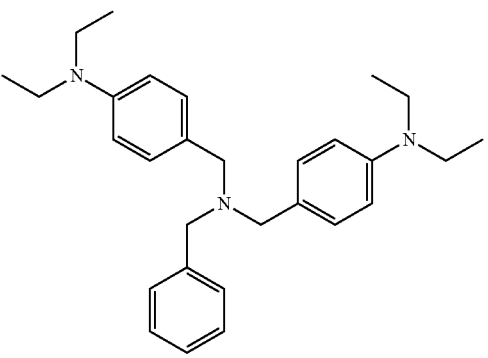 [SMILES: CCN(CC)c1ccc(CN(Cc2ccccc2)Cc2ccc(N(CC)CC)cc2)cc1] | 2.9 μM |
| 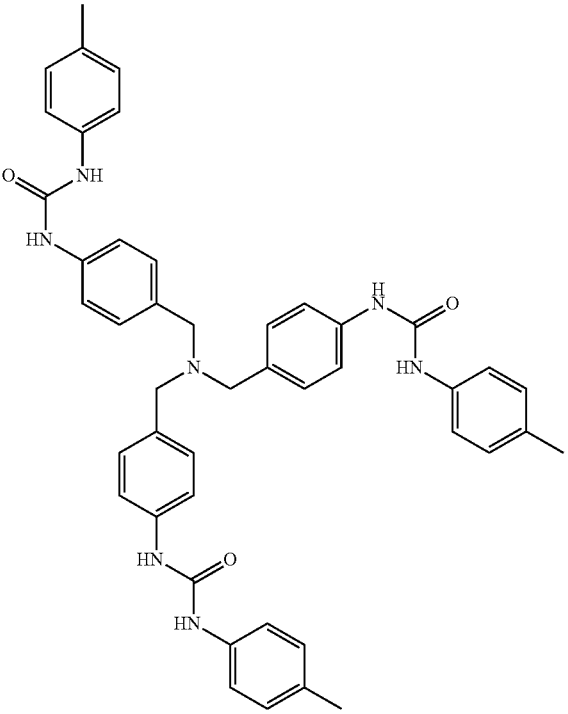 [SMILES: Cc1ccc(NC(=O)Nc2ccc(CN(Cc3ccc(NC(=O)Nc4ccc(C)cc4)cc3)Cc3ccc(NC(=O)Nc4ccc(C)cc4)cc3)cc2)cc1] | 5.2 μM |
| 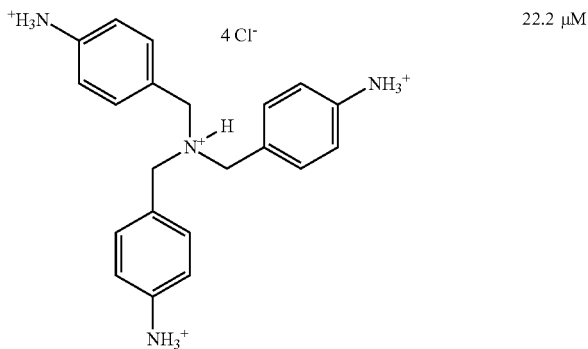 | 22.2 μM |

TABLE 1-continued

Group of compounds of formulae (I)

| Structure | $EC_{50}$ |
|---|---|
| (structure shown) | 2.0 μM |
| (structure shown) | 2.5 μM |

SYNTHETIC EXAMPLES

Synthesis of Intermediate 1

Preparation of N-(4-fluorobenzyl)-1-(pyridin-4-yl)methanamine

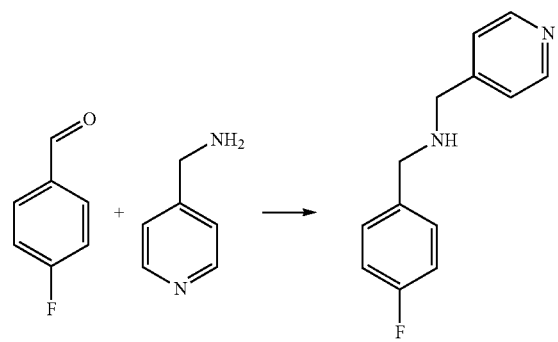

1a
Chemical Formula: C13H13FN2
Molecular Weight: 216.3

To a round bottom flask with a magnetic stirrer bar 4-picolylamine (0.43 g, 4 mmol) and 4-fluorobenzaldehyde (0.63 g, 5 mmol) were added together with 10 ml methanol, $NaCNBH_3$ (0.32 g, 5 mmol) and a few granules of 4 Å molecular sieve. The solution was stirred overnight at room temperature and the progress of the reaction was monitored by thin layer chromatography (TLC). After filtration the solution was concentrated in vacuo and the resulting liquid was diluted with 30 ml dichloromethane and extracted with 3×30 ml 0.05 M HCl. The combined aqueous layer was made basic with NaOH until the pH 10-11 and the solution was extracted with 2×100 ml dichloromethane. The organic layers were combined and dried over anhydrous $MgSO_4$, filtered and evaporated to give N-(4-fluorobenzyl)-1-(pyridin-4-yl)methanamine as a pale yellow oil. Yield: 0.66 g (76%). $^1$H NMR (300 MHz, $CDCl_3$): δ 8.54 (2H, d), 7.30 (4H, m), 7.01 (2H, m), 3.81 (2H, s), 3.77 (2H, s)

Synthesis of Intermediate 2

Preparation of N-(4-(tert-butyl)benzyl)-1-(pyridin-3-yl)methanamine

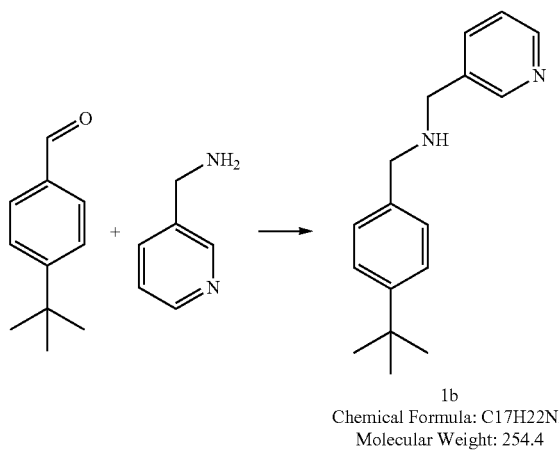

1b
Chemical Formula: C17H22N2
Molecular Weight: 254.4

To a round bottom flask with a magnetic stirrer bar 3-picolylamine (0.43 g, 4 mmol) and 4-tert-butylbenzaldehyde (0.81 g, 5 mmol) were added together with 10 ml methanol, NaCNBH$_3$ (0.32 g, 5 mmol) and a few granules of 4 Å molecular sieve. The solution was stirred for 2-12 hours at room temperature and the progress of the reaction was monitored by thin layer chromatography (TLC). After filtration the solution was concentrated in vacuo and the resulting liquid was diluted with 30 ml dichloromethane and extracted with 3×30 ml 0.05 M HCl. The combined aqueous layer was made basic with NaOH until the pH 10-11 and the solution was extracted with 2×100 ml dichloromethane. The organic layers were combined and dried over anhydrous MgSO$_4$, filtered and evaporated to give N-(4-(tert-butyl)benzyl)-1-(pyridin-3-yl)methanamine as a pale yellow oil. Yield: 0.61 g (60%). $^1$H NMR (300 MHz, CDCl$_3$): δ 8.59 (1H, d), 8.53 (1H, d), 7.78 (1H, d), 7.39 (2H, d), 7.29 (3H, m), 3.86 (2H, s), 3.81 (2H, s), 1.33 (9H, s). $^{13}$C NMR (75 MHz, CDCl$_3$): δ 150.5, 150, 148.9, 136.2, 135.9, 134.8, 128.2, 125.6, 123.6, 52.5, 50.1, 34.6, 31.5.

Synthesis of Intermediate 3

Preparation of 2-(((pyridin-4-ylmethyl)amino)methyl)benzene-1,4-diol)

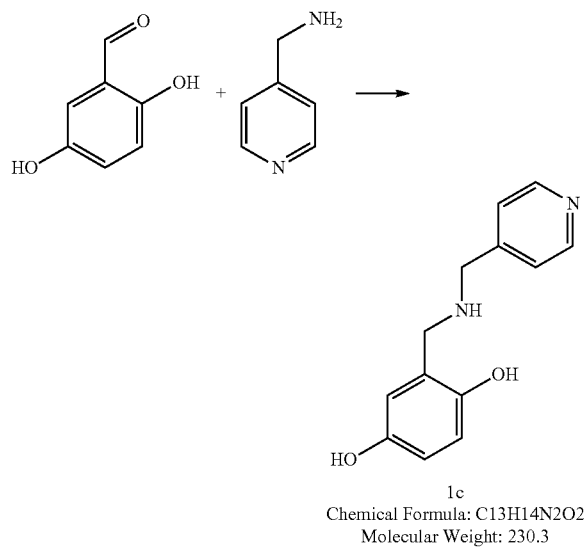

1c
Chemical Formula: C13H14N2O2
Molecular Weight: 230.3

To a round bottom flask with a magnetic stirrer bar 4-picolylamine (0.43 g, 4 mmol) and 2,5-dihydroxybenzaldehyde (0.69 g, 5 mmol) were added together with 10 ml methanol, NaCNBH$_3$ (0.32 g, 5 mmol) and a few granules of 4 Å molecular sieve. The solution was stirred for 2-12 hours at room temperature and the progress of the reaction was monitored by thin layer chromatography (TLC). After filtration the solution was concentrated in vacuo and the resulting liquid was diluted with 50 ml dichloromethane and extracted with 3×50 ml 0.05 M HCl. The combined aqueous layer was made basic with NaOH until the pH was 10 and the solution was extracted with 2×150 ml dichloromethane. The organic layers were combined and dried over anhydrous MgSO$_4$, filtered and evaporated to give 2-(((pyridin-4-ylmethyl)amino)methyl)-benzene-1,4-diol as a highly viscous brown oil. Yield: 0.26 g (28%). $^1$H NMR (300 MHz, DMSO): δ 8.51 (2H, m), 7.34 (2H, d), 6.51 (2H, m). $^{13}$C NMR (75 MHz, DMSO): δ 149.3, 149.2, 148.8, 148.5, 125, 122.7, 115.2, 113.7, 78.8, 50.4, 48.7.

Synthesis of Intermediate 4

Preparation of N,N-dimethyl-4-(((pyridin-4-ylmethyl)amino)methyl)aniline

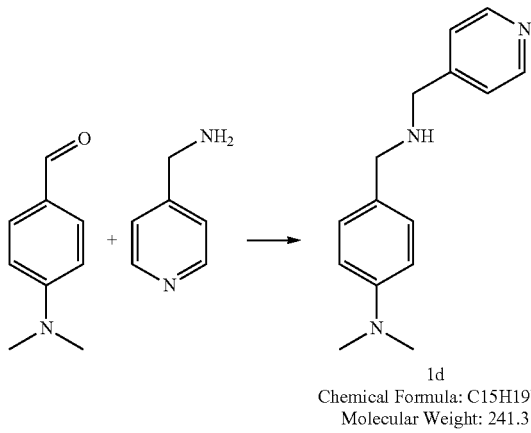

1d
Chemical Formula: C15H19N3
Molecular Weight: 241.3

To a round bottom flask with a magnetic stirrer bar 4-picolylamine (0.43 g, 4 mmol) and 4-(dimethylamino) benzaldehyde (1.34 g, 9 mmol) were added together with 10 ml methanol, NaCNBH$_3$ (0.57 g, 9 mmol) and a few granules of 4 Å molecular sieve. The solution was stirred for 2-12 hours at room temperature and the progress of the reaction was monitored by thin layer chromatography (TLC). After filtration the solution was concentrated in vacuo and the resulting liquid was diluted with 50 ml dichloromethane and extracted with 3×50 ml 0.05 M HCl. The combined aqueous layer was made basic with NaOH until the pH was 10 and the solution was extracted with 2×150 ml dichloromethane. The organic layers were combined and dried over anhydrous MgSO$_4$, filtered and evaporated to give N,N-dimethyl-4-(((pyridin-4-ylmethyl)amino) methyl)aniline as a dark brown oil. Yield: 0.85 g (88%). $^1$H NMR (300 MHz, CDCl$_3$): δ 8.56 (2H, d), 7.25 (4H, m), 6.74 (2, d), 3.82 (2H, s), 3.73 (2H, s), 2.96 (6H, s). $^{13}$C NMR (75 MHz, CDCl$_3$): δ 150.1, 149.9, 149.7, 129.2, 128.7, 127.7, 123.2, 112.8, 52.8, 51.7, 40.8.

Synthesis of Intermediate 5

Preparation of methyl 4-((benzylamino)methyl)benzoate

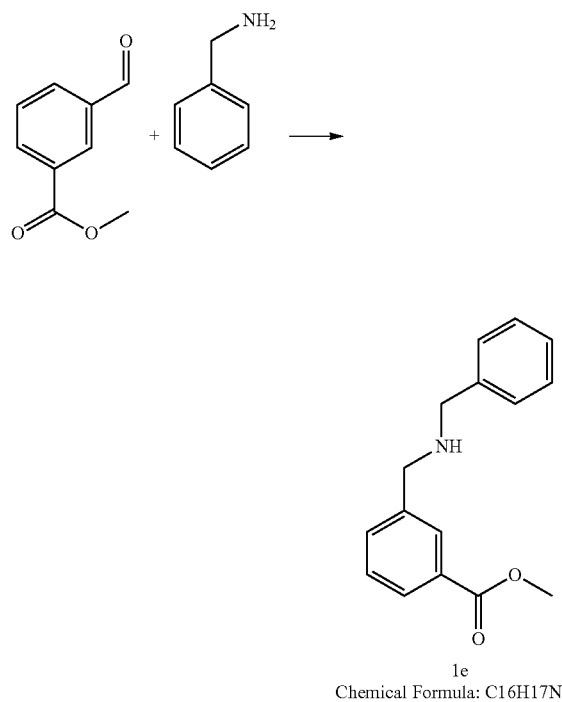

1e
Chemical Formula: C16H17NO2
Molecular Weight: 255.3

To a round bottom flask with a magnetic stirrer bar benzylamine (0.215 g, 2 mmol) and methyl 3-formylbenzoate (0.41 g, 2.5 mmol) were added together with 10 ml methanol, NaCNBH$_3$ (0.16 g, 2.5 mmol) and a few granules of 4 Å molecular sieve. The solution was stirred for 2-12 hours at room temperature and the progress of the reaction was monitored by thin layer chromatography (TLC). After filtration the solution was concentrated in vacuo and the resulting liquid was diluted with 50 ml dichloromethane and extracted with 3×50 ml 0.05 M HCl. The combined aqueous layer was made basic with NaOH until the pH 10-11 and the solution was extracted with 2×150 ml dichloromethane. The organic layers were combined and dried over anhydrous MgSO$_4$, filtered and evaporated to give methyl 4-((benzylamino)methyl)benzoate as a light brown oil. Yield: 0.37 g (36%). $^1$H NMR (300 MHz, CDCl$_3$): δ 8.00 (2H, m), 7.59 (1H, d), 7.36 (6H, m), 3.94 (3H, s), 3.87 (2H, s), 3.83 (2H, s) $^{13}$C NMR (75 MHz, CDCl$_3$): δ 167.3, 140.9, 140.3, 132.9, 130.4, 129.4, 128.6, 128.4, 128.3, 127.2, 53.4, 52.9, 52.2.

Synthesis of Intermediate 6

Preparation of 4-((benzylamino)methyl)-N,N-dimethylaniline

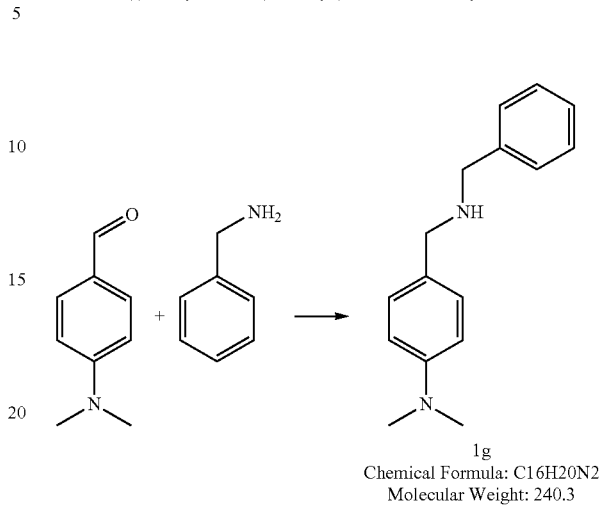

1g
Chemical Formula: C16H20N2
Molecular Weight: 240.3

To a round bottom flask with a magnetic stirrer bar benzylamine (1.07 g, 10 mmol) and 4-(dimethylamino) benzaldehyde (1.79 g, 12 mmol) were added together with 10 ml methanol, NaCNBH$_3$ (0.76 g, 12 mmol) and a few granules of 4 Å molecular sieve. The solution was stirred for 3 hours at room temperature and the progress of the reaction was monitored by thin layer chromatography (TLC). After filtration the mixture was concentrated in vacuo and 300 mg of the crude product was purified by flash chromatography using ethyl acetate/CH$_2$Cl$_2$ (1:9) giving 4-((benzylamino) methyl)-N,N-dimethylaniline as a yellow/brown oil. $^1$H NMR (300 MHz, CDCl$_3$): δ 7.34 (5H, m), 7.19 (2H, d), 6.68 (2H, d), 3.81 (2H, s), 3.75 (2H, s), 2.92 (6H, s).

Synthesis of Intermediate 7

Preparation of N-(4-methoxybenzyl)-1-(pyridin-4-yl)methanamine

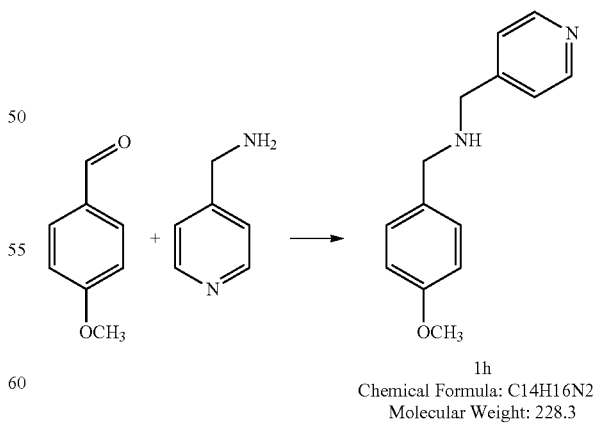

1h
Chemical Formula: C14H16N2O
Molecular Weight: 228.3

To a round bottom flask with a magnetic stirrer bar, 4-picolylamine (0.43 g, 4 mmol) and 4-methoxybenzaldehyde (1.22 g, 9 mmol) were added with 10 ml methanol, NaCNBH$_3$ (0.57 g, 9 mmol) and a few granules of 4 Å molecular sieve. The solution was stirred for 2-12 hours at room temperature and the progress of the reaction was monitored by thin layer chromatography (TLC). After filtration the solution was concentrated in vacuo and to the resulting liquid was added 50 ml dichloromethane and extracted with 3×50 ml 0.05 M HCl. The combined aqueous layer was made basic with NaOH until the pH 10-11 and the solution was extracted with 2×150 ml dichloromethane. The organic layers were combined and dried over anhydrous MgSO$_4$, filtered and evaporated to give N-(4-methoxybenzyl)-1-(pyridin-4-yl)methanamine as a brown oil. Yield: 0.36 g (38%), $^1$H NMR (300 MHz, CDCl$_3$): δ 8.56 (2H, d), 7.28 (4H, m), 6.90 (2H, m), 3.82 (5H, s), 3.76 (2H, s), $^{13}$C NMR (75 MHz, CDCl$_3$): δ 158.9, 149.9, 149.6, 132, 129.4, 128.7, 123.1, 114. 65. 55.4. 52.7, 51.8.

Synthesis of Intermediate 8

Preparation of N-benzyl-2,2-diphenylethanamine

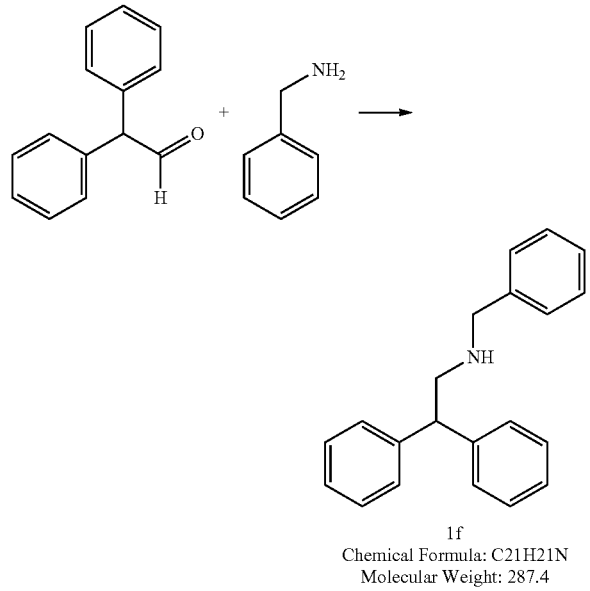

1f
Chemical Formula: C21H21N
Molecular Weight: 287.4

To a round bottom flask with a magnetic stirrer bar benzylamine (0.86 g, 8 mmol) and diphenylacetaldehyde (1.96 g, 10 mmol) were added together with 10 ml methanol, NaCNBH$_3$ (0.64 g, 10 mmol) and a few granules of 4 Å molecular sieve. The solution was stirred for 2-12 hours at room temperature and the progress of the reaction was monitored by thin layer chromatography (TLC). After filtration the mixture was concentrated in vacuo and purified by flash chromatography using ethyl acetate/CH$_2$Cl$_2$ (1:9) giving N-benzyl-2,2-diphenylethanamine as a viscous yellow oil. Yield: 0.45 g (20%), $^1$H NMR (300 MHz, CDCl$_3$): δ 7.19 (15H, m), 4.16 (1H, m), 3.74 (2H, s), 3.18 (2H, m), $^{13}$C NMR (75 MHz, CDCl$_3$): δ 142.5, 139.7, 128.3, 128.1, 128, 127.8, 126.7, 126.3, 125.8, 53.5, 50.9.

Example 2

Preparation of N,N-bis(4-fluorobenzyl)-1-(pyridin-4-yl)methanamine

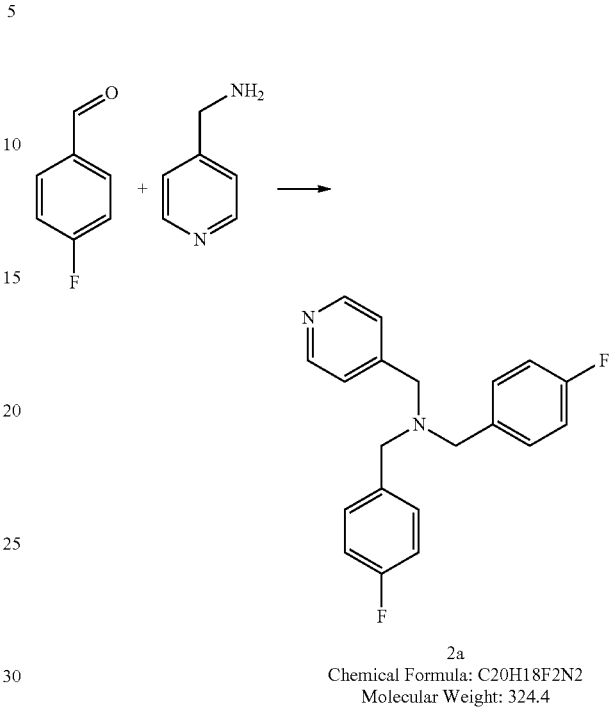

2a
Chemical Formula: C20H18F2N2
Molecular Weight: 324.4

To a round bottom flask with a magnetic stirrer bar 4-picolylamine (0.43 g, 4 mmol) and 4-fluorobenzaldehyde (1.12 g, 9 mmol) were added together with 10 ml methanol, NaCNBH$_3$ (0.57 g, 9 mmol) and a few granules of 4 Å molecular sieve. The solution was stirred for 4 hours at room temperature and the progress of the reaction was monitored by thin layer chromatography (TLC). After filtration the mixture was concentrated in vacuo and the resulting liquid was diluted with 50 ml dichloromethane and extracted with 3×50 ml 0.05 M HCl. The combined aqueous layer was made basic with NaOH until the pH was 10-11 and the solution was extracted with 2×150 ml dichloromethane. The organic layers were combined and dried over anhydrous MgSO$_4$, filtered and evaporated to give N,N-bis(4-fluorobenzyl)-1-(pyridin-4-yl)methanamine as a yellow oil. Yield: 0.49 g (38%) $^1$H NMR (300 MHz, CDCl$_3$): δ 8.53 (2H, d), 7.17 (10H, m), 3.76 (4H, d), 2.34 (2H, s), $^{13}$C NMR (75 MHz, CDCl$_3$): δ 163.4, 160.1, 149.4, 148.9, 135.1, 135, 129.4, 129.3, 128.3, 122.7, 115.1, 114.8, 64.1, 52.1, 51.4.

Example 3

Preparation of 2,2'-(((pyridin-4-ylmethyl)azanediyl) bis(methylene))bis(benzene-1,4-diol)

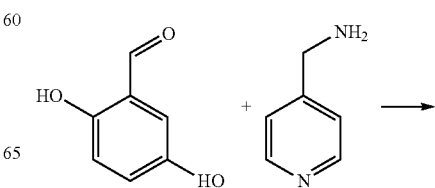

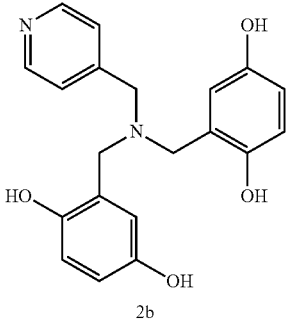

2b
Chemical Formula: C20H20N2O4
Molecular Weight: 352.4

To a round bottom flask with a magnetic stirrer bar 4-picolylamine (0.43 g, 4 mmol) and 2,5-dihydroxybenzaldehyde (1.24 g, 9 mmol) were added together with 10 ml methanol, NaCNBH₃ (0.57 g, 9 mmol) and a few granules of 4 Å molecular sieve. The solution was stirred for 4 hours at room temperature and the progress of the reaction was monitored by thin layer chromatography (TLC). After filtration the mixture was concentrated in vacuo and the resulting liquid was diluted with 50 ml dichloromethane and extracted with 3×50 ml 0.05 M HCl. The combined aqueous layer was made basic with NaOH until the pH was 10-11 and the solution was extracted with 2×150 ml dichloromethane. The organic layers were combined and dried over anhydrous MgSO₄, filtered and evaporated to give 2,2'-(((pyridin-4-ylmethyl)azanediyl)bis(methylene))bis(benzene-1,4-diol) as highly viscous dark brown oil. Yield: 0.88 g (62%), ¹H NMR (300 MHz, DMSO): δ 8.5 (5H, m), 7.35 (4H, m), 6.55 (8H, m), 3.69 (3H, d), 3.16 (4H, s), ¹³C NMR (75 MHz, DMSO): δ 150.6, 150.4, 150, 149.3, 126.1, 124.8, 124.7, 123.9, 116.6, 116.5, 116.3, 114.8, 60, 51.5, 49.8, 49.5.

Example 4

Preparation of N,N-bis(4-fluorobenzyl)-1-(thiazol-2-yl)methanamine

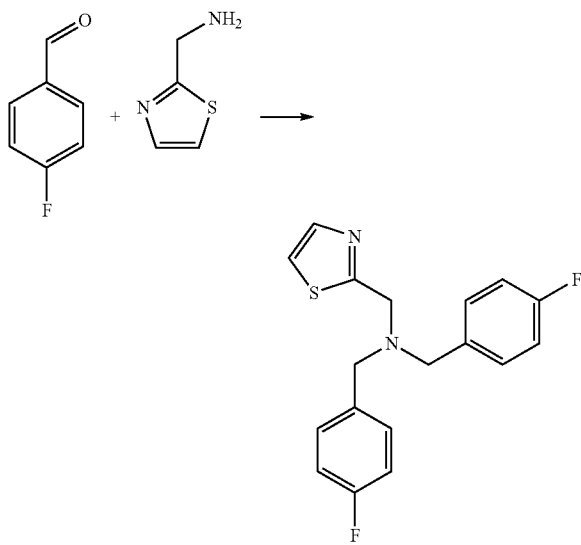

2c
Chemical Formula: C18H16F2N2S
Molecular Weight: 330.4

To a round bottom flask with a magnetic stirrer bar 2-(aminomethyl)thiazole (0.46 g, 4 mmol) and 4-fluorobenzaldehyde (1.12 g, 9 mmol) were added together with 10 ml methanol, NaCNBH₃ (0.57 g, 9 mmol) and a few granules of 4 Å molecular sieve. The solution was stirred overnight at room temperature and the progress of the reaction was monitored by thin layer chromatography (TLC). After filtration the mixture was concentrated in vacuo and the resulting liquid was diluted with 50 ml dichloromethane and extracted with 3×50 ml 0.05 M HCl. The combined aqueous layer was made basic with NaOH until the pH was 10-11 and the solution was extracted with 2×150 ml dichloromethane. The organic layers were combined and dried over anhydrous MgSO₄, filtered and evaporated to give N,N-bis(4-fluorobenzyl)-1-(thiazol-2-yl)methanamine as a dark brown oil. Yield: 0.91 g (69%), ¹H NMR (300 MHz, CDCl₃): δ 7.73 (1H, d), 7.32 (5H, m), 7.04 (4H, m), 4.67 (2H, s), 4.14 (2H, s), 3.86 (2H, s), ¹³C NMR (75 MHz, CDCl₃): δ 171.7, 164, 163.8, 160.8, 160.6, 142.7, 135.5, 135.4, 129.9, 129.8, 128.8, 119, 115.6, 115.5, 115.3, 115.2, 64.6, 52.5, 50.2.

Example 5

Preparation of N,N-bis(4-methoxybenzyl)-1-(thiazol-2-yl)methanamine

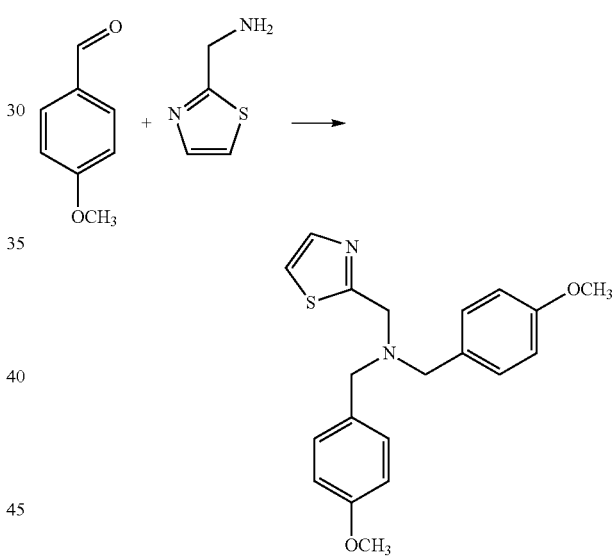

2d
Chemical Formula: C20H22N2O2S
Molecular Weight: 354.5

To a round bottom flask with a magnetic stirrer bar 2-(aminomethyl)thiazole (0.46 g, 4 mmol) and 4-methoxybenzaldehyde (1.22 g, 9 mmol) were added together with 10 ml methanol, NaCNBH₃ (0.57 g, 9 mmol) and a few granules of 4 Å molecular sieve. The solution was stirred overnight at room temperature and the progress of the reaction was monitored by thin layer chromatography (TLC). After filtration the mixture was concentrated in vacuo and the resulting liquid was diluted with 50 ml dichloromethane and extracted with 3×50 ml 0.05 M HCl. The combined aqueous layer was made basic with NaOH until the pH was 10-11 and the solution was extracted with 2×150 ml dichloromethane. The organic layers were combined and dried over anhydrous MgSO₄, filtered and evaporated to give N,N-bis(4-methoxybenzyl)-1-(thiazol-2-yl)methanamine as a dark brown oil. Yield: 1 g (70%), ¹H NMR (300 MHz, CDCl$_3$): δ 7.73 (1H, d), 7.29 (5H, m), 6.9 (4H, m), 4.62 (2H, s), 4.13 (2H, s), 3.81 (8H, s), $^{13}$C NMR (75 MHz, CDCl$_3$): δ 172, 159.2, 158.9, 142.6, 133.4, 131.8, 129.5, 128.7, 118.9, 114, 65, 55.4, 52.7, 50.1.

Example 6

Preparation of N-benzyl-N-(4-methoxybenzyl)-1-(4-methoxyphenyl)methanamine

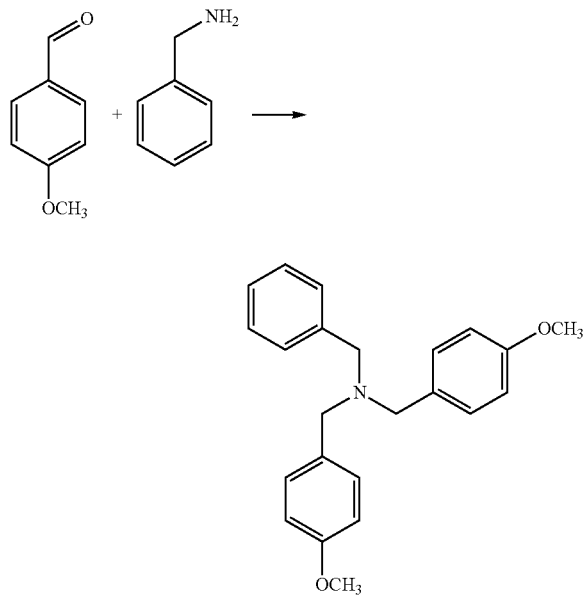

2e
Chemical Formula: C23H25NO2
Molecular Weight: 347.5

To a round bottom flask with a magnetic stirrer bar benzylamine (0.43 g, 4 mmol) and 4-methoxybenzaldehyde (1.22 g, 9 mmol) were added together with 10 ml methanol, NaCNBH$_3$ (0.57 g, 9 mmol) and a few granules of 4 Å molecular sieve. The solution was stirred for 6 hours at room temperature and the progress of the reaction was monitored by thin layer chromatography (TLC). After filtration the mixture was concentrated in vacuo and the resulting liquid was diluted with 50 ml dichloromethane and extracted with 3×50 ml 0.05 M HCl. The combined aqueous layer was made basic with NaOH until the pH was 10-11 and the solution was extracted with 2×150 ml dichloromethane. The organic layers were combined and dried over anhydrous MgSO$_4$, filtered and evaporated to give N-benzyl-N-(4-methoxybenzyl)-1-(4-methoxyphenyl)methanamine as a pale yellow oil. Yield: 0.29 g (20%), $^1$H NMR (300 MHz, CDCl$_3$): δ 7.35 (9H, m), 6.91 (4H, m), 3.8 (12H, m), $^{13}$C NMR (75 MHz, CDCl$_3$): δ 159.2, 140.9, 133, 129.9, 129.2, 128.9, 128.7, 127.5, 114.5, 114.3, 65.6, 55.8, 53.6, 53.1.

Example 7

Preparation of dimethyl 4,4'-((benzylazanediyl)bis(methylene))dibenzoate

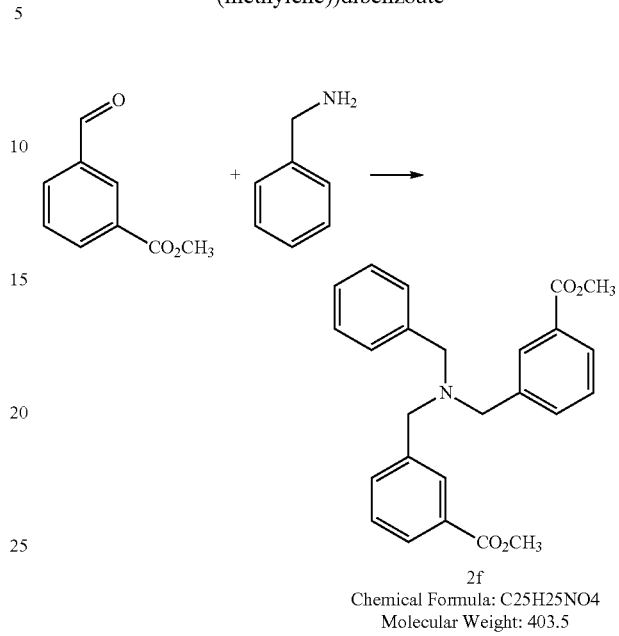

2f
Chemical Formula: C25H25NO4
Molecular Weight: 403.5

To a round bottom flask with a magnetic stirrer bar benzylamine (0.107 g, 1 mmol) and methyl 3-formylbenzoate (0.49 g, 3 mmol) were added together with 10 ml methanol, NaCNBH$_3$ (0.19 g, 3 mmol) and a few granules of 4 Å molecular sieve. The solution was stirred for 6 hours at room temperature and the progress of the reaction was monitored by thin layer chromatography (TLC). After filtration the mixture was concentrated in vacuo and the resulting liquid was diluted with 20 ml dichloromethane and extracted with 3×20 ml 0.05 M HCl. The combined aqueous layer was made basic with NaOH until the pH was 10-11 and the solution was extracted with 3×60 ml dichloromethane. The organic layers were combined and dried over anhydrous MgSO$_4$, filtered and evaporated to give dimethyl 4,4'-((benzylazanediyl)bis(methylene))dibenzoate as a pale yellow oil. Yield: 0.14 g (18%), $^{13}$C NMR (75 MHz, CDCl$_3$): δ 169.3, 167.1, 141.5, 140.7, 140, 132.9, 131.5, 130.5, 130.4, 129.4, 128.9, 128.7, 128.6, 128.4, 128.3, 128, 127.2, 64.8, 53.3, 52.8, 52.3, 52.4.

Example 8

Preparation of 4-((benzyl(4-(dimethylamino)benzyl)amino)methyl)-N,N-dimethylaniline

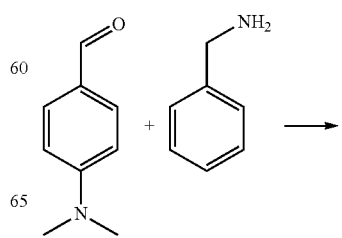

-continued

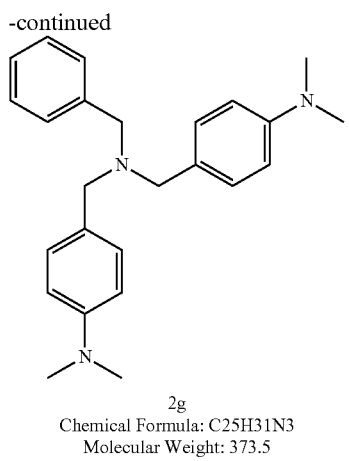

2g
Chemical Formula: C25H31N3
Molecular Weight: 373.5

To a round bottom flask with a magnetic stirrer bar benzylamine (0.43 g, 4 mmol) and 4-(dimethylamino)benzaldehyde (1.6 g, 10.7 mmol) were added together with 10 ml methanol, NaCNBH$_3$ (0.57 g, 9 mmol) and a few granules of 4 Å molecular sieve. The solution was stirred overnight at room temperature and the progress of the reaction was monitored by thin layer chromatography (TLC). After filtration the mixture was concentrated in vacuo and 100 mg of the crude product was purified by flash chromatography using ethyl acetate/CH$_2$Cl$_2$ (1:9) giving 4-((benzyl(4-(dimethylamino)benzyl)amino)methyl)-N,N-dimethylaniline as a highly viscous brown oil. $^{13}$C NMR (75 MHz, CDCl$_3$): δ 150.3, 140.9, 130.2, 129.3, 128.6, 128.3, 127.1, 113.1, 57.9, 57.5, 41.4.

Example 9

Preparation of 4-(((4-(dimethylamino)benzyl)(1-phenylethyl)amino)methyl)-N,N-dimethylaniline

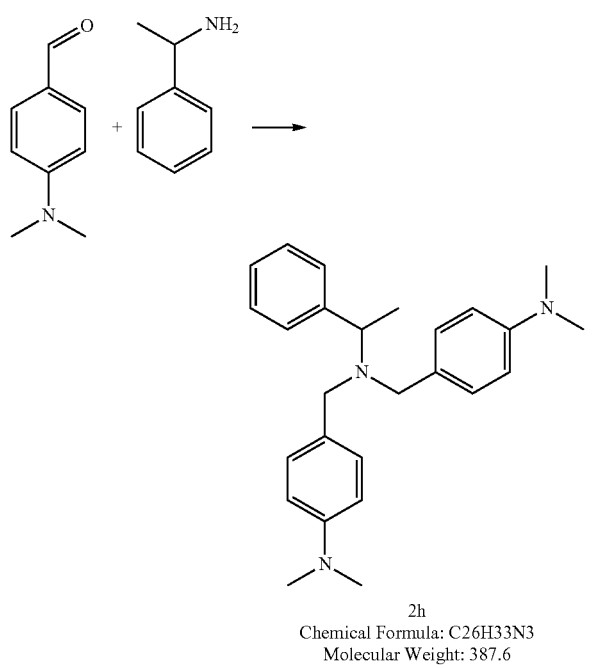

2h
Chemical Formula: C26H33N3
Molecular Weight: 387.6

To a round bottom flask with a magnetic stirrer bar 1-phenylethylamine (0.48 g, 4 mmol) and 4-(dimethylamino)benzaldehyde (1.34 g, 9 mmol) were weighed in and added 10 ml methanol, NaCNBH$_3$ (0.57 g, 9 mmol) and a few granules of molecular sieve 4 Å. The solution was stirred for 6 hours at room temperature and the progress of the reaction was monitored by thin layer chromatography (TLC). After filtration the mixture was concentrated in vacuo and 100 mg of the crude product was purified by flash chromatography using ethyl acetate/CH$_2$Cl$_2$ (1:9) giving 4-(((4-(dimethylamino)benzyl)(1-phenylethyl)amino)methyl)-N,N-dimethylaniline as a highly viscous brown oil.
$^1$H NMR (300 MHz, CDCl$_3$): δ 7.28 (10H, m), 3.72 (2H, d), 3.84 (1H, q), 2.94 (6H, s), 2.19 (12H, s), 1.38 (3H, d), $^{13}$C NMR (75 MHz, CDCl$_3$): δ 150, 146.1, 145.5, 129.3, 129.2, 128.6, 128.4, 127.1, 126.9, 125.4, 112.9, 57.4, 51.1, 40.9, 25.5, 24.4.

Example 10

Preparation of N-(4-(tert-butyl)benzyl)-N-(4-fluorobenzyl)-1-(pyridin-4-yl)methanamine

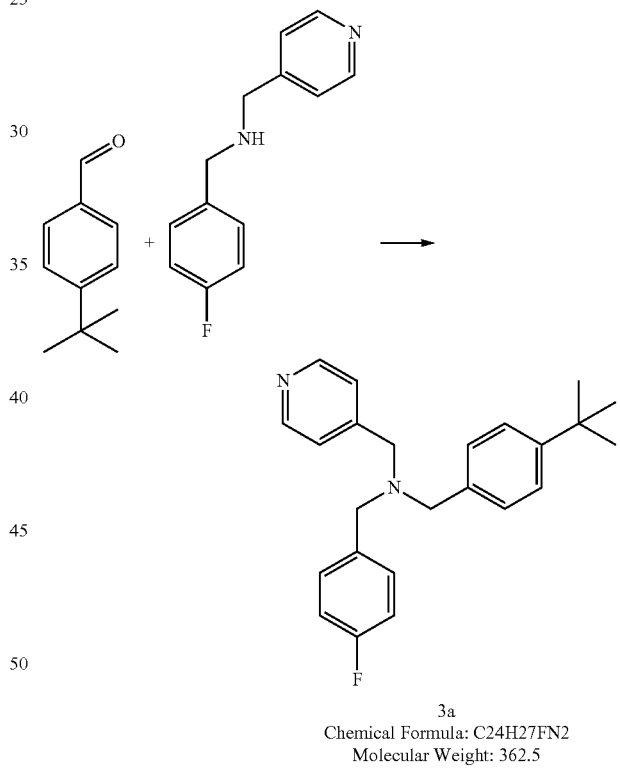

3a
Chemical Formula: C24H27FN2
Molecular Weight: 362.5

To a round bottom flask with a magnetic stirrer bar Intermediate 1 (0.66 g, 3 mmol) and 4-tert-butylbenzaldehyde (1.29 g, 8 mmol) were added together with 10 ml methanol, NaCNBH$_3$ (0.50 g, 8 mmol) and a few granules of 4 Å molecular sieve. The solution was stirred for 8 hours at room temperature and the progress of the reaction was monitored by thin layer chromatography (TLC). After filtration the mixture was concentrated in vacuo and the resulting liquid was diluted with 30 ml dichloromethane and extracted with 3×30 ml 0.05 M HCl. The combined aqueous layer was made basic with NaOH until the pH was 10-11 and the solution was extracted with 2×100 ml dichloromethane.

The organic layers were combined and dried over anhydrous MgSO$_4$, filtered and evaporated to give N-(4-(tert-butyl)benzyl)-N-(4-fluorobenzyl)-1-(pyridin-4-yl)methanamine as a yellow oil. Yield: 0.19 g (18%), $^1$H NMR (300 MHz, CDCl$_3$): δ 8.57 (2H, d), 7.2 (10H, m), 3.81 (4H, d), 3.55 (2H, m), 1.3 (9H, m), $^{13}$C NMR (75 MHz, CDCl$_3$): δ 149.6, 149, 135.2, 129.4, 129.3, 126.6, 125.2, 125, 123.3, 122.7, 115.1, 114.9, 52.1, 51.5, 31.1, 29.4.

Example 11

Preparation of 2-(((4-fluorobenzyl)(pyridin-4-ylmethyl)amino)methyl)benzene-1,4-diol

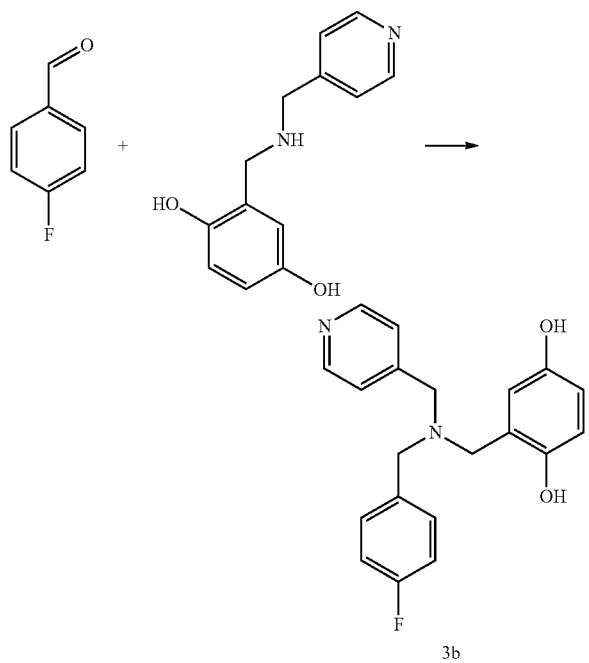

3b
Chemical Formula :
C20H19FN2O2
Molecular Weight: 338.4

To a round bottom flask with a magnetic stirrer bar Intermediate 3 (0.23 g, 1 mmol) and 4-fluorobenzaldehyde (0.37 g, 3 mmol) were added together with 10 ml methanol, NaCNBH$_3$ (0.19 g, 3 mmol) and a few granules of 4 Å molecular sieve. The solution was stirred for 8 hours at room temperature and the progress of the reaction was monitored by thin layer chromatography (TLC). After filtration the mixture was concentrated in vacuo and the resulting liquid was diluted with 30 ml dichloromethane and extracted with 3×30 ml 0.05 M HCl. The combined aqueous layer was made basic with NaOH until the pH was 10-11 and the solution was extracted with 2×100 ml dichloromethane. The organic layers were combined and dried over anhydrous MgSO$_4$, filtered and evaporated to give 2-(((4-fluorobenzyl)(pyridin-4-ylmethyl)amino)methyl)benzene-1,4-diol as a brown oil. Yield: 0.39 g (100%), $^1$H NMR (300 MHz, DMSO): δ 8.51 (2H, d), 7.36 (4H, m), 7.14 (2H, m), 6.80 (1H, s), 6.60 (1H, s), 6.48 (1H, s), 3.32 (6H, s), $^{13}$C NMR (75 MHz, DMSO): δ 149.9, 149.6, 148.2, 148, 138.7, 134.6, 130.5, 130.4, 128.4, 128.3, 124.4, 123.5, 115.7, 115.6, 115.2, 114.9, 114.6, 114.3, 62.1, 56.5, 56, 52.1.

Example 12

Preparation of 4-((benzyl(2,2-diphenylethyl)amino)methyl)-N,N-dimethylaniline

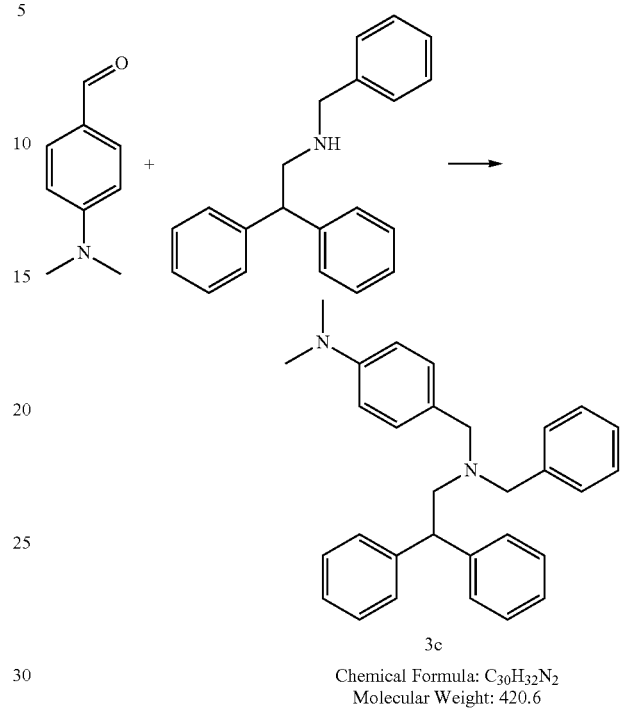

3c
Chemical Formula: C30H32N2
Molecular Weight: 420.6

To a round bottom flask with a magnetic stirrer bar Intermediate 8 (0.24 g, 0.83 mmol) and 4-(dimethylamino)benzaldehyde (0.18 g, 1.2 mmol) were added together with 10 ml methanol, NaCNBH$_3$ (0.10 g, 1.59 mmol) and a few granules of 4 Å molecular sieve. The solution was stirred for 6 hours at room temperature and the progress of the reaction was monitored by thin layer chromatography (TLC). After filtration the mixture was concentrated in vacuo and the crude product was purified by flash chromatography using ethyl acetate/CH$_2$Cl$_2$ (1:9) giving 4-((benzyl(2,2-diphenylethyl)amino)methyl)-N,N-dimethylaniline as a yellow oil. $^1$H NMR (300 MHz, CDCl$_3$): δ 7.15 (15H, m), 6.91 (2H, d), 6.57 (2H, d), 4.17 (1H, t), 3.47 (4H, d), 2.96 (2H, d). 2.84 (6H, s).

Example 13

Preparation of 4-((benzyl((2,3-dihydrobenzofuran-6-yl)methyl)amino)methyl)-N,N dimethylaniline

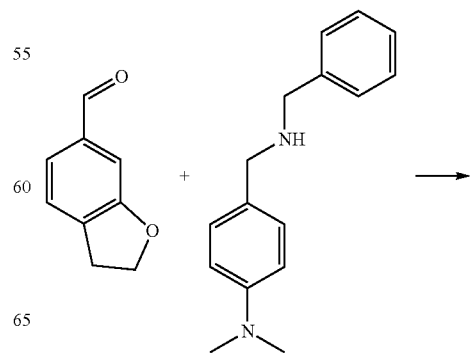

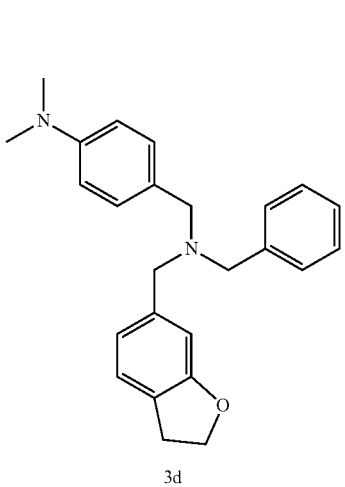

3d
Chemical Formula: C$_{25}$H$_{28}$N$_2$O
Molecular Weight: 372.5

To a round bottom flask with a magnetic stirrer bar Intermediate 6 (0.4 g, 1.4 mmol) and 2,3-dihydrobenzofuran-5-carboxaldehyde (0.37 g, 2.5 mmol) were added together with 10 ml methanol, NaCNBH$_3$ (0.16 g, 2.5 mmol) and a few granules of 4 Å molecular sieve. The solution was stirred for 8 hours at room temperature and the progress of the reaction was monitored by thin layer chromatography (TLC). After filtration the mixture was concentrated in vacuo and 100 mg of the crude product was purified by flash chromatography using 5-10% ethyl acetate in dichloromethane giving 4-((benzyl((2,3-dihydrobenzofuran-6-yl)methyl) amino)methyl)-N,N-dimethylaniline as a viscous yellow oil. $^1$H NMR (300 MHz, CDCl$_3$): δ 7.22 (9H, m), 7.02 (1H, d), 6.64 (2H, d), 4.47 (2H, t), 3.45 (2H, s), 3.38 (4H, s), 3.12 (2H, t), 2.85 (6H, s), $^{13}$C NMR (75 MHz, CDCl$_3$): δ 159.4, 150.1, 140.5, 132.2, 130, 129.1, 128.9, 128.5, 127.9, 127.1, 127, 125.8, 113, 109, 71.6, 57.9, 57.7, 57.4, 51.2, 30.2.

Example 14

Preparation of methyl 4-((benzyl(4-fluorobenzyl)amino)methyl)benzoate

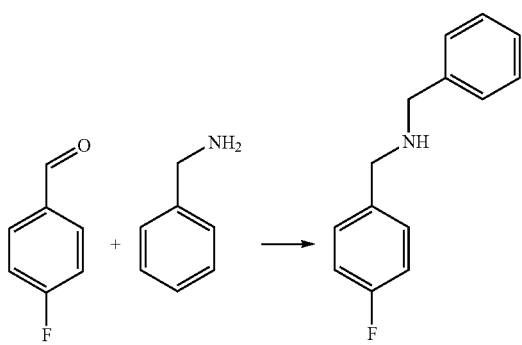

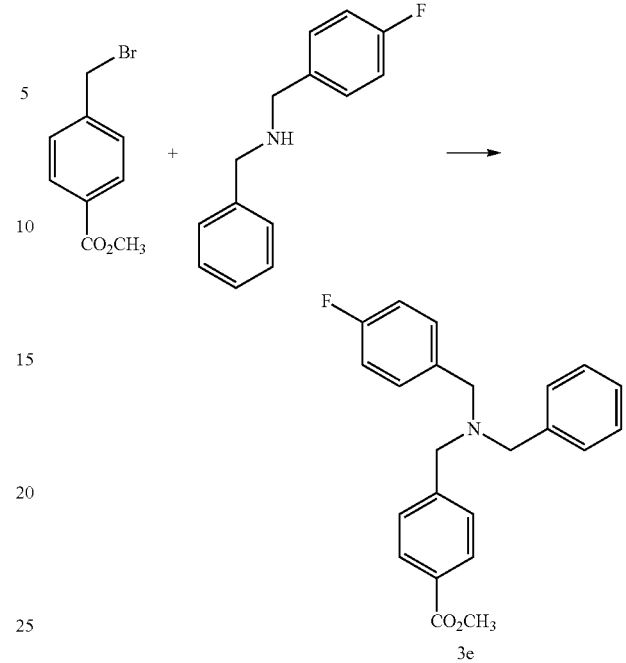

3e
Chemical Formula: C$_{23}$H$_{22}$FNO$_2$
Molecular Weight: 363.4

First Step

To a round bottom flask with a magnetic stirrer bar benzylamine (2.14 g, 10 mmol) and 4-fluorobenzaldehyde (1.55 g, 12.5 mmol) were added together with 10 ml methanol, NaCNBH$_3$ (0.79 g, 12.5 mmol) and a few granules of 4 Å molecular sieve. The solution was stirred for 4 hours at room temperature and the progress of the reaction was monitored by thin layer chromatography (TLC). After filtration the solution was concentrated in vacuo and the resulting liquid was diluted with 50 ml dichloromethane and extracted with 3×50 ml 0.05 M HCl. The combined aqueous layer was made basic with NaOH until the pH was 10-11 and the solution was extracted with 2×150 ml dichloromethane. The organic layers were combined and dried over anhydrous MgSO$_4$, filtered and evaporated to give N-benzyl-1-(4-fluorophenyl)methanamine.

Second Step

N-benzyl-1-(4-fluorophenyl)methanamine (0.61 g, 2.7 mmol) was added to 20 ml acetone in a round bottom flask. To the solution methyl 4-(bromomethyl)benzoate (1.15 g, 5 mmol) and K$_2$CO$_3$ (1.38 g, 10 mmol) were added and the reaction mixture was stirred for 4 hours at 55° C. at reflux. The progress of the reaction was monitored by thin layer chromatography (TLC), and when the reaction was complete the mixture was filtered and concentrated in vacuo. The crude product was purified by flash chromatography using 5-10% ethyl acetate in dichloromethane giving methyl 4-((benzyl(4-fluorobenzyl)amino)methyl)benzoate as a pale yellow oil. $^1$H NMR (300 MHz, CDCl$_3$): δ 7.92 (2H, d), 7.38 (2H, d), 7.24 (7H, m), 6.92 (2H, t), 3.83 (3H, s), 3.5 (2H, s), 3.46 (2H, s), 3.43 (2H, s).

Example 15

Preparation of 4-((benzyl(4-fluorobenzyl)amino)methyl)benzoic acid

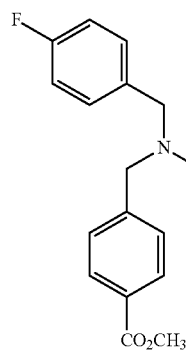

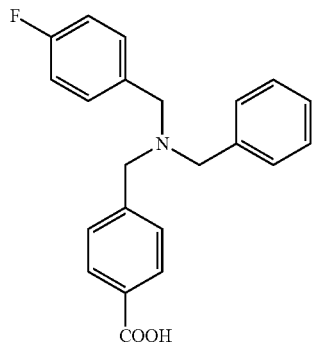

3f
Chemical Formula: $C_{22}H_{20}FNO_2$
Molecular Weight: 349.4

The product from Example 13 was diluted in 0.1 M NaOH (15 ml) and added to 10 ml methanol. The reaction mixture was stirred for 8 hours at 60° C. at reflux, and methanol was evaporated off on rotary evaporator. The remaining aqueous phase was acidified with HCl until pH 5 and extracted with 3×20 ml dichloromethane. The combined organic phase was dried over anhydrous $MgSO_4$ and concentrated in vacuo to give 4-((benzyl(4-fluorobenzyl)amino)methyl)benzoic acid as a pale yellow oil. $^1$H NMR (300 MHz, $CDCl_3$): δ 7.98 (2H, d), 7.41 (2H, d), 7.24 (7H, m), 6.92 (2H, t), 3.52 (2H, s), 3.46 (2H, s), 3.44 (2H, s).

Example 16

Preparation of 1-(2'-(2H-tetrazol-5-yl)-[1,1'-biphenyl]-4-yl)-N-benzyl-N-(4-fluorobenzyl)methanamine

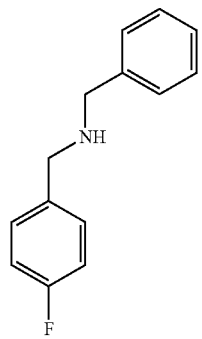

+

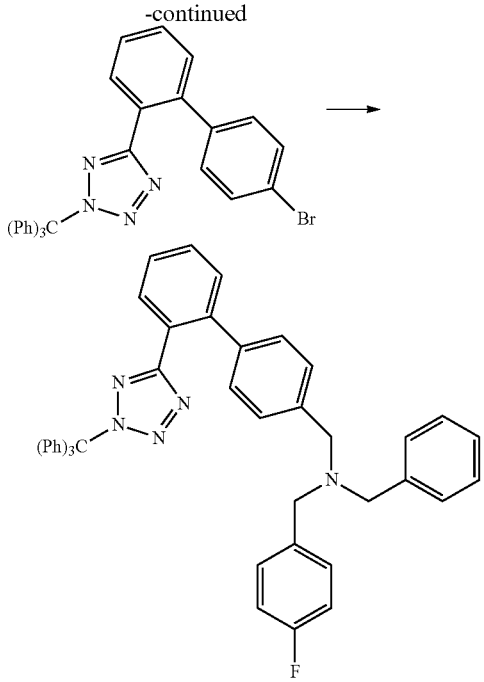

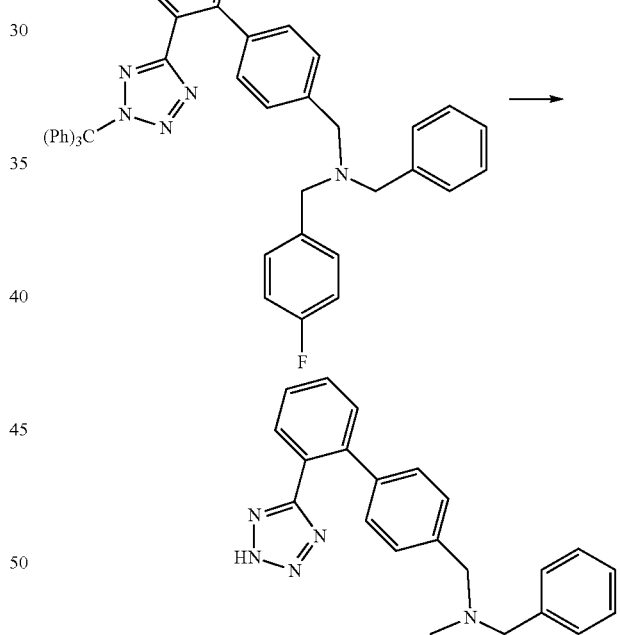

Chemical Formula: $C_{28}H_{24}FN_5$
Molecular Weight: 449.5

First Step

To a round bottom flask with a magnetic stirrer bar N-benzyl-1-(4-fluorophenyl)methanamine (0.4 g, 1.97 mmol) and 5-(4'-bromo-[1,1'-biphenyl]-2-yl)-2-trityl-2H-tetrazole (1.4 g, 2.5 mmol) were added together with 10 ml acetone and K$_2$CO$_3$ (0.69 g, 5 mmol). The reaction mixture was stirred for 4 hours at 55° C. at reflux. The progress of the reaction was monitored by thin layer chromatography (TLC). After filtration the solution was concentrated in vacuo and the crude product was purified by flash chromatography using 5-10% ethyl acetate in dichloromethane giving 0.2 g of the tertiary amine.

Second Step

The tertiary amine from the first step of the reaction (0.2 g, 0.29 mmol) was added 10 ml of a solution of trifluoro acetic acid/dichloromethane/methanol (2:1:1) and stirred for 3 hours at room temperature. The crude product was purified by flash chromatography using 5-10% ethyl acetate in dichloromethane giving 1-(2'-(2H-tetrazol-5-yl)-[1,1'-biphenyl]-4-yl)-N-benzyl-N-(4-fluorobenzyl)methanamine as a pale brown oil. $^1$H NMR (300 MHz, CDCl$_3$): δ 10.77 (1H, s), 8.08 (2H, d), 7.42 (10H, m), 7.03 (2H, t), 3.57 (6H, m), $^{13}$C NMR (75 MHz, CDCl$_3$): δ 164, 160.7, 146.3, 139.4, 135.2, 130.6, 130.5, 129.1, 129, 128.7, 127.5, 115.6, 115.4, 58.4, 58, 57.7.

Example 17

Synthesis of dimethyl 4,4'-((benzylazanediyl)bis(methylene))dibenzoate

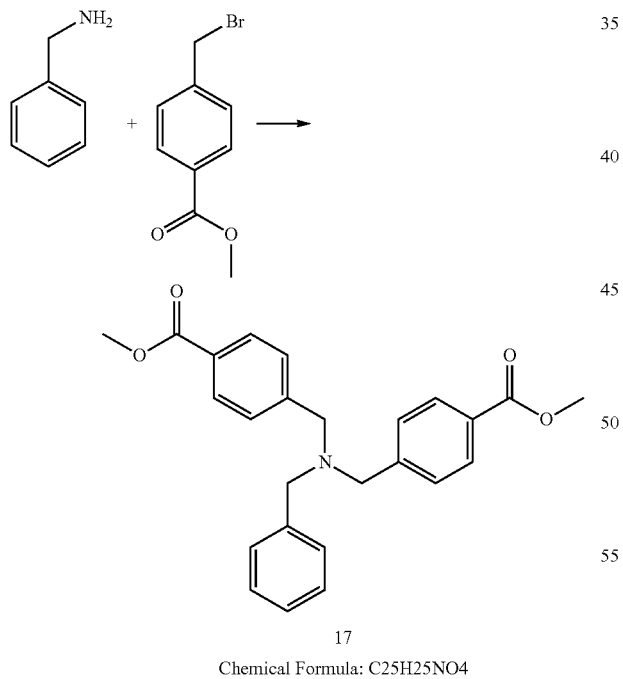

17
Chemical Formula: C25H25NO4
Molecular Weight: 403.5

To a suspension of benzylamine (1.07 g, 10 mmol) and potassium carbonate (2.76 g, 20 mmol) in acetone (20 ml) was added methyl 4-(bromomethyl)benzoate (4.58 g, 20 mmol) and the reaction mixture was heated to reflux overnight, cooled to room temperature and evaporated in vacuo. The residue was separated with flash chromatography (dichloromethane) to give dimethyl 4,4'-((benzylazanediyl)bis(methylene))dibenzoate as a brown viscous oil. Yield: 1.4 g (35%); TLC: R$_f$: 0.85 (10% methanol in dichloromethane); $^1$H NMR (400 MHz, CDCl$_3$): δ 7.91 (4H, d), 7.38 (4H, d), 7.23 (5H, m), 3.81 (6H, s), 3.51 (4H, s), 3.46 (2H, s); $^{13}$C NMR (400 MHz, CDCl$_3$): δ 167.0, 144.9, 138.8, 129.7, 129.0, 128.8, 128.6, 128.3, 127.2, 58.2, 57.8, 52.0 ($^{13}$C NMR had some overlapping signals).

Example 18

Synthesis of 4,4'-((benzylazanediyl)bis(methylene)dibenzoic acid

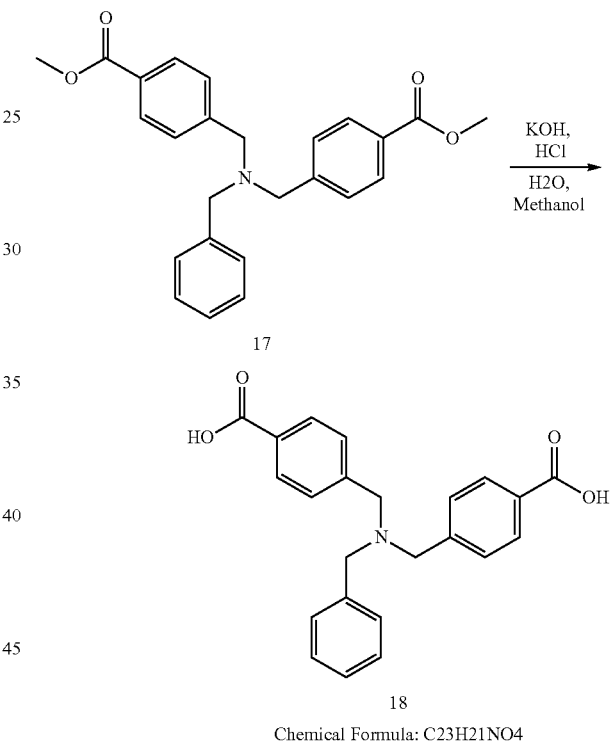

18
Chemical Formula: C23H21NO4
Molecular Weight: 375.4

Compound 17 (0.4 g, 1 mmol) was added to a suspension of potassium hydroxide (0.17 g, 3 mmol) in 2 ml of 50:50 water/methanol. After 15 minutes 1M HCl was added until the mixture became acidic and then washed with water. The residue was subsequently suspended in toluene and dried in vacuo. Removal of toluene (as an azeotropic mixture with water) yielded 4,4'-((benzylazanediyl)bis(methylene)dibenzoic acid as light brown crystals. Yield: 0.21 g (56%); TLC: R$_f$: 0.17 (10% methanol in dichloromethane); $^1$H NMR (400 MHz, DMSO): δ 12.83 (2H, s), 7.93 (4H, d), 7.52 (4H, d), 7.38 (5H, m), 3.58 (4H, s), 3.52 (2H, s); $^{13}$C NMR (400 MHz, DMSO): δ 167.1, 144.2, 138.6, 129.6, 129.4, 128.5, 128.3, 127.0, 57.2, 56.8 ($^{13}$C NMR had some overlapping signals).

Example 19

Synthesis of N-benzyl-N-(4-(tert-butyl)benzyl)-1-(4-(tert-butyl)phenyl)methanamine

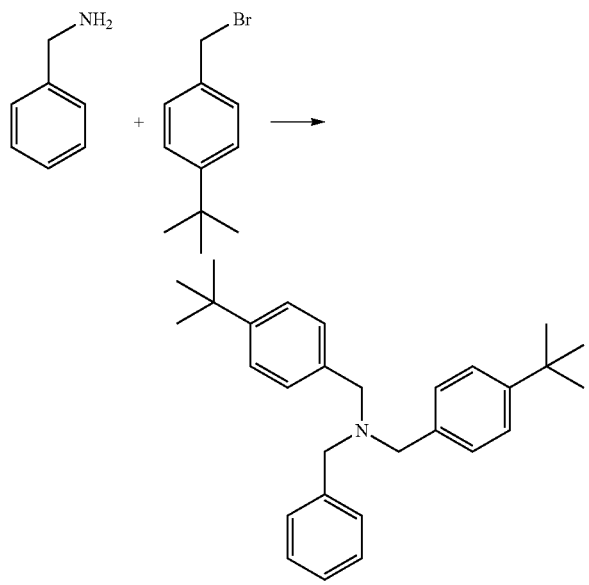

19

Chemical Formula: C29H37N
Molecular Weight: 399.6

Benzylamine (0.536 g, 5 mmol), sodium hydrogen carbonate (0.92 g, 11 mmol) and sodium dodecyl sulfate (approx. 20 mg) were added to water (20 ml) in a 50 ml round-bottom flask, along with a stirring magnet. The mixture was heated at 80° C. for 5 min. 4-tert-Butylbenzyl bromide (2.5 g, 11 mmol) was added to the mixture and subsequently heated to 80° C. for 1 hour. The reaction mixture was cooled to room temperature and the residue filtered and dried, before being recrystallized from a 1:1 mixture of hexane and ethyl acetate to yield N-benzyl-N-(4-(tert-butyl)benzyl)-1-(4-(tert-butyl)phenyl)methanamine as a white crystalline powder. Yield: 1.55 g (78%); TLC: $R_f$: 0.88 (10% methanol in dichloromethane); $^1$H NMR (400 MHz, CDCl$_3$): δ 7.38 (13H, m), 3.60 (6H, d), 1.34 (18H, s); $^{13}$C NMR (400 MHz, CDCl$_3$): δ 127.7, 127.3, 126.6, 125.9, 124.7, 124.5, 124.3, 124.1 ($^{13}$C NMR had some overlapping signals).

Example 20

Synthesis of N-benzyl-N-(4-nitrobenzyl)-1-(4-nitrophenyl)methanamine

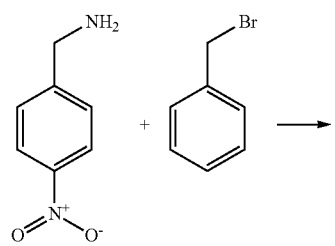

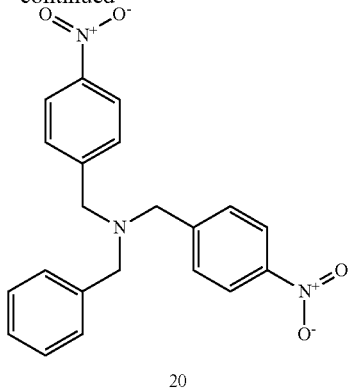

20

Chemical Formula: C21H19N3O4
Molecular Weight: 377.4

Benzylamine (0.536 g, 5 mmol), sodium hydrogen carbonate (0.92 g, 11 mmol) and sodium dodecyl sulfate (approx. 20 mg) were added to water (20 ml) in a 50 ml round-bottom flask, along with a stirring magnet. The mixture was heated at 80° C. for 5 min. 4-nitrobenzylbromide (2.37 g, 11 mmol) was added to the mixture and subsequently heated to 80° C. for 1 hour. The reaction mixture was cooled to room temperature and the residue filtered and dried, before being recrystallized from a 1:1 mixture of hexane and ethyl acetate to yield N-benzyl-N-(4-nitrobenzyl)-1-(4-nitrophenyl)methanamine as a white crystalline powder. Yield: 0.94 g (50%); TLC: $R_f$=0.86 (10% methanol in dichloromethane); $^1$H NMR (400 MHz, CDCl$_3$): δ 8.21 (4H, d), 7.58 (4H, d), 7.32 (5H, m), 3.69 (4H, s), 3.60 (2H, s); $^{13}$C NMR (400 MHZ, CDCl$_3$): δ 147.3, 146.8, 138.0, 129.2, 128.7, 128.6, 127.6, 123.7, 58.5, 57.6.

Example 21

Synthesis of tris(4-nitrobenzyl)amine

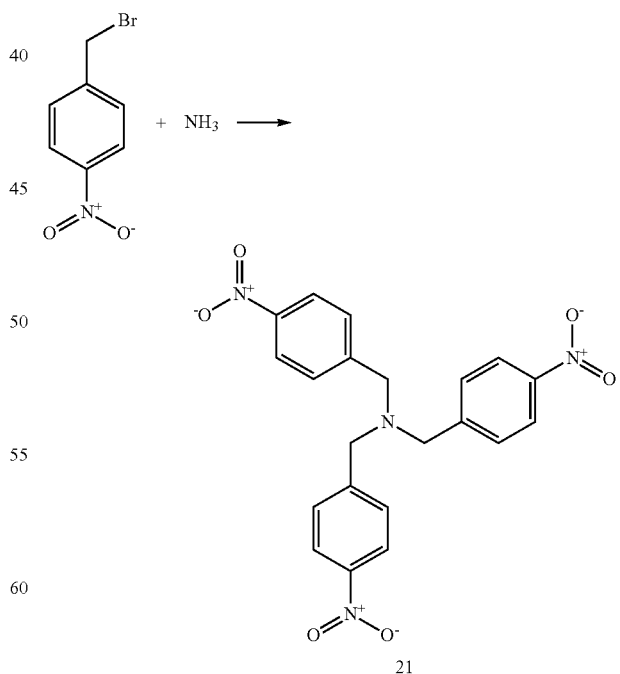

21

Chemical Formula: C21H18N4O6
Molecular Weight: 422.4

A mixture of 4-nitrobenzyl bromide (6.48 g, 30 mmol) and aqueous ammonia solution (30-33%, 2 ml) in methanol (15 ml) was heated in a sealed tube at 100° C. for 4 hours. Then it was cooled to room temperature and poured into water (80 ml). The resulting mixture was extracted three times with dichloromethane and the combined organic layers were dried over sodium sulfate. Removal of the solvents yielded a yellow solid, which was recrystallized in ethyl acetate to give tris(4-nitrobenzyl)amine as a light yellow crystal. Yield: 0.63 g (15%); TLC: $R_f$: 0.87 (10% methanol in dichloromethane); $^1$H NMR (400 MHz, CDCl$_3$): δ 8.25 (6H, d), 7.56 (6H, d), 3.70 (6H, s); $^{13}$C NMR (400 MHz, CDCl$_3$): δ 147.5, 145.8, 129.2, 123.9, 57.8.

Example 22

Synthesis of 4-(((4-aminobenzyl)(benzyl)amino)methyl)aniline

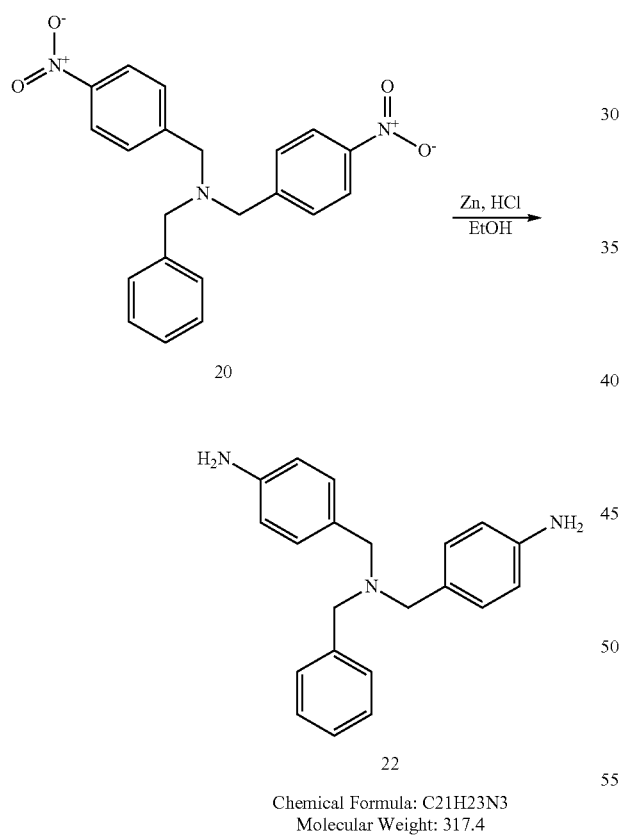

22

Chemical Formula: C21H23N3
Molecular Weight: 317.4

N-benzyl-N-(4-nitrobenzyl)-1-(4-nitrophenyl)methanamine (compound 20) (2.19 g, 5.81 mmol), calcium chloride (0.782 g, 5.32 mmol) and acid-washed zinc (15 g) were suspended in 125 ml of ethanol. The mixture was refluxed for 2 hours, cooled to room temperature, filtered and dried in vacuo, before being recrystallized from a 1:1 mixture of hexane and diethyl ether to yield 4-(((4-aminobenzyl)(benzyl)amino)methyl)aniline as a light yellow crystalline powder. Yield: 0.37 g (20%); TLC: $R_f$: 0.51 (10% methanol in dichloromethane); $^1$H NMR (400 MHz, DMSO): δ 7.33 (5H, m), 7.21 (4H, d), 6.97 (4H, d), 4.90 (4H, s), 3.40 (2H, s), 3.27 (4H, s); $^{13}$C NMR (400 MHz, DMSO): δ 147.3, 139.9, 129.2, 128.3, 128.1, 126.7, 125.4, 113.7, 56.4, 48.6.

Example 23

Synthesis of 4-((benzyl(4-(diethylamino)benzyl)amino)methyl)-N,N-diethylaniline

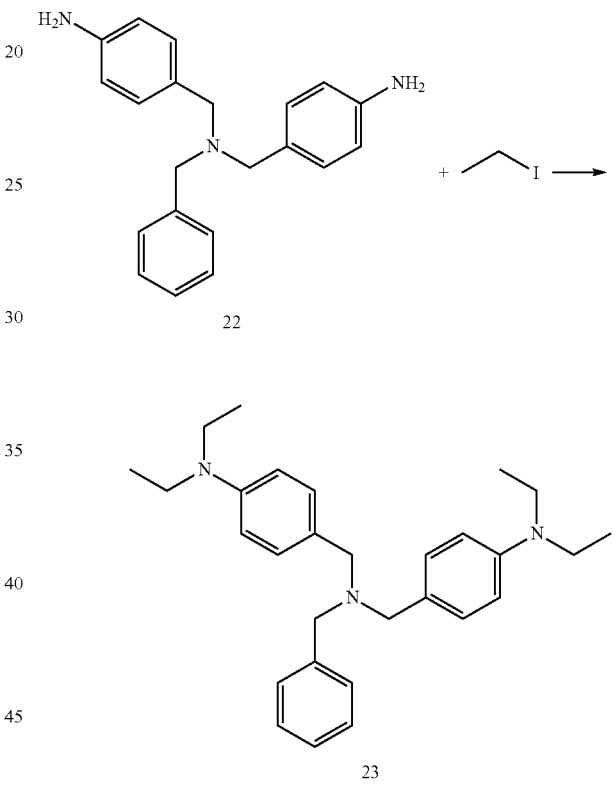

23

Chemical Formula: C29H39N3
Molecular Weight: 429.7

A suspension of 4-((benzyl(4-(diethylamino)benzyl)amino)methyl)-N,N-diethylaniline (compound 22) (0.6 g, 1.9 mmol) and potassium carbonate (2.76 g, 20 mmol) in acetone (50 ml) was added ethyl iodide (3.92 g, 20 mmol) and the reaction mixture was heated to reflux overnight, cooled to room temperature and evaporated in vacuo. The residue was separated with flash chromatography (10% methanol in dichloromethane) to give 4-((benzyl(4-(diethylamino)benzyl)amino)methyl)-N,N-diethylaniline as a viscous brown oil. Yield: 0.05 g (6.1%-NB $^1$H NMR indicated that the substance was not completely dry); TLC: $R_f$: 0.82 (10% methanol in dichloromethane); $^1$H NMR (300 MHz, CDCl$_3$): δ 7.40 (9H, m), 6.74 (4H, m), 3.66 (2H, s), 3.58 (4H, s), 3.42 (8H, q), 1.25 (12H, t).

Example 24

Synthesis of 4-((bis(4-aminobenzyl)amino)methyl)aniline

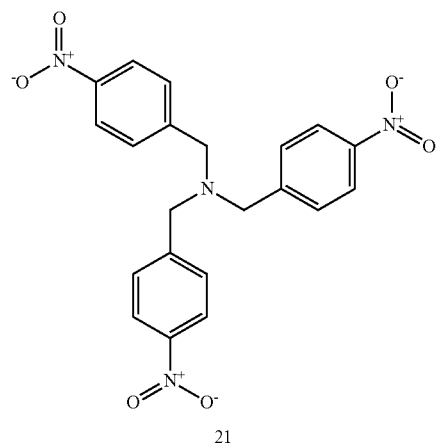

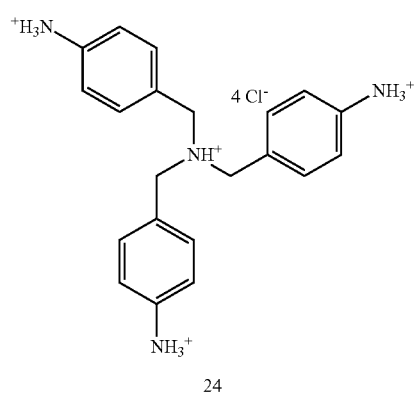

Chemical Formula: C21H28N4 4+
Molecular Weight: 336.5

A mixture of tris(4-nitrobenzyl)amine (compound 21) (848 mg, 2 mmol), 10% Pd—C (42.4 mg) and aqueous HCl (37%, 4 ml) in methanol (30 ml) was hydrogenated at room temperature and atmospheric hydrogen pressure for 3 hours. After the catalyst was filtered off and methanol was evaporated, the residue was dissolved in ethanol and toluene. Removal of these solvents (as azeotropic mixtures with water) yielded a light yellow solid which was washed with diethyl ether to give 4-((bis(4-ammoniobenzyl)ammonio) methyl)benzenaminium as light yellow crystals. Yield: 0.56 g (84% NB the NMR indicated that the substance was not completely dried); TLC: $R_f$: 0.16 (10 methanol in dichloromethane); $^1$H NMR (300 MHz, D$_2$O): δ 7.39 (6H, d), 7.33 (6H, d), 4.33 (6H, s).

Example 25

Synthesis of 1,1'-(((benzylazanediyl)bis(methylene))bis(4,1-phenylene))bis(3-(p-tolyl)urea)

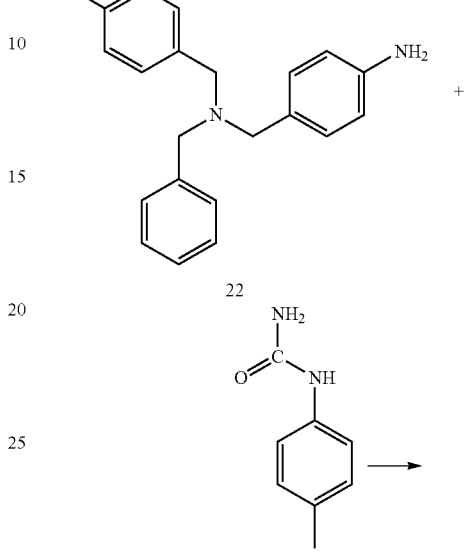

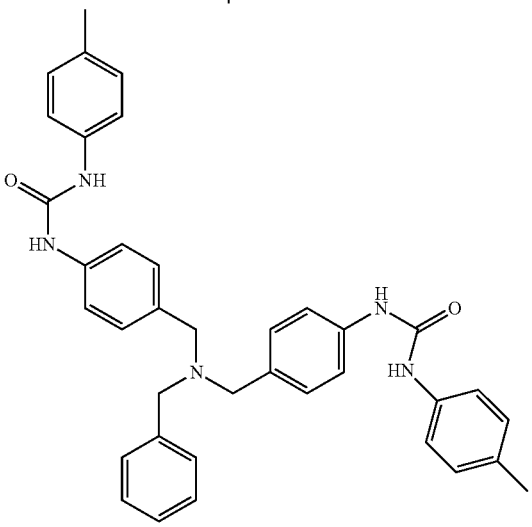

Chemical Formula: C37H37N5O2
Molecular Weight: 583.7

4-(((4-Aminobenzyl)(benzyl)amino)methyl)aniline (compound 22) (0.1 g, 0.315 mmol) was dissolved in dry dichloromethane (4 ml) and p-tolyl isocyanate (0.084 g, 0.63 mmol) was slowly added at 0° C. After stirring at room temperature for 18 hours, the solvent was removed and diethyl ether (3 ml) was added. The white solid was filtered off and dried to yield 1,1'-(((benzylazanediyl)bis(methylene))bis(4,1-phenylene))bis(3-(p-tolyl)urea) as a white powder. Yield: 0.147 g (80%); TLC: $R_f$: 0.54 (10% methanol in dichloromethane); $^1$H NMR (400 MHz, DMSO): δ 8.54 (4H, d), 7.36 (17H, m), 7.07 (4H, d), 3.45 (6H, d), 2.24 (6H, s); $^{13}$C NMR (400 MHz, DMSO): δ 152.5, 138.6, 137.1, 132.2, 130.5, 129.1, 128.9, 128.4, 128.2, 118.2, 118.1, 56.7, 56.3, 20.3 ($^{13}$C NMR had some overlapping signals).

Example 26

Synthesis of 1,1'-(((benzylazanediyl)bis(methylene))bis(4,1-phenylene))bis(3-(4-fluorophenyl)urea)

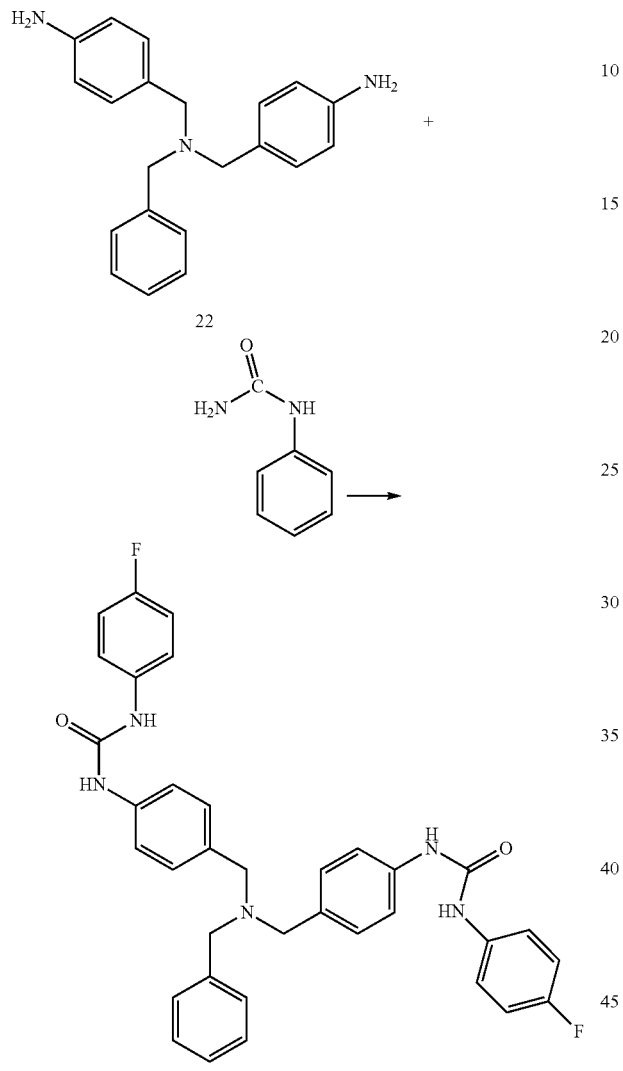

26
Chemical Formula: C35H31F2N5O2
Molecular Weight: 591.7

4-(((4-Aminobenzyl)(benzyl)amino)methyl)aniline (compound 22) (0.1 g, 0.315 mmol) was dissolved in dry dichloromethane (4 ml) and 4-fluorophenyl isocyanate (0.084 g, 0.63 mmol) was slowly added at 0° C. After stirring at room temperature for 18 hours, the solvent was removed and diethyl ether (3 ml) was added. The white solid was filtered off and dried to yield 1,1'-(((benzylazanediyl)bis(methylene))bis(4,1-phenylene))bis(3-(4-fluorophenyl)urea) as a white powder. Yield 0.14 g (75%); TLC: $R_f$: 0.59 (10% methanol in dichloromethane); $^1$H NMR (400 MHz, DMSO): δ 8.66 (4H, d), 7.27 (21H, m), 3.48 (2H, s), 3.42 (4H, s); $^{13}$C NMR (300 MHz, DMSO): δ 153.5, 139.3, 136.94, 136.90, 133.2, 129.8, 129.3, 129.1, 120.8, 120.6, 119.1, 116.3, 116.0, 80.3, 80.1 ($^{13}$C NMR had some overlapping signals).

Example 27

Synthesis of 1,1'-(((benzylazanediyl)bis(methylene))bis(4,1-phenylene))bis(3-phenylurea)

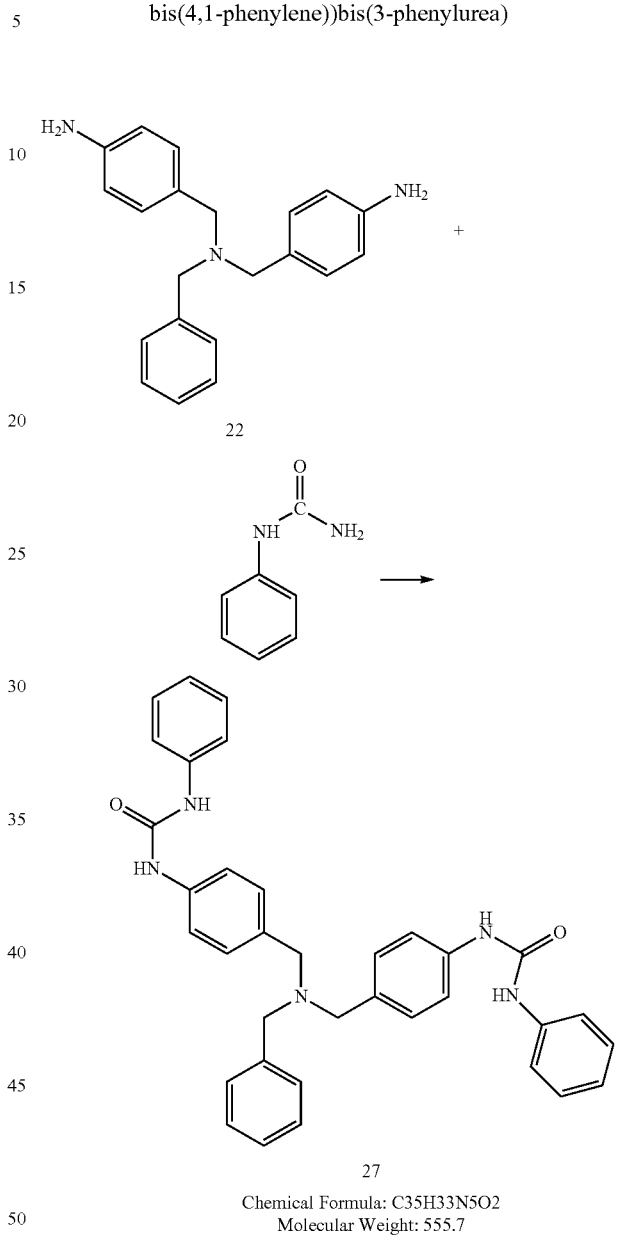

27
Chemical Formula: C35H33N5O2
Molecular Weight: 555.7

4-(((4-Aminobenzyl)(benzyl)amino)methyl)aniline (compound 22) (0.1 g, 0.315 mmol) was dissolved in dry dichloromethane (4 ml) and phenyl isocyanate (0.075 g, 0.63 mmol) was slowly added at 0° C. After stirring at room temperature for 18 hours, the solvent was removed and diethyl ether (3 ml) was added. The white solid was filtered off and dried to yield 1,1'-(((benzylazanediyl)bis(methylene))bis(4,1-phenylene))bis(3-phenylurea) as a white powder. Yield: 0.08 g (46%); TLC: $R_f$: 0.76 (10% methanol in dichloromethane); $^1$H NMR (400 MHz, DMSO): δ 8.61 (4H, s), 7.22 (23H, m), 3.49 (4H, s), 3.43 (2H, s); $^{13}$C NMR (400 MHz, DMSO): δ 152.5, 139.7, 139.3, 138.5, 132.4, 128.9, 128.7, 128.4, 128.2, 126.8, 121.7, 118.1, 56.7, 56.3.

Example 28

Synthesis of 1,1',1''-((nitrilotris(methylene))tris(benzene-4,1-diyl))tris(3-(p-tolyl)urea)

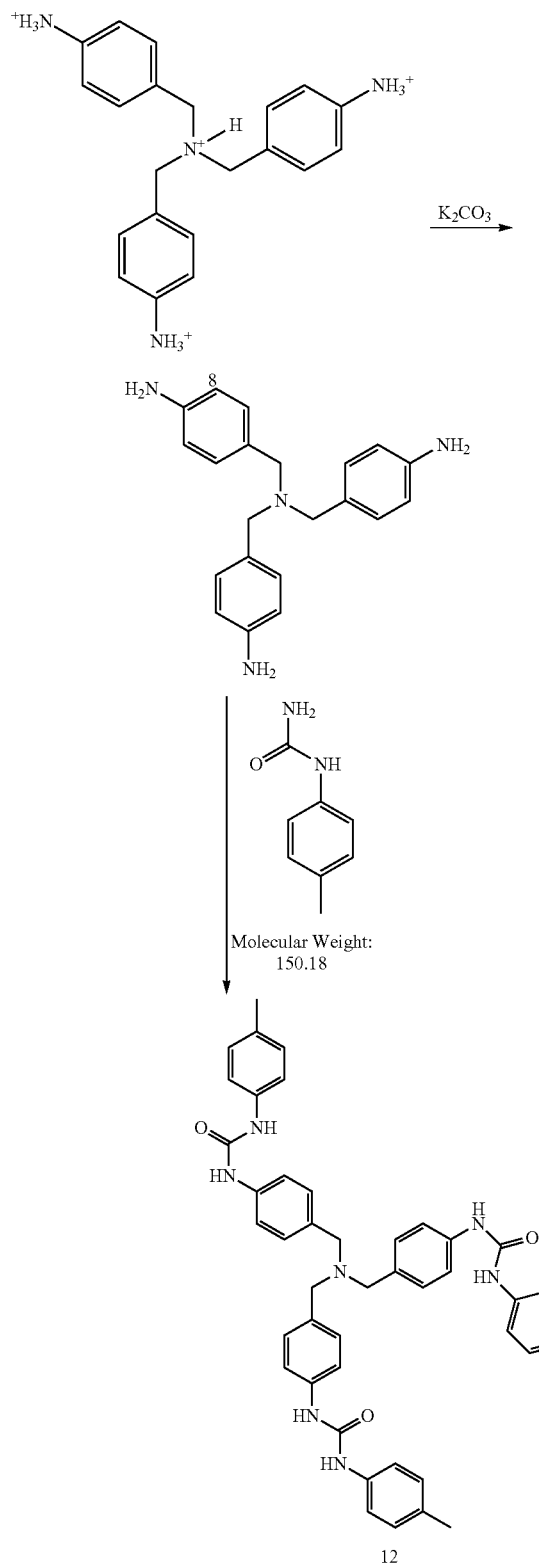

12

Chemical Formula: C45H45N7O3
Molecular Weight: 731.9

4-((Bis(4-ammoniobenzyl)ammonio)methyl)benzenaminium (compound 24) (100 mg, 0,297 mmol) was dissolved in water and stirred at room temperature, before potassium carbonate was added until the pH became 11-12. The mixture was extracted three times with dichloromethane and subsequently dried in vacuo. The residue was dissolved in dry dichloromethane (4 ml) and p-tolyl isocyanate (0.136 g, 0.9 mmol) was slowly added at 0° C. After stirring at room temperature for 18 hours, the solvent was removed and diethylether (3 ml) was added. The white solid was filtered off to give 1,1',1''-((nitrilotris(methylene))tris(benzene-4,1-diyl))tris(3-(p-tolyl)urea) as a white powder. Yield: 0.07 g (32%); TLC: $R_f$: 0.76 (10% methanol in dichloromethane); $^1$H NMR (300 MHz, DMSO): δ 8.57 (6H, d), 7.25 (24H, m), 3.41 (6H, s), 2.24 (9H, s).

Example 29

Synthesis of 4-((benzyl(4-(dimethylamino)benzyl)amino)methyl)-N,N-dimethylaniline

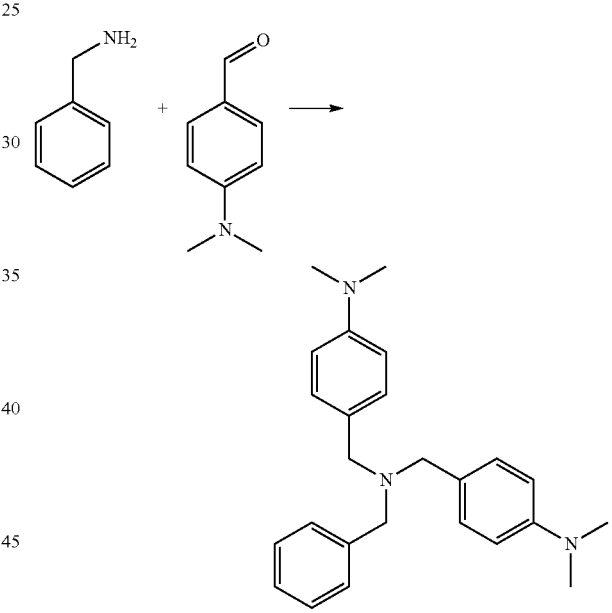

29
Chemical Formula: C25H31N3
Molecular Weight: 373.5

A solution of benzylamine (1.29 g, 12 mmol) and 4-(dimethylamino)benzaldehyde (3.75 g, 25 mmol) in methanol (50 ml) was stirred for 30 minutes before sodium cyanoborohydride (1.6 g, 25 mmol) and 4 Å molecular sieves were added. The mixture was stirred overnight, filtered and thereafter dried in vacuo. The residue was separated with flash chromatography (5-10% ethyl acetate in dichloromethane) to give 4-((benzyl(4-(dimethylamino)benzyl)amino)methyl)-N,N-dimethylaniline as a brown viscous oil. Yield: 1.6 g (35%); TLC: $R_f$: 0.83 (10% methanol in dichloromethane); $^1$H NMR (400 MHz, CDCl$_3$): δ 7.32 (2H, m), 7.18 (7H, m), 6.63 (4H, d), 3.45 (2H, s), 3.38 (4H, s), 2.84 (12H, s); $^{13}$C NMR (400 MHz, CDCl$_3$): δ 149.7, 140.3, 129.7, 128.7, 128.0, 127.7, 126.5, 112.7, 57.4, 57.0, 40.8.

Example 30

Synthesis of N-benzyl-N-(4-(methoxycarbonyl)benzyl)-1-(4(methoxycarbonyl)phenyl)methanaminium chloride

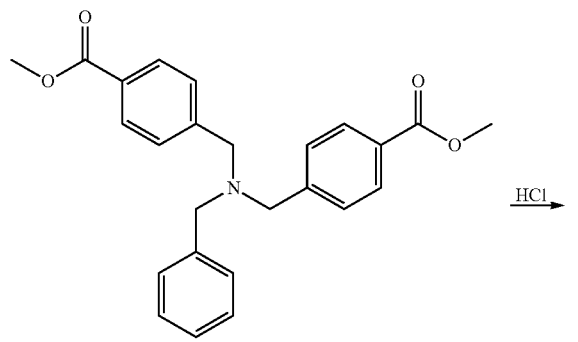

17

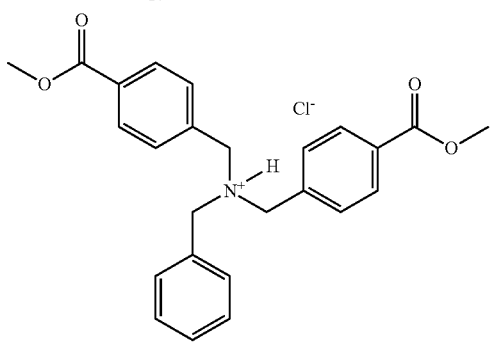

Chemical Formula: C25H26ClNO4
Molecular Weight: 439.9

Dimethyl 4,4'-((benzylazanediyl)bis(methylene))dibenzoate (compound 17) (0.2 g, 0.5 mmol) was added to stirring diethyl ether in a round bottom flask and 2.0 M hydrochloride solution in diethyl ether (0.3 mL, 0.6 mmol) was slowly added. After 5 minutes, the precipitate was filtered off and dried under vacuum to yield N-benzyl-N-(4-(methoxycarbonyl)benzyl)-1-(4-(methoxycarbonyl)phenyl)methanaminium chloride as a light brown powder.

Example 31

Synthesis of N-benzyl-N-(4-(methoxycarbonyl)benzyl)-1-(4-(methoxycarbonyl)phenyl)methanaminium methanesulfonate

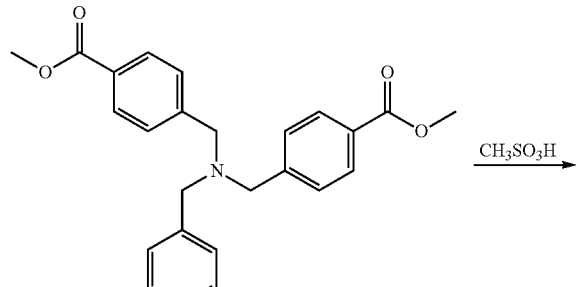

17

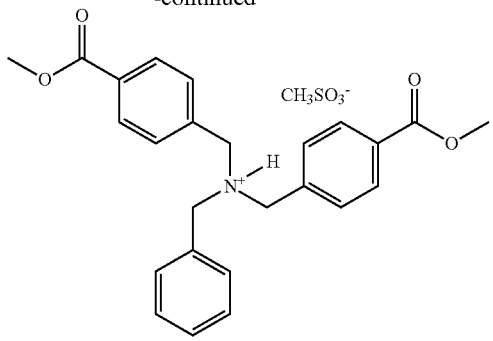

Chemical Formula: C26H29NO7S
Molecular Weight: 499.6

Dimethyl 4,4'-((benzylazanediyl)bis(methylene))dibenzoate (compound 17) (0.2 g, 0.5 mmol) was added to stirring diethyl ether in a round bottom flask and methane sulfonic acid (0.05 g, 0.52 mmol) was slowly added. After 5 minutes, the precipitate was filtered off and dried under vacuum to yield N-benzyl-N-(4-(methoxycarbonyl)benzyl)-1-(4-(methoxycarbonyl)phenyl)methanaminium methanesulfonate as a brown viscous substance.

Example 32

Synthesis of N-benzyl-N-(4-carboxybenzyl)-1-(4-carboxyphenyl)methanaminium chloride

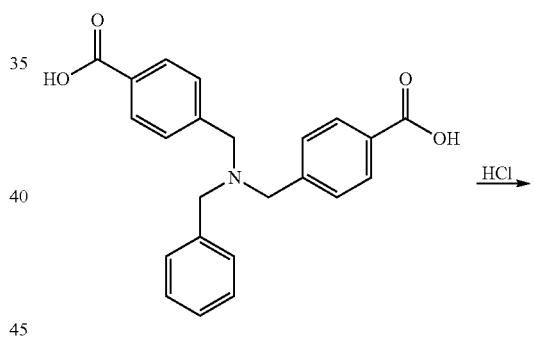

18

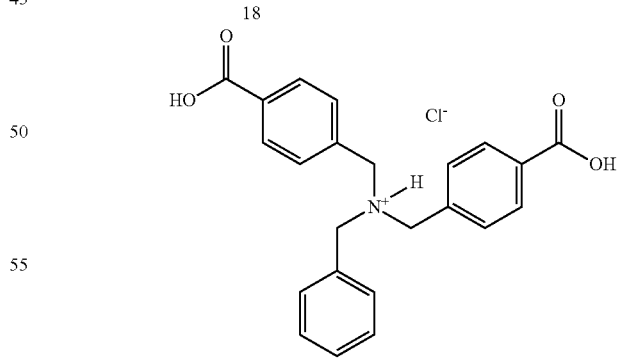

Chemical Formula: C23H22ClNO4
Molecular Weight: 411.9

4,4'-((Benzylazanediyl)bis(methylene)dibenzoic acid (compound 18) (0.2 g, 0.53 mmol) was added to stirring diethyl ether in a round bottom flask and 2.0 M hydrochloride solution in diethyl ether (0.3 mL, 0.6 mmol) was slowly added. After 5 minutes, the precipitate was filtered off and dried under vacuum to yield N-benzyl-N-(4-carboxybenzyl)-1-(4-carboxyphenyl)methanaminium chloride as a light grey crystal-like powder.

Example 33

Synthesis of N-benzyl-N-(4-carboxybenzyl)-1-(4-carboxyphenyl)methanaminium methanesulfonate

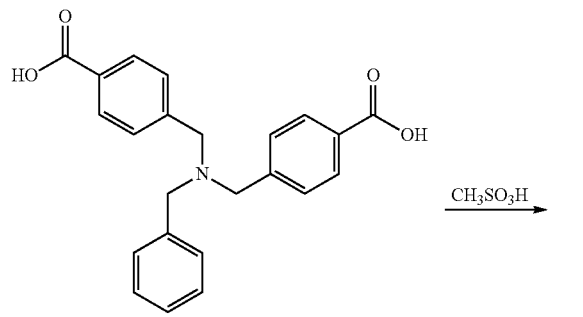

18

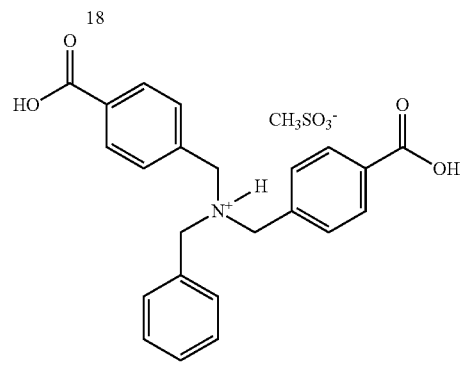

Chemical Formula: C24H25NO7S
Molecular Weight: 471.5

4,4'-((Benzylazanediyl)bis(methylene)dibenzoic acid (compound 18) (0.2 g, 0.53 mmol) was added to stirring diethyl ether in a round bottom flask and methane sulfonic acid (0.06 g, 0.62 mmol) was slowly added. After 5 minutes, the precipitate was filtered off and dried under vacuum to yield N-benzyl-N-(4-carboxybenzyl)-1-(4-carboxyphenyl)methanaminium methanesulfonate chloride as a red viscous substance.

Example 34

Synthesis of N-benzyl-N-(4-(tert-butyl)benzyl)-1-(4-(tert-butyl)phenyl)methanaminium chloride

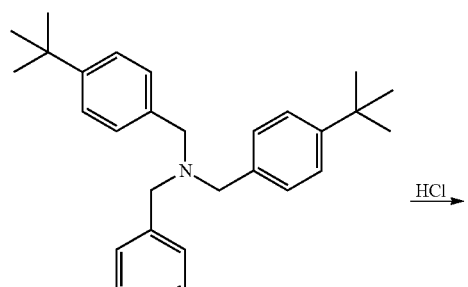

19

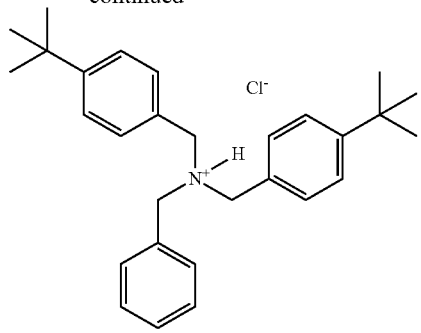

Chemical Formula: C29H38ClN
Molecular Weight: 436.1

N-Benzyl-N-(4-(tert-butyl)benzyl)-1-(4-(tert-butyl)phenyl)methanamine (compound 19) (0.2 g, 0.46 mmol) was added to stirring diethyl ether in a round bottom flask and 2.0 M hydrochloride solution in diethyl ether (0.25 mL, 0.5 mmol) was slowly added. After 5 minutes, the precipitate was filtered off and dried under vacuum to yield of N-benzyl-N-(4-(tert-butyl)benzyl)-1-(4-(tert-butyl)phenyl)methanaminium chloride as a white crystal-like powder.

Example 35

Synthesis of N-benzyl-N-(4-(tert-butyl)benzyl)-1-(4-(tert-butyl)phenyl)methanaminium methanesulfonate

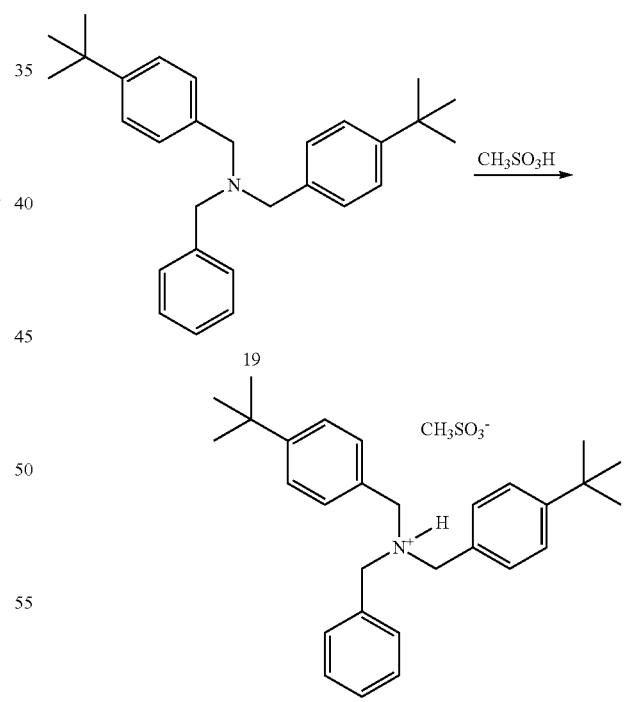

Chemical Formula: C30H41NO3S
Molecular Weight: 495.7

N-Benzyl-N-(4-(tert-butyl)benzyl)-1-(4-(tert-butyl)phenyl)methanamine (compound 19) (0.2 g, 0.46 mmol) was added to stirring diethyl ether in a round bottom flask and methane sulfonic acid (0.05 g, 0.52 mmol) was slowly added. After 5 minutes, the precipitate was filtered off and

Example 36

Synthesis of N-benzyl-N-(4-nitrobenzyl)-1-(4-nitrophenyl)methanaminium chloride)

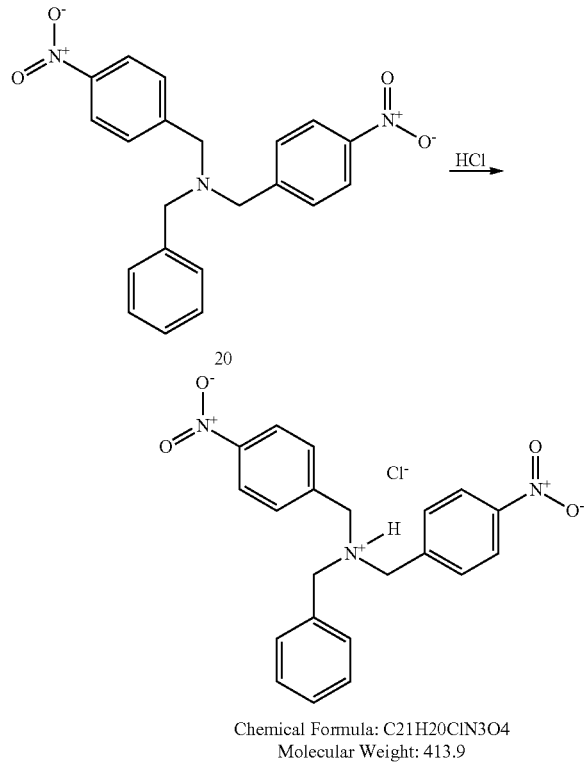

N-Benzyl-N-(4-nitrobenzyl)-1-(4-nitrophenyl)methanamine (compound 20) (0.2 g, 0.53 mmol) was added to stirring diethyl ether in a round bottom flask and 2.0 M hydrochloride solution in diethyl ether (0.3 mL, 0.6 mmol) was slowly added. After 5 minutes, the precipitate was filtered off and dried under vacuum to N-benzyl-N-(4-nitrobenzyl)-1-(4-nitrophenyl)methanaminium chloride as a light yellow crystal-like powder.

Example 37

Synthesis of N-benzyl-N-(4-nitrobenzyl)-1-(4-nitrophenyl)methanaminium methanesulfonate

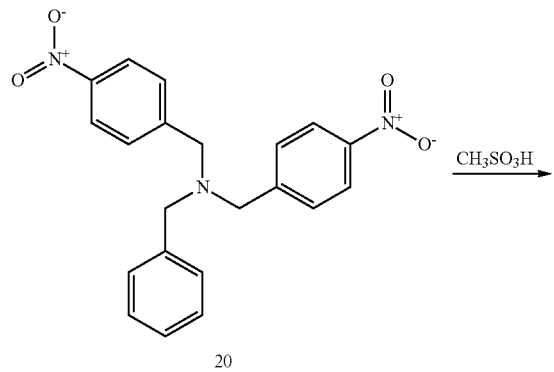

-continued

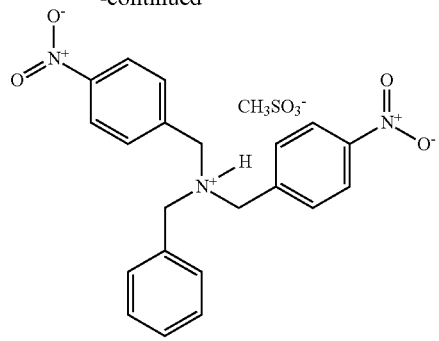

Chemical Formula: C22H23N3O7S
Molecular Weight: 473.5

N-benzyl-N-(4-nitrobenzyl)-1-(4-nitrophenyl)methanamine (compound 20) (0.2 g, 0.53 mmol) was added to stirring diethyl ether in a round bottom flask and methane sulfonic acid (0.06 g, 0.62 mmol) was slowly added. After 5 minutes, the precipitate was filtered off and dried under vacuum to yield N-benzyl-N-(4-(dimethylamino)benzyl)-1-(4-(dimethylamino)phenyl)methanaminium methanesulfonate as a light yellow viscous substance.

Example 38

Synthesis of N,N-bis(4-aminobenzyl)-1-phenylmethanaminium chloride

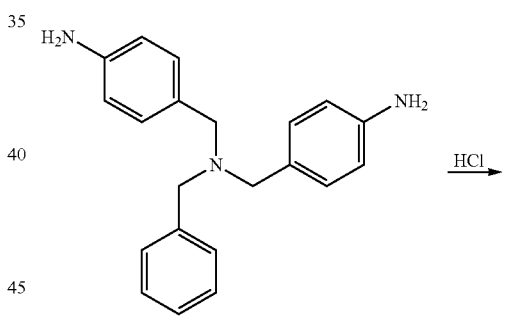

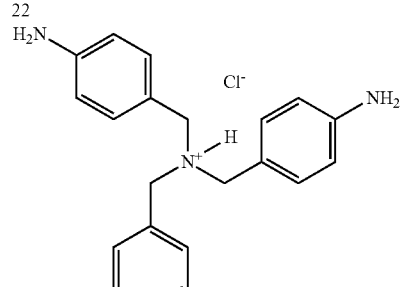

Chemical Formula: C21H24ClN3
Molecular Weight: 353.9

4-(((4-Aminobenzyl)(benzyl)amino)methyl)aniline (compound 22) (0.2 g, 0.63 mmol) was added to stirring diethyl ether in a round bottom flask and 2.0 M hydrochloride solution in diethyl ether (0.35 mL, 0.7 mmol) was slowly added. After 5 minutes, the precipitate was filtered off and dried under vacuum to yield N,N-bis(4-aminobenzyl)-1-phenylmethanaminium chloride as a light yellow crystal-like powder.

Example 39

Synthesis of N,N-bis(4-aminobenzyl)-1-phenylmethanaminium methanesulfonate

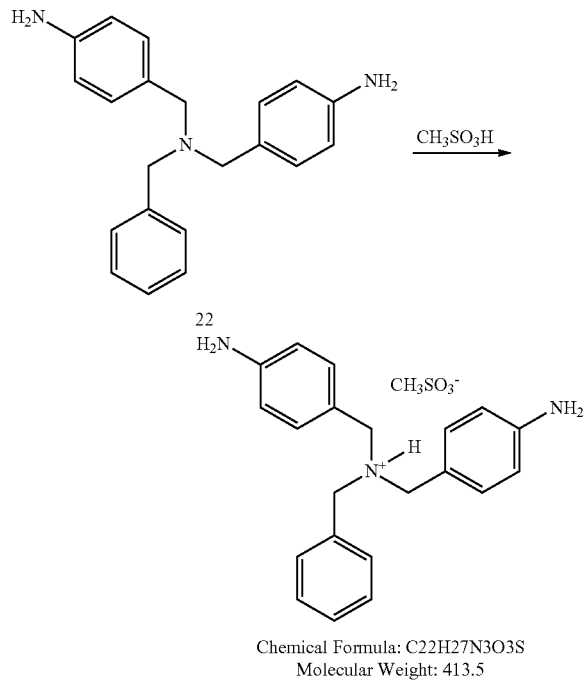

Chemical Formula: C22H27N3O3S
Molecular Weight: 413.5

4-(((4-Aminobenzyl)(benzyl)amino)methyl)aniline (compound 22) (0.2 g, 0.63 mmol) was added to stirring diethyl ether in a round bottom flask and methane sulfonic acid (0.07 g, 0.73 mmol) was slowly added. After 5 minutes, the precipitate was filtered off and dried under vacuum to yield N,N-bis(4-aminobenzyl)-1-phenylmethanaminium methanesulfonate as a light yellow viscous substance.

Example 40

Synthesis of N-benzyl-N-(4-(diethylamino)benzyl)-1-(4-(diethylamino)phenyl)methanaminium chloride

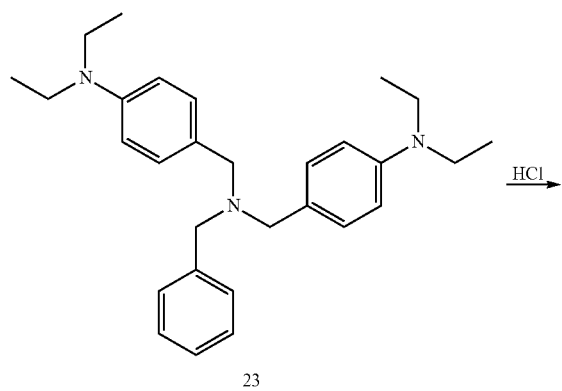

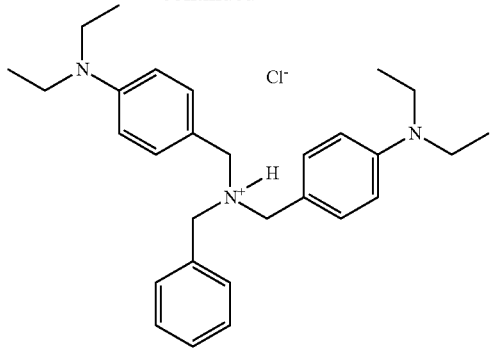

Chemical Formula: C29H40ClN3
Molecular Weight: 466.1

4-((Benzyl(4-(diethylamino)benzyl)amino)methyl)-N,N-diethylaniline (compound 23) (0.2 g, 0.47 mmol) was added to stirring diethyl ether in a round bottom flask and 2.0 M hydrochloride solution in diethyl ether (0.25 mL, 0.5 mmol) was slowly added. After 5 minutes, the precipitate was filtered off and dried under vacuum to yield N-benzyl-N-(4-(diethylamino)benzyl)-1-(4-(diethylamino)phenyl)methanaminium chloride as a light yellow crystal-like powder.

Example 41

Synthesis of N-benzyl-N-(4-(diethylamino)benzyl)-1-(4-(diethylamino)phenyl)methanaminium methanesulfonate

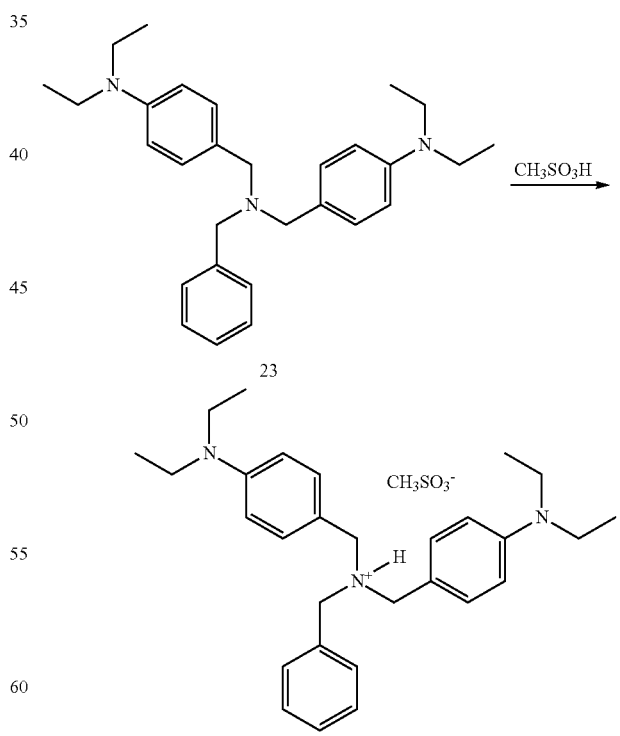

Chemical Formula: C30H43N3O3S
Molecular Weight: 525.8

4-((Benzyl(4-(diethylamino)benzyl)amino)methyl)-N,N-diethylaniline (compound 23) (0.2 g, 0.47 mmol) was added to stirring diethyl ether in a round bottom flask and methane sulfonic acid (0.25 mL, 0.5 mmol) was slowly added. After 5 minutes, the precipitate was filtered off and dried under vacuum to yield N-benzyl-N-(4-(diethylamino)benzyl)-1-(4-(diethylamino)phenyl)methanaminium methanesulfonate as a light yellow viscous substance.

Example 42

Synthesis of N-benzyl-N-(4-(3-(p-tolyl)ureido)benzyl)-1-(4-(3-(p-tolyl)ureido)phenyl)methanaminium chloride

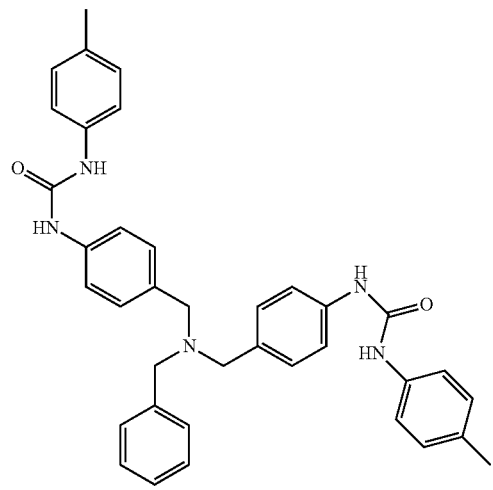

25

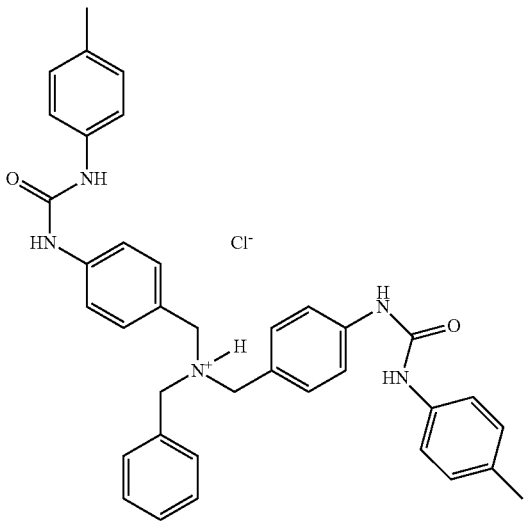

Chemical Formula: C37H38ClN5O2
Molecular Weight: 620.2

1,1'-(((Benzylazanediyl)bis(methylene))bis(4,1-phenylene))bis(3-(p-tolyl)urea) (compound 25) (0.2 g, 0.34 mmol) was added to stirring diethyl ether in a round bottom flask and 2.0 M hydrochloride solution in diethyl ether (0.2 mL, 0.4 mmol) was slowly added. After 5 minutes, the precipitate was filtered off and dried under vacuum to yield N-benzyl-N-(4-(3-(p-tolyl)ureido)benzyl)-1-(4-(3-(p-tolyl)ureido)phenyl)methanaminium chloride as a yellow crystal-like powder.

Example 43

Synthesis of N-benzyl-N-(4-(3-(p-tolyl)ureido)benzyl)-1-(4-(3-(p-tolyl)ureido)phenyl)methanaminium methanesulfonate

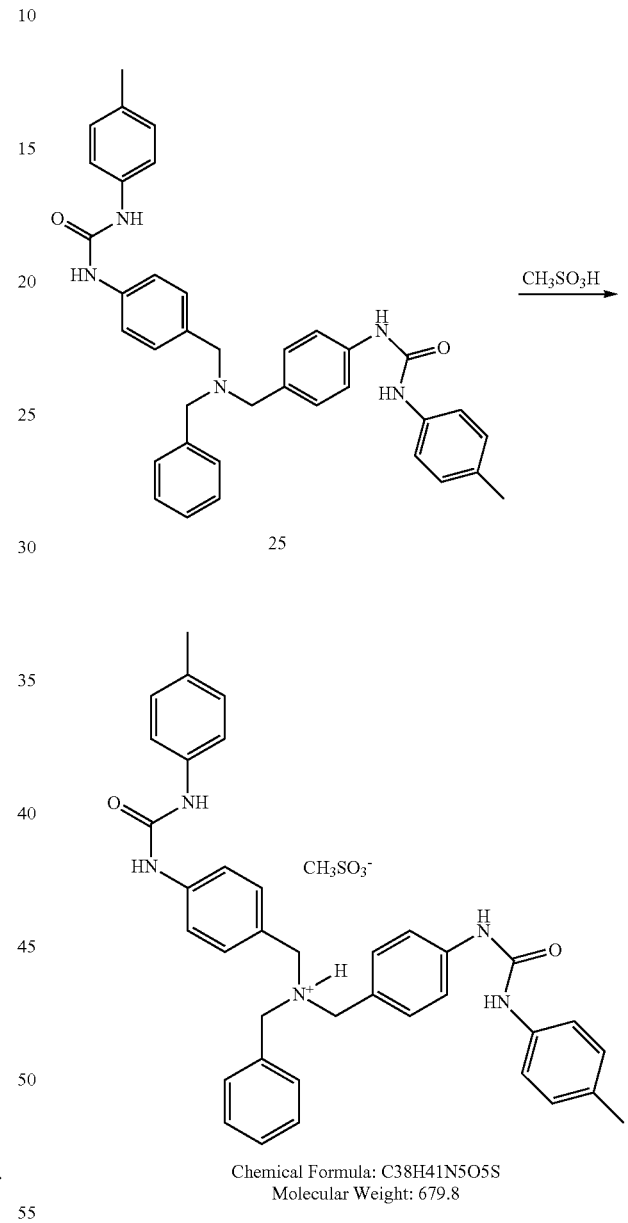

1,1'-(((Benzylazanediyl)bis(methylene))bis(4,1-phenylene))bis(3-(p-tolyl)urea) (compound 25) (0.2 g, 0.34 mmol) was added to stirring diethyl ether in a round bottom flask and methane sulfonic acid (0.04 g, 0.42 mmol) was slowly added. After 5 minutes, the precipitate was filtered off and dried under vacuum to yield N-benzyl-N-(4-(3-(p-tolyl)ureido)benzyl)-1-(4-(3-(p-tolyl)ureido)phenyl)methanaminium methanesulfonate as a yellow powder.

Example 44

Synthesis of N-benzyl-N-(4-(3-(4-fluorophenyl)ureido)benzyl)-1-(4-(3-(4-fluorophenyl)ureido)phenyl)methanaminium chloride

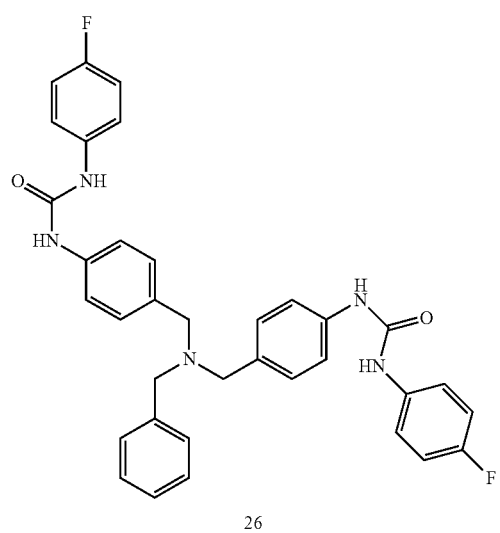

Chemical Formula: C35H32ClF2N5O2
Molecular Weight: 628.1

1,1'-(((Benzylazanediyl)bis(methylene))bis(4,1-phenylene))bis(3-(4-fluorophenyl)urea) (compound 26) (0.2 g, 0.34 mmol) was added to stirring diethyl ether in a round bottom flask and 2.0 M hydrochloride solution in diethyl ether (0.2 mL, 0.4 mmol) was slowly added. After 5 minutes, the precipitate was filtered off and dried under vacuum to yield N-benzyl-N-(4-(3-(4-fluorophenyl)ureido)benzyl)-1-(4-(3-(4-fluorophenyl)ureido)phenyl)methanaminium chloride as a yellow powder.

Example 45

Synthesis of N-benzyl-N-(4-(3-(4-fluorophenyl)ureido)benzyl)-1-(4-(3-(4-fluorophenyl)ureido)phenyl)methanaminium methanesulfonate

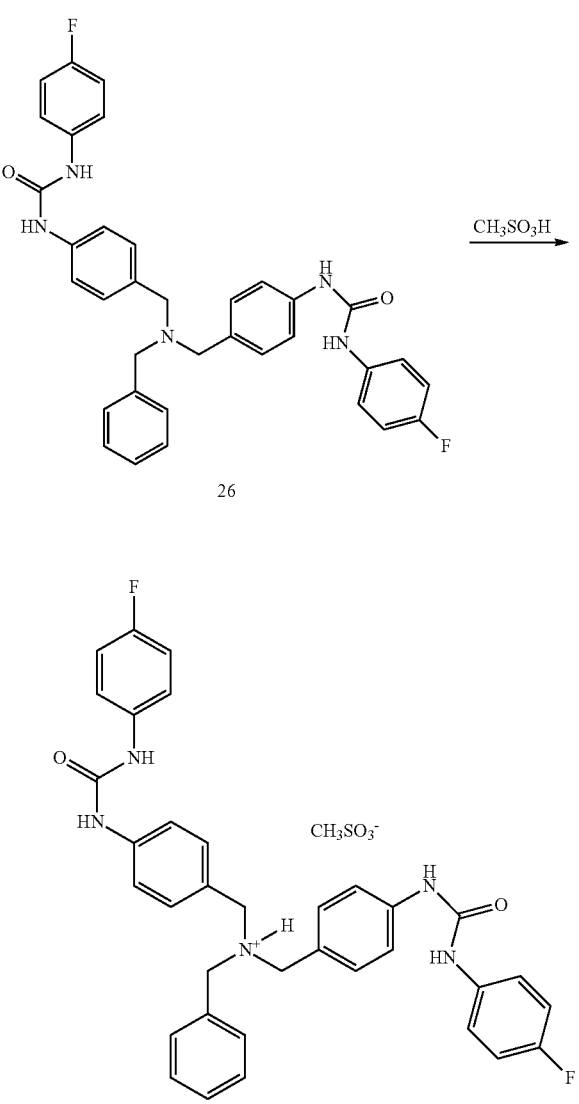

Chemical Formula: C36H35F2N5O5S
Molecular Weight: 687.8

1,1'-(((Benzylazanediyl)bis(methylene))bis(4,1-phenylene))bis(3-(4-fluorophenyl)urea) (compound 26) (0.2 g, 0.34 mmol) was added to stirring diethyl ether in a round bottom flask and methane sulfonic acid (0.04 g, 0.42 mmol) was slowly added. After 5 minutes, the precipitate was filtered off and dried under vacuum to yield N-benzyl-N-(4-(3-(4-fluorophenyl)ureido)benzyl)-1-(4-(3-(4-fluorophenyl)ureido)phenyl)methanaminium methanesulfonate as a yellow substance.

Example 46

Synthesis of N-benzyl-N-(4-(3-phenylureido)benzyl)-1-(4-(3-phenylureido)phenyl)methanaminium chloride

Example 47

Synthesis of N-benzyl-N-(4-(3-phenylureido)benzyl)-1-(4-(3-phenylureido)phenyl)methanaminium methanesulfonate

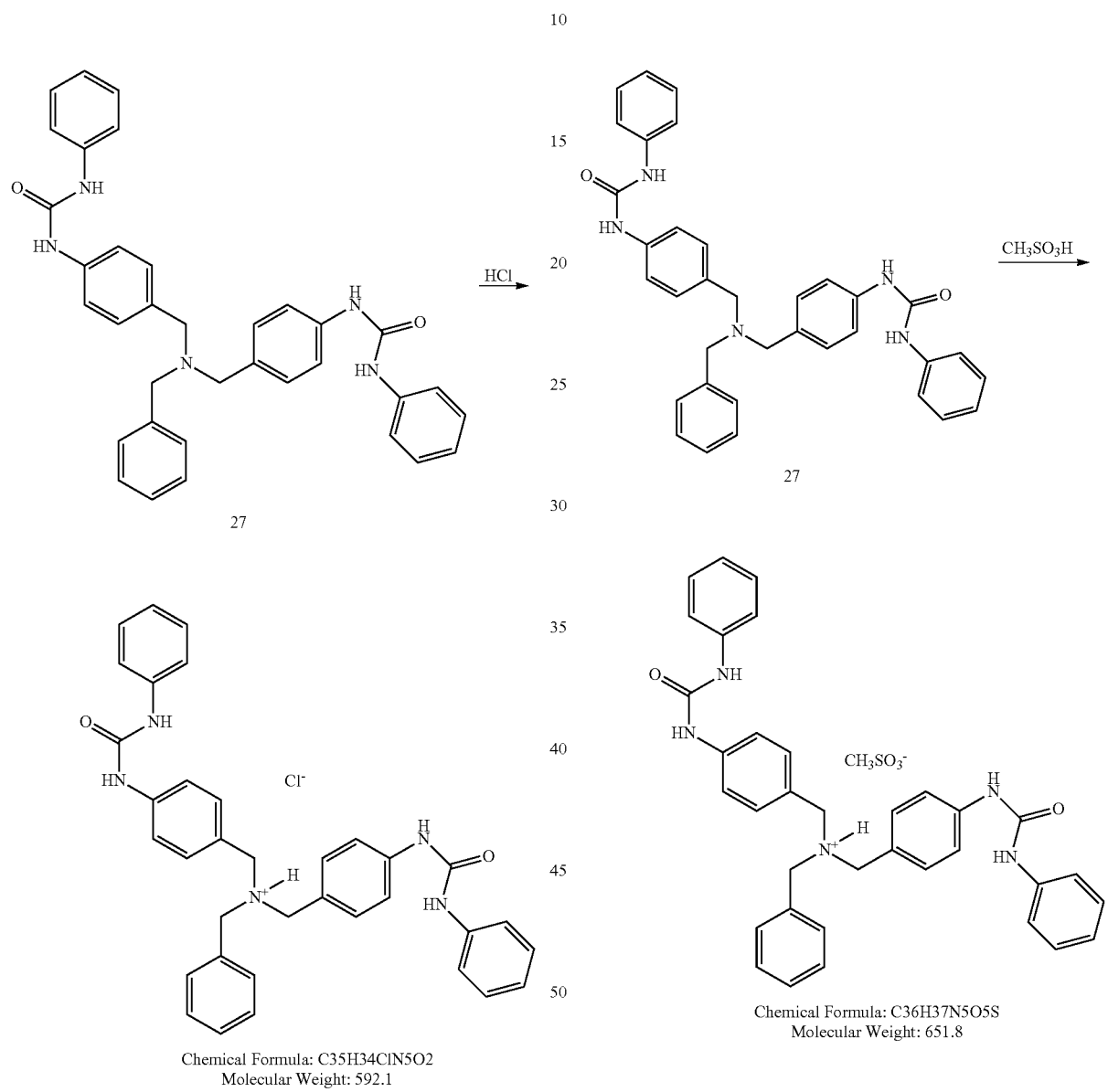

1,1'-(((Benzylazanediyl)bis(methylene))bis(4,1-phenylene))bis(3-phenylurea) (compound 27) (0.2 g, 0.36 mmol) was added to stirring diethyl ether in a round bottom flask and 2.0 M hydrochloride solution in diethyl ether (0.2 mL, 0.4 mmol) was slowly added. After 5 minutes, the precipitate was filtered off and dried under vacuum to yield N-benzyl-N-(4-(3-phenylureido)benzyl)-1-(4-(3-phenylureido)phenyl)methanaminium chloride as a yellow powder.

1,1'-(((Benzylazanediyl)bis(methylene))bis(4,1-phenylene))bis(3-phenylurea) (compound 27) (0.2 g, 0.36 mmol) was added to stirring diethyl ether in a round bottom flask and methane sulfonic acid (0.04 g, 0.42 mmol) was slowly added. After 5 minutes, the precipitate was filtered off and dried under vacuum to yield N-benzyl-N-(4-(3-phenylureido)benzyl)-1-(4-(3-phenylureido)phenyl)methanaminium methanesulfonate as a viscous yellow substance.

Example 48

Synthesis of N-benzyl-N-(4-(dimethylamino)benzyl)-1-(4-(dimethylamino)phenyl)methanaminium chloride

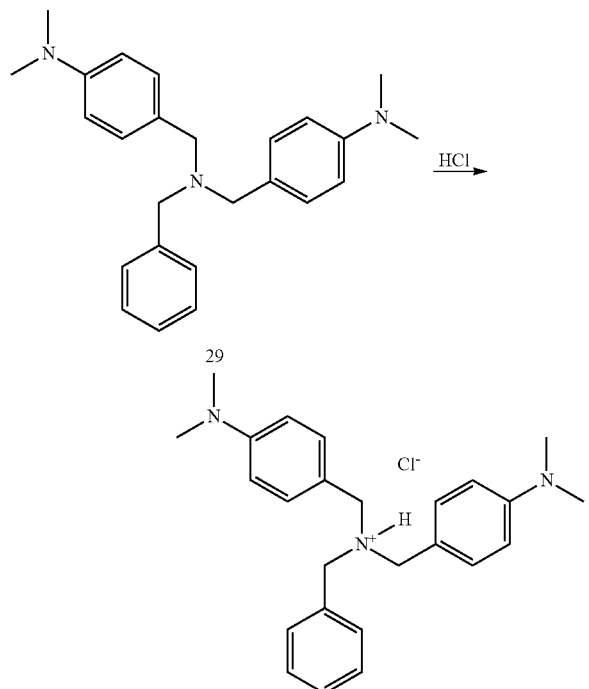

Chemical Formula: C25H32ClN3
Molecular Weight: 410.0

4-(Benzyl(4-(dimethylamino)benzyl)amino)methyl)-N,N-dimethylaniline (compound 29) (0.2 g, 0.54 mmol) was added to stirring diethyl ether in a round bottom flask and 2.0 M hydrochloride solution in diethyl ether (0.3 mL, 0.6 mmol) was slowly added. After 5 minutes, the precipitate was filtered off and dried under vacuum to yield N-benzyl-N-(4-(dimethylamino)benzyl)-1-(4-(dimethylamino)phenyl)methanaminium chloride as a light yellow crystal-like powder.

Example 49

Synthesis of N-benzyl-N-(4-(dimethylamino)benzyl)-1-(4-(dimethylamino)phenyl)methanaminium methanesulfonate

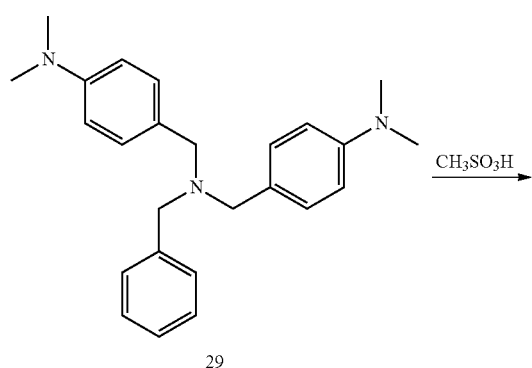

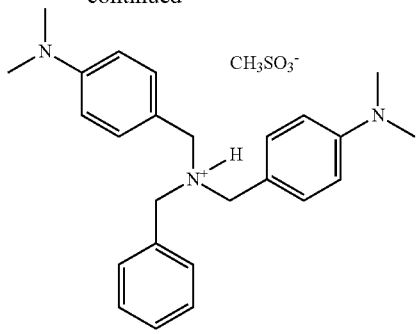

Chemical Formula: C26H35N3O3S
Molecular Weight: 469.6

4-((Benzyl(4-(dimethylamino)benzyl)amino)methyl)-N,N-dimethylaniline (compound 29) (0.2 g, 0.54 mmol) was added to stirring diethyl ether in a round bottom flask and methane sulfonic acid (0.06 g, 0.62 mmol) was slowly added. After 5 minutes, the precipitate was filtered off and dried under vacuum to yield N-benzyl-N-(4-(dimethylamino)benzyl)-1-(4-(dimethylamino)phenyl)methanaminium methanesulfonate as a light brown viscous substance.

Example 50

Aqueous Solubility of Free Bases and Various Salts

The aqueous solubility of various amine compounds and their corresponding salts were determined by dissolution of various amounts of the respective compounds at room temperature.

| Compound | Solubility free base (mg/ml) | Solubility HCl salt | Solubility Mesylate salt |
|---|---|---|---|
| 17 | <0.36 | <0.36 | <0.36 |
| 18 | <0.05 | <0.05 | <0.05 |
| 19 | <0.05 | <0.05 | <0.05 |
| 20 | <3 | <3 | <3 |
| 22 | <0.05 | 4.5 | >22 |
| 23 | <0.05 | 15 | >34 |
| 25 | <0.05 | <0.05 | <0.05 |
| 26 | <1.5 | <1.5 | <1.5 |
| 27 | <0.5 | <0.5 | <0.5 |
| 29 | <0.16 | 6 | 94 |

Example 51

Aqueous Solubility of Tribenzylamine as Free Bases and Various Salts

Tribenzylamine and the corresponding salts were dissolved in water and the solubility was quantified (area under curve (AUC)) by HPLC Solubility of Tribenzylamine and its Corresponding HCl and Mesylate Salts, Tested on HPLC.

| Compound | Free base (mAu*s) | HCl salt (mAu*s) | Mesylate salt (mAu*s) |
|---|---|---|---|
| AUC | ≈0 | 406 | 1975 |

Examples 52-54

Example 52

Testing of Derivatized and Newly Synthesized Tertiary Amines in the AKAP18δ-PLB AlphaScreen Assay The compounds of formula (I) and (I') were made in two groups that differed in their substituents on the aromatic rings. Tertiary amines where two of three substituents were similar were defined in one group (Series 2, 2a-2h), while those containing three unique substituents were in the other (Series 3, 3a-3g).

Two compounds in the group 2a-2h were found to have particularly low $EC_{50}$ values. Compound 2b contained four hydrogen-bond donors and two hydrogen-bond acceptors, increasing the possibility of binding to the protein complex through hydrogen binding. In compound 2g two nitrogens were introduced in substituents coupled to the aromatic rings, leaving the molecule with three hydrogen-binding domains. FIGS. 2 and 3 show the concentration-response curves of compounds 2b and 2g in the AKAP18δ assay.

In the last group of derivatized compounds, the central nitrogen had three different substituents, and by using fragments of the compounds giving a low $EC_{50}$ value further highly active compounds where obtained. Compound 3b was based on the structure of 2b, having one substituent with hydroxyl groups, and the other with fluorine in para-position. The $EC_{50}$ value of 3b was approximately the same as for 2b, as shown in FIG. 4.

Two compounds were synthesized based on 2g, keeping one of the two dimethylamino substituents. In 3c the other part of the molecule was a diphenyl group, a hydrophobic moiety like the one to be found in some of the original compounds. This resulted in an $EC_{50}$ value of 0.327 µM and was the most potent compound described. Compound 3d also contained the dimethylamino group, this time in combination with a benzofuran. This compound had an $EC_{50}$ of 2.79 µM. The concentration response curves of compounds 3c and 3d are shown in FIGS. 5 and 6.

In order to find out whether an acidic moiety was favorable, a compound containing both a basic moiety and a carboxylic acid was synthesised. The synthesis started with making the methylether. After completion of the reaction, a small amount of compound 3e was isolated to before hydrolysis to provide compound 3f. In 3f a carboxylic acid was introduced on the benzene ring, giving the molecule both basic- and acidic properties, like the original group of analogues had. However, compound 3e ($EC_{50}$ 34.84 µM) and compound 3f (36.55 µM) were found to have slightly higher $EC_{50}$ values.

In the last compound synthesized another acidic group was introduced, this time a tetrazole. The tetrazole is a part of the pharmacophore of a group of existing drugs, angiotensin-II blockers, commonly used in the treatment of hypertension.

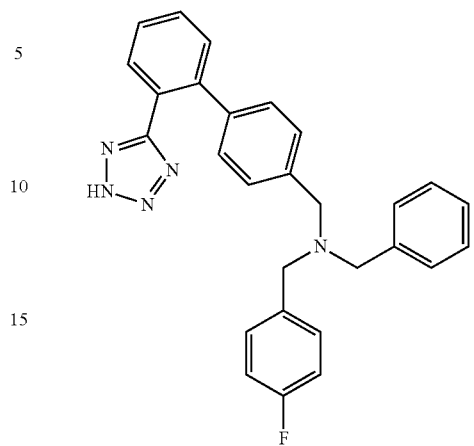

Compound 3g

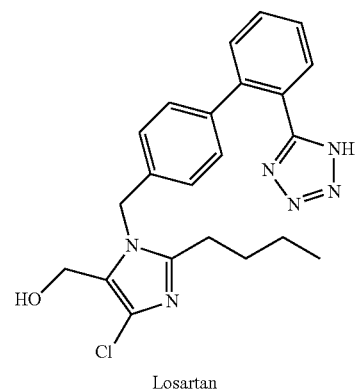

Losartan

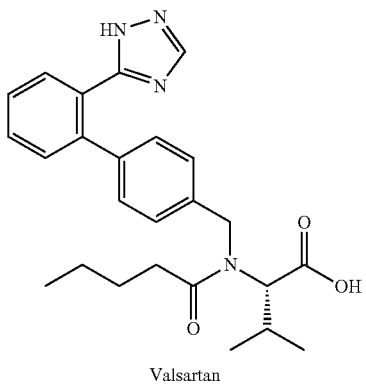

Valsartan

The rationale for introducing this group was that it had the acidic properties similar to the originally identified compound, and earlier testing had shown that substituents containing nitrogen seemed to be preferable in terms of low $EC_{50}$. In this case, four nitrogens were introduced to the molecule, making molecule able to act both as hydrogen binding acceptor and donor. In addition to this an extra benzene ring was added, giving the molecule a larger hydrophobic site. However, compound 3g was found to have the highest $EC_{50}$ value of this screen with 47.07 µM.

Example 53

Cell-Based Testing of Derivatized Compounds in Cardiomyocytes

Based on data from studies in cardiomyocytes assay using a peptide that blocks AKAP18δ-PLB interaction, it was expected that effective compounds would also cause disruption of the AKAP18δ-PLB complex and decrease PLB-$Ser^{16}$ phosphorylation (Lygren et al. in EMBO Reports, volume 8, issue 11, page 1061-1067 (2007). A small selection of hits from the derivatized compounds were tested in this cell-based assay, performed as described in Lygren et al.

Briefly, compounds were added to primary cultures of rat neonatal cardiomyocytes were added compounds about 24 hour prior stimulation with isoproterenol, and amount of phosphorylated $Ser^{16}$-PLB was analyzed by western blotting using a $pSer^{16}$-PLB phosphospecific antibody. Actin was used as a loading control.

Four synthesized compounds were tested, as shown below:

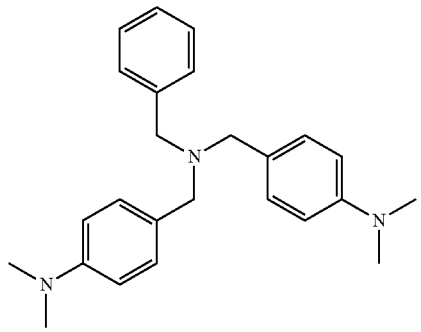

2g

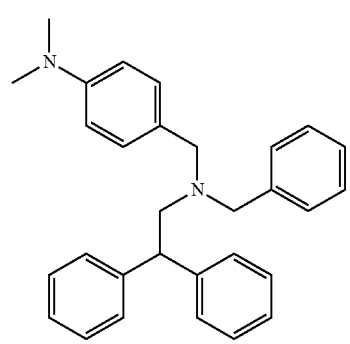

3c

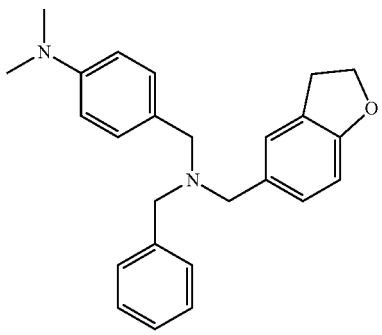

3d

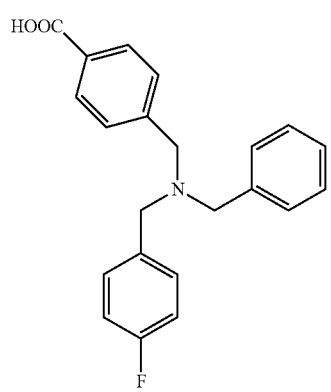

3f

Compound 2g displayed a concentration dependent inhibition of PLB-phosphorylation. Even though compound 3c had the lowest $EC_{50}$ value of the synthesized compounds in vitro, the effect on PLB phosphorylation in cardiomyovcytes was somewhat weaker than that of 2g. Compounds 3d and 3f were tested in the same experiment, but did not appear to have an effect on the phosphorylation of PLB in this assay.

The results are shown in FIG. 7. Rat neonatal cardiomyocytes treated with compounds 24 hours prior stimulation with isoproterenol (100 nM, 5 minutes). The histogram shows levels of phosphorylated $Ser^{16}$-PLB quantified by densiometery relative to actin levels.

Example 54

Cell Viability Assay on Derivatized Compounds

Compound toxicity was measured in a luminescence assay that gives a signal proportional to the amount of metabolically active cells in the sample; the assay was performed as described by the supplier. All synthesized compounds were tested in the viability assay, and viability was registered at 24 hours and 72 hours. The results after 24 hours incubation with the synthesised compounds is shown in FIG. 8.

Examples 52-54

Summary of Test Results on Derivatized Compounds

TABLE 2

Overview of effect and viability of synthesized tertiary amines with two different substituents.
$EC_{50}$ average is given with ±standard deviation (n = 3) or ±half range (n = 2).

| Compound | Structure | $EC_{50}$ in μM (n) | Effect on PLB phosphorylation in cardiomyocytes | Viability (100 μM) 24 hours |
| --- | --- | --- | --- | --- |
| 2a | 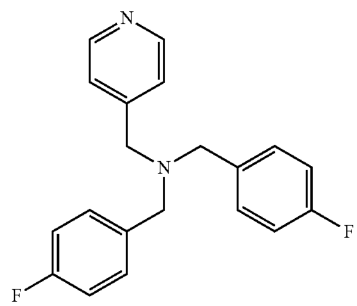 [SMILES: Fc1ccc(CN(Cc2ccncc2)Cc2ccc(F)cc2)cc1] | – | n.d | 0.85 |
| 2b | 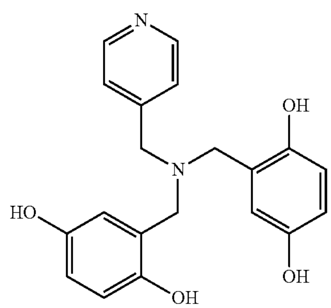 [SMILES: Oc1ccc(O)c(CN(Cc2ccncc2)Cc2cc(O)ccc2O)c1] | 12.33 ± 3.08 (2) | – | 0.10 |
| 2c | 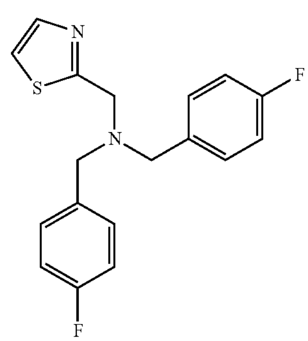 [SMILES: Fc1ccc(CN(Cc2ccc(F)cc2)Cc2nccs2)cc1] | – | n.d | 1.11 |
| 2d | 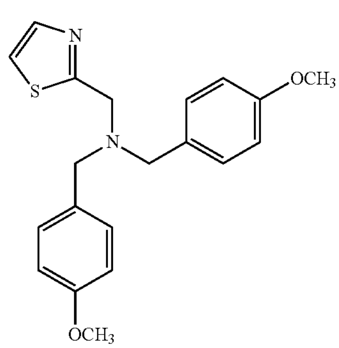 [SMILES: COc1ccc(CN(Cc2ccc(OC)cc2)Cc2nccs2)cc1] | – | n.d | 1.15 |

TABLE 2-continued

Overview of effect and viability of synthesized tertiary amines with two different substituents.
$EC_{50}$ average is given with ±standard deviation (n = 3) or ±half range (n = 2).

| Compound | Structure | $EC_{50}$ in μM (n) | Effect on PLB phosphorylation in cardiomyocytes | Viability (100 μM) 24 hours |
|---|---|---|---|---|
| 2e | *N-benzyl-N-(4-methoxybenzyl)-1-(4-methoxyphenyl)methanamine* | − | n.d | 1.01 |
| 2f | *methyl 4-((benzyl(4-(methoxycarbonyl)benzyl)amino)methyl)benzoate* | − | n.d | 0.92 |
| 2g | *N1-(4-((benzyl(4-(dimethylamino)benzyl)amino)methyl)phenyl)-N,N-dimethylamine* | 1.7 ± 0.91 (3) | ++ | 0.56 |
| 2h | *N1-(4-(((4-(dimethylamino)benzyl)(1-phenylethyl)amino)methyl)phenyl)-N,N-dimethylamine* | − | n.d | 0.91 |

− = no activity, + = possible effect, ++ = effect, n.d = not done

TABLE 3
Overview of effect and viability of synthesized tertiary amines with three different substituents.
$EC_{50}$ average is given with ±standard deviation (n = 3) or ±half range (n = 2).
| Compound | Structure | $EC_{50}$ (n) | Effect on PLB phosphorylation in cardiomyocytes | Viability (100 μM) 24 hours |
|---|---|---|---|---|
| 3a | 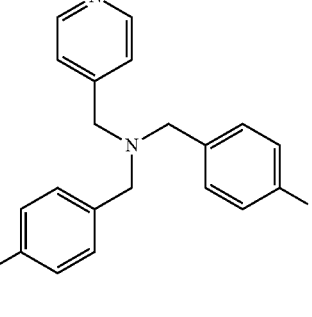 | – | n.d | 0.79 |
| 3b | 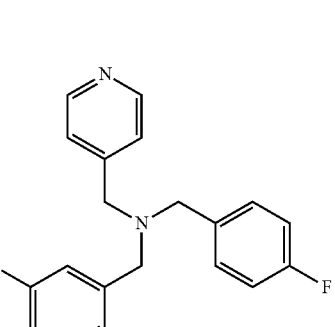 | 5.43 ± 1.11 (2) | n.d. | 0.03 |
| 3c | 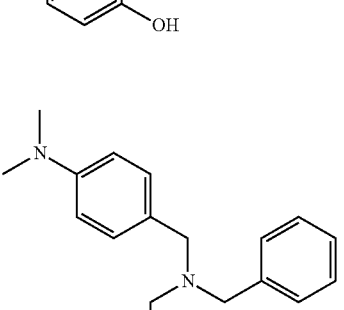 | 0.44 ± 0.18 (3) | + | 0.74 |
| 3d | 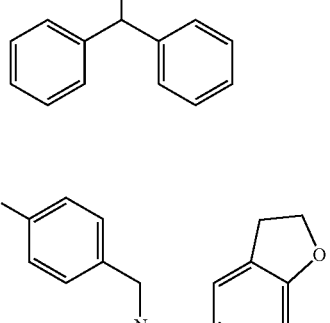 | 2.45 ± 0.73 (3) | – | 0.58 |

TABLE 3-continued

Overview of effect and viability of synthesized tertiary amines with three different substituents.
EC$_{50}$ average is given with ±standard deviation (n = 3) or ±half range (n = 2).

| Compound | Structure | EC$_{50}$ (n) | Effect on PLB phosphorylation in cardiomyocytes | Viability (100 μM) 24 hours |
|---|---|---|---|---|
| 3e | H$_3$CO$_2$C–C$_6$H$_4$–CH$_2$–N(CH$_2$–C$_6$H$_5$)(CH$_2$–C$_6$H$_4$–F) | 34.84 (1) | n.d | 0.57 |
| 3f | HOOC–C$_6$H$_4$–CH$_2$–N(CH$_2$–C$_6$H$_5$)(CH$_2$–C$_6$H$_4$–F) | 40.56 ± 7.4 (3) | + | 0.98 |
| 3g | (tetrazole-biphenyl)–CH$_2$–N(CH$_2$–C$_6$H$_5$)(CH$_2$–C$_6$H$_4$–F) | 47.07 (1) | n.d | 0.80 |

− = no activity, + = possible effect, ++ = effect, n.d = not done

Example 55

Following on Example 53, two compounds, 2g and 3d (FIGS. 9A.B and 9C, respectively), were tested in more detail for their ability to interfere with phosphorylation of phospholamban after stimulation of neonatal (FIGS. 9A and 9C) or adult (FIG. 9B) primary cultures of cardiomyocytes. As can be seen from the Figure, compound 2g inhibited phospholamban phosphorylation with a half-maximal effect of approximately 40 and 100 μM in neonatal and adult cardiomyocytes, respectively whereas compound 3d had a half-maximal effect of approximately 100 μM in neonatal cells.

Example 56

Adult rat cardiomyocytes were isolated and perfused with external solution (NaCl-125, CsCl 20, D-glucose 5, MgCl$_2$ 1, CaCl$_2$ 1.8, Hepes 10, 4-aminopyridine 5, probenecid 2, pH 7.4 by NaOH). Cell dialysis was achieved by 1-2 MO patch pipettes, filled with (in mM): CsCl 115, TEACl 20, Hepes 10, MgATP 5, Na2-Phosphocreatinine 5, EGTA 0.04, cAMP 0.005, adjusted to pH=7.2 with CsOH. Compound 2g (mesylate salt dissolved in water) was included at a concentration of 10 uM. Whole-cell Ca fluorescence measured from voltage-clamped cells was performed with Cairn Research Optoscan Monochromator (Excitation 488 nm, emission 515 nm long pass) (Cain Research Ltd., Faverham, UK). By applying 100 ms square voltage step from −45 to 0 mV at 0.125 Hz by an Axoclamp 2B amplifier (Axon Instruments, Foster City, Calif., USA), basal Ca transients were recorded, and tau values were obtained by monoexponential fitting of the $Ca^{2+}$ extrusion phase from regular transients ($\tau$) and caffeine transients ($\tau$caff) after rapid applications of 10 mM caffeine. SERCA2 rate constant were calculated as: k_SERCA=$1/\tau - 1/\tau$caff.

As can been seen from the figure, incubation with compound 2g in the presence of cAMP increased SERCA2 activity leading to a faster calcium reuptake in sarcoplasmic reticulum and relaxation of the heart to allow filling. This indicates an ability of this class of compounds to regulation SERCA2 activity, positively or negatively, possibly depending on concentration or other aspects of the structure activity relationship.

The invention claimed is:

1. A method of treating a cardiovascular disease or disorder associated with phospholamban phoshorylation, comprising administering to a patient in need thereof a therapeutically effective amount of at least one compound of formula (I) or a physiologically acceptable salt thereof:

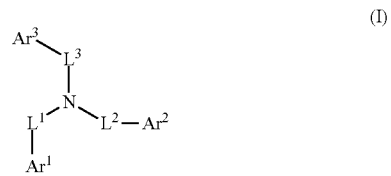

wherein
$L^1$, $L^2$ and $L^3$ independently denote $C_1$-$C_4$-alkylene optionally substituted with one phenyl;
$Ar^1$, $Ar^2$ and $Ar^3$ independently denote phenyl optionally substituted with one or more R;
wherein R independently denotes F, Cl, Br, I, $C_1$-$C_4$-haloalkyl, $OR^1$, $SR^1$, $NO_2$, $NR^2R^3$, $R^4$, C(=O)Y, $SO_3H$, $C_1$-$C_4$-alkyl, $C_1$-$C_4$-alkyl-phenyl, a 5-membered heteroaryl; or a phenyl substituted with a 5-membered heteroaryl;
$R^1$ denotes H, $C_1$-$C_4$-alkyl or $C_1$-$C_4$-alkyl-phenyl; or together two adjacent $OR^1$ groups denote —O—$CH_2$—O—;
$R^2$ and $R^3$ independently denote H or $C_1$-$C_4$-alkyl; or $NR^2R^3$ denotes —NHC(=O)—$NHAr^5$; or
together two adjacent $NR^2R^3$ groups denote —$NR^2$—CH—N— or —$NR^2$—$CH_2$—$NR^2$—; or
together with an adjacent $OR^1$ group, $NR^2R^3$ denotes —$NR^2$—$CH_2$—O— or —N—CH—O—; or
together with an adjacent $SR^1$ group, $NR^2R^3$ denotes —$NR^2$—$CH_2$—S— or —N—CH—S—;
$Ar^5$ denotes phenyl optionally substituted with $R^h$;
$R^h$ denotes halogen or $C_1$-$C_4$ alkyl;
$R^4$ denotes $C_1$-$C_4$-alkyl; or
together with an adjacent $OR^1$ group, $R^4$ denotes —$CH_2CH_2$—O—; or
together two adjacent $R^4$ groups denote —(CH)$_4$— or —(CH$_2$)$_4$—;
Y denotes $OR^5$ or $NR^6R^7$;

$R^5$ denotes H or $C_1$-$C_4$-alkyl; and
$R^6$ and $R^7$ independently denote H, $C_1$-$C_8$-alkyl or $C_3$-$C_6$ cycloalkyl;
wherein the cardiovascular disease or disorder associated with phospholamban phosphorylation is selected from congenital heart failure, myocardial infarction, post infarction heart failure, congestive heart failure, reperfusion damage, dilated cardiomyopathy, and arrhythmia.

2. The method of claim 1, wherein the compound has formula (I'):

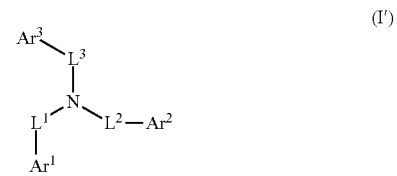

wherein
$L^1$, $L^2$ and $L^3$ independently denote $C_1$-$C_4$-alkylene optionally substituted with one phenyl;
$Ar^1$, $Ar^2$ and $Ar^3$ independently denote phenyl optionally substituted with one or more R;
wherein R independently denotes F, Cl, Br, I, $C_1$-$C_4$-haloalkyl, $OR^1$, $SR^1$, $NO_2$, $NR^2R^3$, $R^4$, C(=O)Y, $SO_3H$, $C_1$-$C_4$-alkyl, $C_1$-$C_4$-alkyl-phenyl, a 5-membered heteroaryl; or a phenyl substituted with a 5-membered heteroaryl;
$R^1$ denotes H, $C_1$-$C_4$-alkyl or $C_1$-$C_4$-alkyl-phenyl; or together two adjacent $OR^1$ groups denote —O—$CH_2$—O—;
$R^2$ and $R^3$ independently denote H or $C_1$-$C_4$-alkyl; or together two adjacent $NR^2R^3$ groups denote —$NR^2$—CH—N— or —$NR^2$—$CH_2$—$NR^2$—; or
together with an adjacent $OR^1$ group, $NR^2R^3$ denotes —$NR^2$—$CH_2$—O— or —N—CH—O—; or
together with an adjacent $SR^1$ group, $NR^2R^3$ denotes —$NR^2$—$CH_2$—S— or —N—CH—S—;
$R^4$ denotes $C_1$-$C_4$-alkyl; or
together with an adjacent $OR^1$ group, $R^4$ denotes —$CH_2CH_2$—O—; or
together two adjacent $R^4$ groups denote —(CH)$_4$— or —(CH$_2$)$_4$—;
Y denotes $OR^5$ or $NR^6R^7$;
$R^5$ denotes H or $C_1$-$C_4$-alkyl; and
$R^6$ and $R^7$ independently denote H, $C_1$-$C_8$-alkyl or $C_3$-$C_6$ cycloalkyl.

3. The method of claim 1, wherein the compound has formula (Ia):

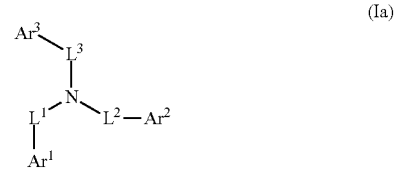

wherein
$L^1$, $L^2$ and $L^3$ independently denote $C_1$-$C_4$-alkylene optionally substituted with one phenyl;
$Ar^1$, $Ar^2$ and $Ar^3$ independently denote phenyl optionally substituted with one or more R;
wherein R independently denotes F, Cl, $CF_3$, $OR^1$, $NO_2$, $NR^2R^3$, $R^4$, C(=O)Y, $C_1$-$C_4$-alkyl, $C_1$-$C_4$-alkyl-phenyl, 5-tetrazolyl or

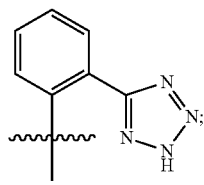 [SMILES: *c1ccccc1-c1nn[nH]n1]

$R^1$ denotes H, $C_1$-$C_4$-alkyl or $C_1$-$C_4$-alkyl-phenyl; or together two adjacent $OR^1$ groups denote —O—$CH_2$—O—;

$R^2$ and $R^3$ independently denote H or $C_1$-$C_4$-alkyl;

$R^4$ denotes $C_1$-$C_4$-alkyl; or together with an adjacent $OR^1$ group, $R^4$ denotes —$CH_2CH_2$—O—;

Y denotes $OR^5$ or $NR^6R^7$;

$R^5$ denotes H or $C_1$-$C_4$-alkyl;

$R^6$ and $R^7$ independently denote H, $C_1$-$C_8$-alkyl or $C_3$-$C_6$ cycloalkyl.

4. The method of claim 1, wherein $L^1$, $L^2$ and $L^3$ in formula (I) independently denote $C_1$-$C_3$-alkylene optionally substituted with one phenyl.

5. The method of claim 1, wherein the compound has formula (II):

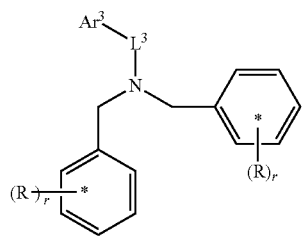

wherein
r denotes 0, 1 or 2;
$L^3$ denotes $C_1$-$C_3$-alkylene optionally substituted with one phenyl; and
$Ar^3$ denotes phenyl optionally substituted with one or two R.

6. The method of claim 1, wherein R independently denotes F, Cl, $CF_3$, $OR^1$, $NO_2$, $NR^2R^3$, $R^4$, C(=O)Y, $C_1$-$C_4$-alkyl, $C_1$-$C_4$-alkyl-phenyl, or

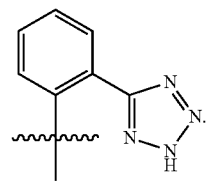 [SMILES: *c1ccccc1-c1nn[nH]n1]

7. The method of claim 1, wherein the compound contains at least one group capable of acting as a hydrogen bond donor, and/or at least one group capable of acting as a hydrogen bond acceptor.

8. The method of claim 1 wherein $L^1$, $L^2$, and $L^3$ are $C_1$-$C_4$ alkylene, $Ar^1$ is phenyl, and $Ar^2$ and $Ar^3$ are phenyl substituted with one or more R.

9. The method of claim 8 wherein $L^1$, $L^2$, and $L^3$ are methylene.

10. The method of claim 9 wherein each R is $NR^2R^3$.

11. The method of claim 10 wherein each $R^2$ and $R^3$ is methyl.

12. The method of claim 1, wherein the disease or disorder associated with phospholamban phosphorylation is myocardial infarction.

13. The method of claim 1 wherein the disease or disorder associated with phospholamban phosphorylation is reperfusion damage.

* * * * *

UNITED STATES PATENT AND TRADEMARK OFFICE
CERTIFICATE OF CORRECTION

PATENT NO. : 9,556,111 B2
APPLICATION NO. : 14/402037
DATED : January 31, 2017
INVENTOR(S) : Kjetil Tasken et al.

It is certified that error appears in the above-identified patent and that said Letters Patent is hereby corrected as shown below:

In the Drawings

Delete Drawing Sheets 1, 3, and 4 and substitute therefore with the attached Drawing Sheets 1, 3, and 4

In the Specification

At Column 5, Line 8:
(AKAP) 18ß to bind to the PKA
Should read:
(AKAP) 18δ to bind to the PKA At Column 18, Line 60:

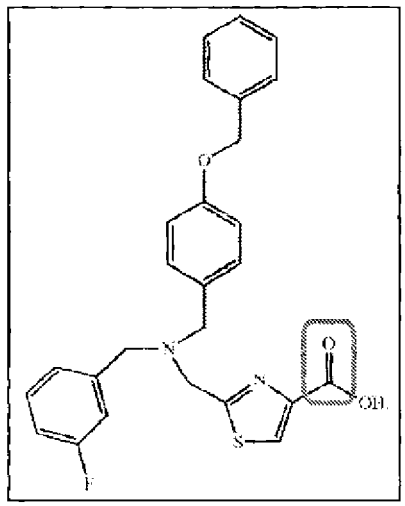 should be: 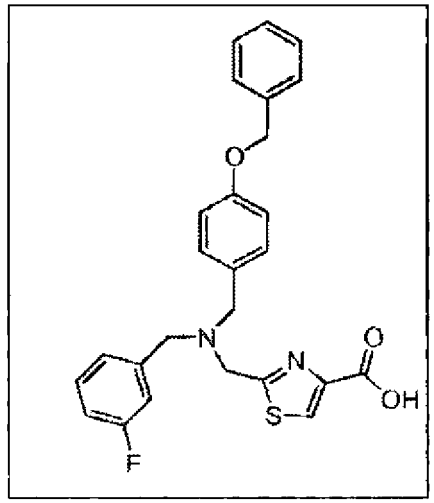

Signed and Sealed this
Nineteenth Day of December, 2017

Joseph Matal
*Performing the Functions and Duties of the*
*Under Secretary of Commerce for Intellectual Property and*
*Director of the United States Patent and Trademark Office*

At Column 208, Line 65:
solution (NaCl-125,
Should read:
solution (NaCl 125,

At Column 208, Line 67:
achieved by 1-2 MO
Should read:
achieved by 1-2 MΩ

In the Claims

At Column 212, Line 32, Claim 12, Line 1:
The method of claim 1, wherein
Should read:
The method of claim 1 wherein